US012534744B2

(12) United States Patent
Juillerat et al.

(10) Patent No.: US 12,534,744 B2
(45) Date of Patent: Jan. 27, 2026

(54) METHODS TO GENETICALLY MODIFY CELLS FOR DELIVERY OF THERAPEUTIC PROTEINS

(71) Applicant: CELLECTIS S.A., Paris (FR)

(72) Inventors: Alexandre Juillerat, New York, NY (US); Philippe Duchateau, Draveil (FR); Patrick Hong, New York, NY (US); Laurent Poirot, Paris (FR); Brian Busser, New York, NY (US); Alex Boyne, Jersey City, NJ (US)

(73) Assignee: CELLECTIS S.A., Paris (FR)

( * ) Notice: Subject to any disclaimer, the term of this patent is extended or adjusted under 35 U.S.C. 154(b) by 748 days.

(21) Appl. No.: 17/996,701

(22) PCT Filed: May 6, 2021

(86) PCT No.: PCT/EP2021/062054
§ 371 (c)(1),
(2) Date: Oct. 20, 2022

(87) PCT Pub. No.: WO2021/224416
PCT Pub. Date: Nov. 11, 2021

(65) Prior Publication Data
US 2023/0279440 A1 Sep. 7, 2023

Related U.S. Application Data

(60) Provisional application No. 63/020,894, filed on May 6, 2020.

(51) Int. Cl.
*C12N 15/90* (2006.01)
*C12N 15/86* (2006.01)

(52) U.S. Cl.
CPC ........... *C12N 15/907* (2013.01); *C12N 15/86* (2013.01); *C12N 2750/14143* (2013.01); *C12N 2830/42* (2013.01)

(58) Field of Classification Search
None
See application file for complete search history.

(56) References Cited

U.S. PATENT DOCUMENTS

2016/0060656 A1 3/2016 Rebar
2018/0214490 A1 8/2018 Rebar

FOREIGN PATENT DOCUMENTS

WO 2019/118875 A1 6/2019

OTHER PUBLICATIONS

Suzuki et al. Precise in vivo genome editing via single homology arm donor mediated intron-targeting gene integration for genetic disease correction. Cell Research, 2019, 29, 804-819.
Rio et al. Targeted gene therapy and cell reprogramming in Fanconi anemia. EMBO Mol Med, 2014, 6(6), 835-848.
(Continued)

*Primary Examiner* — Tracy Vivlemore
*Assistant Examiner* — Hanna Marie Thueson
(74) *Attorney, Agent, or Firm* — Arrigo, Lee, Guttman & Mouta-Bellum LLP

(57) ABSTRACT

The present disclosure provides methods to genetically modify cells by insertion of an artificial exon (ArtEx) for delivery of therapeutic proteins in specific cell types and more particularly engineered cells for expression of a transgene into the brain of a patient.

19 Claims, 15 Drawing Sheets

Specification includes a Sequence Listing.

(56) References Cited

OTHER PUBLICATIONS

Hockeymeyer et al. Highly efficient gene targeting of expressed and silent genes in human ESCs and iPSCs using zinc finger nucleases. Nat Biotechnol, 2009, 27(9), 851-857.
Diez et al. Therapeutic gene editing in CD34+ hematopoietic progenitors from Fanconi anemia patients. EMBO Mol Med, 2017, 9, 1574-1588.
Gomez-Ospina et al. Human genome- edited hematopoietic stem cells phenotypically correct Mucopolysaccharidosis type I. Nature Communications, 2019, 10(4045), 1-14.
Serebrenik et al. Efficient and flexible tagging of endogenous genes by homology-independent intron targeting. Genome Research, 2019, 29, 1322-1328.

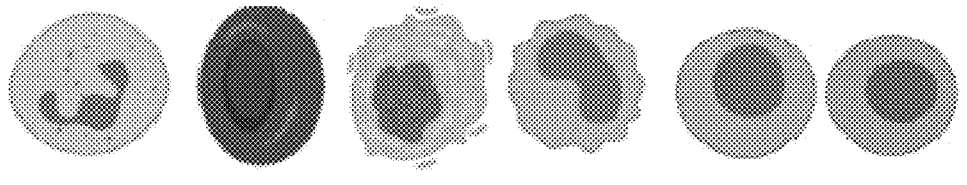

| Targeted expression | Gene inserted | Disease |
|---|---|---|
| Granulocyte | HAX1<br>CYBA, CYBB, NCF1... | Kostmann's Syndrome<br>Chronic Granulomatous disease |
| RBC | HBB<br>RPS19<br>PKLR | Beta Thalassemia<br>Diamond-Blakfan anemia<br>Pyruvate Kinase deficiency |
| Megakaryocyte<br>Platelets | F8<br>F9<br>FXI<br>WAS | Haemophilia A<br>Haemophilia B<br>Haemophilia C<br>Wiskott-Aldrich Syndrome |
| Monocyte | IDUA, IDS, ARSB, GUSB, ABCD1,<br>GALC, ARSA, PSAP, GBA, FUCA1,<br>MAN2B1, AGA, ASAH1, HEXA,<br>GAA, SMPD1, LIPA, CDKL5... | LSD diseases |
| T cell<br>B cell | ADA<br>WAS<br>BTK<br>IL2RG | ADA-SCID<br>Wiskott-Aldrich Syndrome<br>X-linked agammaglobulinemia<br>X-linked SCID |

FIG. 14

SEQUENCE LISTING

```
<160> NUMBER OF SEQ ID NOS: 226

<210> SEQ ID NO 1
<211> LENGTH: 1962
<212> TYPE: DNA
<213> ORGANISM: homo sapiens
<220> FEATURE:
<223> OTHER INFORMATION: IDUA polynucleote sequence

<400> SEQUENCE: 1

atgcgtcccc tgcgcccccg cgccgcgctg ctggcgctcc tggcctcgct cctggccgcg      60

cccccggtgg ccccggccga ggccccgcac ctggtgcatg tggacgcggc ccgcgcgctg     120

tggcccctgc ggcgcttctg gaggagcaca ggcttctgcc ccccgctgcc acacagccag     180

gctgaccagt acgtcctcag ctgggaccag cagctcaacc tcgcctatgt gggcgccgtc     240

cctcaccgcg gcatcaagca ggtccggacc cactggctgc tggagcttgt caccaccagg     300

gggtccactg gacggggcct gagctacaac ttcacccacc tggacgggta cctggacctt     360

ctcagggaga accagctcct cccagggttt gagctgatgg gcagcgcctc gggccacttc     420

actgactttg aggacaagca gcaggtgttt gagtggaagg acttggtctc cagcctggcc     480

aggagataca tcggtaggta cggactggcg catgtttcca agtggaactt cgagacgtgg     540

aatgagccag accaccacga ctttgacaac gtctccatga ccatgcaagg cttcctgaac     600

tactacgatg cctgctcgga gggtctgcgc gccgccagcc ccgccctgcg gctgggaggc     660

cccggcgact ccttccacac cccaccgcga tccccgctga gctggggcct cctgcgccac     720

tgccacgacg gtaccaactt cttcactggg gaggcgggcg tgcggctgga ctacatctcc     780

ctccacagga agggtgcgcg cagctccatc tccatcctgg agcaggagaa ggtcgtcgcg     840

cagcagatcc ggcagctctt ccccaagttc gcggacaccc ccatttacaa cgacgaggcg     900

gacccgctgg tgggctggtc cctgccacag ccgtggaggg cggacgtgac ctacgcggcc     960

atggtggtga aggtcatcgc gcagcatcag aacctgctac tggccaacac cacctccgcc    1020

ttcccctacg cgctcctgag caacgacaat gccttcctga gctaccaccc gcaccccttc    1080

gcgcagcgca cgctcaccgc gcgcttccag gtcaacaaca cccgcccgcc gcacgtgcag    1140

ctgttgcgca agccggtgct cacggccatg gggctgctgg cgctgctgga tgaggagcag    1200

ctctgggccg aagtgtcgca ggccgggacc gtcctggaca gcaaccacac ggtgggcgtc    1260

ctggccagcg cccaccgccc ccagggcccg gccgacgcct ggcgcgccgc ggtgctgatc    1320

tacgcgagcg acgacacccg cgcccacccc aaccgcagcg tcgcggtgac cctgcggctg    1380

cgcggggtgc ccccggccc gggcctggtc tacgtcacgc gctacctgga caacgggctc    1440

tgcagccccg acggcgagtg gcggcgcctg ggccggcccg tcttccccac ggcagagcag    1500

ttccggcgca tgcgcgcggc tgaggacccg gtggccgcgg cgcccccgccc cttacccgcc    1560

ggcggccgcc tgaccctgcg ccccgcgctg cggctgccgt cgcttttgct ggtgcacgtg    1620

tgtgcgcgcc ccgagaagcc gcccgggcag gtcacgcggc tccgcgccct gcccctgacc    1680

caagggcagc tggttctggt ctggtcggat gaacacgtgg gctccaagtg cctgtggaca    1740

tacgagatcc agttctctca ggacggtaag gcgtacaccc cggtcagcag gaagccatcg    1800

accttcaacc tctttgtgtt cagcccagac acaggtgctg tctctggctc ctaccgagtt    1860
```

```
cgagccctgg actactgggc ccgaccaggc cccttctcgg accctgtgcc gtacctggag   1920

gtccctgtgc caagagggcc cccatccccg ggcaatccat ga                      1962


<210> SEQ ID NO 2
<211> LENGTH: 653
<212> TYPE: PRT
<213> ORGANISM: homo sapiens
<220> FEATURE:
<223> OTHER INFORMATION: IDUA polypeptide sequence

<400> SEQUENCE: 2

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350
```

```
Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650
```

<210> SEQ ID NO 3
<211> LENGTH: 1383
<212> TYPE: DNA
<213> ORGANISM: homo sapiens
<220> FEATURE:
<223> OTHER INFORMATION: IDS polynucleotide sequence

<400> SEQUENCE: 3

```
atgcctttgc gcaggagacc tgacaccacc cgcctgtacg acttcaactc ctactggagg      60

gtgcacgctg gaaacttctc caccatcccc cagtacttca aggagaatgg ctatgtgacc     120

atgtcggtgg gaaaagtctt tcaccctggg atatcttcta accataccga tgattctccg     180

tatagctggt cttttccacc ttatcatcct tcctctgaga agtatgaaaa cactaagaca     240

tgtcgagggc cagatggaga actccatgcc aacctgcttt gccctgtgga tgtgctggat     300

gttcccgagg gcaccttgcc tgacaaacag agcactgagc aagccataca gttgttggaa     360
```

```
aagatgaaaa cgtcagccag tcctttcttc ctggccgttg ggtatcataa gccacacatc    420

cccttcagat accccaagga atttcagaag ttgtatccct tggagaacat caccctggcc    480

cccgatcccg aggtccctga tggcctaccc cctgtggcct acaacccctg gatggacatc    540

aggcaacggg aagacgtcca agccttaaac atcagtgtgc cgtatggtcc aattcctgtg    600

gactttcagc ggaaaatccg ccagagctac tttgcctctg tgtcatattt ggatacacag    660

gtcggccgcc tcttgagtgc tttggacgat cttcagctgg ccaacagcac catcattgca    720

tttacctcgg atcatgggtg ggctctaggt gaacatggag aatgggccaa atacagcaat    780

tttgatgttg ctacccatgt tcccctgata ttctatgttc ctggaaggac ggcttcactt    840

ccggaggcag gcgagaagct ttcccttac ctcgaccctt ttgattccgc ctcacagttg    900

atggagccag gcaggcaatc catggacctt gtggaacttg tgtctctttt tcccacgctg    960

gctggacttg caggactgca ggttccacct cgctgccccg ttccttcatt tcacgttgag   1020

ctgtgcagag aaggcaagaa ccttctgaag cattttcgat tccgtgactt ggaagaggat   1080

ccgtacctcc ctggtaatcc ccgtgaactg attgcctata gccagtatcc ccggccttca   1140

gacatccctc agtggaattc tgacaagccg agtttaaaag atataaagat catgggctat   1200

tccatacgca ccatagacta taggtatact gtgtgggttg gcttcaatcc tgatgaattt   1260

ctagctaact tttctgacat ccatgcaggg gaactgtatt ttgtggattc tgacccattg   1320

caggatcaca atatgtataa tgattcccaa ggtggagatc ttttccagtt gttgatgcct   1380

tga                                                                 1383
```

<210> SEQ ID NO 4
<211> LENGTH: 460
<212> TYPE: PRT
<213> ORGANISM: homo sapiens
<220> FEATURE:
<223> OTHER INFORMATION: IDS polypeptide sequence

<400> SEQUENCE: 4

```
Met Pro Leu Arg Arg Arg Pro Asp Thr Thr Arg Leu Tyr Asp Phe Asn
1               5                   10                  15

Ser Tyr Trp Arg Val His Ala Gly Asn Phe Ser Thr Ile Pro Gln Tyr
            20                  25                  30

Phe Lys Glu Asn Gly Tyr Val Thr Met Ser Val Gly Lys Val Phe His
        35                  40                  45

Pro Gly Ile Ser Ser Asn His Thr Asp Asp Ser Pro Tyr Ser Trp Ser
    50                  55                  60

Phe Pro Pro Tyr His Pro Ser Ser Glu Lys Tyr Glu Asn Thr Lys Thr
65                  70                  75                  80

Cys Arg Gly Pro Asp Gly Glu Leu His Ala Asn Leu Leu Cys Pro Val
                85                  90                  95

Asp Val Leu Asp Val Pro Glu Gly Thr Leu Pro Asp Lys Gln Ser Thr
            100                 105                 110

Glu Gln Ala Ile Gln Leu Leu Glu Lys Met Lys Thr Ser Ala Ser Pro
        115                 120                 125

Phe Phe Leu Ala Val Gly Tyr His Lys Pro His Ile Pro Phe Arg Tyr
    130                 135                 140

Pro Lys Glu Phe Gln Lys Leu Tyr Pro Leu Glu Asn Ile Thr Leu Ala
145                 150                 155                 160

Pro Asp Pro Glu Val Pro Asp Gly Leu Pro Pro Val Ala Tyr Asn Pro
                165                 170                 175
```

```
Trp Met Asp Ile Arg Gln Arg Glu Asp Val Gln Ala Leu Asn Ile Ser
            180                 185                 190

Val Pro Tyr Gly Pro Ile Pro Val Asp Phe Gln Arg Lys Ile Arg Gln
        195                 200                 205

Ser Tyr Phe Ala Ser Val Ser Tyr Leu Asp Thr Gln Val Gly Arg Leu
    210                 215                 220

Leu Ser Ala Leu Asp Asp Leu Gln Leu Ala Asn Ser Thr Ile Ile Ala
225                 230                 235                 240

Phe Thr Ser Asp His Gly Trp Ala Leu Gly Glu His Gly Glu Trp Ala
                245                 250                 255

Lys Tyr Ser Asn Phe Asp Val Ala Thr His Val Pro Leu Ile Phe Tyr
            260                 265                 270

Val Pro Gly Arg Thr Ala Ser Leu Pro Glu Ala Gly Glu Lys Leu Phe
        275                 280                 285

Pro Tyr Leu Asp Pro Phe Asp Ser Ala Ser Gln Leu Met Glu Pro Gly
    290                 295                 300

Arg Gln Ser Met Asp Leu Val Glu Leu Val Ser Leu Phe Pro Thr Leu
305                 310                 315                 320

Ala Gly Leu Ala Gly Leu Gln Val Pro Pro Arg Cys Pro Val Pro Ser
                325                 330                 335

Phe His Val Glu Leu Cys Arg Glu Gly Lys Asn Leu Leu Lys His Phe
            340                 345                 350

Arg Phe Arg Asp Leu Glu Glu Asp Pro Tyr Leu Pro Gly Asn Pro Arg
        355                 360                 365

Glu Leu Ile Ala Tyr Ser Gln Tyr Pro Arg Pro Ser Asp Ile Pro Gln
    370                 375                 380

Trp Asn Ser Asp Lys Pro Ser Leu Lys Asp Ile Lys Ile Met Gly Tyr
385                 390                 395                 400

Ser Ile Arg Thr Ile Asp Tyr Arg Tyr Thr Val Trp Val Gly Phe Asn
                405                 410                 415

Pro Asp Glu Phe Leu Ala Asn Phe Ser Asp Ile His Ala Gly Glu Leu
            420                 425                 430

Tyr Phe Val Asp Ser Asp Pro Leu Gln Asp His Asn Met Tyr Asn Asp
        435                 440                 445

Ser Gln Gly Gly Asp Leu Phe Gln Leu Leu Met Pro
    450                 455                 460
```

<210> SEQ ID NO 5
<211> LENGTH: 1956
<212> TYPE: DNA
<213> ORGANISM: homo sapiens
<220> FEATURE:
<223> OTHER INFORMATION: ARSB polynucleotide sequence

<400> SEQUENCE: 5

```
atggcccggg ggtcggcggt tgcctgggcg gcgctcgggc cgttgttgtg gggctgcgcg      60

ctggggctgc agggcgggat gctgtacccc caggagagcc cgtcgcggga gtgcaaggag     120

ctggacggcc tctggagctt ccgcgccgac ttctctgaca accgacgccg gggcttcgag     180

gagcagtggt accggcggcc gctgtgggag tcaggcccca ccgtggacat gccagttccc     240

tccagcttca atgacatcag ccaggactgg cgtctgcggc attttgtcgg ctgggtgtgg     300

tacgaacggg aggtgatcct gccggagcga tggacccagg acctgcgcac aagagtggtg     360

ctgaggattg gcagtgccca ttcctatgcc atcgtgtggg tgaatggggt cgacacgcta     420
```

-continued

```
gagcatgagg ggggctacct ccccttcgag gccgacatca gcaacctggt ccaggtgggg     480

cccctgccct cccggctccg aatcactatc gccatcaaca acacactcac ccccaccacc     540

ctgccaccag ggaccatcca atacctgact gacacctcca agtatcccaa gggttacttt     600

gtccagaaca catattttga ctttttcaac tacgctggac tgcagcggtc tgtacttctg     660

tacacgacac ccaccaccta catcgatgac atcaccgtca ccaccagcgt ggagcaagac     720

agtgggctgg tgaattacca gatctctgtc aagggcagta acctgttcaa gttggaagtg     780

cgtcttttgg atgcagaaaa caaagtcgtg gcgaatggga ctgggaccca gggccaactt     840

aaggtgccag gtgtcagcct ctggtggccg tacctgatgc acgaacgccc tgcctatctg     900

tattcattgg aggtgcagct gactgcacag acgtcactgg ggcctgtgtc tgacttctac     960

acactccctg tggggatccg cactgtggct gtcaccaaga gccagttcct catcaatggg    1020

aaacctttct atttccacgg tgtcaacaag catgaggatg cggacatccg agggaagggc    1080

ttcgactggc cgctgctggt gaaggacttc aacctgcttc gctggcttgg tgccaacgct    1140

ttccgtacca gccactaccc ctatgcagag gaagtgatgc agatgtgtga ccgctatggg    1200

attgtggtca tcgatgagtg tcccggcgtg ggcctggcgc tgccgcagtt cttcaacaac    1260

gtttctctgc atcaccacat gcaggtgatg gaagaagtgg tgcgtaggga caagaaccac    1320

cccgcggtcg tgatgtggtc tgtggccaac gagcctgcgt cccacctaga atctgctggc    1380

tactacttga agatggtgat cgctcacacc aaatccttgg acccctcccg gcctgtgacc    1440

tttgtgagca actctaacta tgcagcagac aagggggctc cgtatgtgga tgtgatctgt    1500

ttgaacagct actactcttg gtatcacgac tacgggcacc tggagttgat tcagctgcag    1560

ctggccaccc agtttgagaa ctggtataag aagtatcaga agcccattat tcagagcgag    1620

tatggagcag aaacgattgc agggtttcac caggatccac ctctgatgtt cactgaagag    1680

taccagaaaa gtctgctaga gcagtaccat ctgggtctgg atcaaaaacg cagaaaatac    1740

gtggttggag agctcatttg gaattttgcc gatttcatga ctgaacagtc accgacgaga    1800

gtgctgggga ataaaaaggg gatcttcact cggcagagac aaccaaaaag tgcagcgttc    1860

cttttgcgag agagatactg gaagattgcc aatgaaacca ggtatcccca ctcagtagcc    1920

aagtcacaat gtttggaaaa cagcctgttt acttga                              1956
```

<210> SEQ ID NO 6
<211> LENGTH: 533
<212> TYPE: PRT
<213> ORGANISM: homo sapiens
<220> FEATURE:
<223> OTHER INFORMATION: ARSB polypeptide sequence

<400> SEQUENCE: 6

```
Met Gly Pro Arg Gly Ala Ala Ser Leu Pro Arg Gly Pro Gly Pro Arg
1               5                   10                  15

Arg Leu Leu Leu Pro Val Val Leu Pro Leu Leu Leu Leu Leu Leu Leu
            20                  25                  30

Ala Pro Pro Gly Ser Gly Ala Gly Ala Ser Arg Pro Pro His Leu Val
        35                  40                  45

Phe Leu Leu Ala Asp Asp Leu Gly Trp Asn Asp Val Gly Phe His Gly
    50                  55                  60

Ser Arg Ile Arg Thr Pro His Leu Asp Ala Leu Ala Ala Gly Gly Val
65                  70                  75                  80

Leu Leu Asp Asn Tyr Tyr Thr Gln Pro Leu Cys Thr Pro Ser Arg Ser
                85                  90                  95
```

```
Gln Leu Leu Thr Gly Arg Tyr Gln Ile Arg Thr Gly Leu Gln His Gln
            100                 105                 110

Ile Ile Trp Pro Cys Gln Pro Ser Cys Val Pro Leu Asp Glu Lys Leu
        115                 120                 125

Leu Pro Gln Leu Leu Lys Glu Ala Gly Tyr Thr Thr His Met Val Gly
    130                 135                 140

Lys Trp His Leu Gly Met Tyr Arg Lys Glu Cys Leu Pro Thr Arg Arg
145                 150                 155                 160

Gly Phe Asp Thr Tyr Phe Gly Tyr Leu Leu Gly Ser Glu Asp Tyr Tyr
                165                 170                 175

Ser His Glu Arg Cys Thr Leu Ile Asp Ala Leu Asn Val Thr Arg Cys
            180                 185                 190

Ala Leu Asp Phe Arg Asp Gly Glu Glu Val Ala Thr Gly Tyr Lys Asn
        195                 200                 205

Met Tyr Ser Thr Asn Ile Phe Thr Lys Arg Ala Ile Ala Leu Ile Thr
    210                 215                 220

Asn His Pro Pro Glu Lys Pro Leu Phe Leu Tyr Leu Ala Leu Gln Ser
225                 230                 235                 240

Val His Glu Pro Leu Gln Val Pro Glu Glu Tyr Leu Lys Pro Tyr Asp
                245                 250                 255

Phe Ile Gln Asp Lys Asn Arg His His Tyr Ala Gly Met Val Ser Leu
            260                 265                 270

Met Asp Glu Ala Val Gly Asn Val Thr Ala Ala Leu Lys Ser Ser Gly
        275                 280                 285

Leu Trp Asn Asn Thr Val Phe Ile Phe Ser Thr Asp Asn Gly Gly Gln
    290                 295                 300

Thr Leu Ala Gly Gly Asn Asn Trp Pro Leu Arg Gly Arg Lys Trp Ser
305                 310                 315                 320

Leu Trp Glu Gly Gly Val Arg Gly Val Gly Phe Val Ala Ser Pro Leu
                325                 330                 335

Leu Lys Gln Lys Gly Val Lys Asn Arg Glu Leu Ile His Ile Ser Asp
            340                 345                 350

Trp Leu Pro Thr Leu Val Lys Leu Ala Arg Gly His Thr Asn Gly Thr
        355                 360                 365

Lys Pro Leu Asp Gly Phe Asp Val Trp Lys Thr Ile Ser Glu Gly Ser
    370                 375                 380

Pro Ser Pro Arg Ile Glu Leu Leu His Asn Ile Asp Pro Asn Phe Val
385                 390                 395                 400

Asp Ser Ser Pro Cys Pro Arg Asn Ser Met Ala Pro Ala Lys Asp Asp
                405                 410                 415

Ser Ser Leu Pro Glu Tyr Ser Ala Phe Asn Thr Ser Val His Ala Ala
            420                 425                 430

Ile Arg His Gly Asn Trp Lys Leu Leu Thr Gly Tyr Pro Gly Cys Gly
        435                 440                 445

Tyr Trp Phe Pro Pro Pro Ser Gln Tyr Asn Val Ser Glu Ile Pro Ser
    450                 455                 460

Ser Asp Pro Pro Thr Lys Thr Leu Trp Leu Phe Asp Ile Asp Arg Asp
465                 470                 475                 480

Pro Glu Glu Arg His Asp Leu Ser Arg Glu Tyr Pro His Ile Val Thr
                485                 490                 495

Lys Leu Leu Ser Arg Leu Gln Phe Tyr His Lys His Ser Val Pro Val
            500                 505                 510
```

```
Tyr Phe Pro Ala Gln Asp Pro Arg Cys Asp Pro Lys Ala Thr Gly Val
        515                 520                 525

Trp Gly Pro Trp Met
    530


<210> SEQ ID NO 7
<211> LENGTH: 1956
<212> TYPE: DNA
<213> ORGANISM: homo sapiens
<220> FEATURE:
<223> OTHER INFORMATION: GUSB polynucleotide sequence

<400> SEQUENCE: 7

atggcccggg ggtcggcggt tgcctgggcg gcgctcgggc cgttgttgtg ggctgcgcg     60

ctggggctgc agggcgggat gctgtacccc caggagagcc cgtcgcggga gtgcaaggag    120

ctggacggcc tctggagctt ccgcgccgac ttctctgaca accgacgccg gggcttcgag    180

gagcagtggt accggcggcc gctgtgggag tcaggcccca ccgtggacat gccagttccc    240

tccagcttca atgacatcag ccaggactgg cgtctgcggc attttgtcgg ctgggtgtgg    300

tacgaacggg aggtgatcct gccggagcga tggacccagg acctgcgcac aagagtggtg    360

ctgaggattg gcagtgccca ttcctatgcc atcgtgtggg tgaatggggt cgacacgcta    420

gagcatgagg ggggctacct ccccttcgag gccgacatca gcaacctggt ccaggtgggg    480

cccctgccct cccggctccg aatcactatc gccatcaaca acacactcac ccccaccacc    540

ctgccaccag ggaccatcca atacctgact gacacctcca agtatcccaa gggttacttt    600

gtccagaaca catattttga ctttttcaac tacgctggac tgcagcggtc tgtacttctg    660

tacacgacac ccaccaccta catcgatgac atcaccgtca ccaccagcgt ggagcaagac    720

agtgggctgg tgaattacca gatctctgtc aagggcagta acctgttcaa gttggaagtg    780

cgtcttttgg atgcagaaaa caaagtcgtg gcgaatggga ctgggaccca gggccaactt    840

aaggtgccag gtgtcagcct ctggtggccg tacctgatgc acgaacgccc tgcctatctg    900

tattcattgg aggtgcagct gactgcacag acgtcactgg ggcctgtgtc tgacttctac    960

acactccctg tggggatccg cactgtggct gtcaccaaga gccagttcct catcaatggg   1020

aaacctttct atttccacgg tgtcaacaag catgaggatg cggacatccg agggaagggc   1080

ttcgactggc cgctgctggt gaaggacttc aacctgcttc gctggcttgg tgccaacgct   1140

ttccgtacca gccactaccc ctatgcagag gaagtgatgc agatgtgtga ccgctatggg   1200

attgtggtca tcgatgagtg tcccggcgtg ggcctggcgc tgccgcagtt cttcaacaac   1260

gtttctctgc atcaccacat gcaggtgatg gaagaagtgg tgcgtaggga caagaaccac   1320

cccgcggtcg tgatgtggtc tgtggccaac gagcctgcgt cccacctaga atctgctggc   1380

tactacttga agatggtgat cgctcacacc aaatccttgg acccctcccg gcctgtgacc   1440

tttgtgagca actctaacta tgcagcagac aagggggctc cgtatgtgga tgtgatctgt   1500

ttgaacagct actactcttg gtatcacgac tacgggcacc tggagttgat tcagctgcag   1560

ctggccaccc agtttgagaa ctggtataag aagtatcaga agcccattat tcagagcgag   1620

tatggagcag aaacgattgc agggtttcac caggatccac ctctgatgtt cactgaagag   1680

taccagaaaa gtctgctaga gcagtaccat ctgggtctgg atcaaaaacg cagaaaatac   1740

gtggttggag agctcatttg gaattttgcc gatttcatga ctgaacagtc accgacgaga   1800

gtgctgggga ataaaaaggg gatcttcact cggcagagac aaccaaaaag tgcagcgttc   1860

cttttgcgag agagatactg gaagattgcc aatgaaacca ggtatcccca ctcagtagcc   1920
```

```
aagtcacaat gtttggaaaa cagcctgttt acttga                         1956


<210> SEQ ID NO 8
<211> LENGTH: 651
<212> TYPE: PRT
<213> ORGANISM: homo sapiens
<220> FEATURE:
<223> OTHER INFORMATION: GUSB polypeptide sequence

<400> SEQUENCE: 8

Met Ala Arg Gly Ser Ala Val Ala Trp Ala Ala Leu Gly Pro Leu Leu
1               5                   10                  15

Trp Gly Cys Ala Leu Gly Leu Gln Gly Gly Met Leu Tyr Pro Gln Glu
            20                  25                  30

Ser Pro Ser Arg Glu Cys Lys Glu Leu Asp Gly Leu Trp Ser Phe Arg
        35                  40                  45

Ala Asp Phe Ser Asp Asn Arg Arg Arg Gly Phe Glu Glu Gln Trp Tyr
    50                  55                  60

Arg Arg Pro Leu Trp Glu Ser Gly Pro Thr Val Asp Met Pro Val Pro
65                  70                  75                  80

Ser Ser Phe Asn Asp Ile Ser Gln Asp Trp Arg Leu Arg His Phe Val
                85                  90                  95

Gly Trp Val Trp Tyr Glu Arg Glu Val Ile Leu Pro Glu Arg Trp Thr
            100                 105                 110

Gln Asp Leu Arg Thr Arg Val Val Leu Arg Ile Gly Ser Ala His Ser
        115                 120                 125

Tyr Ala Ile Val Trp Val Asn Gly Val Asp Thr Leu Glu His Glu Gly
    130                 135                 140

Gly Tyr Leu Pro Phe Glu Ala Asp Ile Ser Asn Leu Val Gln Val Gly
145                 150                 155                 160

Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
            180                 185                 190

Ser Lys Tyr Pro Lys Gly Tyr Phe Val Gln Asn Thr Tyr Phe Asp Phe
        195                 200                 205

Phe Asn Tyr Ala Gly Leu Gln Arg Ser Val Leu Leu Tyr Thr Thr Pro
    210                 215                 220

Thr Thr Tyr Ile Asp Asp Ile Thr Val Thr Thr Ser Val Glu Gln Asp
225                 230                 235                 240

Ser Gly Leu Val Asn Tyr Gln Ile Ser Val Lys Gly Ser Asn Leu Phe
                245                 250                 255

Lys Leu Glu Val Arg Leu Leu Asp Ala Glu Asn Lys Val Val Ala Asn
            260                 265                 270

Gly Thr Gly Thr Gln Gly Gln Leu Lys Val Pro Gly Val Ser Leu Trp
        275                 280                 285

Trp Pro Tyr Leu Met His Glu Arg Pro Ala Tyr Leu Tyr Ser Leu Glu
    290                 295                 300

Val Gln Leu Thr Ala Gln Thr Ser Leu Gly Pro Val Ser Asp Phe Tyr
305                 310                 315                 320

Thr Leu Pro Val Gly Ile Arg Thr Val Ala Val Thr Lys Ser Gln Phe
                325                 330                 335

Leu Ile Asn Gly Lys Pro Phe Tyr Phe His Gly Val Asn Lys His Glu
            340                 345                 350
```

```
Asp Ala Asp Ile Arg Gly Lys Gly Phe Asp Trp Pro Leu Leu Val Lys
        355                 360                 365

Asp Phe Asn Leu Leu Arg Trp Leu Gly Ala Asn Ala Phe Arg Thr Ser
    370                 375                 380

His Tyr Pro Tyr Ala Glu Glu Val Met Gln Met Cys Asp Arg Tyr Gly
385                 390                 395                 400

Ile Val Val Ile Asp Glu Cys Pro Gly Val Gly Leu Ala Leu Pro Gln
                405                 410                 415

Phe Phe Asn Asn Val Ser Leu His His His Met Gln Val Met Glu Glu
            420                 425                 430

Val Val Arg Arg Asp Lys Asn His Pro Ala Val Val Met Trp Ser Val
        435                 440                 445

Ala Asn Glu Pro Ala Ser His Leu Glu Ser Ala Gly Tyr Tyr Leu Lys
    450                 455                 460

Met Val Ile Ala His Thr Lys Ser Leu Asp Pro Ser Arg Pro Val Thr
465                 470                 475                 480

Phe Val Ser Asn Ser Asn Tyr Ala Ala Asp Lys Gly Ala Pro Tyr Val
                485                 490                 495

Asp Val Ile Cys Leu Asn Ser Tyr Tyr Ser Trp Tyr His Asp Tyr Gly
            500                 505                 510

His Leu Glu Leu Ile Gln Leu Gln Leu Ala Thr Gln Phe Glu Asn Trp
        515                 520                 525

Tyr Lys Lys Tyr Gln Lys Pro Ile Ile Gln Ser Glu Tyr Gly Ala Glu
    530                 535                 540

Thr Ile Ala Gly Phe His Gln Asp Pro Pro Leu Met Phe Thr Glu Glu
545                 550                 555                 560

Tyr Gln Lys Ser Leu Leu Glu Gln Tyr His Leu Gly Leu Asp Gln Lys
                565                 570                 575

Arg Arg Lys Tyr Val Val Gly Glu Leu Ile Trp Asn Phe Ala Asp Phe
            580                 585                 590

Met Thr Glu Gln Ser Pro Thr Arg Val Leu Gly Asn Lys Lys Gly Ile
        595                 600                 605

Phe Thr Arg Gln Arg Gln Pro Lys Ser Ala Ala Phe Leu Leu Arg Glu
    610                 615                 620

Arg Tyr Trp Lys Ile Ala Asn Glu Thr Arg Tyr Pro His Ser Val Ala
625                 630                 635                 640

Lys Ser Gln Cys Leu Glu Asn Ser Leu Phe Thr
                645                 650
```

<210> SEQ ID NO 9
<211> LENGTH: 2238
<212> TYPE: DNA
<213> ORGANISM: homo sapiens
<220> FEATURE:
<223> OTHER INFORMATION: ABCD1 polynucleotide sequence

<400> SEQUENCE: 9

```
atgccggtgc tctccaggcc ccggccctgg cgggggaaca cgctgaagcg cacggccgtg      60

ctcctggccc tcgcggccta tggagcccac aaagtctacc ccttggtgcg ccagtgcctg     120

gccccggcca ggggtcttca ggcgcccgcc ggggagccca cgcaggaggc ctccggggtc     180

gcggcggcca aagctggcat gaaccgggta ttcctgcagc ggctcctgtg gctcctgcgg     240

ctgctgttcc cccgggtcct gtgccgggag acggggctgc tggccctgca ctcggccgcc     300

ttggtgagcc gcaccttcct gtcggtgtat gtggcccgcc tggacggaag gctggcccgc     360
```

-continued

```
tgcatcgtcc gcaaggaccc gcgggctttt ggctggcagc tgctgcagtg gctcctcatc    420

gccctccctg ctaccttcgt caacagtgcc atccgttacc tggagggcca actggccctg    480

tcgttccgca gccgtctggt ggcccacgcc taccgcctct acttctccca gcagacctac    540

taccgggtca gcaacatgga cgggcggctt cgcaaccctg accagtctct gacggaggac    600

gtggtggcct ttgcggcctc tgtggcccac ctctactcca acctgaccaa gccactcctg    660

gacgtggctg tgacttccta caccctgctt cgggcggccc gctcccgtgg agccggcaca    720

gcctggccct cggccatcgc cggcctcgtg gtgttcctca cggccaacgt gctgcgggcc    780

ttctcgccca agttcgggga gctggtggca gaggaggcgc ggcggaaggg ggagctgcgc    840

tacatgcact cgcgtgtggt ggccaactcg gaggagatcg ccttctatgg gggccatgag    900

gtggagctgg ccctgctaca gcgctcctac caggacctgg cctcgcagat caacctcatc    960

cttctggaac gcctgtggta tgttatgctg gagcagttcc tcatgaagta tgtgtggagc   1020

gcctcgggcc tgctcatggt ggctgtcccc atcatcactg ccactggcta ctcagagtca   1080

gatgcagagg ccgtgaagaa ggcagccttg gaaaagaagg aggaggagct ggtgagcgag   1140

cgcacagaag ccttcactat tgcccgcaac ctcctgacag cggctgcaga tgccattgag   1200

cggatcatgt cgtcgtacaa ggaggtgacg gagctggctg gctacacagc ccgggtgcac   1260

gagatgttcc aggtatttga agatgttcag cgctgtcact tcaagaggcc cagggagcta   1320

gaggacgctc aggcggggtc tgggaccata ggccggtctg gtgtccgtgt ggagggcccc   1380

ctgaagatcc gaggccaggt ggtggatgtg gaacagggga tcatctgcga gaacatcccc   1440

atcgtcacgc cctcaggaga ggtggtggtg gccagcctca acatcagggt ggaggaaggc   1500

atgcatctgc tcatcacagg ccccaatggc tgcggcaaga gctccctgtt ccggatcctg   1560

ggtgggctct ggcccacgta cggtggtgtg ctctacaagc ccccacccca gcgcatgttc   1620

tacatcccgc agaggcccta catgtctgtg ggctccctgc gtgaccaggt gatctacccg   1680

gactcagtgg aggacatgca aaggaagggc tactcggagc aggacctgga agccatcctg   1740

gacgtcgtgc acctgcacca catcctgcag cgggagggag gttgggaggc tatgtgtgac   1800

tggaaggacg tcctgtcggg tggcgagaag cagagaatcg gcatggcccg catgttctac   1860

cacaggccca agtacgccct cctggatgaa tgcaccagcg ccgtgagcat cgacgtggaa   1920

ggcaagatct tccaggcggc caaggacgcg ggcattgccc tgctctccat cacccaccgg   1980

ccctccctgt ggaaatacca cacacacttg ctacagttcg atggggaggg cggctggaag   2040

ttcgagaagc tggactcagc tgcccgcctg agcctgacgg aggagaagca gcggctggag   2100

cagcagctgg cgggcattcc caagatgcag cggcgcctcc aggagctctg ccagatcctg   2160

ggcgaggccg tggccccagc gcatgtgccg gcacctagcc cgcaaggccc tggtggcctc   2220

cagggtgcct ccacctga                                                 2238
```

<210> SEQ ID NO 10
<211> LENGTH: 745
<212> TYPE: PRT
<213> ORGANISM: homo sapiens
<220> FEATURE:
<223> OTHER INFORMATION: ABCD1 polypeptide sequence

<400> SEQUENCE: 10

```
Met Pro Val Leu Ser Arg Pro Arg Pro Trp Arg Gly Asn Thr Leu Lys
1               5                   10                  15

Arg Thr Ala Val Leu Leu Ala Leu Ala Ala Tyr Gly Ala His Lys Val
            20                  25                  30
```

```
Tyr Pro Leu Val Arg Gln Cys Leu Ala Pro Ala Arg Gly Leu Gln Ala
        35                  40                  45

Pro Ala Gly Glu Pro Thr Gln Glu Ala Ser Gly Val Ala Ala Ala Lys
    50                  55                  60

Ala Gly Met Asn Arg Val Phe Leu Gln Arg Leu Leu Trp Leu Leu Arg
65                  70                  75                  80

Leu Leu Phe Pro Arg Val Leu Cys Arg Glu Thr Gly Leu Leu Ala Leu
                85                  90                  95

His Ser Ala Ala Leu Val Ser Arg Thr Phe Leu Ser Val Tyr Val Ala
            100                 105                 110

Arg Leu Asp Gly Arg Leu Ala Arg Cys Ile Val Arg Lys Asp Pro Arg
        115                 120                 125

Ala Phe Gly Trp Gln Leu Leu Gln Trp Leu Leu Ile Ala Leu Pro Ala
    130                 135                 140

Thr Phe Val Asn Ser Ala Ile Arg Tyr Leu Glu Gly Gln Leu Ala Leu
145                 150                 155                 160

Ser Phe Arg Ser Arg Leu Val Ala His Ala Tyr Arg Leu Tyr Phe Ser
                165                 170                 175

Gln Gln Thr Tyr Tyr Arg Val Ser Asn Met Asp Gly Arg Leu Arg Asn
            180                 185                 190

Pro Asp Gln Ser Leu Thr Glu Asp Val Val Ala Phe Ala Ala Ser Val
        195                 200                 205

Ala His Leu Tyr Ser Asn Leu Thr Lys Pro Leu Leu Asp Val Ala Val
    210                 215                 220

Thr Ser Tyr Thr Leu Leu Arg Ala Ala Arg Ser Arg Gly Ala Gly Thr
225                 230                 235                 240

Ala Trp Pro Ser Ala Ile Ala Gly Leu Val Val Phe Leu Thr Ala Asn
                245                 250                 255

Val Leu Arg Ala Phe Ser Pro Lys Phe Gly Glu Leu Val Ala Glu Glu
            260                 265                 270

Ala Arg Arg Lys Gly Glu Leu Arg Tyr Met His Ser Arg Val Val Ala
        275                 280                 285

Asn Ser Glu Glu Ile Ala Phe Tyr Gly Gly His Glu Val Glu Leu Ala
    290                 295                 300

Leu Leu Gln Arg Ser Tyr Gln Asp Leu Ala Ser Gln Ile Asn Leu Ile
305                 310                 315                 320

Leu Leu Glu Arg Leu Trp Tyr Val Met Leu Glu Gln Phe Leu Met Lys
                325                 330                 335

Tyr Val Trp Ser Ala Ser Gly Leu Leu Met Val Ala Val Pro Ile Ile
            340                 345                 350

Thr Ala Thr Gly Tyr Ser Glu Ser Asp Ala Glu Ala Val Lys Lys Ala
        355                 360                 365

Ala Leu Glu Lys Lys Glu Glu Glu Leu Val Ser Glu Arg Thr Glu Ala
    370                 375                 380

Phe Thr Ile Ala Arg Asn Leu Leu Thr Ala Ala Ala Asp Ala Ile Glu
385                 390                 395                 400

Arg Ile Met Ser Ser Tyr Lys Glu Val Thr Glu Leu Ala Gly Tyr Thr
                405                 410                 415

Ala Arg Val His Glu Met Phe Gln Val Phe Glu Asp Val Gln Arg Cys
            420                 425                 430

His Phe Lys Arg Pro Arg Glu Leu Glu Asp Ala Gln Ala Gly Ser Gly
        435                 440                 445
```

Thr Ile Gly Arg Ser Gly Val Arg Val Glu Gly Pro Leu Lys Ile Arg
450 455 460

Gly Gln Val Val Asp Val Glu Gln Gly Ile Ile Cys Glu Asn Ile Pro
465 470 475 480

Ile Val Thr Pro Ser Gly Glu Val Val Val Ala Ser Leu Asn Ile Arg
485 490 495

Val Glu Glu Gly Met His Leu Leu Ile Thr Gly Pro Asn Gly Cys Gly
500 505 510

Lys Ser Ser Leu Phe Arg Ile Leu Gly Gly Leu Trp Pro Thr Tyr Gly
515 520 525

Gly Val Leu Tyr Lys Pro Pro Pro Gln Arg Met Phe Tyr Ile Pro Gln
530 535 540

Arg Pro Tyr Met Ser Val Gly Ser Leu Arg Asp Gln Val Ile Tyr Pro
545 550 555 560

Asp Ser Val Glu Asp Met Gln Arg Lys Gly Tyr Ser Glu Gln Asp Leu
565 570 575

Glu Ala Ile Leu Asp Val Val His Leu His His Ile Leu Gln Arg Glu
580 585 590

Gly Gly Trp Glu Ala Met Cys Asp Trp Lys Asp Val Leu Ser Gly Gly
595 600 605

Glu Lys Gln Arg Ile Gly Met Ala Arg Met Phe Tyr His Arg Pro Lys
610 615 620

Tyr Ala Leu Leu Asp Glu Cys Thr Ser Ala Val Ser Ile Asp Val Glu
625 630 635 640

Gly Lys Ile Phe Gln Ala Ala Lys Asp Ala Gly Ile Ala Leu Leu Ser
645 650 655

Ile Thr His Arg Pro Ser Leu Trp Lys Tyr His Thr His Leu Leu Gln
660 665 670

Phe Asp Gly Glu Gly Gly Trp Lys Phe Glu Lys Leu Asp Ser Ala Ala
675 680 685

Arg Leu Ser Leu Thr Glu Glu Lys Gln Arg Leu Glu Gln Gln Leu Ala
690 695 700

Gly Ile Pro Lys Met Gln Arg Arg Leu Gln Glu Leu Cys Gln Ile Leu
705 710 715 720

Gly Glu Ala Val Ala Pro Ala His Val Pro Ala Pro Ser Pro Gln Gly
725 730 735

Pro Gly Gly Leu Gln Gly Ala Ser Thr
740 745

<210> SEQ ID NO 11
<211> LENGTH: 2058
<212> TYPE: DNA
<213> ORGANISM: homo sapiens
<220> FEATURE:
<223> OTHER INFORMATION: GALC polynucleotide sequence

<400> SEQUENCE: 11
atggctgagt ggctactctc ggcttcctgg caacgccgag cgaaagctat gactgcggcc 60
gcgggttcgg cgggccgcgc cgcggtgccc ttgctgctgt gtgcgctgct ggcgcccggc 120
ggcgcgtacg tgctcgacga ctccgacggg ctgggccggg agttcgacgg catcggcgcg 180
gtcagcggcg gcggggcaac ctcccgactt ctagtaaatt acccagagcc ctatcgttct 240
cagatattgg attatctctt taagccgaat tttggtgcct ctttgcatat tttaaaagtg 300
gaaataggtg gtgatgggca gacaacagac ggcactgagc cctcccacat gcattatgca 360

```
ctagatgaga attatttccg aggatacgag tggtggttga tgaaagaagc taagaagagg    420

aatcccaata ttacactcat tgggttgcca tggtcattcc ctggatggct gggaaaaggt    480

ttcgactggc cttatgtcaa tcttcagctg actgcctatt atgtcgtgac ctggattgtg    540

ggcgccaagc gttaccatga tttggacatt gattatattg gaatttggaa tgagaggtca    600

tataatgcca attatattaa gatattaaga aaaatgctga attatcaagg tctccagcga    660

gtgaaaatca tagcaagtga taatctctgg gagtccatct ctgcatccat gctccttgat    720

gccgaactct tcaaggtggt tgatgttata ggggctcatt atcctggaac ccattcagca    780

aaagatgcaa agttgactgg gaagaagctt tggtcttctg aagactttag cactttaaat    840

agtgacatgg gtgcaggctg ctggggtcgc attttaaatc agaattatat caatggctat    900

atgacttcca caatcgcatg gaatttagtg gctagttact atgaacagtt gccttatggg    960

agatgcgggt tgatgacggc ccaggagcca tggagtgggc actacgtggt agaatctcct   1020

gtctgggtat cagctcatac cactcagttt actcaacctg gctggtatta cctgaagaca   1080

gttggccatt tagagaaagg aggaagctac gtagctctga ctgatggctt agggaacctc   1140

accatcatca ttgaaaccat gagtcataaa cattctaagt gcatacggcc atttcttcct   1200

tatttcaatg tgtcacaaca atttgccacc tttgttctta agggatcttt tagtgaaata   1260

ccagagctac aggtatggta taccaaactt ggaaaaacat ccgaaagatt tctttttaag   1320

cagctggatt ctctatggct ccttgacagc gatggcagtt tcacactgag cctgcatgaa   1380

gatgagctgt tcacactcac cactctcacc actggtcgca aaggcagcta cccgcttcct   1440

ccaaaatccc agcccttccc aagtacctat aaggatgatt tcaatgttga ttacccattt   1500

tttagtgaag ctccaaactt tgctgatcaa actggtgtat ttgaatattt tacaaatatt   1560

gaagaccctg gcgagcatca cttcacgcta cgccaagttc tcaaccagag acccattaca   1620

tgggctgccg atgcatccaa cacaatcagt attataggag actacaactg gaccaatctg   1680

actataaagt gtgatgtata catagagacc cctgacacag gaggtgtgtt cattgcagga   1740

agagtaaata aaggtggtat tttgattaga agtgccagag gaattttctt ctggattttt   1800

gcaaatggat cttacagggt tacaggtgat ttagctggat ggattatata tgctttagga   1860

cgtgttgaag ttacagcaaa aaaatggtat acactcacgt taactattaa gggtcatttc   1920

acctctggca tgctgaatga caagtctctg tggacagaca tccctgtgaa ttttccaaag   1980

aatggctggg ctgcaattgg aactcactcc tttgaatttg cacagtttga caactttctt   2040

gtggaagcca cacgctaa                                                 2058

<210> SEQ ID NO 12
<211> LENGTH: 685
<212> TYPE: PRT
<213> ORGANISM: homo sapiens
<220> FEATURE:
<223> OTHER INFORMATION: GALC  polypeptide sequence

<400> SEQUENCE: 12

Met Ala Glu Trp Leu Leu Ser Ala Ser Trp Gln Arg Arg Ala Lys Ala
1               5                   10                  15

Met Thr Ala Ala Ala Gly Ser Ala Gly Arg Ala Ala Val Pro Leu Leu
            20                  25                  30

Leu Cys Ala Leu Leu Ala Pro Gly Gly Ala Tyr Val Leu Asp Asp Ser
        35                  40                  45

Asp Gly Leu Gly Arg Glu Phe Asp Gly Ile Gly Ala Val Ser Gly Gly
    50                  55                  60
```

```
Gly Ala Thr Ser Arg Leu Leu Val Asn Tyr Pro Glu Pro Tyr Arg Ser
65                  70                  75                  80

Gln Ile Leu Asp Tyr Leu Phe Lys Pro Asn Phe Gly Ala Ser Leu His
                85                  90                  95

Ile Leu Lys Val Glu Ile Gly Gly Asp Gly Gln Thr Thr Asp Gly Thr
            100                 105                 110

Glu Pro Ser His Met His Tyr Ala Leu Asp Glu Asn Tyr Phe Arg Gly
        115                 120                 125

Tyr Glu Trp Trp Leu Met Lys Glu Ala Lys Lys Arg Asn Pro Asn Ile
    130                 135                 140

Thr Leu Ile Gly Leu Pro Trp Ser Phe Pro Gly Trp Leu Gly Lys Gly
145                 150                 155                 160

Phe Asp Trp Pro Tyr Val Asn Leu Gln Leu Thr Ala Tyr Tyr Val Val
                165                 170                 175

Thr Trp Ile Val Gly Ala Lys Arg Tyr His Asp Leu Asp Ile Asp Tyr
            180                 185                 190

Ile Gly Ile Trp Asn Glu Arg Ser Tyr Asn Ala Asn Tyr Ile Lys Ile
        195                 200                 205

Leu Arg Lys Met Leu Asn Tyr Gln Gly Leu Gln Arg Val Lys Ile Ile
    210                 215                 220

Ala Ser Asp Asn Leu Trp Glu Ser Ile Ser Ala Ser Met Leu Leu Asp
225                 230                 235                 240

Ala Glu Leu Phe Lys Val Val Asp Val Ile Gly Ala His Tyr Pro Gly
                245                 250                 255

Thr His Ser Ala Lys Asp Ala Lys Leu Thr Gly Lys Lys Leu Trp Ser
            260                 265                 270

Ser Glu Asp Phe Ser Thr Leu Asn Ser Asp Met Gly Ala Gly Cys Trp
        275                 280                 285

Gly Arg Ile Leu Asn Gln Asn Tyr Ile Asn Gly Tyr Met Thr Ser Thr
    290                 295                 300

Ile Ala Trp Asn Leu Val Ala Ser Tyr Tyr Glu Gln Leu Pro Tyr Gly
305                 310                 315                 320

Arg Cys Gly Leu Met Thr Ala Gln Glu Pro Trp Ser Gly His Tyr Val
                325                 330                 335

Val Glu Ser Pro Val Trp Val Ser Ala His Thr Thr Gln Phe Thr Gln
            340                 345                 350

Pro Gly Trp Tyr Tyr Leu Lys Thr Val Gly His Leu Glu Lys Gly Gly
        355                 360                 365

Ser Tyr Val Ala Leu Thr Asp Gly Leu Gly Asn Leu Thr Ile Ile Ile
    370                 375                 380

Glu Thr Met Ser His Lys His Ser Lys Cys Ile Arg Pro Phe Leu Pro
385                 390                 395                 400

Tyr Phe Asn Val Ser Gln Gln Phe Ala Thr Phe Val Leu Lys Gly Ser
                405                 410                 415

Phe Ser Glu Ile Pro Glu Leu Gln Val Trp Tyr Thr Lys Leu Gly Lys
            420                 425                 430

Thr Ser Glu Arg Phe Leu Phe Lys Gln Leu Asp Ser Leu Trp Leu Leu
        435                 440                 445

Asp Ser Asp Gly Ser Phe Thr Leu Ser Leu His Glu Asp Glu Leu Phe
    450                 455                 460

Thr Leu Thr Thr Leu Thr Thr Gly Arg Lys Gly Ser Tyr Pro Leu Pro
465                 470                 475                 480
```

```
Pro Lys Ser Gln Pro Phe Pro Ser Thr Tyr Lys Asp Asp Phe Asn Val
                485                 490                 495

Asp Tyr Pro Phe Phe Ser Glu Ala Pro Asn Phe Ala Asp Gln Thr Gly
            500                 505                 510

Val Phe Glu Tyr Phe Thr Asn Ile Glu Asp Pro Gly Glu His His Phe
        515                 520                 525

Thr Leu Arg Gln Val Leu Asn Gln Arg Pro Ile Thr Trp Ala Ala Asp
    530                 535                 540

Ala Ser Asn Thr Ile Ser Ile Ile Gly Asp Tyr Asn Trp Thr Asn Leu
545                 550                 555                 560

Thr Ile Lys Cys Asp Val Tyr Ile Glu Thr Pro Asp Thr Gly Gly Val
                565                 570                 575

Phe Ile Ala Gly Arg Val Asn Lys Gly Gly Ile Leu Ile Arg Ser Ala
            580                 585                 590

Arg Gly Ile Phe Phe Trp Ile Phe Ala Asn Gly Ser Tyr Arg Val Thr
        595                 600                 605

Gly Asp Leu Ala Gly Trp Ile Ile Tyr Ala Leu Gly Arg Val Glu Val
    610                 615                 620

Thr Ala Lys Lys Trp Tyr Thr Leu Thr Leu Thr Ile Lys Gly His Phe
625                 630                 635                 640

Thr Ser Gly Met Leu Asn Asp Lys Ser Leu Trp Thr Asp Ile Pro Val
                645                 650                 655

Asn Phe Pro Lys Asn Gly Trp Ala Ala Ile Gly Thr His Ser Phe Glu
            660                 665                 670

Phe Ala Gln Phe Asp Asn Phe Leu Val Glu Ala Thr Arg
        675                 680                 685
```

```
<210> SEQ ID NO 13
<211> LENGTH: 1530
<212> TYPE: DNA
<213> ORGANISM: homo sapiens
<220> FEATURE:
<223> OTHER INFORMATION: ARSA polynucleotide sequence

<400> SEQUENCE: 13

atgtccatgg gggcaccgcg gtccctcctc ctggccctgg ctgctggcct ggccgttgcc      60

cgtccgccca acatcgtgct gatctttgcc gacgacctcg gctatgggga cctgggctgc     120

tatgggcacc ccagctctac cactcccaac ctggaccagc tggcggcggg agggctgcgg     180

ttcacagact tctacgtgcc tgtgtctctg tgcacaccct ctagggccgc cctcctgacc     240

ggccggctcc cggttcggat gggcatgtac cctggcgtcc tggtgcccag ctcccggggg     300

ggcctgcccc tggaggaggt gaccgtggcc gaagtcctgg ctgcccgagg ctacctcaca     360

ggaatggccg gcaagtggca ccttggggtg gggcctgagg gggccttcct gcccccccat     420

cagggcttcc atcgatttct aggcatcccg tactcccacg accagggccc ctgccagaac     480

ctgacctgct tcccgccggc cactccttgc gacggtggct gtgaccaggg cctggtcccc     540

atcccactgt tggccaacct gtccgtggag gcgcagcccc cctggctgcc cggactagag     600

gcccgctaca tggctttcgc ccatgacctc atggccgacg cccagcgcca ggatcgcccc     660

ttcttcctgt actatgcctc tcaccacacc cactaccctc agttcagtgg gcagagcttt     720

gcagagcgtt caggccgcgg gccatttggg gactccctga tggagctgga tgcagctgtg     780

gggaccctga tgacagccat aggggacctg gggctgcttg aagagacgct ggtcatcttc     840

actgcagaca atggacctga gaccatgcgt atgtcccgag gcggctgctc cggtctcttg     900
```

```
cggtgtggaa agggaacgac ctacgagggc ggtgtccgag agcctgcctt ggccttctgg    960

ccaggtcata tcgctcccgg cgtgacccac gagctggcca gctccctgga cctgctgcct   1020

accctggcag ccctggctgg ggccccactg cccaatgtca ccttggatgg ctttgacctc   1080

agccccctgc tgctgggcac aggcaagagc cctcggcagt ctctcttctt ctacccgtcc   1140

tacccagacg aggtccgtgg ggtttttgct gtgcggactg gaaagtacaa ggctcacttc   1200

ttcacccagg gctctgccca cagtgatacc actgcagacc ctgcctgcca cgcctccagc   1260

tctctgactg ctcatgagcc cccgctgctc tatgacctgt ccaaggaccc tggtgagaac   1320

tacaacctgc tgggggtgt ggccggggcc accccagagg tgctgcaagc cctgaaacag   1380

cttcagctgc tcaaggccca gttagacgca gctgtgacct tcggccccag ccaggtggcc   1440

cggggcgagg accccgccct gcagatctgc tgtcatcctg gctgcacccc ccgcccagct   1500

tgctgccatt gcccagatcc ccatgcctga                                    1530
```

<210> SEQ ID NO 14
<211> LENGTH: 509
<212> TYPE: PRT
<213> ORGANISM: homo sapiens
<220> FEATURE:
<223> OTHER INFORMATION: ARSA  polypeptide sequence

<400> SEQUENCE: 14

```
Met Ser Met Gly Ala Pro Arg Ser Leu Leu Leu Ala Leu Ala Ala Gly
1               5                   10                  15

Leu Ala Val Ala Arg Pro Pro Asn Ile Val Leu Ile Phe Ala Asp Asp
            20                  25                  30

Leu Gly Tyr Gly Asp Leu Gly Cys Tyr Gly His Pro Ser Ser Thr Thr
        35                  40                  45

Pro Asn Leu Asp Gln Leu Ala Ala Gly Gly Leu Arg Phe Thr Asp Phe
    50                  55                  60

Tyr Val Pro Val Ser Leu Cys Thr Pro Ser Arg Ala Ala Leu Leu Thr
65                  70                  75                  80

Gly Arg Leu Pro Val Arg Met Gly Met Tyr Pro Gly Val Leu Val Pro
                85                  90                  95

Ser Ser Arg Gly Gly Leu Pro Leu Glu Glu Val Thr Val Ala Glu Val
            100                 105                 110

Leu Ala Ala Arg Gly Tyr Leu Thr Gly Met Ala Gly Lys Trp His Leu
        115                 120                 125

Gly Val Gly Pro Glu Gly Ala Phe Leu Pro Pro His Gln Gly Phe His
    130                 135                 140

Arg Phe Leu Gly Ile Pro Tyr Ser His Asp Gln Gly Pro Cys Gln Asn
145                 150                 155                 160

Leu Thr Cys Phe Pro Pro Ala Thr Pro Cys Asp Gly Gly Cys Asp Gln
                165                 170                 175

Gly Leu Val Pro Ile Pro Leu Leu Ala Asn Leu Ser Val Glu Ala Gln
            180                 185                 190

Pro Pro Trp Leu Pro Gly Leu Glu Ala Arg Tyr Met Ala Phe Ala His
        195                 200                 205

Asp Leu Met Ala Asp Ala Gln Arg Gln Asp Arg Pro Phe Phe Leu Tyr
    210                 215                 220

Tyr Ala Ser His His Thr His Tyr Pro Gln Phe Ser Gly Gln Ser Phe
225                 230                 235                 240

Ala Glu Arg Ser Gly Arg Gly Pro Phe Gly Asp Ser Leu Met Glu Leu
                245                 250                 255
```

```
Asp Ala Ala Val Gly Thr Leu Met Thr Ala Ile Gly Asp Leu Gly Leu
            260                 265                 270

Leu Glu Glu Thr Leu Val Ile Phe Thr Ala Asp Asn Gly Pro Glu Thr
        275                 280                 285

Met Arg Met Ser Arg Gly Gly Cys Ser Gly Leu Leu Arg Cys Gly Lys
    290                 295                 300

Gly Thr Thr Tyr Glu Gly Gly Val Arg Glu Pro Ala Leu Ala Phe Trp
305                 310                 315                 320

Pro Gly His Ile Ala Pro Gly Val Thr His Glu Leu Ala Ser Ser Leu
                325                 330                 335

Asp Leu Leu Pro Thr Leu Ala Ala Leu Ala Gly Ala Pro Leu Pro Asn
            340                 345                 350

Val Thr Leu Asp Gly Phe Asp Leu Ser Pro Leu Leu Leu Gly Thr Gly
        355                 360                 365

Lys Ser Pro Arg Gln Ser Leu Phe Phe Tyr Pro Ser Tyr Pro Asp Glu
    370                 375                 380

Val Arg Gly Val Phe Ala Val Arg Thr Gly Lys Tyr Lys Ala His Phe
385                 390                 395                 400

Phe Thr Gln Gly Ser Ala His Ser Asp Thr Thr Ala Asp Pro Ala Cys
                405                 410                 415

His Ala Ser Ser Ser Leu Thr Ala His Glu Pro Pro Leu Leu Tyr Asp
            420                 425                 430

Leu Ser Lys Asp Pro Gly Glu Asn Tyr Asn Leu Leu Gly Gly Val Ala
        435                 440                 445

Gly Ala Thr Pro Glu Val Leu Gln Ala Leu Lys Gln Leu Gln Leu Leu
    450                 455                 460

Lys Ala Gln Leu Asp Ala Ala Val Thr Phe Gly Pro Ser Gln Val Ala
465                 470                 475                 480

Arg Gly Glu Asp Pro Ala Leu Gln Ile Cys Cys His Pro Gly Cys Thr
                485                 490                 495

Pro Arg Pro Ala Cys Cys His Cys Pro Asp Pro His Ala
            500                 505
```

```
<210> SEQ ID NO 15
<211> LENGTH: 1584
<212> TYPE: DNA
<213> ORGANISM: homo sapiens
<220> FEATURE:
<223> OTHER INFORMATION: PSAP polynucleotide sequence

<400> SEQUENCE: 15

atgtacgccc tcttcctcct ggccagcctc ctgggcgcgg ctctagccgg cccggtcctt      60

ggactgaaag aatgcaccag ggctcggca gtgtggtgcc agaatgtgaa gacggcgtcc      120

gactgcgggg cagtgaagca ctgcctgcag accgtttgga acaagccaac agtgaaatcc     180

cttccctgcg acatatgcaa agacgttgtc accgcagctg gtgatatgct gaaggacaat     240

gccactgagg aggagatcct tgtttacttg gagaagacct gtgactggct tccgaaaccg     300

aacatgtctg cttcatgcaa ggagatagtg gactcctacc tccctgtcat cctggacatc     360

attaaaggag aaatgagccg tcctggggag gtgtgctctg ctctcaacct ctgcgagtct     420

ctccagaagc acctagcaga gctgaatcac cagaagcagc tggagtccaa taagatccca     480

gagctggaca tgactgaggt ggtggccccc ttcatggcca acatccctct cctcctctac     540

cctcaggacg gcccccgcag caagccccag ccaaaggata atggggacgt ttgccaggac     600
```

```
tgcattcaga tggtgactga catccagact gctgtacgga ccaactccac ctttgtccag    660

gccttggtgg aacatgtcaa ggaggagtgt gaccgcctgg gccctggcat ggccgacata    720

tgcaagaact atatcagcca gtattctgaa attgctatcc agatgatgat gcacatgcag    780

gatcagcaac ccaaggagat ctgtgcgctg gttgggttct gtgatgaggt gaaagagatg    840

cccatgcaga ctctggtccc cgccaaagtg gcctccaaga atgtcatccc tgccctggaa    900

ctggtggagc ccattaagaa gcacgaggtc ccagcaaagt ctgatgttta ctgtgaggtg    960

tgtgaattcc tggtgaagga ggtgaccaag ctgattgaca acaacaagac tgagaaagaa   1020

atactcgacg cttttgacaa aatgtgctcg aagctgccga agtccctgtc ggaagagtgc   1080

caggaggtgg tggacacgta cggcagctcc atcctgtcca tcctgctgga ggaggtcagc   1140

cctgagctgg tgtgcagcat gctgcacctc tgctctggca cgcggctgcc tgcactgacc   1200

gttcacgtga ctcagccaaa ggacggtggc ttctgcgaag tgtgcaagaa gctggtgggt   1260

tatttggatc gcaacctgga gaaaaacagc accaagcagg agatcctggc tgctcttgag   1320

aaaggctgca gcttcctgcc agacccttac cagaagcagt gtgatcagtt tgtggcagag   1380

tacgagcccg tgctgatcga gatcctggtg gaggtgatgg atccttcctt cgtgtgcttg   1440

aaaattggag cctgcccctc ggcccataag cccttgttgg gaactgagaa gtgtatatgg   1500

ggcccaagct actggtgcca gaacacagag acagcagccc agtgcaatgc tgtcgagcat   1560

tgcaaacgcc atgtgtggaa ctag                                          1584
```

<210> SEQ ID NO 16
<211> LENGTH: 527
<212> TYPE: PRT
<213> ORGANISM: homo sapiens
<220> FEATURE:
<223> OTHER INFORMATION: PSAP polypeptide sequence

<400> SEQUENCE: 16

```
Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190
```

```
Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Asp Gln Gln Pro Lys Glu Ile Cys Ala Leu Val Gly
            260                 265                 270

Phe Cys Asp Glu Val Lys Glu Met Pro Met Gln Thr Leu Val Pro Ala
        275                 280                 285

Lys Val Ala Ser Lys Asn Val Ile Pro Ala Leu Glu Leu Val Glu Pro
    290                 295                 300

Ile Lys Lys His Glu Val Pro Ala Lys Ser Asp Val Tyr Cys Glu Val
305                 310                 315                 320

Cys Glu Phe Leu Val Lys Glu Val Thr Lys Leu Ile Asp Asn Asn Lys
                325                 330                 335

Thr Glu Lys Glu Ile Leu Asp Ala Phe Asp Lys Met Cys Ser Lys Leu
            340                 345                 350

Pro Lys Ser Leu Ser Glu Glu Cys Gln Glu Val Val Asp Thr Tyr Gly
        355                 360                 365

Ser Ser Ile Leu Ser Ile Leu Leu Glu Glu Val Ser Pro Glu Leu Val
    370                 375                 380

Cys Ser Met Leu His Leu Cys Ser Gly Thr Arg Leu Pro Ala Leu Thr
385                 390                 395                 400

Val His Val Thr Gln Pro Lys Asp Gly Gly Phe Cys Glu Val Cys Lys
                405                 410                 415

Lys Leu Val Gly Tyr Leu Asp Arg Asn Leu Glu Lys Asn Ser Thr Lys
            420                 425                 430

Gln Glu Ile Leu Ala Ala Leu Glu Lys Gly Cys Ser Phe Leu Pro Asp
        435                 440                 445

Pro Tyr Gln Lys Gln Cys Asp Gln Phe Val Ala Glu Tyr Glu Pro Val
    450                 455                 460

Leu Ile Glu Ile Leu Val Glu Val Met Asp Pro Ser Phe Val Cys Leu
465                 470                 475                 480

Lys Ile Gly Ala Cys Pro Ser Ala His Lys Pro Leu Leu Gly Thr Glu
                485                 490                 495

Lys Cys Ile Trp Gly Pro Ser Tyr Trp Cys Gln Asn Thr Glu Thr Ala
            500                 505                 510

Ala Gln Cys Asn Ala Val Glu His Cys Lys Arg His Val Trp Asn
        515                 520                 525
```

<210> SEQ ID NO 17
<211> LENGTH: 1611
<212> TYPE: DNA
<213> ORGANISM: homo sapiens
<220> FEATURE:
<223> OTHER INFORMATION: GBA polynucleotide sequence

<400> SEQUENCE: 17

```
atggagtttt caagtccttc cagagaggaa tgtcccaagc ctttgagtag ggtaagcatc     60

atggctggca gcctcacagg attgcttcta cttcaggcag tgtcgtgggc atcaggtgcc    120

cgcccctgca tccctaaaag cttcggctac agctcggtgg tgtgtgtctg caatgccaca    180
```

```
tactgtgact cctttgaccc cccgaccttt cctgcccttg gtaccttcag ccgctatgag    240

agtacacgca gtgggcgacg gatggagctg agtatggggc ccatccaggc taatcacacg    300

ggcacaggcc tgctactgac cctgcagcca gaacagaagt tccagaaagt gaagggattt    360

ggaggggcca tgacagatgc tgctgctctc aacatccttg ccctgtcacc ccctgcccaa    420

aatttgctac ttaaatcgta cttctctgaa gaaggaatcg gatataacat catccgggta    480

cccatggcca gctgtgactt ctccatccgc acctacacct atgcagacac ccctgatgat    540

ttccagttgc acaacttcag cctcccagag gaagatacca agctcaagat acccctgatt    600

caccgagccc tgcagttggc ccagcgtccc gtttcactcc ttgccagccc ctggacatca    660

cccacttggc tcaagaccaa tggagcggtg aatgggaagg ggtcactcaa gggacagccc    720

ggagacatct accaccagac ctgggccaga tactttgtga agttcctgga tgcctatgct    780

gagcacaagt tacagttctg ggcagtgaca gctgaaaatg agccttctgc tgggctgttg    840

agtggatacc ccttccagtg cctgggcttc acccctgaac atcagcgaga cttcattgcc    900

cgtgacctag gtcctaccct cgccaacagt actcaccaca atgtccgcct actcatgctg    960

gatgaccaac gcttgctgct gccccactgg gcaaaggtgg tactgacaga cccagaagca   1020

gctaaatatg ttcatggcat tgctgtacat tggtacctgg actttctggc tccagccaaa   1080

gccaccctag gggagacaca ccgcctgttc cccaacacca tgctctttgc ctcagaggcc   1140

tgtgtgggct ccaagttctg ggagcagagt gtgcggctag gctcctggga tcgagggatg   1200

cagtacagcc acagcatcat cacgaacctc ctgtaccatg tggtcggctg gaccgactgg   1260

aaccttgccc tgaaccccga aggaggaccc aattgggtgc gtaactttgt cgacagtccc   1320

atcattgtag acatcaccaa ggacacgttt tacaaacagc ccatgttcta ccaccttggc   1380

cacttcagca agttcattcc tgagggctcc cagagagtgg ggctggttgc cagtcagaag   1440

aacgacctgg acgcagtggc actgatgcat cccgatggct ctgctgttgt ggtcgtgcta   1500

aaccgctcct ctaaggatgt gcctcttacc atcaaggatc ctgctgtggg cttcctggag   1560

acaatctcac ctggctactc cattcacacc tacctgtggc gtcgccagtg a            1611
```

<210> SEQ ID NO 18
<211> LENGTH: 536
<212> TYPE: PRT
<213> ORGANISM: homo sapiens
<220> FEATURE:
<223> OTHER INFORMATION: GBA polypeptide sequence

<400> SEQUENCE: 18

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110
```

```
Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
    130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525
```

His Thr Tyr Leu Trp Arg Arg Gln
530 535

<210> SEQ ID NO 19
<211> LENGTH: 1401
<212> TYPE: DNA
<213> ORGANISM: homo sapiens
<220> FEATURE:
<223> OTHER INFORMATION: FUCA1 polynucleotide sequence

<400> SEQUENCE: 19
atgcgggctc cggggatgag gtcgcggccg gcgggtcccg cgctgttgct gctgctgctc 60
ttcctcggag cggccgagtc ggtgcgtcgg gcccagcctc cgcgccgcta caccccagac 120
tggccgagcc tggattctcg gccgctgccg gcctggttcg acgaagccaa gttcggggtg 180
ttcatccact ggggcgtgtt ctcggtgccc gcctggggca gcgagtggtt ctggtggcac 240
tggcagggcg aggggcggcc gcagtaccag cgcttcatgc gcgacaacta cccgcccggc 300
ttcagctacg ccgacttcgg accgcagttc actgcgcgct tcttccaccc ggaggagtgg 360
gccgacctct tccaggccgc gggcgccaag tatgtagttt tgacgacaaa gcatcacgaa 420
ggcttcacaa actggccgag tcctgtgtct tggaactgga actccaaaga cgtggggcct 480
catcgggatt tggttggtga attgggaaca gctctccgga agaggaacat ccgctatgga 540
ctataccact cactcttaga gtggttccat ccactctatc tacttgataa gaaaaatggc 600
ttcaaaacac agcattttgt cagtgcaaaa acaatgccag agctgtacga ccttgttaac 660
agctataaac ctgatctgat ctggtctgat ggggagtggg aatgtcctga tacttactgg 720
aactccacaa attttctttc atggctctac aatgacagcc ctgtcaagga tgaggtggta 780
gtaaatgacc gatggggtca gaactgttcc tgtcaccatg gaggatacta taactgtgaa 840
gataaattca agccacagag cttgccagat cacaagtggg agatgtgcac cagcattgac 900
aagttttcct ggggctatcg tcgtgacatg gcattgtctg atgttacaga agaatctgaa 960
atcatttcgg aactggttca gacagtaagt ttgggaggca actatcttct gaacattgga 1020
ccaactaaag atggactgat tgttcccatc ttccaagaaa ggcttcttgc tgttgggaaa 1080
tggctgagca tcaatgggga ggctatctat gcctccaaac catggcgggt gcaatgggaa 1140
aagaacacaa catctgtatg gtatacctca aagggatcgg ctgtttatgc catttttctg 1200
cactggccag aaaatggagt cttaaacctt gaatccccca taactacctc aactacaaag 1260
ataacaatgc tgggaattca aggagatctg aagtggtcca cagatccaga taaaggtctc 1320
ttcatctctc taccccagtt gccaccctct gctgtccccg cagagtttgc ttggactata 1380
aagctgacag gagtgaagta a 1401

<210> SEQ ID NO 20
<211> LENGTH: 466
<212> TYPE: PRT
<213> ORGANISM: homo sapiens
<220> FEATURE:
<223> OTHER INFORMATION: FUCA1 polypeptide sequence

<400> SEQUENCE: 20

Met Arg Ala Pro Gly Met Arg Ser Arg Pro Ala Gly Pro Ala Leu Leu
1 5 10 15

Leu Leu Leu Leu Phe Leu Gly Ala Ala Glu Ser Val Arg Arg Ala Gln
20 25 30

Pro Pro Arg Arg Tyr Thr Pro Asp Trp Pro Ser Leu Asp Ser Arg Pro
35 40 45

-continued

```
Leu Pro Ala Trp Phe Asp Glu Ala Lys Phe Gly Val Phe Ile His Trp
    50                  55                  60

Gly Val Phe Ser Val Pro Ala Trp Gly Ser Glu Trp Phe Trp Trp His
65                  70                  75                  80

Trp Gln Gly Glu Gly Arg Pro Gln Tyr Gln Arg Phe Met Arg Asp Asn
                85                  90                  95

Tyr Pro Pro Gly Phe Ser Tyr Ala Asp Phe Gly Pro Gln Phe Thr Ala
            100                 105                 110

Arg Phe Phe His Pro Glu Glu Trp Ala Asp Leu Phe Gln Ala Ala Gly
        115                 120                 125

Ala Lys Tyr Val Val Leu Thr Thr Lys His His Glu Gly Phe Thr Asn
    130                 135                 140

Trp Pro Ser Pro Val Ser Trp Asn Trp Asn Ser Lys Asp Val Gly Pro
145                 150                 155                 160

His Arg Asp Leu Val Gly Glu Leu Gly Thr Ala Leu Arg Lys Arg Asn
                165                 170                 175

Ile Arg Tyr Gly Leu Tyr His Ser Leu Leu Glu Trp Phe His Pro Leu
            180                 185                 190

Tyr Leu Leu Asp Lys Lys Asn Gly Phe Lys Thr Gln His Phe Val Ser
        195                 200                 205

Ala Lys Thr Met Pro Glu Leu Tyr Asp Leu Val Asn Ser Tyr Lys Pro
    210                 215                 220

Asp Leu Ile Trp Ser Asp Gly Glu Trp Glu Cys Pro Asp Thr Tyr Trp
225                 230                 235                 240

Asn Ser Thr Asn Phe Leu Ser Trp Leu Tyr Asn Asp Ser Pro Val Lys
                245                 250                 255

Asp Glu Val Val Val Asn Asp Arg Trp Gly Gln Asn Cys Ser Cys His
            260                 265                 270

His Gly Gly Tyr Tyr Asn Cys Glu Asp Lys Phe Lys Pro Gln Ser Leu
        275                 280                 285

Pro Asp His Lys Trp Glu Met Cys Thr Ser Ile Asp Lys Phe Ser Trp
    290                 295                 300

Gly Tyr Arg Arg Asp Met Ala Leu Ser Asp Val Thr Glu Glu Ser Glu
305                 310                 315                 320

Ile Ile Ser Glu Leu Val Gln Thr Val Ser Leu Gly Gly Asn Tyr Leu
                325                 330                 335

Leu Asn Ile Gly Pro Thr Lys Asp Gly Leu Ile Val Pro Ile Phe Gln
            340                 345                 350

Glu Arg Leu Leu Ala Val Gly Lys Trp Leu Ser Ile Asn Gly Glu Ala
        355                 360                 365

Ile Tyr Ala Ser Lys Pro Trp Arg Val Gln Trp Glu Lys Asn Thr Thr
    370                 375                 380

Ser Val Trp Tyr Thr Ser Lys Gly Ser Ala Val Tyr Ala Ile Phe Leu
385                 390                 395                 400

His Trp Pro Glu Asn Gly Val Leu Asn Leu Glu Ser Pro Ile Thr Thr
                405                 410                 415

Ser Thr Thr Lys Ile Thr Met Leu Gly Ile Gln Gly Asp Leu Lys Trp
            420                 425                 430

Ser Thr Asp Pro Asp Lys Gly Leu Phe Ile Ser Leu Pro Gln Leu Pro
        435                 440                 445

Pro Ser Ala Val Pro Ala Glu Phe Ala Trp Thr Ile Lys Leu Thr Gly
    450                 455                 460
```

Val Lys
465

<210> SEQ ID NO 21
<211> LENGTH: 3036
<212> TYPE: DNA
<213> ORGANISM: homo sapiens
<220> FEATURE:
<223> OTHER INFORMATION: MAN2B1 polynucleotide sequence

<400> SEQUENCE: 21
atgggcgcct acgcgcgggc ttcgggggtc tgcgctcgcg gctgcctgga ctcagcaggc 60
ccctggacca tgtcccgcgc cctgcggcca ccgctcccgc ctctctgctt tttccttttg 120
ttgctggcgg ctgccggtgc tcgggccggg ggatacgaga catgccccac agtgcagccg 180
aacatgctga acgtgcacct gctgcctcac acacatgatg acgtgggctg gctcaaaacc 240
gtggaccagt acttttatgg aatcaagaat gacatccagc acgccggtgt gcagtacatc 300
ctggactcgg tcatctctgc cttgctggca gatcccaccc gtcgcttcat ttacgtggag 360
attgccttct tctcccgttg gtggcaccag cagacaaatg ccacacagga agtcgtgcga 420
gaccttgtgc gccaggggcg cctggagttc gccaatggtg gctgggtgat gaacgatgag 480
gcagccaccc actacggtgc catcgtggac cagatgacac ttgggctgcg ctttctggag 540
gacacatttg gcaatgatgg gcgaccccgt gtggcctggc acattgaccc cttcggccac 600
tctcgggagc aggcctcgct gtttgcgcag atgggcttcg acggcttctt ctttgggcgc 660
cttgattatc aagataagtg ggtacggatg cagaagctgg agatggagca ggtgtggcgg 720
gccagcacca gcctgaagcc cccgaccgcg gacctcttca ctggtgtgct tcccaatggt 780
tacaacccgc caaggaatct gtgctgggat gtgctgtgtg tcgatcagcc gctggtggag 840
gaccctcgca gccccgagta caacgccaag gagctggtcg attacttcct aaatgtggcc 900
actgcccagg gccggtatta ccgcaccaac cacactgtga tgaccatggg ctcggacttc 960
caatatgaga atgccaacat gtggttcaag aaccttgaca agctcatccg gctggtaaat 1020
gcgcagcagg caaaaggaag cagtgtccat gttctctact ccacccccgc ttgttacctc 1080
tgggagctga acaaggccaa cctcacctgg tcagtgaaac atgacgactt cttcccttac 1140
gcggatggcc cccaccagtt ctggaccggt tacttttcca gtcggccggc cctcaaacgc 1200
tacgagcgcc tcagctacaa cttcctgcag gtgtgcaacc agctggaggc gctggtgggc 1260
ctggcggcca acgtgggacc ctatggctcc ggagacagtg caccccctcaa tgaggcgatg 1320
gctgtgctcc agcatcacga cgccgtcagc ggcacctccc gccagcacgt ggccaacgac 1380
tacgcgcgcc agcttgcggc aggctggggg ccttgcgagg ttcttctgag caacgcgctg 1440
gcgcggctca gaggcttcaa agatcacttc accttttgcc aacagctaaa catcagcatc 1500
tgcccgctca gccagacggc ggcgcgcttc caggtcatcg tttataatcc cctggggcgg 1560
aaggtgaatt ggatggtacg gctgccggtc agcgaaggcg ttttcgttgt gaaggacccc 1620
aatggcagga cagtgcccag cgatgtggta atatttccca gctcagacag ccaggcgcac 1680
cctccggagc tgctgttctc agcctcactg cccgccctgg gcttcagcac ctattcagta 1740
gcccaggtgc ctcgctggaa gccccaggcc cgcgcaccac agcccatccc cagaagatcc 1800
tggtcccctg ctttaaccat cgaaaatgag cacatccggg caacgtttga tcctgacaca 1860
gggctgttga tggagattat gaacatgaat cagcaactcc tgctgcctgt tcgccagacc 1920
ttcttctggt acaacgccag tataggtgac aacgaaagtg accaggcctc aggtgcctac 1980
atcttcagac ccaaccaaca gaaaccgctg cctgtgagcc gctgggctca gatccacctg 2040
gtgaagacac ccttggtgca ggaggtgcac cagaacttct cagcttggtg ttcccaggtg 2100
gttcgcctgt acccaggaca gcggcacctg gagctagagt ggtcggtggg gccgatacct 2160
gtgggcgaca cctgggggaa ggaggtcatc agccgttttg acacaccgct ggagacaaag 2220
ggacgcttct acacagacag caatggccgg gagatcctgg agaggaggcg ggattatcga 2280
cccacctgga aactgaacca gacggagccc gtggcaggaa actactatcc agtcaacacc 2340
cggatttaca tcacggatgg aaacatgcag ctgactgtgc tgactgaccg ctcccagggg 2400
ggcagcagcc tgagagatgg ctcgctggag ctcatggtgc accgaaggct gctgaaggac 2460
gatggacgcg gagtatcgga gccactaatg gagaacgggt cgggggcgtg ggtgcgaggg 2520
cgccacctgg tgctgctgga cacagcccag gctgcagccg ccggacaccg gctcctggcg 2580
gagcaggagg tcctggcccc tcaggtggtg ctggccccgg gtggcggcgc cgcctacaat 2640
ctcggggctc ctccgcgcac gcagttctca gggctgcgca gggacctgcc gccctcggtg 2700
cacctgctca cgctggccag ctggggcccc gaaatggtgc tgctgcgctt ggagcaccag 2760
tttgccgtag gagaggattc cggacgtaac ctgagcgccc ccgttacctt gaacttgagg 2820
gacctgttct ccaccttcac catcacccgc ctgcaggaga ccacgctggt ggccaaccag 2880
ctccgcgagg cagcctccag gctcaagtgg acaacaaaca caggccccac accccaccaa 2940
actccgtacc agctggaccc ggccaacatc acgctggaac ccatggaaat ccgcactttc 3000
ctggcctcag ttcaatggaa ggaggtggat ggttag 3036

<210> SEQ ID NO 22
<211> LENGTH: 1011
<212> TYPE: PRT
<213> ORGANISM: homo sapiens
<220> FEATURE:
<223> OTHER INFORMATION: MAN2B1 polypeptide sequence

<400> SEQUENCE: 22

Met Gly Ala Tyr Ala Arg Ala Ser Gly Val Cys Ala Arg Gly Cys Leu
1 5 10 15

Asp Ser Ala Gly Pro Trp Thr Met Ser Arg Ala Leu Arg Pro Pro Leu
20 25 30

Pro Pro Leu Cys Phe Phe Leu Leu Leu Leu Ala Ala Ala Gly Ala Arg
35 40 45

Ala Gly Gly Tyr Glu Thr Cys Pro Thr Val Gln Pro Asn Met Leu Asn
50 55 60

Val His Leu Leu Pro His Thr His Asp Asp Val Gly Trp Leu Lys Thr
65 70 75 80

Val Asp Gln Tyr Phe Tyr Gly Ile Lys Asn Asp Ile Gln His Ala Gly
85 90 95

Val Gln Tyr Ile Leu Asp Ser Val Ile Ser Ala Leu Leu Ala Asp Pro
100 105 110

Thr Arg Arg Phe Ile Tyr Val Glu Ile Ala Phe Phe Ser Arg Trp Trp
115 120 125

His Gln Gln Thr Asn Ala Thr Gln Glu Val Val Arg Asp Leu Val Arg
130 135 140

Gln Gly Arg Leu Glu Phe Ala Asn Gly Gly Trp Val Met Asn Asp Glu
145 150 155 160

Ala Ala Thr His Tyr Gly Ala Ile Val Asp Gln Met Thr Leu Gly Leu
165 170 175

-continued

```
Arg Phe Leu Glu Asp Thr Phe Gly Asn Asp Gly Arg Pro Arg Val Ala
            180                 185                 190

Trp His Ile Asp Pro Phe Gly His Ser Arg Glu Gln Ala Ser Leu Phe
        195                 200                 205

Ala Gln Met Gly Phe Asp Gly Phe Phe Phe Gly Arg Leu Asp Tyr Gln
    210                 215                 220

Asp Lys Trp Val Arg Met Gln Lys Leu Glu Met Glu Gln Val Trp Arg
225                 230                 235                 240

Ala Ser Thr Ser Leu Lys Pro Pro Thr Ala Asp Leu Phe Thr Gly Val
                245                 250                 255

Leu Pro Asn Gly Tyr Asn Pro Pro Arg Asn Leu Cys Trp Asp Val Leu
            260                 265                 270

Cys Val Asp Gln Pro Leu Val Glu Asp Pro Arg Ser Pro Glu Tyr Asn
        275                 280                 285

Ala Lys Glu Leu Val Asp Tyr Phe Leu Asn Val Ala Thr Ala Gln Gly
    290                 295                 300

Arg Tyr Tyr Arg Thr Asn His Thr Val Met Thr Met Gly Ser Asp Phe
305                 310                 315                 320

Gln Tyr Glu Asn Ala Asn Met Trp Phe Lys Asn Leu Asp Lys Leu Ile
                325                 330                 335

Arg Leu Val Asn Ala Gln Gln Ala Lys Gly Ser Ser Val His Val Leu
            340                 345                 350

Tyr Ser Thr Pro Ala Cys Tyr Leu Trp Glu Leu Asn Lys Ala Asn Leu
        355                 360                 365

Thr Trp Ser Val Lys His Asp Asp Phe Phe Pro Tyr Ala Asp Gly Pro
    370                 375                 380

His Gln Phe Trp Thr Gly Tyr Phe Ser Ser Arg Pro Ala Leu Lys Arg
385                 390                 395                 400

Tyr Glu Arg Leu Ser Tyr Asn Phe Leu Gln Val Cys Asn Gln Leu Glu
                405                 410                 415

Ala Leu Val Gly Leu Ala Ala Asn Val Gly Pro Tyr Gly Ser Gly Asp
            420                 425                 430

Ser Ala Pro Leu Asn Glu Ala Met Ala Val Leu Gln His His Asp Ala
        435                 440                 445

Val Ser Gly Thr Ser Arg Gln His Val Ala Asn Asp Tyr Ala Arg Gln
    450                 455                 460

Leu Ala Ala Gly Trp Gly Pro Cys Glu Val Leu Leu Ser Asn Ala Leu
465                 470                 475                 480

Ala Arg Leu Arg Gly Phe Lys Asp His Phe Thr Phe Cys Gln Gln Leu
                485                 490                 495

Asn Ile Ser Ile Cys Pro Leu Ser Gln Thr Ala Ala Arg Phe Gln Val
            500                 505                 510

Ile Val Tyr Asn Pro Leu Gly Arg Lys Val Asn Trp Met Val Arg Leu
        515                 520                 525

Pro Val Ser Glu Gly Val Phe Val Val Lys Asp Pro Asn Gly Arg Thr
    530                 535                 540

Val Pro Ser Asp Val Val Ile Phe Pro Ser Ser Asp Ser Gln Ala His
545                 550                 555                 560

Pro Pro Glu Leu Leu Phe Ser Ala Ser Leu Pro Ala Leu Gly Phe Ser
                565                 570                 575

Thr Tyr Ser Val Ala Gln Val Pro Arg Trp Lys Pro Gln Ala Arg Ala
            580                 585                 590

Pro Gln Pro Ile Pro Arg Arg Ser Trp Ser Pro Ala Leu Thr Ile Glu
```

-continued

```
        595                 600                 605

Asn Glu His Ile Arg Ala Thr Phe Asp Pro Asp Thr Gly Leu Leu Met
    610                 615                 620

Glu Ile Met Asn Met Asn Gln Gln Leu Leu Leu Pro Val Arg Gln Thr
625                 630                 635                 640

Phe Phe Trp Tyr Asn Ala Ser Ile Gly Asp Asn Glu Ser Asp Gln Ala
                645                 650                 655

Ser Gly Ala Tyr Ile Phe Arg Pro Asn Gln Gln Lys Pro Leu Pro Val
            660                 665                 670

Ser Arg Trp Ala Gln Ile His Leu Val Lys Thr Pro Leu Val Gln Glu
        675                 680                 685

Val His Gln Asn Phe Ser Ala Trp Cys Ser Gln Val Val Arg Leu Tyr
    690                 695                 700

Pro Gly Gln Arg His Leu Glu Leu Glu Trp Ser Val Gly Pro Ile Pro
705                 710                 715                 720

Val Gly Asp Thr Trp Gly Lys Glu Val Ile Ser Arg Phe Asp Thr Pro
                725                 730                 735

Leu Glu Thr Lys Gly Arg Phe Tyr Thr Asp Ser Asn Gly Arg Glu Ile
            740                 745                 750

Leu Glu Arg Arg Arg Asp Tyr Arg Pro Thr Trp Lys Leu Asn Gln Thr
        755                 760                 765

Glu Pro Val Ala Gly Asn Tyr Tyr Pro Val Asn Thr Arg Ile Tyr Ile
    770                 775                 780

Thr Asp Gly Asn Met Gln Leu Thr Val Leu Thr Asp Arg Ser Gln Gly
785                 790                 795                 800

Gly Ser Ser Leu Arg Asp Gly Ser Leu Glu Leu Met Val His Arg Arg
                805                 810                 815

Leu Leu Lys Asp Asp Gly Arg Gly Val Ser Glu Pro Leu Met Glu Asn
            820                 825                 830

Gly Ser Gly Ala Trp Val Arg Gly Arg His Leu Val Leu Leu Asp Thr
        835                 840                 845

Ala Gln Ala Ala Ala Ala Gly His Arg Leu Leu Ala Glu Gln Glu Val
    850                 855                 860

Leu Ala Pro Gln Val Val Leu Ala Pro Gly Gly Gly Ala Ala Tyr Asn
865                 870                 875                 880

Leu Gly Ala Pro Pro Arg Thr Gln Phe Ser Gly Leu Arg Arg Asp Leu
                885                 890                 895

Pro Pro Ser Val His Leu Leu Thr Leu Ala Ser Trp Gly Pro Glu Met
            900                 905                 910

Val Leu Leu Arg Leu Glu His Gln Phe Ala Val Gly Glu Asp Ser Gly
        915                 920                 925

Arg Asn Leu Ser Ala Pro Val Thr Leu Asn Leu Arg Asp Leu Phe Ser
    930                 935                 940

Thr Phe Thr Ile Thr Arg Leu Gln Glu Thr Thr Leu Val Ala Asn Gln
945                 950                 955                 960

Leu Arg Glu Ala Ala Ser Arg Leu Lys Trp Thr Thr Asn Thr Gly Pro
                965                 970                 975

Thr Pro His Gln Thr Pro Tyr Gln Leu Asp Pro Ala Asn Ile Thr Leu
            980                 985                 990

Glu Pro Met Glu Ile Arg Thr Phe Leu Ala Ser Val Gln Trp Lys Glu
        995                 1000                1005

Val Asp Gly
    1010
```

<210> SEQ ID NO 23
<211> LENGTH: 1041
<212> TYPE: DNA
<213> ORGANISM: homo sapiens
<220> FEATURE:
<223> OTHER INFORMATION: AGA polynucleotide sequence

<400> SEQUENCE: 23

```
atggcgcgga agtcgaactt gcctgtgctt ctcgtgccgt ttctgctctg ccaggcccta     60

gtgcgctgct ccagccctct gcccctggtc gtcaacactt ggccctttaa gaatgcaacc    120

gaagcagcgt ggagggcatt agcatctgga ggctctgccc tggatgcagt ggagagcggc    180

tgtgccatgt gtgagagaga gcagtgtgac ggctctgtag gctttggagg aagtcctgat    240

gaacttggag aaaccacact agatgccatg atcatggatg gcactactat ggatgtagga    300

gcagtaggag atctcagacg aattaaaaat gctattggtg tggcacggaa agtactggaa    360

catacaacac acacactttt agtaggagag tcagccacca catttgctca aagtatgggg    420

tttatcaatg aagacttatc taccactgct tctcaagctc ttcattcaga ttggcttgct    480

cggaattgcc agccaaatta ttggaggaat gttataccag atccctcaaa atactgcgga    540

ccctacaaac cacctggtat cttaaagcag gatattccta tccataaaga aacagaagat    600

gatcgtggtc atgacactat tggcatggtt gtaatccata agacaggaca tattgctgct    660

ggtacatcta caaatggtat aaaattcaaa atacatggcc gtgtaggaga ctcaccaata    720

cctggagctg gagcctatgc tgacgatact gcaggggcag ccgcagccac tgggaatggt    780

gatatattga tgcgcttcct gccaagctac caagctgtag aatacatgag aagaggagaa    840

gatccaacca tagcttgcca aaaagtgatt tcaagaatcc agaagcattt tccagaattc    900

tttggggctg ttatatgtgc caatgtgact ggaagttacg gtgctgcttg caataaactt    960

tcaacattta ctcagtttag tttcatggtt tataattccg aaaaaaatca gccaactgag   1020

gaaaaagtgg actgcatcta a                                             1041
```

<210> SEQ ID NO 24
<211> LENGTH: 346
<212> TYPE: PRT
<213> ORGANISM: homo sapiens
<220> FEATURE:
<223> OTHER INFORMATION: AGA polypeptide sequence

<400> SEQUENCE: 24

```
Met Ala Arg Lys Ser Asn Leu Pro Val Leu Leu Val Pro Phe Leu Leu
1               5                   10                  15

Cys Gln Ala Leu Val Arg Cys Ser Ser Pro Leu Pro Leu Val Val Asn
            20                  25                  30

Thr Trp Pro Phe Lys Asn Ala Thr Glu Ala Ala Trp Arg Ala Leu Ala
        35                  40                  45

Ser Gly Gly Ser Ala Leu Asp Ala Val Glu Ser Gly Cys Ala Met Cys
    50                  55                  60

Glu Arg Glu Gln Cys Asp Gly Ser Val Gly Phe Gly Gly Ser Pro Asp
65                  70                  75                  80

Glu Leu Gly Glu Thr Thr Leu Asp Ala Met Ile Met Asp Gly Thr Thr
                85                  90                  95

Met Asp Val Gly Ala Val Gly Asp Leu Arg Arg Ile Lys Asn Ala Ile
            100                 105                 110

Gly Val Ala Arg Lys Val Leu Glu His Thr Thr His Thr Leu Leu Val
```

```
        115                 120                 125

Gly Glu Ser Ala Thr Thr Phe Ala Gln Ser Met Gly Phe Ile Asn Glu
    130                 135                 140

Asp Leu Ser Thr Thr Ala Ser Gln Ala Leu His Ser Asp Trp Leu Ala
145                 150                 155                 160

Arg Asn Cys Gln Pro Asn Tyr Trp Arg Asn Val Ile Pro Asp Pro Ser
                165                 170                 175

Lys Tyr Cys Gly Pro Tyr Lys Pro Pro Gly Ile Leu Lys Gln Asp Ile
            180                 185                 190

Pro Ile His Lys Glu Thr Glu Asp Asp Arg Gly His Asp Thr Ile Gly
        195                 200                 205

Met Val Val Ile His Lys Thr Gly His Ile Ala Ala Gly Thr Ser Thr
    210                 215                 220

Asn Gly Ile Lys Phe Lys Ile His Gly Arg Val Gly Asp Ser Pro Ile
225                 230                 235                 240

Pro Gly Ala Gly Ala Tyr Ala Asp Asp Thr Ala Gly Ala Ala Ala Ala
                245                 250                 255

Thr Gly Asn Gly Asp Ile Leu Met Arg Phe Leu Pro Ser Tyr Gln Ala
            260                 265                 270

Val Glu Tyr Met Arg Arg Gly Glu Asp Pro Thr Ile Ala Cys Gln Lys
        275                 280                 285

Val Ile Ser Arg Ile Gln Lys His Phe Pro Glu Phe Phe Gly Ala Val
    290                 295                 300

Ile Cys Ala Asn Val Thr Gly Ser Tyr Gly Ala Ala Cys Asn Lys Leu
305                 310                 315                 320

Ser Thr Phe Thr Gln Phe Ser Phe Met Val Tyr Asn Ser Glu Lys Asn
                325                 330                 335

Gln Pro Thr Glu Glu Lys Val Asp Cys Ile
            340                 345


<210> SEQ ID NO 25
<211> LENGTH: 1236
<212> TYPE: DNA
<213> ORGANISM: homo sapiens
<220> FEATURE:
<223> OTHER INFORMATION: ASAH1 polynucleotide sequence

<400> SEQUENCE: 25

atgaactgct gcatcgggct gggagagaaa gctcgcgggt cccaccgggc ctcctaccca      60

agtctcagcg cgcttttcac cgaggcctca attctgggat ttggcagctt tgctgtgaaa     120

gcccaatgga cagaggactg cagaaaatca acctatcctc cttcaggacc aacgtacaga     180

ggtgcagttc catggtacac cataaatctt gacttaccac cctacaaaag atggcatgaa     240

ttgatgcttg acaaggcacc agtgctaaag gttatagtga attctctgaa gaatatgata     300

aatacattcg tgccaagtgg aaaaattatg caggtggtgg atgaaaaatt gcctggccta     360

cttggcaact ttcctggccc ttttgaagag gaaatgaagg gtattgccgc tgttactgat     420

atacctttag gagagattat ttcattcaat attttttatg aattatttac catttgtact     480

tcaatagtag cagaagacaa aaaaggtcat ctaatacatg ggagaaacat ggattttgga     540

gtatttcttg ggtggaacat aaataatgat acctgggtca taactgagca actaaaacct     600

ttaacagtga atttggattt ccaaagaaac aacaaaactg tcttcaaggc ttcaagcttt     660

gctggctatg tgggcatgtt aacaggattc aaaccaggac tgttcagtct tacactgaat     720

gaacgtttca gtataaatgg tggttatctg ggtattctag aatggattct gggaaagaaa     780
```

```
gatgtcatgt ggatagggtt cctcactaga acagttctgg aaaatagcac aagttatgaa    840

gaagccaaga atttattgac caagaccaag atattggccc cagcctactt tatcctggga    900

ggcaaccagt ctggggaagg ttgtgtgatt acacgagaca gaaaggaatc attggatgta    960

tatgaactcg atgctaagca gggtagatgg tatgtggtac aaacaaatta tgaccgttgg   1020

aaacatccct tcttccttga tgatcgcaga acgcctgcaa agatgtgtct gaaccgcacc   1080

agccaagaga atatctcatt tgaaaccatg tatgatgtcc tgtcaacaaa acctgtcctc   1140

aacaagctga ccgtatacac aaccttgata gatgttacca aaggtcaatt cgaaacttac   1200

ctgcgggact gccctgaccc ttgtataggt tggtga                              1236


<210> SEQ ID NO 26
<211> LENGTH: 411
<212> TYPE: PRT
<213> ORGANISM: homo sapiens
<220> FEATURE:
<223> OTHER INFORMATION: ASAH1 polypeptide sequence

<400> SEQUENCE: 26

Met Asn Cys Cys Ile Gly Leu Gly Glu Lys Ala Arg Gly Ser His Arg
1               5                   10                  15

Ala Ser Tyr Pro Ser Leu Ser Ala Leu Phe Thr Glu Ala Ser Ile Leu
            20                  25                  30

Gly Phe Gly Ser Phe Ala Val Lys Ala Gln Trp Thr Glu Asp Cys Arg
        35                  40                  45

Lys Ser Thr Tyr Pro Pro Ser Gly Pro Thr Tyr Arg Gly Ala Val Pro
    50                  55                  60

Trp Tyr Thr Ile Asn Leu Asp Leu Pro Pro Tyr Lys Arg Trp His Glu
65                  70                  75                  80

Leu Met Leu Asp Lys Ala Pro Val Leu Lys Val Ile Val Asn Ser Leu
                85                  90                  95

Lys Asn Met Ile Asn Thr Phe Val Pro Ser Gly Lys Ile Met Gln Val
            100                 105                 110

Val Asp Glu Lys Leu Pro Gly Leu Leu Gly Asn Phe Pro Gly Pro Phe
        115                 120                 125

Glu Glu Glu Met Lys Gly Ile Ala Ala Val Thr Asp Ile Pro Leu Gly
    130                 135                 140

Glu Ile Ile Ser Phe Asn Ile Phe Tyr Glu Leu Phe Thr Ile Cys Thr
145                 150                 155                 160

Ser Ile Val Ala Glu Asp Lys Lys Gly His Leu Ile His Gly Arg Asn
                165                 170                 175

Met Asp Phe Gly Val Phe Leu Gly Trp Asn Ile Asn Asn Asp Thr Trp
            180                 185                 190

Val Ile Thr Glu Gln Leu Lys Pro Leu Thr Val Asn Leu Asp Phe Gln
        195                 200                 205

Arg Asn Asn Lys Thr Val Phe Lys Ala Ser Ser Phe Ala Gly Tyr Val
    210                 215                 220

Gly Met Leu Thr Gly Phe Lys Pro Gly Leu Phe Ser Leu Thr Leu Asn
225                 230                 235                 240

Glu Arg Phe Ser Ile Asn Gly Gly Tyr Leu Gly Ile Leu Glu Trp Ile
                245                 250                 255

Leu Gly Lys Lys Asp Val Met Trp Ile Gly Phe Leu Thr Arg Thr Val
            260                 265                 270

Leu Glu Asn Ser Thr Ser Tyr Glu Glu Ala Lys Asn Leu Leu Thr Lys
```

```
        275                 280                 285

Thr Lys Ile Leu Ala Pro Ala Tyr Phe Ile Leu Gly Gly Asn Gln Ser
    290                 295                 300

Gly Glu Gly Cys Val Ile Thr Arg Asp Arg Lys Glu Ser Leu Asp Val
305                 310                 315                 320

Tyr Glu Leu Asp Ala Lys Gln Gly Arg Trp Tyr Val Val Gln Thr Asn
                325                 330                 335

Tyr Asp Arg Trp Lys His Pro Phe Phe Leu Asp Asp Arg Arg Thr Pro
            340                 345                 350

Ala Lys Met Cys Leu Asn Arg Thr Ser Gln Glu Asn Ile Ser Phe Glu
        355                 360                 365

Thr Met Tyr Asp Val Leu Ser Thr Lys Pro Val Leu Asn Lys Leu Thr
    370                 375                 380

Val Tyr Thr Thr Leu Ile Asp Val Thr Lys Gly Gln Phe Glu Thr Tyr
385                 390                 395                 400

Leu Arg Asp Cys Pro Asp Pro Cys Ile Gly Trp
                405                 410


<210> SEQ ID NO 27
<211> LENGTH: 1590
<212> TYPE: DNA
<213> ORGANISM: homo sapiens
<220> FEATURE:
<223> OTHER INFORMATION: HEXA polynucleotide sequence

<400> SEQUENCE: 27

atgacaagct ccaggctttg gttttcgctg ctgctggcgg cagcgttcgc aggacgggcg     60

acggccctct ggccctggcc tcagaacttc caaacctccg accagcgcta cgtcctttac    120

ccgaacaact ttcaattcca gtacgatgtc agctcggccg cgcagcccgg ctgctcagtc    180

ctcgacgagg ccttccagcg ctatcgtgac ctgcttttcg gttccgggtc ttggccccgt    240

ccttacctca cagggaaacg gcatacactg gagaagaatg tgttggttgt ctctgtagtc    300

acacctggat gtaaccagct tcctactttg gagtcagtgg agaattatac cctgaccata    360

aatgatgacc agtgtttact cctctctgag actgtctggg gagctctccg aggtctggag    420

acttttagcc agcttgtttg gaaatctgct gagggcacat tctttatcaa caagactgag    480

attgaggact ttccccgctt tcctcaccgg ggcttgctgt tggatacatc tcgccattac    540

ctgccactct ctagcatcct ggacactctg gatgtcatgg cgtacaataa attgaacgtg    600

ttccactggc atctggtaga tgatccttcc ttcccatatg agagcttcac ttttccagag    660

ctcatgagaa aggggtccta caaccctgtc acccacatct acacagcaca ggatgtgaag    720

gaggtcattg aatacgcacg gctccggggt atccgtgtgc ttgcagagtt tgacactcct    780

ggccacactt tgtcctgggg accaggtatc cctggattac tgactccttg ctactctggg    840

tctgagccct ctggcacctt tggaccagtg aatcccagtc tcaataatac ctatgagttc    900

atgagcacat tcttcttaga agtcagctct gtcttcccag atttttatct tcatcttgga    960

ggagatgagg ttgatttcac ctgctggaag tccaacccag agatccagga ctttatgagg   1020

aagaaaggct tcggtgagga cttcaagcag ctggagtcct tctacatcca gacgctgctg   1080

gacatcgtct cttcttatgg caagggctat gtggtgtggc aggaggtgtt tgataataaa   1140

gtaaagattc agccagacac aatcatacag gtgtggcgag aggatattcc agtgaactat   1200

atgaaggagc tggaactggt caccaaggcc ggcttccggg cccttctctc tgccccctgg   1260

tacctgaacc gtatatccta tggccctgac tggaaggatt tctacatagt ggaacccctg   1320
```

```
gcatttgaag gtacccctga gcagaaggct ctggtgattg gtggagaggc ttgtatgtgg   1380

ggagaatatg tggacaacac aaacctggtc cccaggctct ggcccagagc aggggctgtt   1440

gccgaaaggc tgtggagcaa caagttgaca tctgacctga catttgccta tgaacgtttg   1500

tcacacttcc gctgtgaatt gctgaggcga ggtgtccagg cccaacccct caatgtaggc   1560

ttctgtgagc aggagtttga acagacctga                                    1590


<210> SEQ ID NO 28
<211> LENGTH: 529
<212> TYPE: PRT
<213> ORGANISM: homo sapiens
<220> FEATURE:
<223> OTHER INFORMATION: HEXA polypeptide sequence

<400> SEQUENCE: 28

Met Thr Ser Ser Arg Leu Trp Phe Ser Leu Leu Leu Ala Ala Ala Phe
1               5                   10                  15

Ala Gly Arg Ala Thr Ala Leu Trp Pro Trp Pro Gln Asn Phe Gln Thr
            20                  25                  30

Ser Asp Gln Arg Tyr Val Leu Tyr Pro Asn Asn Phe Gln Phe Gln Tyr
        35                  40                  45

Asp Val Ser Ser Ala Ala Gln Pro Gly Cys Ser Val Leu Asp Glu Ala
    50                  55                  60

Phe Gln Arg Tyr Arg Asp Leu Leu Phe Gly Ser Gly Ser Trp Pro Arg
65                  70                  75                  80

Pro Tyr Leu Thr Gly Lys Arg His Thr Leu Glu Lys Asn Val Leu Val
                85                  90                  95

Val Ser Val Val Thr Pro Gly Cys Asn Gln Leu Pro Thr Leu Glu Ser
            100                 105                 110

Val Glu Asn Tyr Thr Leu Thr Ile Asn Asp Asp Gln Cys Leu Leu Leu
        115                 120                 125

Ser Glu Thr Val Trp Gly Ala Leu Arg Gly Leu Glu Thr Phe Ser Gln
    130                 135                 140

Leu Val Trp Lys Ser Ala Glu Gly Thr Phe Phe Ile Asn Lys Thr Glu
145                 150                 155                 160

Ile Glu Asp Phe Pro Arg Phe Pro His Arg Gly Leu Leu Leu Asp Thr
                165                 170                 175

Ser Arg His Tyr Leu Pro Leu Ser Ser Ile Leu Asp Thr Leu Asp Val
            180                 185                 190

Met Ala Tyr Asn Lys Leu Asn Val Phe His Trp His Leu Val Asp Asp
        195                 200                 205

Pro Ser Phe Pro Tyr Glu Ser Phe Thr Phe Pro Glu Leu Met Arg Lys
    210                 215                 220

Gly Ser Tyr Asn Pro Val Thr His Ile Tyr Thr Ala Gln Asp Val Lys
225                 230                 235                 240

Glu Val Ile Glu Tyr Ala Arg Leu Arg Gly Ile Arg Val Leu Ala Glu
                245                 250                 255

Phe Asp Thr Pro Gly His Thr Leu Ser Trp Gly Pro Gly Ile Pro Gly
            260                 265                 270

Leu Leu Thr Pro Cys Tyr Ser Gly Ser Glu Pro Ser Gly Thr Phe Gly
        275                 280                 285

Pro Val Asn Pro Ser Leu Asn Asn Thr Tyr Glu Phe Met Ser Thr Phe
    290                 295                 300

Phe Leu Glu Val Ser Ser Val Phe Pro Asp Phe Tyr Leu His Leu Gly
```

```
305                 310                 315                 320

Gly Asp Glu Val Asp Phe Thr Cys Trp Lys Ser Asn Pro Glu Ile Gln
                325                 330                 335

Asp Phe Met Arg Lys Lys Gly Phe Gly Glu Asp Phe Lys Gln Leu Glu
            340                 345                 350

Ser Phe Tyr Ile Gln Thr Leu Leu Asp Ile Val Ser Ser Tyr Gly Lys
        355                 360                 365

Gly Tyr Val Val Trp Gln Glu Val Phe Asp Asn Lys Val Lys Ile Gln
    370                 375                 380

Pro Asp Thr Ile Ile Gln Val Trp Arg Glu Asp Ile Pro Val Asn Tyr
385                 390                 395                 400

Met Lys Glu Leu Glu Leu Val Thr Lys Ala Gly Phe Arg Ala Leu Leu
                405                 410                 415

Ser Ala Pro Trp Tyr Leu Asn Arg Ile Ser Tyr Gly Pro Asp Trp Lys
            420                 425                 430

Asp Phe Tyr Ile Val Glu Pro Leu Ala Phe Glu Gly Thr Pro Glu Gln
        435                 440                 445

Lys Ala Leu Val Ile Gly Gly Glu Ala Cys Met Trp Gly Glu Tyr Val
    450                 455                 460

Asp Asn Thr Asn Leu Val Pro Arg Leu Trp Pro Arg Ala Gly Ala Val
465                 470                 475                 480

Ala Glu Arg Leu Trp Ser Asn Lys Leu Thr Ser Asp Leu Thr Phe Ala
                485                 490                 495

Tyr Glu Arg Leu Ser His Phe Arg Cys Glu Leu Leu Arg Arg Gly Val
            500                 505                 510

Gln Ala Gln Pro Leu Asn Val Gly Phe Cys Glu Gln Glu Phe Glu Gln
        515                 520                 525

Thr
```

<210> SEQ ID NO 29
<211> LENGTH: 2859
<212> TYPE: DNA
<213> ORGANISM: homo sapiens
<220> FEATURE:
<223> OTHER INFORMATION: GAA polynucleotide sequence

<400> SEQUENCE: 29

```
atgggagtga ggcacccgcc ctgctcccac cggctcctgg ccgtctgcgc cctcgtgtcc      60

ttggcaaccg ctgcactcct ggggcacatc ctactccatg atttcctgct ggttccccga     120

gagctgagtg gctcctcccc agtcctggag gagactcacc cagctcacca gcagggagcc     180

agcagaccag ggccccggga tgcccaggca caccccggcc gtcccagagc agtgcccaca     240

cagtgcgacg tcccccccaa cagccgcttc gattgcgccc ctgacaaggc catcacccag     300

gaacagtgcg aggcccgcgg ctgttgctac atccctgcaa agcaggggct gcagggagcc     360

cagatggggc agccctggtg cttcttccca cccagctacc ccagctacaa gctggagaac     420

ctgagctcct ctgaaatggg ctacacggcc accctgaccc gtaccacccc caccttcttc     480

cccaaggaca tcctgaccct gcggctggac gtgatgatgg agactgagaa ccgcctccac     540

ttcacgatca aagatccagc taacaggcgc tacgaggtgc ccttggagac cccgcatgtc     600

cacagccggg caccgtcccc actctacagc gtggagttct ccgaggagcc cttcggggtg     660

atcgtgcgcc ggcagctgga cggccgcgtg ctgctgaaca cgacggtggc gcccctgttc     720

tttgcggacc agttccttca gctgtccacc tcgctgccct cgcagtatat cacaggcctc     780
```

```
gccgagcacc tcagtcccct gatgctcagc accagctgga ccaggatcac cctgtggaac    840
cgggaccttg cgcccacgcc cggtgcgaac ctctacgggt ctcacccttt ctacctggcg    900
ctggaggacg gcgggtcggc acacggggtg ttcctgctaa acagcaatgc catggatgtg    960
gtcctgcagc cgagccctgc ccttagctgg aggtcgacag gtgggatcct ggatgtctac   1020
atcttcctgg gcccagagcc caagagcgtg gtgcagcagt acctggacgt tgtgggatac   1080
ccgttcatgc cgccatactg gggcctgggc ttccacctgt gccgctgggg ctactcctcc   1140
accgctatca cccgccaggt ggtggagaac atgaccaggg cccacttccc cctggacgtc   1200
cagtggaacg acctggacta catggactcc cggagggact tcacgttcaa caaggatggc   1260
ttccgggact tcccggccat ggtgcaggag ctgcaccagg gcggccggcg ctacatgatg   1320
atcgtggatc ctgccatcag cagctcgggc cctgccggga gctacaggcc ctacgacgag   1380
ggtctgcgga gggggtttt catcaccaac gagaccggcc agccgctgat tgggaaggta    1440
tggcccgggt ccactgcctt ccccgacttc accaacccca cagccctggc ctggtgggag   1500
gacatggtgg ctgagttcca tgaccaggtg cccttcgacg gcatgtggat tgacatgaac   1560
gagccttcca acttcatcag ggctctgag gacggctgcc ccaacaatga gctggagaac    1620
ccaccctacg tgcctggggt ggttggggg accctccagg cggccaccat ctgtgcctcc    1680
agccaccagt ttctctccac acactacaac ctgcacaacc tctacggcct gaccgaagcc   1740
atcgcctccc acagggcgct ggtgaaggct cgggggacac gcccatttgt gatctcccgc   1800
tcgacctttg ctggccacgg ccgatacgcc ggccactgga cgggggacgt gtggagctcc   1860
tgggagcagc tcgcctcctc cgtgccagaa atcctgcagt ttaacctgct ggggggtgcct  1920
ctggtcgggg ccgacgtctg cggcttcctg ggcaacacct cagaggagct gtgtgtgcgc   1980
tggacccagc tgggggcctt ctaccccttc atgcggaacc acaacagcct gctcagtctg   2040
ccccaggagc cgtacagctt cagcgagccg gcccagcagg ccatgaggaa ggccctcacc   2100
ctgcgctacg cactcctccc ccacctctac acactgttcc accaggccca cgtcgcgggg   2160
gagaccgtgg cccggcccct cttcctggag ttccccaagg actctagcac ctggactgtg   2220
gaccaccagc tcctgtgggg ggaggccctg ctcatcaccc cagtgctcca ggccgggaag   2280
gccgaagtga ctggctactt cccccttgggc acatggtacg acctgcagac ggtgccagta   2340
gaggcccttg gcagcctccc acccccacct gcagctcccc gtgagccagc catccacagc   2400
gaggggcagt gggtgacgct gccggccccc ctggacacca tcaacgtcca cctccgggct   2460
gggtacatca tcccccctgca gggccctggc ctcacaacca cagagtcccg ccagcagccc  2520
atggccctgg ctgtggccct gaccaagggt ggggaggccc gaggggagct gttctgggac   2580
gatggagaga gcctggaagt gctggagcga ggggcctaca cacaggtcat cttcctggcc   2640
aggaataaca cgatcgtgaa tgagctggta cgtgtgacca gtgagggagc tggcctgcag   2700
ctgcagaagg tgactgtcct gggcgtggcc acggcgcccc agcaggtcct ctccaacggt   2760
gtccctgtct ccaacttcac ctacagcccc gacaccaagg tcctggacat ctgtgtctcg   2820
ctgttgatgg gagagcagtt tctcgtcagc tggtgttag                          2859
```

<210> SEQ ID NO 30
<211> LENGTH: 952
<212> TYPE: PRT
<213> ORGANISM: homo sapiens
<220> FEATURE:
<223> OTHER INFORMATION: GAA polypeptide sequence

<400> SEQUENCE: 30

-continued

```
Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415
```

```
Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Val Glu Ala Leu Gly
    770                 775                 780

Ser Leu Pro Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
```

835 840 845

Lys Gly Gly Glu Ala Arg Gly Glu Leu Phe Trp Asp Asp Gly Glu Ser
850 855 860

Leu Glu Val Leu Glu Arg Gly Ala Tyr Thr Gln Val Ile Phe Leu Ala
865 870 875 880

Arg Asn Asn Thr Ile Val Asn Glu Leu Val Arg Val Thr Ser Glu Gly
885 890 895

Ala Gly Leu Gln Leu Gln Lys Val Thr Val Leu Gly Val Ala Thr Ala
900 905 910

Pro Gln Gln Val Leu Ser Asn Gly Val Pro Val Ser Asn Phe Thr Tyr
915 920 925

Ser Pro Asp Thr Lys Val Leu Asp Ile Cys Val Ser Leu Leu Met Gly
930 935 940

Glu Gln Phe Leu Val Ser Trp Cys
945 950

<210> SEQ ID NO 31
<211> LENGTH: 1896
<212> TYPE: DNA
<213> ORGANISM: homo sapiens
<220> FEATURE:
<223> OTHER INFORMATION: SMPD1 polynucleotide sequence

<400> SEQUENCE: 31
atgccccgct acggagcgtc actccgccag agctgcccca ggtccggccg ggagcaggga 60
caagacggga ccgccggagc cccggactc ctttggatgg gcctggtgct ggcgctggcg 120
ctggcgctgg cgctggcgct ggctctgtct gactctcggg ttctctgggc tccggcagag 180
gctcaccctc tttctcccca aggccatcct gccaggttac atcgcatagt gccccggctc 240
cgagatgtct ttgggtgggg gaacctcacc tgcccaatct gcaaaggtct attcaccgcc 300
atcaacctcg ggctgaagaa ggaacccaat gtggctcgcg tgggctccgt ggccatcaag 360
ctgtgcaatc tgctgaagat agcaccacct gccgtgtgcc aatccattgt ccacctcttt 420
gaggatgaca tggtggaggt gtggagacgc tcagtgctga gcccatctga ggcctgtggc 480
ctgctcctgg gctccacctg tgggcactgg gacattttct catcttggaa catctctttg 540
cctactgtgc cgaagccgcc ccccaaaccc cctagccccc cagccccagg tgcccctgtc 600
agccgcatcc tcttcctcac tgacctgcac tgggatcatg actacctgga gggcacggac 660
cctgactgtg cagacccact gtgctgccgc cggggttctg gcctgccgcc cgcatcccgg 720
ccaggtgccg gatactgggg cgaatacagc aagtgtgacc tgcccctgag gaccctggag 780
agcctgttga gtgggctggg cccagccggc ccttttgata tggtgtactg gacaggagac 840
atccccgcac atgatgtctg gcaccagact cgtcaggacc aactgcgggc cctgaccacc 900
gtcacagcac ttgtgaggaa gttcctgggg ccagtgccag tgtaccctgc tgtgggtaac 960
catgaaagca cacctgtcaa tagcttccct cccccccttca ttgagggcaa ccactcctcc 1020
cgctggctct atgaagcgat ggccaaggct tgggagccct ggctgcctgc cgaagccctg 1080
cgcaccctca gaattggggg gttctatgct ctttccccat accccggtct ccgcctcatc 1140
tctctcaata tgaatttttg ttcccgtgag aacttctggc tcttgatcaa ctccacggat 1200
cccgcaggac agctccagtg gctggtgggg gagcttcagg ctgctgagga tcgaggagac 1260
aaagtgcata taattggcca cattccccca gggcactgtc tgaagagctg gagctggaat 1320
tattaccgaa ttgtagccag gtatgagaac accctggctg ctcagttctt tggccacact 1380

```
catgtggatg aatttgaggt cttctatgat gaagagactc tgagccggcc gctggctgta   1440

gccttcctgg cacccagtgc aactacctac atcggcctta atcctggtta ccgtgtgtac   1500

caaatagatg gaaactactc cgggagctct cacgtggtcc tggaccatga gacctacatc   1560

ctgaatctga cccaggcaaa cataccggga gccataccgc actggcagct tctctacagg   1620

gctcgagaaa cctatgggct gcccaacaca ctgcctaccg cctggcacaa cctggtatat   1680

cgcatgcggg gcgacatgca acttttccag accttctggt ttctctacca taagggccac   1740

ccaccctcgg agccctgtgg cacgccctgc cgtctggcta ctctttgtgc ccagctctct   1800

gcccgtgctg acagccctgc tctgtgccgc cacctgatgc cagatgggag cctcccagag   1860

gcccagagcc tgtggccaag gccactgttt tgctag                             1896
```

<210> SEQ ID NO 32
<211> LENGTH: 631
<212> TYPE: PRT
<213> ORGANISM: homo sapiens
<220> FEATURE:
<223> OTHER INFORMATION: SMPD1 polypeptide sequence

<400> SEQUENCE: 32

```
Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
            20                  25                  30

Met Gly Leu Val Leu Ala Leu Ala Leu Ala Leu Ala Leu Ala Leu Ala
        35                  40                  45

Leu Ser Asp Ser Arg Val Leu Trp Ala Pro Ala Glu Ala His Pro Leu
    50                  55                  60

Ser Pro Gln Gly His Pro Ala Arg Leu His Arg Ile Val Pro Arg Leu
65                  70                  75                  80

Arg Asp Val Phe Gly Trp Gly Asn Leu Thr Cys Pro Ile Cys Lys Gly
                85                  90                  95

Leu Phe Thr Ala Ile Asn Leu Gly Leu Lys Lys Glu Pro Asn Val Ala
            100                 105                 110

Arg Val Gly Ser Val Ala Ile Lys Leu Cys Asn Leu Leu Lys Ile Ala
        115                 120                 125

Pro Pro Ala Val Cys Gln Ser Ile Val His Leu Phe Glu Asp Asp Met
    130                 135                 140

Val Glu Val Trp Arg Arg Ser Val Leu Ser Pro Ser Glu Ala Cys Gly
145                 150                 155                 160

Leu Leu Leu Gly Ser Thr Cys Gly His Trp Asp Ile Phe Ser Ser Trp
                165                 170                 175

Asn Ile Ser Leu Pro Thr Val Pro Lys Pro Pro Pro Lys Pro Pro Ser
            180                 185                 190

Pro Pro Ala Pro Gly Ala Pro Val Ser Arg Ile Leu Phe Leu Thr Asp
        195                 200                 205

Leu His Trp Asp His Asp Tyr Leu Glu Gly Thr Asp Pro Asp Cys Ala
    210                 215                 220

Asp Pro Leu Cys Cys Arg Arg Gly Ser Gly Leu Pro Pro Ala Ser Arg
225                 230                 235                 240

Pro Gly Ala Gly Tyr Trp Gly Glu Tyr Ser Lys Cys Asp Leu Pro Leu
                245                 250                 255

Arg Thr Leu Glu Ser Leu Leu Ser Gly Leu Gly Pro Ala Gly Pro Phe
            260                 265                 270
```

```
Asp Met Val Tyr Trp Thr Gly Asp Ile Pro Ala His Asp Val Trp His
        275                 280                 285

Gln Thr Arg Gln Asp Gln Leu Arg Ala Leu Thr Thr Val Thr Ala Leu
    290                 295                 300

Val Arg Lys Phe Leu Gly Pro Val Pro Val Tyr Pro Ala Val Gly Asn
305                 310                 315                 320

His Glu Ser Thr Pro Val Asn Ser Phe Pro Pro Pro Phe Ile Glu Gly
                325                 330                 335

Asn His Ser Ser Arg Trp Leu Tyr Glu Ala Met Ala Lys Ala Trp Glu
            340                 345                 350

Pro Trp Leu Pro Ala Glu Ala Leu Arg Thr Leu Arg Ile Gly Gly Phe
        355                 360                 365

Tyr Ala Leu Ser Pro Tyr Pro Gly Leu Arg Leu Ile Ser Leu Asn Met
    370                 375                 380

Asn Phe Cys Ser Arg Glu Asn Phe Trp Leu Leu Ile Asn Ser Thr Asp
385                 390                 395                 400

Pro Ala Gly Gln Leu Gln Trp Leu Val Gly Glu Leu Gln Ala Ala Glu
                405                 410                 415

Asp Arg Gly Asp Lys Val His Ile Ile Gly His Ile Pro Pro Gly His
            420                 425                 430

Cys Leu Lys Ser Trp Ser Trp Asn Tyr Tyr Arg Ile Val Ala Arg Tyr
        435                 440                 445

Glu Asn Thr Leu Ala Ala Gln Phe Phe Gly His Thr His Val Asp Glu
    450                 455                 460

Phe Glu Val Phe Tyr Asp Glu Glu Thr Leu Ser Arg Pro Leu Ala Val
465                 470                 475                 480

Ala Phe Leu Ala Pro Ser Ala Thr Thr Tyr Ile Gly Leu Asn Pro Gly
                485                 490                 495

Tyr Arg Val Tyr Gln Ile Asp Gly Asn Tyr Ser Gly Ser Ser His Val
            500                 505                 510

Val Leu Asp His Glu Thr Tyr Ile Leu Asn Leu Thr Gln Ala Asn Ile
        515                 520                 525

Pro Gly Ala Ile Pro His Trp Gln Leu Leu Tyr Arg Ala Arg Glu Thr
    530                 535                 540

Tyr Gly Leu Pro Asn Thr Leu Pro Thr Ala Trp His Asn Leu Val Tyr
545                 550                 555                 560

Arg Met Arg Gly Asp Met Gln Leu Phe Gln Thr Phe Trp Phe Leu Tyr
                565                 570                 575

His Lys Gly His Pro Pro Ser Glu Pro Cys Gly Thr Pro Cys Arg Leu
            580                 585                 590

Ala Thr Leu Cys Ala Gln Leu Ser Ala Arg Ala Asp Ser Pro Ala Leu
        595                 600                 605

Cys Arg His Leu Met Pro Asp Gly Ser Leu Pro Glu Ala Gln Ser Leu
    610                 615                 620

Trp Pro Arg Pro Leu Phe Cys
625                 630
```

<210> SEQ ID NO 33
<211> LENGTH: 1200
<212> TYPE: DNA
<213> ORGANISM: homo sapiens
<220> FEATURE:
<223> OTHER INFORMATION: LIPA polynucleotide sequence

<400> SEQUENCE: 33

```
atgaaaatgc ggttcttggg gttggtggtc tgtttggttc tctggaccct gcattctgag      60
gggtctggag ggaaactgac agctgtggat cctgaaacaa acatgaatgt gagtgaaatt     120
atctcttact ggggattccc tagtgaggaa tacctagttg agacagaaga tggatatatt     180
ctgtgcctta accgaattcc tcatgggagg aagaaccatt ctgacaaagg tcccaaacca     240
gttgtcttcc tgcaacatgg cttgctggca gattctagta actgggtcac aaaccttgcc     300
aacagcagcc tgggcttcat tcttgctgat gctggttttg acgtgtggat gggcaacagc     360
agaggaaata cctggtctcg gaaacataag acactctcag tttctcagga tgaattctgg     420
gctttcagtt atgatgagat ggcaaaatat gacctaccag cttccattaa cttcattctg     480
aataaaactg gccaagaaca agtgtattat gtgggtcatt ctcaaggcac cactataggt     540
tttatagcat tttcacagat ccctgagctg gctaaaagga ttaaaatgtt ttttgccctg     600
ggtcctgtgg cttccgtcgc cttctgtact agccctatgg ccaaattagg acgattacca     660
gatcatctca ttaaggactt atttggagac aaagaatttc ttccccagag tgcgtttttg     720
aagtggctgg gtacccacgt ttgcactcat gtcatactga aggagctctg tggaaatctc     780
tgttttcttc tgtgtggatt taatgagaga aatttaaata tgtctagagt ggatgtatat     840
acaacacatt ctcctgctgg aacttctgtg caaaacatgt tacactggag ccaggctgtt     900
aaattccaaa agtttcaagc ctttgactgg ggaagcagtg ccaagaatta ttttcattac     960
aaccagagtt atcctcccac atacaatgtg aaggacatgc ttgtgccgac tgcagtctgg    1020
agcgggggtc acgactggct tgcagatgtc tacgacgtca atatcttact gactcagatc    1080
accaacttgg tgttccatga gagcattccg gaatgggagc atcttgactt catttggggc    1140
ctggatgccc cttggaggct ttataataaa attattaatc taatgaggaa atatcagtga    1200
```

<210> SEQ ID NO 34
<211> LENGTH: 399
<212> TYPE: PRT
<213> ORGANISM: homo sapiens
<220> FEATURE:
<223> OTHER INFORMATION: LIPA polypeptide sequence

<400> SEQUENCE: 34

```
Met Lys Met Arg Phe Leu Gly Leu Val Val Cys Leu Val Leu Trp Thr
1               5                   10                  15

Leu His Ser Glu Gly Ser Gly Gly Lys Leu Thr Ala Val Asp Pro Glu
            20                  25                  30

Thr Asn Met Asn Val Ser Glu Ile Ile Ser Tyr Trp Gly Phe Pro Ser
        35                  40                  45

Glu Glu Tyr Leu Val Glu Thr Glu Asp Gly Tyr Ile Leu Cys Leu Asn
    50                  55                  60

Arg Ile Pro His Gly Arg Lys Asn His Ser Asp Lys Gly Pro Lys Pro
65                  70                  75                  80

Val Val Phe Leu Gln His Gly Leu Leu Ala Asp Ser Ser Asn Trp Val
                85                  90                  95

Thr Asn Leu Ala Asn Ser Ser Leu Gly Phe Ile Leu Ala Asp Ala Gly
            100                 105                 110

Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
    130                 135                 140

Asp Glu Met Ala Lys Tyr Asp Leu Pro Ala Ser Ile Asn Phe Ile Leu
145                 150                 155                 160
```

```
Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
    210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285

Ser Val Gln Asn Met Leu His Trp Ser Gln Ala Val Lys Phe Gln Lys
    290                 295                 300

Phe Gln Ala Phe Asp Trp Gly Ser Ser Ala Lys Asn Tyr Phe His Tyr
305                 310                 315                 320

Asn Gln Ser Tyr Pro Pro Thr Tyr Asn Val Lys Asp Met Leu Val Pro
                325                 330                 335

Thr Ala Val Trp Ser Gly Gly His Asp Trp Leu Ala Asp Val Tyr Asp
            340                 345                 350

Val Asn Ile Leu Leu Thr Gln Ile Thr Asn Leu Val Phe His Glu Ser
        355                 360                 365

Ile Pro Glu Trp Glu His Leu Asp Phe Ile Trp Gly Leu Asp Ala Pro
    370                 375                 380

Trp Arg Leu Tyr Asn Lys Ile Ile Asn Leu Met Arg Lys Tyr Gln
385                 390                 395
```

<210> SEQ ID NO 35
<211> LENGTH: 3093
<212> TYPE: DNA
<213> ORGANISM: homo sapiens
<220> FEATURE:
<223> OTHER INFORMATION: CDKL5 polynucleotide sequence

<400> SEQUENCE: 35

```
atgaagattc ctaacattgg taatgtgatg aataaatttg agatccttgg ggttgtaggt      60

gaaggagcct atggagttgt acttaaatgc agacacaagg aaacacatga aattgtggcg     120

atcaagaaat tcaaggacag tgaagaaaat gaagaagtca aagaaacgac tttacgagag     180

cttaaaatgc ttcggactct caagcaggaa aacattgtgg agttgaagga agcatttcgt     240

cggaggggaa agttgtactt ggtgtttgag tatgttgaaa aaaatatgct cgaattgctg     300

gaagaaatgc caaatggagt tccacctgag aaagtaaaaa gctacatcta tcagctaatc     360

aaggctattc actggtgcca taagaatgat attgtccatc gagatataaa accagaaaat     420

ctcttaatca gccacaatga tgtcctaaaa ctgtgtgact ttggttttgc tcgtaatctg     480

tcagaaggca ataatgctaa ttacacagag tacgttgcca ccagatggta tcggtcccca     540

gaactcttac ttggcgctcc ctatggaaag tccgtggaca tgtggtcggt gggctgtatt     600

cttggggagc ttagcgatgg acagcccttta tttcctggag aaagtgaaat tgaccaactt     660

tttactattc agaaggtgct aggaccactt ccatctgagc agatgaagct tttctacagt     720
```

```
aatcctcgct tccatgggct ccggtttcca gctgttaacc atcctcagtc cttggaaaga    780
agataccttg gaattttgaa tagtgttcta cttgacctaa tgaagaattt actgaagttg    840
gacccagctg acagatactt gacagaacag tgtttgaatc accctacatt tcaaacccag    900
agacttctgg atcgttctcc ttcaaggtca gcaaaaagaa aaccttacca tgtggaaagc    960
agcacattgt ctaatagaaa ccaagccggc aaaagtactg ctttgcagtc tcaccacaga   1020
tctaacagca aggacatcca gaacctgagt gtaggcctgc cccgggctga cgaaggtctc   1080
cctgccaatg aaagcttcct aaatggaaac cttgctggag ctagtcttag tccactgcac   1140
accaaaacct accaagcaag cagccagcct gggtctacca gcaaagatct caccaacaac   1200
aacataccac accttcttag cccaaaagaa gccaagtcaa aaacagagtt tgattttaat   1260
attgacccaa agccttcaga aggcccaggg acaaagtacc tcaagtcaaa cagcagatct   1320
cagcagaacc gccactcatt catggaaagc tctcaaagca aagctgggac actgcagccc   1380
aatgaaaagc agagtcggca tagctatatt gacacaattc cccagtcctc taggagtccc   1440
tcctacagga ccaaggccaa aagccatggg gcactgagtg actccaagtc tgtgagcaac   1500
ctttctgaag ccagggccca aattgcggag cccagtacca gtaggtactt cccatctagc   1560
tgcttagact tgaattctcc caccagccca acccccacca gacacagtga cacgagaact   1620
ttgctcagcc cttctggaag aaataaccga aatgagggaa cgctggactc acgtcgaacc   1680
acaaccagac attctaagac gatggaggaa ttgaagctgc cggagcacat ggacagtagc   1740
cattcccatt cactgtctgc acctcacgaa tctttttctt atggactggg ctacaccagc   1800
ccctttcctt cccagcaacg tcctcatagg cattctatgt atgtgacccg tgacaaagtg   1860
agagccaagg gcttggatgg aagcttgagc atagggcaag ggatggcagc tagagccaac   1920
agcctgcaac tcttgtcacc ccagcctgga gaacagctcc ctccagagat gactgtggca   1980
agatcttcgg tcaaagagac ctccagagaa ggcacctctt ccttccatac acgccagaag   2040
tctgagggtg gagtgtatca tgacccacac tctgatgatg gcacagcccc caaagaaaat   2100
agacacctat acaatgatcc tgtgccaagg agagttggta gcttttacag agtgccatct   2160
ccacgtccag acaattcttt ccatgaaaat aatgtgtcaa ctagagtttc ttctctacca   2220
tcagagagca gttctggaac caaccactca aaaagacaac cagcattcga tccatggaaa   2280
agtcctgaaa atattagtca ttcagagcaa ctcaaggaaa aagagaagca aggatttttc   2340
aggtcaatga aaaagaaaaa gaagaaatct caaacagtac ccaattccga cagccctgat   2400
cttctgacgt tgcagaaatc cattcattct gctagcactc caagcagcag accaaaggag   2460
tggcgccccg agaagatctc agatctgcag acccaaagcc agccattaaa atcactgcgc   2520
aagttgttac atctctcttc ggcctcaaat cacccggctt cctcagatcc ccgcttccag   2580
cccttaacag ctcaacaaac caaaaattcc ttctcagaaa ttcggattca ccccctgagc   2640
caggcctctg gcgggagcag caacatccgg caggaacccg caccgaaggg caggccagcc   2700
ctccagctgc cagacggtgg atgtgatggc agaagacaga gacaccattc tggaccccaa   2760
gatagacgct tcatgttaag gacgacagaa caacaaggag aatacttctg ctgtggtgac   2820
ccaaagaagc ctcacactcc gtgcgtccca aaccgagccc ttcatcgtcc aatctccagt   2880
cctgctccct atccagtact ccaggtccga ggcacttcca tgtgcccgac actccaggtc   2940
cgaggcactg atgctttcag ctgcccaacc cagcaatccg ggttctcttt cttcgtgaga   3000
cacgttatga gggaagccct gattcacagg gcccaggtaa accaagctgc gctcctgaca   3060
```

taccatgaga atgcggcact gacgggcaag tga 3093

<210> SEQ ID NO 36
<211> LENGTH: 1030
<212> TYPE: PRT
<213> ORGANISM: homo sapiens
<220> FEATURE:
<223> OTHER INFORMATION: CDKL5 polypeptide sequence

<400> SEQUENCE: 36

```
Met Lys Ile Pro Asn Ile Gly Asn Val Met Asn Lys Phe Glu Ile Leu
1               5                   10                  15

Gly Val Val Gly Glu Gly Ala Tyr Gly Val Val Leu Lys Cys Arg His
            20                  25                  30

Lys Glu Thr His Glu Ile Val Ala Ile Lys Lys Phe Lys Asp Ser Glu
        35                  40                  45

Glu Asn Glu Glu Val Lys Glu Thr Thr Leu Arg Glu Leu Lys Met Leu
    50                  55                  60

Arg Thr Leu Lys Gln Glu Asn Ile Val Glu Leu Lys Glu Ala Phe Arg
65                  70                  75                  80

Arg Arg Gly Lys Leu Tyr Leu Val Phe Glu Tyr Val Glu Lys Asn Met
                85                  90                  95

Leu Glu Leu Leu Glu Glu Met Pro Asn Gly Val Pro Pro Glu Lys Val
            100                 105                 110

Lys Ser Tyr Ile Tyr Gln Leu Ile Lys Ala Ile His Trp Cys His Lys
        115                 120                 125

Asn Asp Ile Val His Arg Asp Ile Lys Pro Glu Asn Leu Leu Ile Ser
    130                 135                 140

His Asn Asp Val Leu Lys Leu Cys Asp Phe Gly Phe Ala Arg Asn Leu
145                 150                 155                 160

Ser Glu Gly Asn Asn Ala Asn Tyr Thr Glu Tyr Val Ala Thr Arg Trp
                165                 170                 175

Tyr Arg Ser Pro Glu Leu Leu Leu Gly Ala Pro Tyr Gly Lys Ser Val
            180                 185                 190

Asp Met Trp Ser Val Gly Cys Ile Leu Gly Glu Leu Ser Asp Gly Gln
        195                 200                 205

Pro Leu Phe Pro Gly Glu Ser Glu Ile Asp Gln Leu Phe Thr Ile Gln
    210                 215                 220

Lys Val Leu Gly Pro Leu Pro Ser Glu Gln Met Lys Leu Phe Tyr Ser
225                 230                 235                 240

Asn Pro Arg Phe His Gly Leu Arg Phe Pro Ala Val Asn His Pro Gln
                245                 250                 255

Ser Leu Glu Arg Arg Tyr Leu Gly Ile Leu Asn Ser Val Leu Leu Asp
            260                 265                 270

Leu Met Lys Asn Leu Leu Lys Leu Asp Pro Ala Asp Arg Tyr Leu Thr
        275                 280                 285

Glu Gln Cys Leu Asn His Pro Thr Phe Gln Thr Gln Arg Leu Leu Asp
    290                 295                 300

Arg Ser Pro Ser Arg Ser Ala Lys Arg Lys Pro Tyr His Val Glu Ser
305                 310                 315                 320

Ser Thr Leu Ser Asn Arg Asn Gln Ala Gly Lys Ser Thr Ala Leu Gln
                325                 330                 335

Ser His His Arg Ser Asn Ser Lys Asp Ile Gln Asn Leu Ser Val Gly
            340                 345                 350

Leu Pro Arg Ala Asp Glu Gly Leu Pro Ala Asn Glu Ser Phe Leu Asn
```

```
        355                 360                 365

Gly Asn Leu Ala Gly Ala Ser Leu Ser Pro Leu His Thr Lys Thr Tyr
    370                 375                 380

Gln Ala Ser Ser Gln Pro Gly Ser Thr Ser Lys Asp Leu Thr Asn Asn
385                 390                 395                 400

Asn Ile Pro His Leu Leu Ser Pro Lys Glu Ala Lys Ser Lys Thr Glu
                405                 410                 415

Phe Asp Phe Asn Ile Asp Pro Lys Pro Ser Glu Gly Pro Gly Thr Lys
            420                 425                 430

Tyr Leu Lys Ser Asn Ser Arg Ser Gln Gln Asn Arg His Ser Phe Met
        435                 440                 445

Glu Ser Ser Gln Ser Lys Ala Gly Thr Leu Gln Pro Asn Glu Lys Gln
    450                 455                 460

Ser Arg His Ser Tyr Ile Asp Thr Ile Pro Gln Ser Ser Arg Ser Pro
465                 470                 475                 480

Ser Tyr Arg Thr Lys Ala Lys Ser His Gly Ala Leu Ser Asp Ser Lys
                485                 490                 495

Ser Val Ser Asn Leu Ser Glu Ala Arg Ala Gln Ile Ala Glu Pro Ser
            500                 505                 510

Thr Ser Arg Tyr Phe Pro Ser Ser Cys Leu Asp Leu Asn Ser Pro Thr
        515                 520                 525

Ser Pro Thr Pro Thr Arg His Ser Asp Thr Arg Thr Leu Leu Ser Pro
    530                 535                 540

Ser Gly Arg Asn Asn Arg Asn Glu Gly Thr Leu Asp Ser Arg Arg Thr
545                 550                 555                 560

Thr Thr Arg His Ser Lys Thr Met Glu Glu Leu Lys Leu Pro Glu His
                565                 570                 575

Met Asp Ser Ser His Ser His Ser Leu Ser Ala Pro His Glu Ser Phe
            580                 585                 590

Ser Tyr Gly Leu Gly Tyr Thr Ser Pro Phe Ser Ser Gln Gln Arg Pro
        595                 600                 605

His Arg His Ser Met Tyr Val Thr Arg Asp Lys Val Arg Ala Lys Gly
    610                 615                 620

Leu Asp Gly Ser Leu Ser Ile Gly Gln Gly Met Ala Ala Arg Ala Asn
625                 630                 635                 640

Ser Leu Gln Leu Leu Ser Pro Gln Pro Gly Glu Gln Leu Pro Pro Glu
                645                 650                 655

Met Thr Val Ala Arg Ser Ser Val Lys Glu Thr Ser Arg Glu Gly Thr
            660                 665                 670

Ser Ser Phe His Thr Arg Gln Lys Ser Glu Gly Gly Val Tyr His Asp
        675                 680                 685

Pro His Ser Asp Asp Gly Thr Ala Pro Lys Glu Asn Arg His Leu Tyr
    690                 695                 700

Asn Asp Pro Val Pro Arg Arg Val Gly Ser Phe Tyr Arg Val Pro Ser
705                 710                 715                 720

Pro Arg Pro Asp Asn Ser Phe His Glu Asn Asn Val Ser Thr Arg Val
                725                 730                 735

Ser Ser Leu Pro Ser Glu Ser Ser Ser Gly Thr Asn His Ser Lys Arg
            740                 745                 750

Gln Pro Ala Phe Asp Pro Trp Lys Ser Pro Glu Asn Ile Ser His Ser
        755                 760                 765

Glu Gln Leu Lys Glu Lys Glu Lys Gln Gly Phe Phe Arg Ser Met Lys
    770                 775                 780
```

Lys Lys Lys Lys Lys Ser Gln Thr Val Pro Asn Ser Asp Ser Pro Asp
785 790 795 800

Leu Leu Thr Leu Gln Lys Ser Ile His Ser Ala Ser Thr Pro Ser Ser
805 810 815

Arg Pro Lys Glu Trp Arg Pro Glu Lys Ile Ser Asp Leu Gln Thr Gln
820 825 830

Ser Gln Pro Leu Lys Ser Leu Arg Lys Leu Leu His Leu Ser Ser Ala
835 840 845

Ser Asn His Pro Ala Ser Ser Asp Pro Arg Phe Gln Pro Leu Thr Ala
850 855 860

Gln Gln Thr Lys Asn Ser Phe Ser Glu Ile Arg Ile His Pro Leu Ser
865 870 875 880

Gln Ala Ser Gly Gly Ser Ser Asn Ile Arg Gln Glu Pro Ala Pro Lys
885 890 895

Gly Arg Pro Ala Leu Gln Leu Pro Asp Gly Gly Cys Asp Gly Arg Arg
900 905 910

Gln Arg His His Ser Gly Pro Gln Asp Arg Arg Phe Met Leu Arg Thr
915 920 925

Thr Glu Gln Gln Gly Glu Tyr Phe Cys Cys Gly Asp Pro Lys Lys Pro
930 935 940

His Thr Pro Cys Val Pro Asn Arg Ala Leu His Arg Pro Ile Ser Ser
945 950 955 960

Pro Ala Pro Tyr Pro Val Leu Gln Val Arg Gly Thr Ser Met Cys Pro
965 970 975

Thr Leu Gln Val Arg Gly Thr Asp Ala Phe Ser Cys Pro Thr Gln Gln
980 985 990

Ser Gly Phe Ser Phe Phe Val Arg His Val Met Arg Glu Ala Leu Ile
995 1000 1005

His Arg Ala Gln Val Asn Gln Ala Ala Leu Leu Thr Tyr His Glu Asn
1010 1015 1020

Ala Ala Leu Thr Gly Lys
1025 1030

<210> SEQ ID NO 37
<211> LENGTH: 18
<212> TYPE: PRT
<213> ORGANISM: homo sapiens
<220> FEATURE:
<223> OTHER INFORMATION: Albumin peptide

<400> SEQUENCE: 37

Met Lys Trp Val Thr Phe Ile Ser Leu Leu Phe Leu Phe Ser Ser Ala
1 5 10 15

Tyr Ser

<210> SEQ ID NO 38
<211> LENGTH: 18
<212> TYPE: PRT
<213> ORGANISM: homo sapiens
<220> FEATURE:
<223> OTHER INFORMATION: chymotrypsinogen peptide

<400> SEQUENCE: 38

Met Ala Phe Leu Trp Leu Leu Ser Cys Trp Ala Leu Leu Gly Thr Thr
1 5 10 15

Phe Gly

<210> SEQ ID NO 39
<211> LENGTH: 14
<212> TYPE: PRT
<213> ORGANISM: homo sapiens
<220> FEATURE:
<223> OTHER INFORMATION: interleukin-2 peptide

<400> SEQUENCE: 39

Met Gln Leu Leu Ser Cys Ile Ala Leu Ile Leu Ala Leu Val
1 5 10

<210> SEQ ID NO 40
<211> LENGTH: 15
<212> TYPE: PRT
<213> ORGANISM: homo sapiens
<220> FEATURE:
<223> OTHER INFORMATION: trypsinogen-2 peptide

<400> SEQUENCE: 40

Met Asn Leu Leu Leu Ile Leu Thr Phe Val Ala Ala Ala Val Ala
1 5 10 15

<210> SEQ ID NO 41
<211> LENGTH: 17
<212> TYPE: PRT
<213> ORGANISM: homo sapiens
<220> FEATURE:
<223> OTHER INFORMATION: BM40 peptide

<400> SEQUENCE: 41

Met Arg Ala Trp Ile Phe Phe Leu Leu Cys Leu Ala Gly Arg Ala Leu
1 5 10 15

Ala

<210> SEQ ID NO 42
<211> LENGTH: 21
<212> TYPE: PRT
<213> ORGANISM: artificial
<220> FEATURE:
<223> OTHER INFORMATION: Secrecon

<400> SEQUENCE: 42

Met Trp Trp Arg Leu Trp Trp Leu Leu Leu Leu Leu Leu Leu Leu Trp
1 5 10 15

Pro Met Val Trp Ala
20

<210> SEQ ID NO 43
<211> LENGTH: 20
<212> TYPE: PRT
<213> ORGANISM: artificial
<220> FEATURE:
<223> OTHER INFORMATION: Mouse IgKVIII

<400> SEQUENCE: 43

Met Glu Thr Asp Thr Leu Leu Leu Trp Val Leu Leu Leu Trp Val Pro
1 5 10 15

Gly Ser Thr Gly
20

<210> SEQ ID NO 44
<211> LENGTH: 22
<212> TYPE: PRT
<213> ORGANISM: artificial
<220> FEATURE:

<223> OTHER INFORMATION: Human IgKVIII

<400> SEQUENCE: 44

Met Asp Met Arg Val Pro Ala Gln Leu Leu Gly Leu Leu Leu Leu Trp
1 5 10 15

Leu Arg Gly Ala Arg Cys
20

<210> SEQ ID NO 45
<211> LENGTH: 16
<212> TYPE: PRT
<213> ORGANISM: artificial
<220> FEATURE:
<223> OTHER INFORMATION: CD33

<400> SEQUENCE: 45

Met Pro Leu Leu Leu Leu Leu Pro Leu Leu Trp Ala Gly Ala Leu Ala
1 5 10 15

<210> SEQ ID NO 46
<211> LENGTH: 23
<212> TYPE: PRT
<213> ORGANISM: artificial
<220> FEATURE:
<223> OTHER INFORMATION: tPA

<400> SEQUENCE: 46

Met Asp Ala Met Lys Arg Gly Leu Cys Cys Val Leu Leu Leu Cys Gly
1 5 10 15

Ala Val Phe Val Ser Pro Ser
20

<210> SEQ ID NO 47
<211> LENGTH: 16
<212> TYPE: PRT
<213> ORGANISM: artificial
<220> FEATURE:
<223> OTHER INFORMATION: Consensus

<400> SEQUENCE: 47

Met Leu Leu Leu Leu Leu Leu Leu Leu Leu Leu Ala Leu Ala Leu Ala
1 5 10 15

<210> SEQ ID NO 48
<211> LENGTH: 17
<212> TYPE: PRT
<213> ORGANISM: artificial
<220> FEATURE:
<223> OTHER INFORMATION: Native

<400> SEQUENCE: 48

Met Leu Leu Leu Leu Leu Leu Leu Gly Leu Arg Leu Gln Leu Ser Leu
1 5 10 15

Gly

<210> SEQ ID NO 49
<211> LENGTH: 16
<212> TYPE: PRT
<213> ORGANISM: artificial
<220> FEATURE:
<223> OTHER INFORMATION: Penetratin

<400> SEQUENCE: 49

Arg Gln Ile Lys Ile Trp Phe Gln Asn Arg Arg Met Lys Trp Lys Lys
1 5 10 15

<210> SEQ ID NO 50
<211> LENGTH: 11
<212> TYPE: PRT
<213> ORGANISM: artificial
<220> FEATURE:
<223> OTHER INFORMATION: TAT

<400> SEQUENCE: 50

Tyr Gly Arg Lys Lys Arg Arg Gln Arg Arg Arg
1               5                   10

<210> SEQ ID NO 51
<211> LENGTH: 18
<212> TYPE: PRT
<213> ORGANISM: artificial
<220> FEATURE:
<223> OTHER INFORMATION: SynB1

<400> SEQUENCE: 51

Arg Gly Gly Arg Leu Ser Tyr Ser Arg Arg Arg Phe Ser Thr Ser Thr
1               5                   10                  15

Gly Arg

<210> SEQ ID NO 52
<211> LENGTH: 10
<212> TYPE: PRT
<213> ORGANISM: artificial
<220> FEATURE:
<223> OTHER INFORMATION: SynB3

<400> SEQUENCE: 52

Arg Arg Leu Ser Tyr Ser Arg Arg Arg Phe
1               5                   10

<210> SEQ ID NO 53
<211> LENGTH: 12
<212> TYPE: PRT
<213> ORGANISM: artificial
<220> FEATURE:
<223> OTHER INFORMATION: PTD-4

<400> SEQUENCE: 53

Pro Ile Arg Arg Arg Lys Lys Leu Arg Arg Leu Lys
1               5                   10

<210> SEQ ID NO 54
<211> LENGTH: 12
<212> TYPE: PRT
<213> ORGANISM: artificial
<220> FEATURE:
<223> OTHER INFORMATION: PTD-5

<400> SEQUENCE: 54

Arg Arg Gln Arg Arg Thr Ser Lys Leu Met Lys Arg
1               5                   10

<210> SEQ ID NO 55
<211> LENGTH: 15
<212> TYPE: PRT
<213> ORGANISM: artificial
<220> FEATURE:
<223> OTHER INFORMATION: FHV Coat

<400> SEQUENCE: 55

Arg Arg Arg Arg Asn Arg Thr Arg Arg Asn Arg Arg Arg Val Arg 1 5 10 15

<210> SEQ ID NO 56
<211> LENGTH: 19
<212> TYPE: PRT
<213> ORGANISM: artificial
<220> FEATURE:
<223> OTHER INFORMATION: BMV Gag

<400> SEQUENCE: 56

Lys Met Thr Arg Ala Gln Arg Arg Ala Ala Ala Arg Arg Asn Arg Trp
1 5 10 15

Thr Ala Arg

<210> SEQ ID NO 57
<211> LENGTH: 13
<212> TYPE: PRT
<213> ORGANISM: artificial
<220> FEATURE:
<223> OTHER INFORMATION: HTLV-II Rex

<400> SEQUENCE: 57

Thr Arg Arg Gln Arg Thr Arg Arg Ala Arg Arg Asn Arg
1 5 10

<210> SEQ ID NO 58
<211> LENGTH: 13
<212> TYPE: PRT
<213> ORGANISM: artificial
<220> FEATURE:
<223> OTHER INFORMATION: D-Tat

<400> SEQUENCE: 58

Gly Arg Lys Lys Arg Arg Gln Arg Arg Arg Pro Pro Gln
1 5 10

<210> SEQ ID NO 59
<211> LENGTH: 13
<212> TYPE: PRT
<213> ORGANISM: artificial
<220> FEATURE:
<223> OTHER INFORMATION: R9-Tat

<400> SEQUENCE: 59

Gly Arg Arg Arg Arg Arg Arg Arg Arg Arg Pro Pro Gln
1 5 10

<210> SEQ ID NO 60
<211> LENGTH: 27
<212> TYPE: PRT
<213> ORGANISM: artificial
<220> FEATURE:
<223> OTHER INFORMATION: Transportan

<400> SEQUENCE: 60

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 61
<211> LENGTH: 17
<212> TYPE: PRT
<213> ORGANISM: artificial
<220> FEATURE:
<223> OTHER INFORMATION: MAP

<400> SEQUENCE: 61

Lys Leu Ala Leu Lys Leu Ala Leu Lys Leu Ala Leu Ala Leu Lys Leu
1               5                   10                  15

Ala

<210> SEQ ID NO 62
<211> LENGTH: 27
<212> TYPE: PRT
<213> ORGANISM: artificial
<220> FEATURE:
<223> OTHER INFORMATION: SBP

<400> SEQUENCE: 62

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 63
<211> LENGTH: 27
<212> TYPE: PRT
<213> ORGANISM: artificial
<220> FEATURE:
<223> OTHER INFORMATION: FBP

<400> SEQUENCE: 63

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 64
<211> LENGTH: 27
<212> TYPE: PRT
<213> ORGANISM: artificial
<220> FEATURE:
<223> OTHER INFORMATION: MPG ac

<400> SEQUENCE: 64

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 65
<211> LENGTH: 27
<212> TYPE: PRT
<213> ORGANISM: artificial
<220> FEATURE:
<223> OTHER INFORMATION: MPG(ΔNLS)

<400> SEQUENCE: 65

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 66
<211> LENGTH: 21
<212> TYPE: PRT
<213> ORGANISM: artificial
<220> FEATURE:
<223> OTHER INFORMATION: Pep-1

<400> SEQUENCE: 66

Lys Glu Thr Trp Trp Glu Thr Trp Trp Thr Glu Trp Ser Gln Pro Lys
1 5 10 15

Lys Lys Arg Lys Val
20

<210> SEQ ID NO 67
<211> LENGTH: 21
<212> TYPE: PRT
<213> ORGANISM: artificial
<220> FEATURE:
<223> OTHER INFORMATION: Pep-2

<400> SEQUENCE: 67

Lys Glu Thr Trp Phe Glu Thr Trp Phe Thr Glu Trp Ser Gln Pro Lys
1 5 10 15

Lys Lys Arg Lys Val
20

<210> SEQ ID NO 68
<211> LENGTH: 18
<212> TYPE: PRT
<213> ORGANISM: artificial
<220> FEATURE:
<223> OTHER INFORMATION: ApoE p1

<400> SEQUENCE: 68

Leu Arg Lys Leu Arg Lys Arg Leu Leu Leu Arg Lys Leu Arg Lys Arg
1 5 10 15

Leu Leu

<210> SEQ ID NO 69
<211> LENGTH: 30
<212> TYPE: PRT
<213> ORGANISM: artificial
<220> FEATURE:
<223> OTHER INFORMATION: ApoE p2

<400> SEQUENCE: 69

Leu Arg Lys Leu Arg Lys Arg Leu Leu Arg Asp Ala Asp Asp Leu Leu
1 5 10 15

Arg Lys Leu Arg Lys Arg Leu Leu Arg Asp Ala Asp Asp Leu
20 25 30

<210> SEQ ID NO 70
<211> LENGTH: 17
<212> TYPE: PRT
<213> ORGANISM: artificial
<220> FEATURE:
<223> OTHER INFORMATION: ApoE p3

<400> SEQUENCE: 70

Leu Arg Val Arg Leu Ala Ser His Leu Arg Lys Leu Arg Lys Arg Leu
1 5 10 15

Leu

<210> SEQ ID NO 71
<211> LENGTH: 20
<212> TYPE: PRT
<213> ORGANISM: artificial
<220> FEATURE:
<223> OTHER INFORMATION: ApoE p4

<400> SEQUENCE: 71

Thr Glu Glu Leu Arg Val Arg Leu Ala Ser His Leu Arg Lys Leu Arg
1 5 10 15

Lys Arg Leu Leu
20

<210> SEQ ID NO 72
<211> LENGTH: 34
<212> TYPE: PRT
<213> ORGANISM: artificial
<220> FEATURE:
<223> OTHER INFORMATION: ApoE p5

<400> SEQUENCE: 72

Leu Arg Val Arg Leu Ala Ser His Leu Arg Lys Leu Arg Lys Arg Leu
1 5 10 15

Leu Leu Arg Val Arg Leu Ala Ser His Leu Arg Lys Leu Arg Lys Arg
20 25 30

Leu Leu

<210> SEQ ID NO 73
<211> LENGTH: 40
<212> TYPE: PRT
<213> ORGANISM: artificial
<220> FEATURE:
<223> OTHER INFORMATION: ApoE p6

<400> SEQUENCE: 73

Thr Glu Glu Leu Arg Val Arg Leu Ala Ser His Leu Arg Lys Leu Arg
1 5 10 15

Lys Arg Leu Leu Thr Glu Glu Leu Arg Val Arg Leu Ala Ser His Leu
20 25 30

Arg Lys Leu Arg Lys Arg Leu Leu
35 40

<210> SEQ ID NO 74
<211> LENGTH: 10
<212> TYPE: PRT
<213> ORGANISM: artificial
<220> FEATURE:
<223> OTHER INFORMATION: Myc Peptide

<400> SEQUENCE: 74

Glu Gln Lys Leu Ile Ser Glu Glu Asp Leu
1 5 10

<210> SEQ ID NO 75
<211> LENGTH: 39
<212> TYPE: PRT
<213> ORGANISM: artificial
<220> FEATURE:
<223> OTHER INFORMATION: ApoB Peptide

<400> SEQUENCE: 75

Ser Ser Val Ile Asp Ala Leu Gln Tyr Lys Leu Glu Gly Thr Thr Arg
1 5 10 15

Leu Thr Arg Lys Arg Gly Leu Lys Leu Ala Thr Ala Leu Ser Leu Ser
20 25 30

Asn Lys Phe Val Glu Gly Ser
35

<210> SEQ ID NO 76

<211> LENGTH: 18242
<212> TYPE: DNA
<213> ORGANISM: homo sapiens
<220> FEATURE:
<223> OTHER INFORMATION: CX3CR1_loci

<400> SEQUENCE: 76
ggggcgggcc gtgcttacca ggccgtggac ttaaaccagg atgagagaac ccctggaggc 60
gtttaagttg gcagacttgg atttcaggaa gagctctctg gcttctgggt ggagaatggc 120
cagtggggta agtggtgaga ggaaagacag agaacggaga aggttagatg ggcttgggaa 180
attatccagg ccctggatgg aggtagagat gtgtgctcat gaacacggag gggattactg 240
atgtggggtg gatgagactg tcgtcaagag tgtgggacag gaagagaggg agagtcttgg 300
ccagatccaa gaaaggagcc ctcagaagag gaggggagtc agaggcaagg aaggggctga 360
ggcagccagc ccagctgagt ggaccccagg agaggtatca aggggtggtg tggggtgggg 420
aggggccagt gtcagaaagt ggatggggag cggcctgact ctgcttttgt cctgtggcct 480
tctggccaaa ggcagggaaa ggtggccaaa cactgagacc aagaacaaag aaagaaaact 540
gctggtggac ttcttccacc atgagcaggc caccaagccc gcagcactgc actgcagccc 600
ccagctctgt cctggggttg ggggaggtga ggaggggcaa ggtggggagc acacagagca 660
cccgctgtcc tcggaacacc acagcgacta gaggtaaggg agcaccggat gtggctggga 720
tgtgggcagc aaggggccag aggggccttg aaggggtcac agaccattta atgaaggtgt 780
attgaaggcc accatgggcc aggccctagt tagggatgga tcagaattat atagcatatg 840
ccaggggtca ggcaggtaat gaagtgatcg gaaggtgatg aggcagtggc agttgagatt 900
cacgttgcag tcgccccaag ctggccaggc cagggagcag aagcatggct ggatgccgga 960
gcccaccagg ctccccactg cagggcaaga gtggcagggg gagagactgt gaaaggagca 1020
taggccaggt cctgggtgaa agctgtgtcc tcagccttga ctgatgggta tagggagcca 1080
ctaaatgcct tggggcagag aggtgaggaa aaaaatattt accgagcatc tacaaggtgc 1140
aaggtactca ctagatgcct tcagtaccaa agcttctcaa acttagtatg catatcactc 1200
ttctaagaat ttcattaaaa tgcagattct aattcagcag atatagggca gggcttgagg 1260
tgctgtcttt aataagctcc cagtgcctgg gactgcactt tgaggagaag agctgtgtgt 1320
gccccagtgt ggtccagtga gtactctggg ctccctctcg tgggcaggga agctgagggc 1380
cccatgagct ctcccagctt cctgaaggct ccccattaat gagagctgac tgtgctgtgc 1440
tttgctgact gcagggcctg ctccctgccc cccacctcca ggttggggta agtggcacct 1500
ctctccctcc agctccgcag tcttccctga ggtttagatc ttccaggttt ataaagtcag 1560
gccctcctgt tggcagctgg cctccaccct ggagtatctg agcttgcctg tggcagcatc 1620
taaagatagt ctcccttaca ggaaacaaga tactattggc taactctgca aataaaatgc 1680
tcttagaggg aaggaaaggg aaatactcgt ctctggtaaa gtctgagcag gacagggtgg 1740
ctgactggca gatccagagg ttcccttggc agtccacgcc aggtaggtgc acaggactag 1800
ttgggtacct gtgggtgggg tggagcagtg gacagctaat aggttaataa tgcctgtttg 1860
cttacgtgca gacaatggaa accattttcc tggggatgtt gtagcctaaa tatgtccaag 1920
gggatggaag agtgggaggc aaggggtgat cagatcattt ataatacact caacctggtg 1980
gaatagtatt agaagcatta gtaattacat tttagagaca tggagaaaag ctcatgattt 2040
taaactaact gaaaaaagca tgaaaaattg catctggatg ctgttgagga attattgcta 2100
attttttgag atgagaaatt gtattaaagt ctttttcaaa aaagagtcct taacttttag 2160

-continued

```
agatgcacac aagtgtttat gggtgaaatt aaataattca gtagagacat taagtgggaa   2220
atagaggaaa tattgaccat gggttgctaa tagttgaagc caggtgttgg gtataaggag   2280
gttctcgctg cttttatttg aaaagttgct ttttatttga aaatttaata ataaagagtt   2340
tttaaatttg tatctgtatt ttaatataaa tataaatgca cttaatataa atataaaata   2400
tgtataacat ttagatagag aaaagctaaa agattactgt ggttgattct aggaaactgc   2460
attgcagata gtttcatggg tttttttttc ctttttcttc cactttttgt accatctatg   2520
ggtttttgtt tgttttttgt tttttgggtt ttctttcttg tttgtgtttt gtttttttgag   2580
acggagtttt gctcttgttg cctaagctgg agtgcaatgg cacagtctcg gctcactgca   2640
acctctgcct cctgggttca agtgattctc ctgcctcagc ctcccaagta gctgggatta   2700
taggcatgta ccaccgcccg gctaattttg tatttttagt agaggcgggg tttctccatt   2760
aataaattcc tggcacaaat ttagtgttca attttgatat atgttgttat aaccattgtg   2820
aggatactca ggctcaggtt tgtgtgggtg gaaaacatgg tcttcagaaa gaaattatga   2880
gtgcaagaca ggaggaaatc catcagaggc cccagctgag gactgaccac ggcttgttat   2940
ttctcttgcc ttgcctctgg caatcacagc ctcacagagc ctgcaatcct tgctttgtga   3000
gtttatagct cagtccagag aatggctaag aaagtttagg attctttcaa cacccactcc   3060
acaaaaaaaa aaaaaaaaaa gaaaagaaaa aaaaattaat ttttgaaata cttgaggtag   3120
aaaacttgag gcagaaaaaa attgagccaa aaaaaaagga aaattgaacc acgtgaaagc   3180
aggcaagaaa gcttgcattg ctcagggcat cccaggccca gagggcgctt tggagggagc   3240
tgggtttcct gagaggaggc agggtgggtg acggacctgt gctggagagc cttgaggacc   3300
actgtgggtt gggaatgggg gcagtggatt ggggttcaaa acccctggga atgagaaatg   3360
ggctcaggaa ggctagggtg gattctttca tcttcctctt tgcttggctt tattttcaca   3420
aaggaaggca gggcaggaaa tagtctcagc ccaacttcag tgtggttctt cttagtgctc   3480
aggcttacct ggcacttgcc acacctctgg gatgggagca cctactatcc atcagccacg   3540
tgccagtctc cacaaagtct gctcctgaac cctgctcctc agctggcccc acttcacaga   3600
tggggacata ggcagcttgg ctttggaatg aaggaatgaa gtcaggaatg aagtcctggc   3660
tctgcacttg gtgactgtgc actgggcttg ctaagtctgt ttcctgcttt taaaatggag   3720
attgtccatc agcctttgaa gccatgtaat gggtatgtgt caactttctg caaggattaa   3780
aggcatggta taggaagtcc caaacacact gcctgaccca tctttgatgc tcaagaaacg   3840
atatatgttg ttgtcatgag gaaactgagc ctcagaaagt ttggatacct gaaaaacact   3900
gactactatt gaatgaggtt gtgaagaatc cagagctgta ggggcaggaa agcaaagaac   3960
gtattagagc tgacccagtc aggacgatcg tctatcccct tcctcacccc accccatccc   4020
aggaggaagc ctgcccggcc ctaggcagct atggcacagt ggcaatgtca ggtatggttc   4080
tccctagcca gagaccctag cctcaaaaaa cctccttctt gggatccagg catccaactg   4140
ctcctcccca gccccagcct ctgacccagt atcctgagtc cagagacgtt tggaaccagc   4200
acctgtaatg gaggagctga acaaggaggg gaacttctgc tgctccacag caggtcacgg   4260
tcataggagg gagtggaacc agaatggcag aatccagatc ttggctgcct ttcccaagga   4320
cttgttctga ttcctagcag cacagcccag gcattccgag aagttgggct ctctggcatc   4380
actcactctg cccagaagag ccaggggaaa gttggggctt ctagctgaac cttgatccca   4440
cctgccctct tgaggggctc agaatctgct ggctgcttca caggtgggat tctcacggca   4500
```

cgctggccac agctgatgct tcgacccccct catcttgttt ggccaaagtg cagcttttta 4560
gcttgtgagt aaggaagaaa agctgtatca tatgtcttta aacatcttcc tagaccacct 4620
ttgttttccc cttaaagtgt gcttaaggag aaaatggaaa gtctcttttc agtgtgttgt 4680
attttgttta ttgcaaaata caacacactg aaagaacaat gtctgggtta gcaaagtatt 4740
agatttaatt tcccacatta ctaccatcca ggctgagaaa gagaacccca gaagcctctc 4800
tcatgtccct tcctgaccac agcctcttcc tctcccacaa agaaccacaa gtctgacttc 4860
tatggtgatc acttccttgc ttttccctat agtttgactg aatctaaata tcatccctaa 4920
acaatatagc ttagctttgc ctatttttga tcttcatatt tggattcata ctttttggtt 4980
tggctcaaga ctaaactttt aaaatgcatc cacgttgtag gagatgtaca tgcacaaaaa 5040
ttttcacggc aacattgtcc aaactagcaa caaactgaaa gccacctatg tgtgcattag 5100
cagtagaaat ggcaataaat catggactag tcacacagtg gaatcctacg cagcaaggag 5160
aattagcagt ctacagccaa accaacagca tgggtgagat gcttccagaa atactgagat 5220
gaatttagag ataaaggcac aattggtcca tatctacagg gcacttaatc cagtgcatct 5280
ccactagaca aaatttgtat ttccatgagc aagagtcatt tgcactgcta tctgctataa 5340
cctacggtgc tgtaaaatta gctcaggcaa taaaaggggg aggtagcccc aaagagtatg 5400
ccagaaagga ctcccagtaa tcttcagtgt gtgtctattt caaagtcttt catcattttt 5460
ccttgtagtt acttagtgtg gaatttcaga cccctctcta tgtccctctt ctccctttttc 5520
agccttggct ttctctgcat ccttccccga agccctgcac tcagcctaaa ctgactttcc 5580
tgaacactct gggagcatgt gggctcctcc caactccacc atcttcactg ccttctgttc 5640
ctatttccct ctgcctggcc ttggccccag gaaaccttcc tatgctcaga ccctctgtgc 5700
ctttgtcttc aaagcccacc cactattcac tgccacctcc atcttggtca acctggaaga 5760
ctttccccat ccttaaaaca tcagctcaaa cggcagattt tttttttttt ttttgtgata 5820
tcctcttgat caccctcccc cagtttttaa ggagacagat atagaggttc aatccttggg 5880
cttcccatga cttttcttat attctgttac tgagcaataa taaacacttc taggaactgt 5940
atcttaaaca cttttgcctc tacagaatct agcacagtgc ctagtattgg tgaaatataa 6000
ttaacaaagt cttctttcaa cacagagatt ctctccacaa aaggagtaga gaaagaacag 6060
ttttattatg gaataagcag taaaccaaaa tatgcagagc attataggcc atctactaag 6120
aggttgcaag aacagaaaga aatctccccc ttttgtatag ccaagtagat acaacctgtt 6180
acatacatgt tatcaaggca aacaataact gttcctcaag taagaggtct tgccagcacc 6240
gtttgccgta catggttcac tctaaattta cctggtaatt agggtaacca cttgtgttag 6300
ctaactggct ctacccagag gaaaatcaaa tttatcttta agacaagggg taattttgca 6360
gcactgagca aggctcttca gttaggctca taccttccca cagaaactaa gagatagaag 6420
cactatctcc cttaggtttg tttacatttc aaagagatga cgcccaggtc cttgggaaag 6480
actagcttag ctcataaagc tgacaaaaag cctatctagt ttcaaaagga tttacacatg 6540
ttcaaagaga ggagaaagta tgtaaaagtt ttctaggtgg gcacggtggc tcacacctgt 6600
attcccagca ctttgagagg ctgaggcggg tggatcacct gaagtcagga atttgagatc 6660
agcctggcca acatggtgaa accttgtctc tactaaaaat acaaaaaatta gctgggcatg 6720
gtggtgggcg cctgtaatcc cagctacttg ggaggctgag gcaggagaat cacttgaacc 6780
caggaggtgg aggtggcagt gagccaagat ggcaccattg cactccagcc tgggcgatga 6840
gagtgaaact ccatgtcaaa aaaaaaaaaa gttttctaaa gtaaatgctc tgagaaaaaa 6900

```
acagaaggtg aggagatctc tgtccttatt tttaacaaga ataattaaat gtttttattt   6960
ttaatttcta cttagactag aatatggtac agatgctcaa aaatattgac ttaattaata   7020
attaaacaat taacaagtct atctctttcc taattattaa aaaaattatg aagtatttcc   7080
cttcaaaatt tcacagttta ctttgacata aataaataaa taccataaag tattttgaag   7140
aggaaaggga agggtggggc ttcaaacaca aaataatggc aggttttgta aaggggcaat   7200
tcactaaacc caataggatt ctcctgttgc tatttttttt tttttttttt ttttggtggt   7260
ggttggaggg aagggttggg tgtgcatttg gcctgtgtga aaaactggtg ggtagacaat   7320
gccatgctgt tctagatggg ctcattgcta taggaataga tagtcactga atttacttgc   7380
ataggggatg gggtataaaa tgtttcctta tagctcctta acatggaatt cagcacccct   7440
ctccccatca gccttagctc tctctgaatc ccaagggata tgtgttataa aaatagctgc   7500
catcataaat gagaaaacca tcaggacctg gtaaaacttg gcttcccaaa cagtcagggg   7560
tctgggcatg gcagccgact gagaaccttt ctatctagta caaggtaaac aagatttgcc   7620
aagacttgat caactgatcc agctccctat ctccaaacag aacctcatct gaatgctcac   7680
aggctgtgcc ccagaagtgt agaagtgtca tgttccctgg gcaggctgct gggcagcctc   7740
tctgttgaca atagaccaca cttttgctga cctaggactc atgttgctct ttaagactgc   7800
ttccttggcc aggcatgatg gctcacacct gtaatcctgg cactttgaga ggcccaggca   7860
ggaggatctc ttgaggccag atgttcaaga ccagcctggt caacatagta agaccccata   7920
tctaccaaaa atagctgggc atggtggtgc acacctatac tcccagctac ttaggagact   7980
gaggtgggag gattgctaca tcccaggagt tcaaggctgt agtgagctat gatcatgcca   8040
ctgcactcca gcctgggcaa cagagcgaga tcctgtctca aacaaacagt ttccttctgt   8100
ttgattcttg ctgaaaaatt gagcatgcca gagctagcaa ggctcttaga ggtggtctgg   8160
tccaatgctt taatttcata catcaagaaa ctgaagcaga gcagagtgac ctgcccaggg   8220
tctctcagcc attcatgctc agaaatgtat gggctcctgt gaaacatgtg gctcttaaaa   8280
gcactatcat atatttgaag gcagaaaata ggctaaacct tcagccttca gacttttcct   8340
ctccagagaa aatgacccca gtttcctcac tatggttgct gggagctaga ttcctgggga   8400
tctggcagtg tggaccacct agtggtggct agaggagcaa ataatatccc gcattccatt   8460
ttccactcac caatccctga ggggcagcct gctgggttat gagcccacag ggggagaacc   8520
ccaacgaatt cagagatgca tcatggacca gtttctctta aggggcctgg gtctactatt   8580
ttcagttcta cttcgagaga agtggcctgc aatatcctgc agatttcccc tccagggaga   8640
aaagcattgt gcggtgcaag gagcacaggc tttgtggaaa gaggcatctg ggggttgagat   8700
cctggctctt ttgcttcctt gaacaagtta accaaatctc tgggcctctg ctggttaatt   8760
tataccatgg ggatcatcat ttctccagtg gggttgtgaa gagaatgtgg tgggatcttg   8820
tgtgtggagc atgacactta gcaggcatcc gggaatggca gcctcctccc tttctaaact   8880
ggggctttct gagggtgact tcagattcca caatgtcaac agcacaatgg catcctcata   8940
aggaaagttt gggttggggc tcctcaagca attctctact ctcatttggt acaaagaaaa   9000
aaattaagcc tcacaatttt cttggcacca gactgaacct caaacccagt cttcactttt   9060
actaaaaagc cataaacaga gaccaggagg gtaaaaacta ccagaagata cactggattt   9120
agaaaacagt aagctggatg tgaagccaaa agagagggag aaagcaacat aaaagaatgt   9180
cagattgaag aagaaatgga ttctggccac ctaaagaaga agggaagtat agaaaaggga   9240
```

-continued

```
agctgattgg aaacaatggg taatgatgag tgtccctccc ctaaaaagtt aaaaaataaa   9300
tgagcaggca tgagaaaagg aagtaggcca gaggaagtag accaggatca gccacggatg   9360
tgagtgggga attttacaaa tttctacttg ggtgtgaaac atgtgtacac tcaaagctct   9420
gtctaggttc accgaaactc tcccagctca aggccattta gtaaaacctt ggcttaactg   9480
aatagtgggt aaggaggcct gaggatggcc cagagaaggt ttaaattctt actggctgct   9540
gcactaagtt gtaaagtgca gccttagttg atgatgcctt tattagtgca acatcccaga   9600
atgcatgcgt cttacaaccc ttgtggatat gaaacccagc tgggtagaca ctgcaaagtc   9660
ttctcatttg attcttccac ttggtttcta gtgtccctca gggacaaagg aaagccatgg   9720
tccagtctaa gatgaaaacc aattagacct ctggcaggcc tttgaccacc ctgagggcca   9780
cccccaaggc acggccacac tcgcatctgc tgccaggagg ccctatctta ggctcagctc   9840
ccaaaccttg aacatcttgg aggatccaca aataggaggt acactcagct caggctcagt   9900
cttccttaaa aagcgccttg ctaaagctat caagttcact ggaatacttc tgcgaaggac   9960
acagcttcag cgatgtcaga tttttatgt aaatggtgcc ttcacatgct ctggggcatt  10020
tggctaccaa gggcggtttg aactagctcc agcacacaga atacaagtct cttcagaacc  10080
aggcaaaacc ctatgttgcc caatgactcc tgctgtttct tgagatttgc acagaagaca  10140
gagctgcaat tacccacgct gatatctatt tcatgaccac atatgttcaa aagccacatg  10200
tgagaggtat ggttgaaatg agaggttgtg tttgccaagt tgtcttctga ctgtggagag  10260
ctggtgagcc tcttctcatc tcctggggct ccatattata gagctgacga atctcttttc  10320
ttgctccttg aagtctttca ttcacttatt tattaattca tttaacacat caggcaccta  10380
ctaacttctc agagttcaag gcttcctagc ctatgatcag aaaggacacc tgtgtgctca  10440
tgagcacccc tgggatcagg gtgactgata gggtgctgtc atcactacta gatgaaactc  10500
tttggaacaa aggtctagga tataatattt atccttctgc aaatattcat atggcattcg  10560
ctgtgtacca ggccttctgt tgaacattgg cctgcagagc tgaagaggac gtgggtcttc  10620
tcttaggaac tcctagtctt gggaaaaagg aatggggaag ggctgtaatg tgaagttaaa  10680
aaaaagtgct gaggccgaac acatctgggc cctcactgca gccctattgc acacacactg  10740
catcacctcg aacaagttat tcaccctctc tgaattcatc tatttgccca taaaaataga  10800
gatgatcctt ttatatgttg gctaccactt attatgtgca gcatgcttgt tattgtacta  10860
agttactcat tttttagttt ttcatataac tcatattttt gttgattttt attttaaaat  10920
tccaaacgaa ttaattaaac tattttccaa aatacgtagt atgtgtacat ggtaaaaaac  10980
atttccaaaa gtttaccata aaaactgtct cctttcccat atcctcaatc cttcagaatc  11040
cctctccagg gataattacc accaccagtg tattccttaa gagatattta aactttatac  11100
aaaatacgca cacatcattc ttttccacaa atgacagcat actatgtaca tggtacctca  11160
cctagctttt ttcacttacc agtatatctt agagattgtt gcatgacaga atatacagat  11220
ctgcctgttt ttgttgtttt tcccaagttt ccaagagcta gaaactgttt ggtttttaag  11280
cagctgcttg gtattccatt aattggactt atcgtgcttt gatctgtccc tagtgatgga  11340
cattggggtt gtttcccttc atttatattt gaagcttgtt gcagtgacag tgtacacact  11400
tgcttgagca tgtgtgtgtc tacgataaat cccaataagc aatttaaagt aatttaattc  11460
ttatgctctc aacaaaccta agaggttatt tttttagagg aggaagctaa ggctgttgtt  11520
ttgatgcctt tttaccactg gacttgggac tcaactgttt gatagtcatc gagtccttga  11580
ctcttctccc ctgccaggat ttggccccta agcccagggc ccgagtctcc tccatcttca  11640
```

agggagagtg ggaacagcac aggccttggc ctcagtcctg ctccccctgc ttctagctgt 11700
gggatgggcc aggtgcttca cccagctgtg cctcctgtga ggcacagtgt gtgcaaaatg 11760
gaaatgtgaa catgaagatc aaaaatgtcc ctcaatgacc agtgctgttc ctcagagtca 11820
cgtgggaact catagaaagc gatattggta ctgctctttc ctctgtagca tggtccagat 11880
ggctcatagc agggaccatg atatgctggg tgagcaccca ctgcatgcac ccactgtgcc 11940
agcactgaga gactcctgtg ggagccacag caattctagg gtcttcactg gggactctga 12000
gacagcaggg agctaggatg agggctgcag agtgttcgtc tgccctcact gagcagaccc 12060
cctggatggc agggagcagt cccaagccag atggatgccc ataaccagcc atttggctct 12120
caatacataa tatcaccacg tatcaggcaa aaccatcctg cccagagcat tatctgaatt 12180
tgcatcccat ctgcagaaga tacattcacc cacttcttcc attctgtctt aatcaaagtc 12240
tttatgtgaa ttttccccat tgagaagaca agccccttcc tggcttagac tgtacctgac 12300
tgatcttttc atgagctcct tgccaagcca gaccaccccc agcttatatg gagacttggt 12360
gcaaattaga gatgcccctg tgcacgtggc agccctgagc ccaagcaccc agtaaggcaa 12420
agggcctgat ttgggacccc tctgccactc caccaggcaa tcagttgctt atttctaact 12480
ttcccttcct tctccacatt tgtcccattc cttcctctca tcatgaatat ccccagaggc 12540
attcagcagt gcagtgaatt aaatatagaa cttttttttt tcagaattgc agaacggatt 12600
agatcaatat taatccaaac agagcaatga gcctgacagt ttagtaaaag ctcaataaag 12660
ggtggcttac ctcccccaaa ataatctgaa aagaaagcat gtcttatttc aggggggaaaa 12720
aaaaataaag tgacctttaa agaccaaatt cccaggatac ccagggtgga ggtggaacat 12780
gggagtccac aggcagcctg gatgtttcca aagatccaaa gggcttttgc ttcctcacat 12840
aatgcaggaa acaaattgaa catgtattaa gtgcttgctg tatgtgacac actgtgccag 12900
gtgctcccct taaaacagtt ctgtgggcag gcatgagaat gaatcccgat cttacagaca 12960
aggaatgtta ggctcagagg tttcaagctc acccatcact cagccagaga ggacagatgc 13020
aggattcaat ctcgggagtg cccgagtcca cagaagttcc tgtgctgaag gaccgaccac 13080
aggcacataa agagatgcga gacaattttt actggatttg gccacctctc gaggtcggct 13140
ttgccagctc ttctcactgg gggaagggga gggagaaagt agctagctcc agggtcccta 13200
acatagaacc accaaggact tgactatttt tactcataca gcagcttgtc tgggaagatc 13260
atgctctgtg acaagctgca ggcactaagt agcaatttct gtttcccaca tattagcttg 13320
agtcatataa aactgacatg gatgtggctc aaaaatagct gtatgtcagc cattttatac 13380
catttgactt aaatgttatt aattaacgtc acagccagag attattctct gagaaaaggg 13440
cattgtagcc tgaagcagag aaagcataca cgttccctgg ggttgagaac tcatcacagc 13500
ctgagacagc ttaggttgta aagccccggc ccacttatcc caggagagtc tgggtgagat 13560
gcaggcccca aagcagaggc tggaagcga gaagtgacac accctggctg ggtgggccct 13620
catcttggtg agacaccacc tgggtaaaac catcatggaa agggtgtagt ggggcgtgga 13680
aactccctcg gttaaagcgt gagctttgct gtaagttgtg gtaaggaggg aggcagtgac 13740
aaccaggagg cctgttttga gggtttctga gggacccatc tgtggtatca cgaggagacg 13800
cccagaggag ccgtgtgaaa gggctgcctc ccagccggct ctggagtgaa tgagcagcaa 13860
gtcctggctg cgaaaagaag gggagtgcag cctgcagaag tgtcttcttt tttcaattcc 13920
tgctcagaag gaaacaggag ataagaatag tggggaagtc caaaccaaag tgaactatag 13980

```
ggctggtaat cgtaggggga attagtcacc cggagactag cccagcagac taacggagcc  14040
ccatcctcca tcttgaatca gtcagcccct ctatgactgc agagtcctga atgatggcaa  14100
caccttctct tcacttagcg ttgtaggatg accaacagtc ctgatttgcc tgggactgag  14160
gggttcccaa tagatgggac tttcagggct aaaaccagga aagtcctggg cagcccaaaa  14220
caaggtagtc actctagagt gtatgactct gtctgatacc tgctaagaaa gagaaggact  14280
tgttgattat aaggagaaga ggaggtgaaa tggttctcaa aaaacaaaga tgagggcttc  14340
cgggtgctgt tctgcccaag gctctgggtc tgaggcttct ctctccaggc ctagcttcat  14400
ggaaaagtaa ggggccagag ggtggaaaag gtggaaacaa aggaagagga tggagaattg  14460
ctttggggaa gtttggactg gaagtgtgaa ttacagctgc acccccaatt caccccatct  14520
caccccccctc cccctcctgc tcatggttct ccctttctca tccacacatt ggtcaaacta  14580
gctagctttt ggagagattt tgggcagtaa aagtaaaaca gatctgtctc aagcttcaaa  14640
aagcctagag ctggctgggc gctgtggctc acgcctgtaa tcctagcatt ttgggaggct  14700
gaggcggaag gataatctga ggtcaggagt ttgagaccag cctggctaac atgatgaaac  14760
cccatctcta ctaaaaatac aaaaattagc caggcgtggt agtgcacgcc tataatccca  14820
gctatttggg aggctgaggc aggagaatcg cttgaacccc aggggacaga ggttgcagtg  14880
agctgagatc gcaccactgc actccagcct gggtgacaca gcgagactcc atttaaaaaa  14940
aaaaaaatgc ctagagccaa atgctcacag agccatttac tgcatggctt tgggcaagtc  15000
aaaggagtcc gcctctcctg tcagaagagt ctgttgcagt cttcatcaca agactgttgt  15060
ggggattaaa caagatggca agtgggaagt tgggaaatgt agtgtgcacc caaccaatat  15120
ttgtttcttc ctgcctgcct acatatgagg ccacacagaa ttccaacttt gtttctctga  15180
taactaacac agttacttgt ttttctttct gatccaggcc ttcaccatgg atcagttccc  15240
tgaatcagtg acagaaaact ttgagtacga tgatttggct gaggcctgtt atattgggga  15300
catcgtggtc tttgggactg tgttcctgtc catattctac tccgtcatct ttgccattgg  15360
cctggtggga aatttgttgg tagtgtttgc cctcaccaac agcaagaagc ccaagagtgt  15420
caccgacatt tacctcctga acctggcctt gtctgatctg ctgtttgtag ccactttgcc  15480
cttctggact cactatttga taaatgaaaa gggcctccac aatgccatgt gcaaattcac  15540
taccgccttc ttcttcatcg gcttttttgg aagcatattc ttcatcaccg tcatcagcat  15600
tgataggtac ctggccatcg tcctggccgc caactccatg aacaaccgga ccgtgcagca  15660
tggcgtcacc atcagcctag gcgtctgggc agcagccatt ttggtggcag caccccagtt  15720
catgttcaca aagcagaaag aaaatgaatg ccttggtgac taccccgagg tcctccagga  15780
aatctggccc gtgctccgca atgtggaaac aaattttctt ggcttcctac tccccctgct  15840
cattatgagt tattgctact tcagaatcat ccagacgctg ttttcctgca agaaccacaa  15900
gaaagccaaa gccattaaac tgatccttct ggtggtcatc gtgtttttcc tcttctggac  15960
accctacaac gttatgattt tcctggagac gcttaagctc tatgacttct ttcccagttg  16020
tgacatgagg aaggatctga ggctggccct cagtgtgact gagacggttg catttagcca  16080
ttgttgcctg aatcctctca tctatgcatt tgctggggag aagttcagaa gatacctttta  16140
ccacctgtat gggaaatgcc tggctgtcct gtgtgggcgc tcagtccacg ttgatttctc  16200
ctcatctgaa tcacaaagga gcaggcatgg aagtgttctg agcagcaatt ttacttacca  16260
cacgagtgat ggagatgcat tgctccttct ctgaagggaa tcccaaagcc ttgtgtctac  16320
agagaacctg gagttcctga acctgatgct gactagtgag gaaagatttt tgttgttatt  16380
```

tcttacaggc acaaaatgat ggacccaatg cacacaaaac aaccctagag tgttgttgag 16440
aattgtgctc aaaatttgaa gaatgaacaa attgaactct ttgaatgaca aagagtagac 16500
atttctctta ctgcaaatgt catcagaact ttttggtttg cagatgacaa aaattcaact 16560
cagactagtt tagttaaatg agggtggtga atattgttca tattgtggca caagcaaaag 16620
ggtgtctgag ccctcaaagt gaggggaaac cagggcctga gccaagctag aattccctct 16680
ctctgactct caaatctttt agtcattata gatcccccag actttacatg acacagcttt 16740
atcaccagag agggactgac acccatgttt ctctggcccc aagggcaaaa ttcccaggga 16800
agtgctctga taggccaagt ttgtatcagg tgcccatccc tggaaggtgc tgttatccat 16860
ggggaaggga tatataagat ggaagcttcc agtccaatct catggagaag cagaaataca 16920
tatttccaag aagttggatg ggtgggtact attctgatta cacaaaacaa atgccacaca 16980
tcacccttac catgtgcctg atccagcctc tcccctgatt acaccagcct cgtcttcatt 17040
aagccctctt ccatcatgtc cccaaacctg caagggctcc ccactgccta ctgcatcgag 17100
tcaaaactca aatgcttggc ttctcatacg tccaccatgg ggtcctacca atagattccc 17160
cattgcctcc tccttcccaa aggactccac ccatcctatc agcctgtctc ttccatatga 17220
cctcatgcat ctccacctgc tcccaggcca gtaagggaaa tagaaaaacc ctgcccccaa 17280
ataagaaggg atggattcca accccaactc cagtagcttg ggacaaatca agcttcagtt 17340
tcctggtctg tagaagaggg ataaggtacc tttcacatag agatcatcct ttccagcatg 17400
aggaactagc caccaactct tgcaggtctc aacccttttg tctgcctctt agacttctgc 17460
tttccacacc tggcactgct gtgctgtgcc caagttgtgg tgctgacaaa gcttggaaga 17520
gcctgcaggt gctgctgcgt ggcatagccc agacacagaa gaggctggtt cttacgatgg 17580
cacccagtga gcactcccaa gtctacagag tgatagcctt ccgtaaccca actctcctgg 17640
actgccttga atatcccctc ccagtcacct tgtggcaagc ccctgcccat ctgggaaaat 17700
accccatcat tcatgctact gccaacctgg ggagccaggg ctatgggagc agcttttttt 17760 tccccctag aaacgtttgg aacaatctaa aagtttaaag ctcgaaaaca attgtaataa 17820
tgctaaagaa aaagtcatcc aatctaacca catcaatatt gtcattcctg tattcacccg 17880
tccagacctt gttcacactc tcacatgttt agagttgcaa tcgtaatgta cagatggttt 17940
tataatctga tttgttttcc tcttaacgtt agaccacaaa tagtgctcgc tttctatgta 18000
gtttggtaat tatcatttta gaagactcta ccagactgtg tattcattga agtcagatgt 18060
ggtaactgtt aaattgctgt gtatctgata gctctttggc agtctatatg tttgtataat 18120
gaatgagaga ataagtcatg ttccttcaag atcatgtacc ccaatttact tgccattact 18180
caattgataa acatttaact tgtttccaat gtttagcaaa tacatatttt atagaacttc 18240
ca 18242

<210> SEQ ID NO 77
<211> LENGTH: 49
<212> TYPE: DNA
<213> ORGANISM: artificial
<220> FEATURE:
<223> OTHER INFORMATION: CX3CR1_T01

<400> SEQUENCE: 77
tctttcctct gtagcatggt ccagatggct catagcaggg accatgata 49

<210> SEQ ID NO 78

<211> LENGTH: 49
<212> TYPE: DNA
<213> ORGANISM: artificial
<220> FEATURE:
<223> OTHER INFORMATION: CX3CR1_T02

<400> SEQUENCE: 78
tatgctgggt gagcacccac tgcatgcacc cactgtgcca gcactgaga 49

<210> SEQ ID NO 79
<211> LENGTH: 49
<212> TYPE: DNA
<213> ORGANISM: artificial
<220> FEATURE:
<223> OTHER INFORMATION: CX3CR1_T03

<400> SEQUENCE: 79
tgctgggtga gcacccactg catgcaccca ctgtgccagc actgagaga 49

<210> SEQ ID NO 80
<211> LENGTH: 49
<212> TYPE: DNA
<213> ORGANISM: artificial
<220> FEATURE:
<223> OTHER INFORMATION: CX3CR1_T04

<400> SEQUENCE: 80
tgagagactc ctgtgggagc cacagcaatt ctagggtctt cactgggga 49

<210> SEQ ID NO 81
<211> LENGTH: 49
<212> TYPE: DNA
<213> ORGANISM: artificial
<220> FEATURE:
<223> OTHER INFORMATION: CX3CR1_T05

<400> SEQUENCE: 81
tcctgtggga gccacagcaa ttctagggtc ttcactgggg actctgaga 49

<210> SEQ ID NO 82
<211> LENGTH: 49
<212> TYPE: DNA
<213> ORGANISM: artificial
<220> FEATURE:
<223> OTHER INFORMATION: CX3CR1_T06

<400> SEQUENCE: 82
tgggagccac agcaattcta gggtcttcac tggggactct gagacagca 49

<210> SEQ ID NO 83
<211> LENGTH: 49
<212> TYPE: DNA
<213> ORGANISM: artificial
<220> FEATURE:
<223> OTHER INFORMATION: CX3CR1_T07

<400> SEQUENCE: 83
tcgtctgccc tcactgagca gaccccctgg atggcaggga gcagtccca 49

<210> SEQ ID NO 84
<211> LENGTH: 49
<212> TYPE: DNA
<213> ORGANISM: artificial
<220> FEATURE:
<223> OTHER INFORMATION: CX3CR1_T08

<400> SEQUENCE: 84
tgccctcact gagcagaccc cctggatggc agggagcagt cccaagcca 49

<210> SEQ ID NO 85
<211> LENGTH: 49
<212> TYPE: DNA
<213> ORGANISM: artificial
<220> FEATURE:
<223> OTHER INFORMATION: CX3CR1_T09

<400> SEQUENCE: 85
tggatggcag ggagcagtcc caagccagat ggatgcccat aaccagcca 49

<210> SEQ ID NO 86
<211> LENGTH: 49
<212> TYPE: DNA
<213> ORGANISM: artificial
<220> FEATURE:
<223> OTHER INFORMATION: CX3CR1_T10

<400> SEQUENCE: 86
tctcaataca taatatcacc acgtatcagg caaaaccatc ctgcccaga 49

<210> SEQ ID NO 87
<211> LENGTH: 49
<212> TYPE: DNA
<213> ORGANISM: artificial
<220> FEATURE:
<223> OTHER INFORMATION: CX3CR1_T11

<400> SEQUENCE: 87
tatcaggcaa aaccatcctg cccagagcat tatctgaatt tgcatccca 49

<210> SEQ ID NO 88
<211> LENGTH: 49
<212> TYPE: DNA
<213> ORGANISM: artificial
<220> FEATURE:
<223> OTHER INFORMATION: CX3CR1_T12

<400> SEQUENCE: 88
tcctgcccag agcattatct gaatttgcat cccatctgca gaagataca 49

<210> SEQ ID NO 89
<211> LENGTH: 49
<212> TYPE: DNA
<213> ORGANISM: artificial
<220> FEATURE:
<223> OTHER INFORMATION: CX3CR1_T13

<400> SEQUENCE: 89
tctgaatttg catcccatct gcagaagata cattcaccca cttcttcca 49

<210> SEQ ID NO 90
<211> LENGTH: 49
<212> TYPE: DNA
<213> ORGANISM: artificial
<220> FEATURE:
<223> OTHER INFORMATION: CX3CR1_T14

<400> SEQUENCE: 90
ttccattctg tcttaatcaa agtctttatg tgaattttcc ccattgaga 49

<210> SEQ ID NO 91
<211> LENGTH: 49
<212> TYPE: DNA

<213> ORGANISM: artificial
<220> FEATURE:
<223> OTHER INFORMATION: CX3CR1_T15

<400> SEQUENCE: 91
tccattctgt cttaatcaaa gtctttatgt gaattttccc cattgagaa 49

<210> SEQ ID NO 92
<211> LENGTH: 49
<212> TYPE: DNA
<213> ORGANISM: artificial
<220> FEATURE:
<223> OTHER INFORMATION: CX3CR1_T16

<400> SEQUENCE: 92
ttctgtctta atcaaagtct ttatgtgaat tttccccatt gagaagaca 49

<210> SEQ ID NO 93
<211> LENGTH: 49
<212> TYPE: DNA
<213> ORGANISM: artificial
<220> FEATURE:
<223> OTHER INFORMATION: CX3CR1_T17

<400> SEQUENCE: 93
tctgtcttaa tcaaagtctt tatgtgaatt ttccccattg agaagacaa 49

<210> SEQ ID NO 94
<211> LENGTH: 49
<212> TYPE: DNA
<213> ORGANISM: artificial
<220> FEATURE:
<223> OTHER INFORMATION: CX3CR1_T18

<400> SEQUENCE: 94
tttatgtgaa ttttccccat tgagaagaca agccccttcc tggcttaga 49

<210> SEQ ID NO 95
<211> LENGTH: 49
<212> TYPE: DNA
<213> ORGANISM: artificial
<220> FEATURE:
<223> OTHER INFORMATION: CX3CR1_T19

<400> SEQUENCE: 95
ttcctggctt agactgtacc tgactgatct tttcatgagc tccttgcca 49

<210> SEQ ID NO 96
<211> LENGTH: 49
<212> TYPE: DNA
<213> ORGANISM: artificial
<220> FEATURE:
<223> OTHER INFORMATION: CX3CR1_T20

<400> SEQUENCE: 96
tcctggctta gactgtacct gactgatctt ttcatgagct ccttgccaa 49

<210> SEQ ID NO 97
<211> LENGTH: 23
<212> TYPE: DNA
<213> ORGANISM: artificial
<220> FEATURE:
<223> OTHER INFORMATION: CX3CR1_gRNA1

<400> SEQUENCE: 97
gtacagtcta agccaggaag ggg 23

<210> SEQ ID NO 98
<211> LENGTH: 23
<212> TYPE: DNA
<213> ORGANISM: artificial
<220> FEATURE:
<223> OTHER INFORMATION: CX3CR1_gRNA2

<400> SEQUENCE: 98
gggagcagtc ccaagccaga tgg 23

<210> SEQ ID NO 99
<211> LENGTH: 23
<212> TYPE: DNA
<213> ORGANISM: artificial
<220> FEATURE:
<223> OTHER INFORMATION: CX3CR1_gRNA3

<400> SEQUENCE: 99
gactgctccc tgccatccag ggg 23

<210> SEQ ID NO 100
<211> LENGTH: 23
<212> TYPE: DNA
<213> ORGANISM: artificial
<220> FEATURE:
<223> OTHER INFORMATION: CX3CR1_gRNA4

<400> SEQUENCE: 100
gtgaatgtat cttctgcaga tgg 23

<210> SEQ ID NO 101
<211> LENGTH: 23
<212> TYPE: DNA
<213> ORGANISM: artificial
<220> FEATURE:
<223> OTHER INFORMATION: CX3CR1_gRNA5

<400> SEQUENCE: 101
gtctctcagt gctggcacag tgg 23

<210> SEQ ID NO 102
<211> LENGTH: 23
<212> TYPE: DNA
<213> ORGANISM: artificial
<220> FEATURE:
<223> OTHER INFORMATION: CX3CR1_gRNA6

<400> SEQUENCE: 102
gacagcaggg agctaggatg agg 23

<210> SEQ ID NO 103
<211> LENGTH: 23
<212> TYPE: DNA
<213> ORGANISM: artificial
<220> FEATURE:
<223> OTHER INFORMATION: CX3CR1_gRNA7

<400> SEQUENCE: 103
gaaggggctt gtcttctcaa tgg 23

<210> SEQ ID NO 104
<211> LENGTH: 23
<212> TYPE: DNA
<213> ORGANISM: artificial
<220> FEATURE:

<223> OTHER INFORMATION: CX3CR1_gRNA8

<400> SEQUENCE: 104
gcaaattcag ataatgctct ggg 23

<210> SEQ ID NO 105
<211> LENGTH: 23
<212> TYPE: DNA
<213> ORGANISM: artificial
<220> FEATURE:
<223> OTHER INFORMATION: CX3CR1_gRNA9

<400> SEQUENCE: 105
gagcagaccc cctggatggc agg 23

<210> SEQ ID NO 106
<211> LENGTH: 23
<212> TYPE: DNA
<213> ORGANISM: artificial
<220> FEATURE:
<223> OTHER INFORMATION: CX3CR1_gRNA10

<400> SEQUENCE: 106
gaactcatag aaagcgatat tgg 23

<210> SEQ ID NO 107
<211> LENGTH: 1599
<212> TYPE: DNA
<213> ORGANISM: homo sapiens
<220> FEATURE:
<223> OTHER INFORMATION: CD11b_loci

<400> SEQUENCE: 107
gtgcatgggg gtggggtggg ggactctggg tggggaggag ggtaactttt gggtctgtca 60
taaatagagg gcccagaata tgtaggagtc agtctgggga gaggcaaagg ggatttgggg 120
aaggagaaag ggttcaagaa gaagcaggga gaacagctag acccagacag gctggccagg 180
gaagcctgga tgaatgacca cattcatgga ctgtgcaagg ctgcttgccg gtccccttgc 240
ttcacacatg aggagacgga ggcccaggga ggagaagtga catggctcag ggtgcgcagc 300
aggtgtgaga cccctttcct gagtgcttcc tcctggatcc cctctcacca tctccacttt 360
gcctccggtt ctattttcca aggtcccggg tgcaaatgtt tgttgaatga ctgatgaatg 420
aaaatgattt gagtttgtta ccttttatgc ttatatgttg tggaaaatga aattctcctc 480
aaaagggaag gaaatacttg agagctgcat aggaaggaaa ttatctaatt aagaatgtat 540
agaaacttca ctgttgggca aatcatcgtt gtgacaccgg gggaagaagc catttaggtg 600
ctcagaaggg aggctggaat tcagagcagg actggacgtg ccccacgacg gtggttctta 660
ggtcaggagt cagcaaacag tggcctgggg gcccgatatg gcccacgacc tgtttttgca 720
caacctgcca gctagagatt gaagatgaac actgataatc gatttgatga tagggagcac 780
cacccccaaa gaattctatt tgtctcattt gtaaacccgt attacaaaca aattgtactc 840
aatcattatg tttgaaattt ccctaatgac aaatttgtgg aaaagtattt tctgtcttgt 900
tatataagta cttgtacaac atattctatc agcctcttgg tctgcaaaac ctaaaattta 960
ctatctggct gtttacagaa taagtgtgct aatccccgcc ccaggctaac agagctggac 1020
ctgggaggca gacatctgga tgctgggtta gttagggtga ccgaatggat gggaaaggga 1080
atggagcagg aagacatgct gctatctttt tttttttttt tttttttga tacagggtct 1140 ttctctgttg cccaggctgt agtgcagtgg catgatcatg gttcactgca gccttgacct 1200
cctgggttca agcaatcctc ccacctcagc ctcctgagta ccactacacc cggctaattt 1260
tttatttttt gtagagatgg ggtctcactg tgttgcctag gctggtctta aactcctgag 1320
cccaggtgat cctcccacgt cagcctctta aattattggg ataacaggcc tgagccacca 1380
cacccagcca ttgctttctt ttaaattatt attagttttt gttttttttt tgtatttaat 1440
tttgagatag gatctctctc tgttgctcag gctggagtgc agtggcacaa tcagggctca 1500
agtgatcctc ctgcctcagc cctccaaagt gctaggacta cagcccctaa ctggcatgct 1560
actttcctct gcttgatcct tcccccattc tcccttttag 1599

<210> SEQ ID NO 108
<211> LENGTH: 49
<212> TYPE: DNA
<213> ORGANISM: artificial
<220> FEATURE:
<223> OTHER INFORMATION: CD11b_T01

<400> SEQUENCE: 108
ttcagagcag gactggacgt gccccacgac ggtggttctt aggtcagga 49

<210> SEQ ID NO 109
<211> LENGTH: 49
<212> TYPE: DNA
<213> ORGANISM: artificial
<220> FEATURE:
<223> OTHER INFORMATION: CD11b_T02

<400> SEQUENCE: 109
tatggcccac gacctgtttt tgcacaacct gccagctaga gattgaaga 49

<210> SEQ ID NO 110
<211> LENGTH: 49
<212> TYPE: DNA
<213> ORGANISM: artificial
<220> FEATURE:
<223> OTHER INFORMATION: CD11b_T03

<400> SEQUENCE: 110
tgatgatagg gagcaccacc cccaaagaat tctatttgtc tcatttgta 49

<210> SEQ ID NO 111
<211> LENGTH: 49
<212> TYPE: DNA
<213> ORGANISM: artificial
<220> FEATURE:
<223> OTHER INFORMATION: CD11b_T04

<400> SEQUENCE: 111
ttctatttgt ctcatttgta aacccgtatt acaaacaaat tgtactcaa 49

<210> SEQ ID NO 112
<211> LENGTH: 49
<212> TYPE: DNA
<213> ORGANISM: artificial
<220> FEATURE:
<223> OTHER INFORMATION: CD11b_T05

<400> SEQUENCE: 112
tatttgtctc atttgtaaac ccgtattaca aacaaattgt actcaatca 49

<210> SEQ ID NO 113
<211> LENGTH: 49
<212> TYPE: DNA

<213> ORGANISM: artificial
<220> FEATURE:
<223> OTHER INFORMATION: CD11b_T06

<400> SEQUENCE: 113
tttgtaaacc cgtattacaa acaaattgta ctcaatcatt atgtttgaa 49

<210> SEQ ID NO 114
<211> LENGTH: 49
<212> TYPE: DNA
<213> ORGANISM: artificial
<220> FEATURE:
<223> OTHER INFORMATION: CD11b_T07

<400> SEQUENCE: 114
ttgtaaaccc gtattacaaa caaattgtac tcaatcatta tgtttgaaa 49

<210> SEQ ID NO 115
<211> LENGTH: 49
<212> TYPE: DNA
<213> ORGANISM: artificial
<220> FEATURE:
<223> OTHER INFORMATION: CD11b_T08

<400> SEQUENCE: 115
tacaaacaaa ttgtactcaa tcattatgtt tgaaatttcc ctaatgaca 49

<210> SEQ ID NO 116
<211> LENGTH: 49
<212> TYPE: DNA
<213> ORGANISM: artificial
<220> FEATURE:
<223> OTHER INFORMATION: CD11b_T09

<400> SEQUENCE: 116
ttgtactcaa tcattatgtt tgaaatttcc ctaatgacaa atttgtgga 49

<210> SEQ ID NO 117
<211> LENGTH: 49
<212> TYPE: DNA
<213> ORGANISM: artificial
<220> FEATURE:
<223> OTHER INFORMATION: CD11b_T10

<400> SEQUENCE: 117
tgtactcaat cattatgttt gaaatttccc taatgacaaa tttgtggaa 49

<210> SEQ ID NO 118
<211> LENGTH: 49
<212> TYPE: DNA
<213> ORGANISM: artificial
<220> FEATURE:
<223> OTHER INFORMATION: CD11b_T11

<400> SEQUENCE: 118
tactcaatca ttatgtttga aatttcccta atgacaaatt tgtggaaaa 49

<210> SEQ ID NO 119
<211> LENGTH: 49
<212> TYPE: DNA
<213> ORGANISM: artificial
<220> FEATURE:
<223> OTHER INFORMATION: CD11b_T12

<400> SEQUENCE: 119
tttccctaat gacaaatttg tggaaaagta ttttctgtct tgttatata 49

<210> SEQ ID NO 120
<211> LENGTH: 49
<212> TYPE: DNA
<213> ORGANISM: artificial
<220> FEATURE:
<223> OTHER INFORMATION: CD11b_T13

<400> SEQUENCE: 120
ttccctaatg acaaatttgt ggaaaagtat tttctgtctt gttatataa 49

<210> SEQ ID NO 121
<211> LENGTH: 49
<212> TYPE: DNA
<213> ORGANISM: artificial
<220> FEATURE:
<223> OTHER INFORMATION: CD11b_T14

<400> SEQUENCE: 121
ttgtggaaaa gtattttctg tcttgttata taagtacttg tacaacata 49

<210> SEQ ID NO 122
<211> LENGTH: 49
<212> TYPE: DNA
<213> ORGANISM: artificial
<220> FEATURE:
<223> OTHER INFORMATION: CD11b_T15

<400> SEQUENCE: 122
tgttatataa gtacttgtac aacatattct atcagcctct tggtctgca 49

<210> SEQ ID NO 123
<211> LENGTH: 49
<212> TYPE: DNA
<213> ORGANISM: artificial
<220> FEATURE:
<223> OTHER INFORMATION: CD11b_T16

<400> SEQUENCE: 123
ttatataagt acttgtacaa catattctat cagcctcttg gtctgcaaa 49

<210> SEQ ID NO 124
<211> LENGTH: 49
<212> TYPE: DNA
<213> ORGANISM: artificial
<220> FEATURE:
<223> OTHER INFORMATION: CD11b_T17

<400> SEQUENCE: 124
tatataagta cttgtacaac atattctatc agcctcttgg tctgcaaaa 49

<210> SEQ ID NO 125
<211> LENGTH: 49
<212> TYPE: DNA
<213> ORGANISM: artificial
<220> FEATURE:
<223> OTHER INFORMATION: CD11b_T18

<400> SEQUENCE: 125
tacaacatat tctatcagcc tcttggtctg caaaacctaa aatttacta 49

<210> SEQ ID NO 126
<211> LENGTH: 49
<212> TYPE: DNA
<213> ORGANISM: artificial
<220> FEATURE:

<223> OTHER INFORMATION: CD11b_T19

<400> SEQUENCE: 126
tcttggtctg caaaacctaa aatttactat ctggctgttt acagaataa 49

<210> SEQ ID NO 127
<211> LENGTH: 49
<212> TYPE: DNA
<213> ORGANISM: artificial
<220> FEATURE:
<223> OTHER INFORMATION: CD11b_T20

<400> SEQUENCE: 127
tgcaaaacct aaaatttact atctggctgt ttacagaata agtgtgcta 49

<210> SEQ ID NO 128
<211> LENGTH: 49
<212> TYPE: DNA
<213> ORGANISM: artificial
<220> FEATURE:
<223> OTHER INFORMATION: CD11b_T21

<400> SEQUENCE: 128
tgaaaatgat ttgagtttgt taccttttat gcttatatgt tgtggaaaa 49

<210> SEQ ID NO 129
<211> LENGTH: 49
<212> TYPE: DNA
<213> ORGANISM: artificial
<220> FEATURE:
<223> OTHER INFORMATION: CD11b_T22

<400> SEQUENCE: 129
tttgttacct tttatgctta tatgttgtgg aaaatgaaat tctcctcaa 49

<210> SEQ ID NO 130
<211> LENGTH: 49
<212> TYPE: DNA
<213> ORGANISM: artificial
<220> FEATURE:
<223> OTHER INFORMATION: CD11b_T23

<400> SEQUENCE: 130
ttgttacctt ttatgcttat atgttgtgga aaatgaaatt ctcctcaaa 49

<210> SEQ ID NO 131
<211> LENGTH: 49
<212> TYPE: DNA
<213> ORGANISM: artificial
<220> FEATURE:
<223> OTHER INFORMATION: CD11b_T24

<400> SEQUENCE: 131
tgttaccttt tatgcttata tgttgtggaa aatgaaattc tcctcaaaa 49

<210> SEQ ID NO 132
<211> LENGTH: 49
<212> TYPE: DNA
<213> ORGANISM: artificial
<220> FEATURE:
<223> OTHER INFORMATION: CD11b_T25

<400> SEQUENCE: 132
tttatgctta tatgttgtgg aaaatgaaat tctcctcaaa agggaagga 49

<210> SEQ ID NO 133
<211> LENGTH: 49
<212> TYPE: DNA
<213> ORGANISM: artificial
<220> FEATURE:
<223> OTHER INFORMATION: CD11b_T26

<400> SEQUENCE: 133
ttatgcttat atgttgtgga aaatgaaatt ctcctcaaaa gggaaggaa 49

<210> SEQ ID NO 134
<211> LENGTH: 49
<212> TYPE: DNA
<213> ORGANISM: artificial
<220> FEATURE:
<223> OTHER INFORMATION: CD11b_T27

<400> SEQUENCE: 134
tatgcttata tgttgtggaa aatgaaattc tcctcaaaag ggaaggaaa 49

<210> SEQ ID NO 135
<211> LENGTH: 49
<212> TYPE: DNA
<213> ORGANISM: artificial
<220> FEATURE:
<223> OTHER INFORMATION: CD11b_T28

<400> SEQUENCE: 135
tgcttatatg ttgtggaaaa tgaaattctc ctcaaaaggg aaggaaata 49

<210> SEQ ID NO 136
<211> LENGTH: 49
<212> TYPE: DNA
<213> ORGANISM: artificial
<220> FEATURE:
<223> OTHER INFORMATION: CD11b_T29

<400> SEQUENCE: 136
tggaaaatga aattctcctc aaaagggaag gaaatacttg agagctgca 49

<210> SEQ ID NO 137
<211> LENGTH: 49
<212> TYPE: DNA
<213> ORGANISM: artificial
<220> FEATURE:
<223> OTHER INFORMATION: CD11b_T30

<400> SEQUENCE: 137
tacttgagag ctgcatagga aggaaattat ctaattaaga atgtataga 49

<210> SEQ ID NO 138
<211> LENGTH: 23
<212> TYPE: DNA
<213> ORGANISM: artificial
<220> FEATURE:
<223> OTHER INFORMATION: CD11b_gRNA1

<400> SEQUENCE: 138
ggttgtgcaa aaacaggtcg tgg 23

<210> SEQ ID NO 139
<211> LENGTH: 23
<212> TYPE: DNA
<213> ORGANISM: artificial
<220> FEATURE:
<223> OTHER INFORMATION: CD11b_gRNA2

<400> SEQUENCE: 139
gggaggctgg aattcagagc agg 23

<210> SEQ ID NO 140
<211> LENGTH: 23
<212> TYPE: DNA
<213> ORGANISM: artificial
<220> FEATURE:
<223> OTHER INFORMATION: CD11b_gRNA3

<400> SEQUENCE: 140
ggagtcagca aacagtggcc tgg 23

<210> SEQ ID NO 141
<211> LENGTH: 23
<212> TYPE: DNA
<213> ORGANISM: artificial
<220> FEATURE:
<223> OTHER INFORMATION: CD11b_gRNA4

<400> SEQUENCE: 141
gagtcagcaa acagtggcct ggg 23

<210> SEQ ID NO 142
<211> LENGTH: 23
<212> TYPE: DNA
<213> ORGANISM: artificial
<220> FEATURE:
<223> OTHER INFORMATION: CD11b_gRNA5

<400> SEQUENCE: 142
gacctaagaa ccaccgtcgt ggg 23

<210> SEQ ID NO 143
<211> LENGTH: 23
<212> TYPE: DNA
<213> ORGANISM: artificial
<220> FEATURE:
<223> OTHER INFORMATION: CD11b_gRNA6

<400> SEQUENCE: 143
gcaaatcatc gttgtgacac cgg 23

<210> SEQ ID NO 144
<211> LENGTH: 23
<212> TYPE: DNA
<213> ORGANISM: artificial
<220> FEATURE:
<223> OTHER INFORMATION: CD11b_gRNA7

<400> SEQUENCE: 144
gagacaaata gaattctttg ggg 23

<210> SEQ ID NO 145
<211> LENGTH: 23
<212> TYPE: DNA
<213> ORGANISM: artificial
<220> FEATURE:
<223> OTHER INFORMATION: CD11b_gRNA8

<400> SEQUENCE: 145
gccccacgac ggtggttctt agg 23

<210> SEQ ID NO 146
<211> LENGTH: 23

<212> TYPE: DNA
<213> ORGANISM: artificial
<220> FEATURE:
<223> OTHER INFORMATION: CD11b_gRNA9

<400> SEQUENCE: 146
gaaatacttg agagctgcat agg 23

<210> SEQ ID NO 147
<211> LENGTH: 23
<212> TYPE: DNA
<213> ORGANISM: artificial
<220> FEATURE:
<223> OTHER INFORMATION: CD11b_gRNA10

<400> SEQUENCE: 147
ggtcaggagt cagcaaacag tgg 23

<210> SEQ ID NO 148
<211> LENGTH: 387
<212> TYPE: DNA
<213> ORGANISM: homo sapiens
<220> FEATURE:
<223> OTHER INFORMATION: S100A9_loci

<400> SEQUENCE: 148
gtaagtgagc tgccagcttc cccaggcaga agcctgcctg ccgattcctt ctttccttcc 60
ctgacccaac ttccttccaa atcctcctcc tagaagccct ccttggttgg ccctgcctac 120
tttaaagctt ctttcacatt ttcttaggtc atgttcccct ggggcctcct gccctcaaat 180
gctttgcttt ttggcactct gtagatattc taaaaaatca ttttgtacat gtgtgtgaca 240
ggccatctcc cagttaagtt gcagcctgtg ctttcttttt attttgcact tcccccacta 300
tttctgtgag tgcttagtag gaagtgtcaa agaagcttga cagcattttc ttctaagtgt 360
cccaactctt ggttttccat tacacag 387

<210> SEQ ID NO 149
<211> LENGTH: 49
<212> TYPE: DNA
<213> ORGANISM: artificial
<220> FEATURE:
<223> OTHER INFORMATION: S100A9_T01

<400> SEQUENCE: 149
tttccccgtt gtattggttg aaataagttt cactaattgg taacctcca 49

<210> SEQ ID NO 150
<211> LENGTH: 49
<212> TYPE: DNA
<213> ORGANISM: artificial
<220> FEATURE:
<223> OTHER INFORMATION: S100A9_T02

<400> SEQUENCE: 150
tattggttga aataagtttc actaattggt aacctccaga gggaaggga 49

<210> SEQ ID NO 151
<211> LENGTH: 49
<212> TYPE: DNA
<213> ORGANISM: artificial
<220> FEATURE:
<223> OTHER INFORMATION: S100A9_T03

<400> SEQUENCE: 151
tttcactaat tggtaacctc cagagggaag ggaagggagg gcaggggaa 49

<210> SEQ ID NO 152
<211> LENGTH: 49
<212> TYPE: DNA
<213> ORGANISM: artificial
<220> FEATURE:
<223> OTHER INFORMATION: S100A9_T04

<400> SEQUENCE: 152
tggaactggc ctctaagtca gatctgaatt tgcatgccct caatagtca 49

<210> SEQ ID NO 153
<211> LENGTH: 49
<212> TYPE: DNA
<213> ORGANISM: artificial
<220> FEATURE:
<223> OTHER INFORMATION: S100A9_T05

<400> SEQUENCE: 153
tctaagtcag atctgaattt gcatgccctc aatagtcaag ctgtgaaaa 49

<210> SEQ ID NO 154
<211> LENGTH: 49
<212> TYPE: DNA
<213> ORGANISM: artificial
<220> FEATURE:
<223> OTHER INFORMATION: S100A9_T06

<400> SEQUENCE: 154
tgcatgccct caatagtcaa gctgtgaaaa ctaatgaccc tctctagga 49

<210> SEQ ID NO 155
<211> LENGTH: 49
<212> TYPE: DNA
<213> ORGANISM: artificial
<220> FEATURE:
<223> OTHER INFORMATION: S100A9_T07

<400> SEQUENCE: 155
tgaaaactaa tgaccctctc taggactggt ttcaagtctt cctccagga 49

<210> SEQ ID NO 156
<211> LENGTH: 49
<212> TYPE: DNA
<213> ORGANISM: artificial
<220> FEATURE:
<223> OTHER INFORMATION: S100A9_T08

<400> SEQUENCE: 156
tcttcctcca ggaagatacc attcctagct gttaaagttg ttataagga 49

<210> SEQ ID NO 157
<211> LENGTH: 49
<212> TYPE: DNA
<213> ORGANISM: artificial
<220> FEATURE:
<223> OTHER INFORMATION: S100A9_T09

<400> SEQUENCE: 157
tcctccagga agataccatt cctagctgtt aaagttgtta taaggacca 49

<210> SEQ ID NO 158
<211> LENGTH: 49
<212> TYPE: DNA
<213> ORGANISM: artificial

<220> FEATURE:
<223> OTHER INFORMATION: S100A9_T10

<400> SEQUENCE: 158
ttcctagctg ttaaagttgt tataaggacc aaatgaggtg acatttcca 49

<210> SEQ ID NO 159
<211> LENGTH: 49
<212> TYPE: DNA
<213> ORGANISM: artificial
<220> FEATURE:
<223> OTHER INFORMATION: S100A9_T11

<400> SEQUENCE: 159
ttaaagttgt tataaggacc aaatgaggtg acatttccag gcttactca 49

<210> SEQ ID NO 160
<211> LENGTH: 49
<212> TYPE: DNA
<213> ORGANISM: artificial
<220> FEATURE:
<223> OTHER INFORMATION: S100A9_T12

<400> SEQUENCE: 160
tgaccagggc aagaccctgg aactcagctt cctcttctat aaatagaga 49

<210> SEQ ID NO 161
<211> LENGTH: 49
<212> TYPE: DNA
<213> ORGANISM: artificial
<220> FEATURE:
<223> OTHER INFORMATION: S100A9_T13

<400> SEQUENCE: 161
ttcctcttct ataaatagag aatcagcacc caagtcacag ggtcatgga 49

<210> SEQ ID NO 162
<211> LENGTH: 49
<212> TYPE: DNA
<213> ORGANISM: artificial
<220> FEATURE:
<223> OTHER INFORMATION: S100A9_T14

<400> SEQUENCE: 162
tcttctataa atagagaatc agcacccaag tcacagggtc atggaggga 49

<210> SEQ ID NO 163
<211> LENGTH: 49
<212> TYPE: DNA
<213> ORGANISM: artificial
<220> FEATURE:
<223> OTHER INFORMATION: S100A9_T15

<400> SEQUENCE: 163
tctataaata gagaatcagc acccaagtca cagggtcatg gagggaata 49

<210> SEQ ID NO 164
<211> LENGTH: 49
<212> TYPE: DNA
<213> ORGANISM: artificial
<220> FEATURE:
<223> OTHER INFORMATION: S100A9_T16

<400> SEQUENCE: 164
tataaataga gaatcagcac ccaagtcaca gggtcatgga gggaataaa 49

<210> SEQ ID NO 165
<211> LENGTH: 49
<212> TYPE: DNA
<213> ORGANISM: artificial
<220> FEATURE:
<223> OTHER INFORMATION: S100A9_T17

<400> SEQUENCE: 165
tggagagcgt ttggtatgtg ctcagtgtct gctccattgt gcgcactca 49

<210> SEQ ID NO 166
<211> LENGTH: 49
<212> TYPE: DNA
<213> ORGANISM: artificial
<220> FEATURE:
<223> OTHER INFORMATION: S100A9_T18

<400> SEQUENCE: 166
tggtatgtgc tcagtgtctg ctccattgtg cgcactcagc ctatggtca 49

<210> SEQ ID NO 167
<211> LENGTH: 49
<212> TYPE: DNA
<213> ORGANISM: artificial
<220> FEATURE:
<223> OTHER INFORMATION: S100A9_T19

<400> SEQUENCE: 167
ttgtgcgcac tcagcctatg gtcattttta atttttaaat ccagcccca 49

<210> SEQ ID NO 168
<211> LENGTH: 49
<212> TYPE: DNA
<213> ORGANISM: artificial
<220> FEATURE:
<223> OTHER INFORMATION: S100A9_T20

<400> SEQUENCE: 168
ttcccttgta catttgccag ctggtcattt actgtgctcc cagtcccca 49

<210> SEQ ID NO 169
<211> LENGTH: 49
<212> TYPE: DNA
<213> ORGANISM: artificial
<220> FEATURE:
<223> OTHER INFORMATION: S100A9_T21

<400> SEQUENCE: 169
ttttgttttc ttttcaaatt tggggaaagt cgggaaacag aggcctgca 49

<210> SEQ ID NO 170
<211> LENGTH: 49
<212> TYPE: DNA
<213> ORGANISM: artificial
<220> FEATURE:
<223> OTHER INFORMATION: S100A9_T22

<400> SEQUENCE: 170
tttcttttca aatttgggga aagtcgggaa acagaggcct gcattaaga 49

<210> SEQ ID NO 171
<211> LENGTH: 49
<212> TYPE: DNA
<213> ORGANISM: artificial
<220> FEATURE:
<223> OTHER INFORMATION: S100A9_T23

<400> SEQUENCE: 171
ttcttttcaa atttggggaa agtcgggaaa cagaggcctg cattaagaa 49

<210> SEQ ID NO 172
<211> LENGTH: 49
<212> TYPE: DNA
<213> ORGANISM: artificial
<220> FEATURE:
<223> OTHER INFORMATION: S100A9_T24

<400> SEQUENCE: 172
ttggggaaag tcgggaaaca gaggcctgca ttaagaaggg tggaacaca 49

<210> SEQ ID NO 173
<211> LENGTH: 49
<212> TYPE: DNA
<213> ORGANISM: artificial
<220> FEATURE:
<223> OTHER INFORMATION: S100A9_T25

<400> SEQUENCE: 173
taggtcccca gccctcccag tgcccctccc tccgccttgg taaggtgga 49

<210> SEQ ID NO 174
<211> LENGTH: 49
<212> TYPE: DNA
<213> ORGANISM: artificial
<220> FEATURE:
<223> OTHER INFORMATION: S100A9_T26

<400> SEQUENCE: 174
ttcagagtta ggggccctga cagctctcca taggtggagg cctcaggca 49

<210> SEQ ID NO 175
<211> LENGTH: 49
<212> TYPE: DNA
<213> ORGANISM: artificial
<220> FEATURE:
<223> OTHER INFORMATION: S100A9_T27

<400> SEQUENCE: 175
ttaggggccc tgacagctct ccataggtgg aggcctcagg caggcagga 49

<210> SEQ ID NO 176
<211> LENGTH: 49
<212> TYPE: DNA
<213> ORGANISM: artificial
<220> FEATURE:
<223> OTHER INFORMATION: S100A9_T28

<400> SEQUENCE: 176
tccataggtg gaggcctcag gcaggcagga tgctgggtgg ggtaggcaa 49

<210> SEQ ID NO 177
<211> LENGTH: 49
<212> TYPE: DNA
<213> ORGANISM: artificial
<220> FEATURE:
<223> OTHER INFORMATION: S100A9_T29

<400> SEQUENCE: 177
taggtggagg cctcaggcag gcaggatgct gggtggggta ggcaagaaa 49

<210> SEQ ID NO 178

<211> LENGTH: 49
<212> TYPE: DNA
<213> ORGANISM: artificial
<220> FEATURE:
<223> OTHER INFORMATION: S100A9_T30

<400> SEQUENCE: 178
tgggtggggt aggcaagaaa gggcccagca gagaggccgc atggcaaaa 49

<210> SEQ ID NO 179
<211> LENGTH: 23
<212> TYPE: DNA
<213> ORGANISM: artificial
<220> FEATURE:
<223> OTHER INFORMATION: S100A9_gRNA1

<400> SEQUENCE: 179
gcacaggaga gtgctcgcat tgg 23

<210> SEQ ID NO 180
<211> LENGTH: 23
<212> TYPE: DNA
<213> ORGANISM: artificial
<220> FEATURE:
<223> OTHER INFORMATION: S100A9_gRNA2

<400> SEQUENCE: 180
ggtaccccac aggttctggg agg 23

<210> SEQ ID NO 181
<211> LENGTH: 23
<212> TYPE: DNA
<213> ORGANISM: artificial
<220> FEATURE:
<223> OTHER INFORMATION: S100A9_gRNA3

<400> SEQUENCE: 181
ggagccagac atcctggggt agg 23

<210> SEQ ID NO 182
<211> LENGTH: 23
<212> TYPE: DNA
<213> ORGANISM: artificial
<220> FEATURE:
<223> OTHER INFORMATION: S100A9_gRNA4

<400> SEQUENCE: 182
ggagagtgct cgcattggct ggg 23

<210> SEQ ID NO 183
<211> LENGTH: 23
<212> TYPE: DNA
<213> ORGANISM: artificial
<220> FEATURE:
<223> OTHER INFORMATION: S100A9_gRNA5

<400> SEQUENCE: 183
ggaagcagag cctcatggat ggg 23

<210> SEQ ID NO 184
<211> LENGTH: 23
<212> TYPE: DNA
<213> ORGANISM: artificial
<220> FEATURE:
<223> OTHER INFORMATION: S100A9_gRNA6

<400> SEQUENCE: 184
ggcttactca tgccatgacc agg 23

<210> SEQ ID NO 185
<211> LENGTH: 23
<212> TYPE: DNA
<213> ORGANISM: artificial
<220> FEATURE:
<223> OTHER INFORMATION: S100A9_gRNA7

<400> SEQUENCE: 185
gggaaacacc tagaaaaact agg 23

<210> SEQ ID NO 186
<211> LENGTH: 23
<212> TYPE: DNA
<213> ORGANISM: artificial
<220> FEATURE:
<223> OTHER INFORMATION: S100A9_gRNA8

<400> SEQUENCE: 186 gtgggggtg aagcgggcat agg 23

<210> SEQ ID NO 187
<211> LENGTH: 23
<212> TYPE: DNA
<213> ORGANISM: artificial
<220> FEATURE:
<223> OTHER INFORMATION: S100A9_gRNA9

<400> SEQUENCE: 187
ggggggtgaa gcgggcatag ggg 23

<210> SEQ ID NO 188
<211> LENGTH: 23
<212> TYPE: DNA
<213> ORGANISM: artificial
<220> FEATURE:
<223> OTHER INFORMATION: S100A9_gRNA10

<400> SEQUENCE: 188
gagggctggg gacctacccc agg 23

<210> SEQ ID NO 189
<211> LENGTH: 3424
<212> TYPE: DNA
<213> ORGANISM: homo sapiens
<220> FEATURE:
<223> OTHER INFORMATION: TMEM119

<400> SEQUENCE: 189
gtgagtcctg ggtcccctc ctctgtcctg agagcctgga gctatcttgg agcttaggga 60
ctggggactg ttggagcact ctggggggcc tctctaagtg tgtgtgggct ttgagtgtgt 120
gtttggtgtt gtgtgcatga gtgtggtgga atctgagtcc cgtgtgcggt gctggggtgg 180
gccagggtgg gccggagtgt tgtgtgtgtg cggctggggc cttggtgtag ggggtgtgtt 240
gcttccactt ttctgcaagt ggatgccagg ctgttgcttc caggatctgt gtgagggtga 300
tgtggacggt attgtcctgt gtgcagggat cggctgtgtg tcaggggggtt gtgtatgtat 360 atgtgttgtg tgtccgtgtg tgttctctgt gtattgtgtg catgggccat gagagtgctg 420
ttgggtgtct cagtgctgtg tgagtcggtg tgcctgtgtt gtgtgtcttt atattgtgtg 480
tccatgctgc tctgtgtgtg tgtgtgtgtg tggaggggga ttgtgccccc aggacccccc 540

-continued

```
tccccatcca gacctccagg gcccaggtcc ctgtccttgg ctggccctgg ggtcgggggc    600
atgtgcagtg ctccaaccag aacacccctc cccacaaggg ccactgattg aagccaggtt    660
tccgtgggcc gcccctcccc caaaggccac cagtctctgg gtgggggtgg ggcagccccc    720
ggtcccctag cttcaagtct tggggccccc aggcctcagg ggtgcatctg cactcctcca    780
cagactcagg accatcttag ggcatttgcc acacttacac acggccagcc ctgcctgaca    840
tgtccccagg cagggagtcc tgggcaatca cgtggtacct gctaattggc acccactgtg    900
caccaggcat ggccgcatct tgtcctaaca gcagtccagg gaggtggctc ttatccccat    960
tgtacagata tggaaaccga ggctcagaga ggtgacatgc ccagcccaag gacacatagc   1020
cgggaagtga cctcctctgg gatataccaa gacaggcttc tctgtccagg gctctgctgg   1080
gctcacccct gactttctgt gtgacctggg caggctgttt ccagtctctg gacctgagtt   1140
acctctaagg tgaagcaaga ggcgttgggc ctgaccccag ctcctaatgg cctgttagat   1200
tctgagtcct tgaaaaaatt agggtccggg gggaggtagg cagaataatg acttcagagc   1260
tgcccagaac agtgcttcat tccacagatg ggaaactgag gcccagagag ggcaggggcc   1320
gtccagggcc acacaaccat ctttttgag gctctgctga ctgcaggtgg ggctgggtcc   1380
tccatacgtt gcccccacct ttccctggaa gccaggaggg gttgtggggt gcaggggact   1440
ctgagagtca gggtctcagc cttaaagagc cagtggcagt ttgtgtgttc tcctttcttg   1500
ccctctgcct ctgacttcgt gtgtgtgtgt gtgtgtgtgt tgtatgtata tgtgtgtgta   1560
ggtgtatgtg tgcatgtgtg tgtatgtgta tgtgtgtgca tgtgtgtgtt tggttctgca   1620
ttccttggcg gccagagcta aagaggtttc actgaacggg gtgaaaaggt tggtctttca   1680
ctgggtggcg gccggaccag acagtgagcg catgttccca tccggcgatg gtgctcattt   1740
gtcgactcag ggtgggaaat tgctggctga acctggagtt cggctaggga aggaattcag   1800
ctaccccaga ccctatcttt cctcggggct cagctacttc gcaccaggca ctctctgaaa   1860
gttgtctcat ttggccctaa cagctctgag aggtgctacc tgtggtcacc ctgtcccaac   1920
ttacggatgg ggaaagtgag gcccacagga gccagaccac agagctggat gcgatggagc   1980
cgggattctt gacccagcca gaacttgagt gggtctccag ccacccatgg tcccagctgc   2040
cctctgcagt gagaagtggt agttgttgcc acaaaagctc tctcctaggc ttgactgggg   2100
gtgggaggca gggaggtgac tggcaggtca cagaccccaa agctcaaggt tgtctgtagg   2160
aacctttgct aacaggtgcc agagaggtga gggggtcctt tcctcattta gcatctgaca   2220
ggtgatgtcc accagcggga acaagccatt cctggctcag agtgtgtggt gtgtgcatgt   2280
gtgtgtggtt gtgtaggtga gtgtgtgtgg tgtatgtgta tggttgtgtg tatgtggagt   2340
gtatgcatat atgtgtggtg tgtgcatgtg tgtatgattg tgtgtagtat gtgaatgtgt   2400
gtataggggt gtgtgtgggg catgtgtgta cgtggttgtg tgtggggtgt atatgggtat   2460
gtgtggcgtg tgtgcatgtt tgtgtgtggg gtgtgtgtgc atgtgtgtag atgattgtgt   2520
gtgtagtatg tgcatgtgtg tatatgggtg tgtgagtgtg tgtgtggtat gtgtgtgcat   2580
ggttgtgtgt ggtgtgtgtg catgtgtgta tgattgtgta gtctgtgcat gtgtgtatat   2640
gggtgtgtgt gtgtgtggcg tgtgtgcatg attatgtgtg gggtgtgtat ggggatgtgt   2700
gtgtgagtgt gtggcgtgta tgaatggttg tgtgtgtggt gagtgtgcat gtgtatgtat   2760
ggctgtgtat gagtgtgagt gtggtttgtg tgaatgtgcg tgtaaactcc tgggatcaga   2820
cagaggaagg ttcagatccc agctcagcta cttatcatct gtgtgtcctt ggggaagtca   2880
ctgtctgtct ctgaacctct gtttcctcat ctgtaaaatg ggataatga agctgcctca   2940
```

gggctcctgt aggattaaag gcatgaaaag ggcttagatg agtacccgcg aggaaagcac 3000
aggtgaccag ctcatttaaa atgagcccct gagaagcttt gtctcttttt taaaaaattg 3060
aaatatttta atatatttca tagagatgga ggtttcctta tgttgcccag gctggtcttg 3120
aactcctggg ctcaagcgat cctcccaagt agctgggact acaggcatac accaccaggc 3180
ctggctactt ttttattttt ttgtagaggt ggggtcttac tatgttgctc aaactcctgc 3240
cctcaatcaa tcctccggcc tcggcctccc aaagtgctgg gattacaagt gtgagccacc 3300
acacctggcc aattttgcct ctttttatgt cctggaatta ttttttttatt ttttccatct 3360 aagccagttt gttcacattt aatttctttt ttttcttttc tttctttctt ttttttttg 3420 acag 3424

<210> SEQ ID NO 190
<211> LENGTH: 6273
<212> TYPE: DNA
<213> ORGANISM: homo sapiens
<220> FEATURE:
<223> OTHER INFORMATION: MERTK

<400> SEQUENCE: 190
gtgagtgcgc ccggctgggg gccaggcgag ggggtggggg ctcccaggag gaagcagggg 60
cctctgggga gggagcgcgt ccacaggggc gcgcctggct gctggacaag tttgcaaaca 120
ccctccaccc actgcggtgc cagaggaggg ggcgtaggcg aacctaccgt ccactgaccg 180
cggcgcctca agcgtcccga gggcacccag cctggcttgc gggtgcgcat cgtggtgaag 240
ccgggtcggg gtcggcgttg caggctcccc tcttcaccgc agaggaggaa atcgagctcg 300
gccgggcgcg ctgcaagtcc tgaagttccg acgagtggaa cgtaggtagc aggtctggtc 360
tgggatgcga cgagaacttt ccactagagt tgcatggtgg ggccccgctc tggccggagt 420
cccgggggcc acagatccgg tctcccgagg gaccggcgcg gggcgaacga acgggctgcg 480
ggagtcggag ccgcagtccg ggagccgcga tagactgagg ccgagcgacg ggccaggggg 540
ggacggcagt cctggctgct cccaatgggc ccttacgggc attattagta tcccttttta 600
ggggcaccca gagagtgtgg gaaaagggga gcgttctttt cactcctgtt atggcagaac 660
agaacttaca gtgctcggca gcgtttacgt ttatctggat tcagcgaagt gttgttacag 720
gctttttttt ttttaatttg agaccgagtc tcgccctgtc gcccaggctg gagtgccgcg 780
gcgcgatctc ggctcactgc aggctccgcc tcccgggttc aagcgattct cctgcctcag 840
cctcccgagt agctgagact atagacgcgc gctaccacgt ccggctaatt tttgtatttt 900
tagtagagac ggggtttcac catgttggcc aggatggtct cgatctcttg acctcgtgat 960
ctgctctcct tggcctccca aagttctggg attacagtcg tgagccaccg cgcccggctt 1020
gttccaggca ttttaataca agatgctgga ctgatacgtg gaggcaagga aggccggttt 1080
cattctgctt gaacagctta tttggggagt gagtgatgaa cagatttcaa gtttgatcgc 1140
tgatgcactt cttgaggagg ctggaataaa cttaccaggc tttacccaaa agaaaaagaa 1200
aggggaaaaa tgctaaataa acacattcca agtattttct ctcagctaaa aggtttctat 1260
ttccattcag catgtagatt ttctctcttt tgatcgagaa tgcacttgac tagccttcac 1320
ctattacagt caaagatgtt ttttaggaat acctggaaag ctcagtttat agtcaagtaa 1380
gttacttaaa agtttttcct ttgagatttt cctttgaaag ctcatttact caaatgaaaa 1440
attcttaaac agtgcaccca ctttttgcac gttaaattac ataagcaatt tataatttgg 1500
ggcaacatag caatttgaaa caaactttaa gagccaggca aagaactaaa gcagttctgt 1560
tctccactgc ccctccctcc accaaacctt caaaaattcc tcagcatttc tgccagcccc 1620
atttttcata atctgctgca aatctgttat ttgttgctac tagtgaggac tggccgtgaa 1680
tagtcttgga ggtagtgaat gtggtgagaa ctatggagaa agtaatggga acaatagttt 1740
tgtgttaaat acttaaaaat tggagtgctt ttgtttttct aaaattttaa aaggctgtaa 1800
taacaaattt ttgtagctga caatcaactt taatcagaca atcataaaaa ggccttttaa 1860
aatccaccca gctggaagaa tgaaaagttt caccaatcgt tcttgcactt tttgcttttg 1920
gttttgaact ttacctatga gatgtgtgac agttttacat ctcaccttgt gaaaagctta 1980
aagaatggga ttctcactgg cagaattaca gcacaaagga gtgctgtatg aagaaattaa 2040
acatggaaat tagactcttc atctaatttt aagattttcc tattacacat tgtgggtctg 2100
agtgctttgc tgaccacaca ggggagacag agagagagac aatgagaata tgtgtgtaga 2160
ttctacactg ttagcagtat agaagaatgg gtaaataaaa tttaagcatc actttaaccc 2220
aggaaatccc ctctgccccc caacacacat acacactaca cgtctcacaa agacatgcac 2280
acacagaact ggaactgcca aaccaggagc atttcgaggc tttccagtct ttcctttctg 2340
ctcagtctct gatgggggtg ccattgagca gcaaaatgag gcaagcggtg gctctctgaa 2400
gggccaggga gaggatggag caagataaat ataaatgtgg ataaaaatga atgcattatg 2460
aggacttagc tcatgacgag gctgtgtgtg cagctaaact caacccttag agtaaattag 2520
gcttttaaga ttctttaatg ttaatatttc ttttccaaac tgatattgta acatgtattc 2580
cagtatattg taaacatctt cccagaggga acttttaagt tgttctgttg cttgtgggct 2640
ttattccaaa ggcttcaaat gctttttgaa agtacatcgt gcatatttta aaaatgaata 2700
cttttagaaa attattctga cccattaaag tgctgagtgg aattcttttc ttttctttct 2760
ttcttttttt tttttttttg gcaggttctc attctgccac ccaggctaga gtgcagtggc 2820
accatcacgg ctcactgcaa cctcaacctt ccgggctcaa gtgatcctcc cacctcagcc 2880
tcccaagtag ctatgaccac aggcacatac caccatgcct ggctaatttt ttattttttg 2940
tagagacagg atctcactat gttgcccagg ctggtcttga actcctgggc tcaagcgatc 3000
ttcccacctt agcctctcag agtgtgggga ttataggcat gagccaccat gcacagctga 3060
atacaatttt taaaaaatta acaataatta tgtttttttg tttttgagat agagtttcac 3120
tcttgctgtc caggctagag tgcaatggca caatctcggc tcaccgcaac ttcccgcctc 3180
ccgggttcaa gcagttctcc tgcctcagcc tcctgagtag ctgggattac aggcatgcac 3240
caccacgcct ggctaatttt gtatttttgg tagagacagg gtttctccgt gttggttagg 3300
ttggtctcga actcccaacc tcaggtgatc tgcctgcctt ggcctcccaa agtgctggga 3360
ttacaggcat gagccaccac acccagccaa taattatatt tttaaatctt aatttttgaa 3420
ataatttcca gataattgta gaagggccag tgagttacta gtcagcattg gtcaagaaga 3480
ggttcaatct ttttatgcct gtgaattggg aacatgctgc tgggtagaaa aactgagctg 3540
ggaccttgaa cacacatgtg aaacagtcgc tttccatata atagccagaa tgagattttg 3600
gaaacgaatc tgattgtatt ttccatttga aaatcttcca gtggcttcct gttccctact 3660
agaatttgca gagactcaca gcgaacctct ttgacccatt tccattcact tccctcttgt 3720
tcctaccact ccagccacct gtgtcttctt tctagggcct gagcagcctt tgcagtgact 3780
cttccctctg gctggaacct ttttcccaag atctcggcat gctggcttct tctcatcctt 3840
tgggtttcag ttcagaggtt ctccttgaga agccttcccc aataaccacc ccctgccaaa 3900
gtatcatatg catacacccc actatccctt aaatttaatt tcctgataat gcttctcaca 3960
acctgatcag ttccttcctt ccttccttcc ttcctccctc cctccctccc tctatttctt 4020
tattgacaga gtcttgcaat ggcaaattct ctgctcactg caacctccgc ctcccaggtt 4080
caagcaattc tcctgcctca gccttcccag tagctgggat tacaggcacc tgccaccaca 4140
gctggctaat ttttgtattt ttagtagaga cagggtttca ccatgttggc caggctggtc 4200
tcgaactcct gacctcaggt gatccgccta cctcagcctc ccaaagtgca gagattacag 4260
gcgtgagcta tggcacccag ccttacctct ttgtttactc cttttcctcc actgtccccc 4320
caccacaagg taagctcctg gtggcagggc tgctgtcttt ttcactgcta acacagcatg 4380
gagctcatac gggtgctcag tgagtatcag agcacagcat gaaggaacca agcccctgca 4440
tgtcttacca ggtgctcttc acccttatct tttcctactg gcttttccag aaacagaatt 4500
gctggagctc ccatgccctc acattcgggg cttggttaat agaaaacaat cttttatttt 4560
gctgtgatgc caatgtgatt tcattgctgg aggagctagt caattaaaac cagacagatt 4620
tttgggctgt attaacccca aacatatttt acattgtcct aactattcca actagaaaaa 4680
aaaatgtcag aaggtaattt ttcatgttaa acacagttct aacaactcct tgctcagggg 4740
caggtagccc tgggtgcctt gactttggcc cttgccgtta gtttaatctt aacccaaagc 4800
acatggctct gaattggtat gtttctcagc aggagattaa ttattataaa aactgaaagg 4860
ggtctcacac tgtgtgaggc acactatgcc tctggggact ggaatgaaag tgttaaccgg 4920
gactggcttc tggggctttg ggggtggtga ttaactttca ggacctctgt tcctttttgg 4980
gtacagtggg aggctctttt catagaattg ttaggaggac gtaatgagct aatggcaggt 5040
gatatgtgct taaaatatat ttgccattat taccaatggt tctcctccat tcttctgaac 5100
tcaagtatgg gggaaatgtt tttcctagac aaaaggtgtt gggaggaggg ttcttttctt 5160
attgaagtgt atcctgaatg gtccaccctc cattgttcag aatgctttgg tgaaggggcc 5220
ctccggtgtc gccctagagt gcccaagtcc tttgctgcag ctctttaggt ttttgtttcc 5280
tagtagtttg agcaaaaccc acccaggacc aagcagttct ccagagaagc agggcccgcc 5340
ctgactgcca ttcccctcct actcctgccc ccataccttc ccttatggag ttcaaacttg 5400
acatagtaca ggaatagctt cttgtcatgt gcctctcagg aaggtataaa aatgaagtcc 5460
agttcctgtt caacttttcc cacataactc ttttccaaac tgggtgtggt ttaaattttt 5520
ttatttttat tttttgtgtt tgttttgttt tagggttttt gagtgtgaac atccagaaaa 5580
ttcttttttt tttttttgag atggaatctt gctctgtcgc ccaggctgga gtgcatgtgg 5640
cgcgatctcg gctcactgca acctccgcct cctggcttca agcaattctc tgcctcagcc 5700
tcccaagtag ctgggattac aggtgccctc caccagacct ggctaatttt tgtattttaa 5760
gtagagacgg ggtttcaccg tgttgggcag gctggtcttg aactcctgac ctcgcgatcc 5820
acccacctcg gcctctcaaa gtgctgggat tacaggagtg aaccacctca cccagctcag 5880
aaaattcttt tcctttttac cacatcgagc taggttttcc caatgaggtc agttggctgc 5940
aacatagaga aaatgaggct ttggttctta gagtagattc cgtgtacagg cgtgagtatg 6000
tgtccgcagg tggtcttgta ggaaatgcaa agggcgccag gtgcactcct ggcttctggt 6060
acttcctgct taatggcatg ggtgagccaa ccctcaggtg cccgggaggg agccctgatt 6120
actctccctc tggcactctg ggcattggct aacccgtgac cggagttaaa ccagttccct 6180
ctcttttcat tctatgtctc ccactcctgc ctccagccga agtgctaaaa atgcagcctg 6240
gcaggggcag agaattccat taggatcagc agg 6273

<210> SEQ ID NO 191
<211> LENGTH: 2541
<212> TYPE: DNA
<213> ORGANISM: homo sapiens
<220> FEATURE:
<223> OTHER INFORMATION: CD164

<400> SEQUENCE: 191
gtgggcgcgg gccctgtggg cttcccgccc tcccctgccc agccgagccg cactgcctcc 60
tcgccgtgcg ggcggggccc gggttcgggc cacggtcggg cgggcgggcc gcgctcgggg 120
tgcggcggcg actccggcaa catggcggcc agcctggagt ccactcgtgg ccgggccggg 180
tggggagcgc gctgggggga agcggacgcg cggttcccag tggctgcggg gctggggccc 240
ccctcgaagt gttgcaagtc gaggtgcctt ttaaaagtgc atcgtaattc ctagcctcac 300
ttggggtcgg aaatggggac gtggcttcct tccgcggggg cagcggtggg gttgaggatg 360
gggccgggcg tcgcgcctct gaggttggcg gtggggccga gctgcctctc cctgccactg 420
gttgttcacc ctcccggcgc ctctctccgg aggtagcctt ctccggaagt ccgggaaaga 480
gaaacttaaa gacggtaatg ctcgttcgtg tctcagactt gagtctgaga aggtcgcttg 540
agatttaatt acattggttt tgcagatagg aatagaatgt agctgacgtt tgagcacgta 600
gttagtgaaa acttcacact tcaaagtatg cgaaaaggaa gaaaagtacc catgtatgta 660
ccgggtgttt tgcgtacgta tcctaaggct aaactggaag gtaggtagtg aaacctagga 720
ggtagatgca gagacggaga tgagtaaact ctcctgacat tgtatgttta ttcttttttc 780
aattgttttt aaaatttttct taactatgtc ctgtgctcag atagcgtatg tttagtaggt 840
cgtggaacgg gggtttgtgc ccaggtctgt gggttttcta aaacccgatc aggagcgtgt 900
cttttgttat gtgcagtcgc atagggctgg ttaaggcata catacatttt aaagcagaaa 960
ttgccatata ccgtgacaac acaaaagaga gaaggaagat aagtttgagg taataagcgg 1020
gagaaacact agaggtttaa aacctgcagt ctcgtatgat tggttattct agttaacatt 1080
agttaaggag taatgtttac gtagttaaca ttggcttctt gaccgaagaa tgccgaagtg 1140
taatgatttt tatcacggca ttcatattct acaaattctc ctctagtttt agtattttat 1200
aaaagtttaa taaagtatat agtaaactta atgttttgtt tttagtttaa ggaagatgta 1260
atggtaacat ttcaaaacga gggaagtaaa ttgcagtata atactgggaa ttctaaccgc 1320
actattttaa gatgatagag cagaatatgt ttgtctcagt cttaatttga cagtttcctt 1380
tcagaattgt agtgtgtgtg taagagaagg ttggaagtat caaattaatt tgtctttgtg 1440
taattgaagt gcgtgcaaag gaggtatgta ttttctggaa atcataagtg gatgtagtgt 1500
ggtctgaaag gtagcaagtt tagttcattg taaagaacat ttcagacatt tcactttgct 1560
acacccgtca agcacaaagg tttttaaaca gcatgtttta tctatacaaa cttcagaaaa 1620
tttattttta ctttatgaac ccttccccac cccaccgtac atgtcccagt ctttaataag 1680
tactaatgat gaagtattga aagcagtgcc tctgcagaac tattttttag gcaggagcaa 1740
agcaaacgag aatgtttgga ggcatctagt ttctaggaaa atgaatggag cccaattctt 1800
ttttttcttt tattttgctg ctttttctca ctggaaaata gagcccaatt ttatagtccg 1860
ttcttctcca gaaattgaat tatggtgatg agtacttgtt tctggattgt ttggcctagg 1920
atgaactatt gacaaatacc ttgttaacct gaattgtatg cacttgaata tgggctttta 1980
gatgttgtct ccagttgtgg aggatcctgt cgagagtgga tcatttatga atcgagaatc 2040

```
cctgggaaat tatctttgtt tgcagcagaa tgggcatcat cagtgcttgg gttcaacctg   2100

ttaaactact actgttacta ctaaaaatct cagggtttta tctgatgttt gggggtagtg   2160

gttttcctat gtgtagtgtt ggtattatat caaagccttt ttctcgatat ttttatgtat   2220

taaggatgct ttgaaatgcc taaatcctta gtggctgtgg gtgtcttcca atagttgtcc   2280

tgtgaaaaag gattggttag acagatacca tcaggcactg tactgagagt gaccactagc   2340

ttgtttttct aatgcgttta cttacagctt tgtaatgatt ggaatttctt agtaaaccag   2400

tataaagttt tatcatttat ctgaattagt aattttgatg ctgtatgtaa tgcttattgt   2460

tcaaaaagat aagtaataca gattcaaata agatactaat aaaatcattg atttcatgca   2520

tctctccccc caactcccca g                                             2541
```

<210> SEQ ID NO 192
<211> LENGTH: 357
<212> TYPE: DNA
<213> ORGANISM: homo sapiens
<220> FEATURE:
<223> OTHER INFORMATION: TLR7

<400> SEQUENCE: 192

```
gtattttaaa cattggaaca catatagata atttaagtag gtagatgtat gtgctgttat     60

aaggaagtgg ggaggagaga agagggaacc gaaatcatat gcacaaaaat ttttttaga    120

atataaataa aaaatgtggt agtctaaaat gtcaattctt caaagataaa gttaggcttt   180

cagtaacgtt agaaatggtt ttctggaata tgtctccagt ctacctaact ttgaggaagt   240

aaatactgta aatagatgtt tcaaacgcat tttaaagcaa tgatcctagc atgtctttaa   300

gctacagtat tgtgctgtct ttgaaatgta aactttgatg tcttctcttt ctcttag      357
```

<210> SEQ ID NO 193
<211> LENGTH: 359
<212> TYPE: DNA
<213> ORGANISM: homo sapiens
<220> FEATURE:
<223> OTHER INFORMATION: CD14

<400> SEQUENCE: 193

```
gtagattctc tgggatataa ggtaggggga ttggggggtt ggatagtgca gagtatggta     60

ctggcctaag gcactgagga tcatcctttt cccacaccca ccagagaagg cttaggctcc    120

cgagtcaaca gggcattcac cgcctggggc gcctgagtca tcaggacact gccaggagac    180

acagaaccct agatgccctg cagaatcctt cctgttacgg tccccctccc tgaaacatcc    240

ttcattgcaa tatttccagg aaaggaaggg ggctggctcg gaggaagaga ggtggggagg    300

tgatcagggt tcacagagga gggaactgaa tgacatccca ggattacata aactgtcag     359
```

<210> SEQ ID NO 194
<211> LENGTH: 855
<212> TYPE: DNA
<213> ORGANISM: homo sapiens
<220> FEATURE:
<223> OTHER INFORMATION: FCGR3A (CD16)

<400> SEQUENCE: 194

```
gtaaggagcc ctggagcccc ggctcctagg ctgacagacc agcccagatc cagtggcccg     60

gaggggcctg agctaaatcc gcaggacctg ggtaacacga ggaaggtaaa gagttcctgt    120

cctcgcccct ccccaccccc accttttctg tgatcttttc agcctttcgc tggtgacttg    180
```

ttcttccagg gcccatttct ctaccctacc tgggtttctt ctaacctgga aatctaatga 240
tcaaatcaca ctaaaaagtc agtagctcct gtggattaca tatcccagga gcatatagat 300
tttgaatttt gaattttgaa agaaattctg cgtggagata atattgaggc agagacactg 360
ctagtggtct gaagatttga aaggaccact ttctgtgtgc aggcagggcc tcagctggag 420
atagatgggt ctgggcgagg caggagagtg acaagttctg aggtgaaatg aaggaagccc 480
tcagagaatg ctcctcccac cttgaatctc atccccaggg tctcactgtc ccattcttgg 540
tgctgggtgg atccaaatcc aggagatggg gcaagcatcc tgggatggct gagggcacac 600
tctggcagat tctgtgtgtg tcctcagatg ctcagccaca gacctttgag ggagtaaagg 660
gggcagaccc acccaccttg cctccaggct ctttccttcc tggtcctgtt ctatggtggg 720
gctcccttgc cagacttcag actgagaagt cagatgaagt ttcaagaaaa ggaaattggt 780
gggtgacaga gatgggtgga ggggctgggg aaaggctgtt tacttcctcc tgtctagtcg 840
gtttggtccc tttag 855

<210> SEQ ID NO 195
<211> LENGTH: 2268
<212> TYPE: DNA
<213> ORGANISM: homo sapiens
<220> FEATURE:
<223> OTHER INFORMATION: TBXAS1

<400> SEQUENCE: 195
gtaggagtgg aatgaatgaa tgaaggagtg ggcgcgcgcc gtgctccgga ggagggcggg 60
tgagtggagg agcttcggaa agccacacga ggtcagaggc accgaagccc tgccgtgcac 120
gccgcggaaa tgcagccccc ggggtggtcg ctgggttcct gccggagtct ggcttccacg 180
ccaccctgat cttctcctcc tcgcgtctac actgtcccga gggccgccac tccatcactt 240
gaatgggagc tcacaactct ctgggtcctc gcttttctca gcgctctctc ctatcagggc 300
ttccgctaaa cactctccag actctcccca gccgggagcc tctccaggtt tgcttctcca 360
gctgcctccc ggatgcttgg ataggatgcc ctgccatccc ctccaactta ggaagacttg 420
ttgagtctcc tcttaggcac tgtttttaaa actgtgggtc gtgacacagt aatagatcat 480
aaaataaatg cagcggaagg caaccagctt tcaaaaagaa cgaaatggaa tccaatagaa 540
aatattagag tccattgccc ttagtaaggg caactattgt ttcataaacc ttttgtttcg 600
attataggta ctggacaagt gtactggacc atgatgtcaa ttttatttcc gtctgtgaat 660
cgtgggttta aaaaagttga aaagctatct gtgtaaaata atgatctcta acactgtata 720
actttcttaa aaacaacctc gtgattttct cactacttct tatcctttcc ggtctccatc 780
ctccgttccc atccttcagt ccttcccaaa aaaggcaagc tctttcacac ttttttagtg 840
gtacatcacg acaccttcct ctgtgtgatc ttgtactctg cggtcttcct tgcccccata 900
atcaatgcta cacttcctat cccttctctt aacctaatgc cattcacgtt tgcagaatcc 960
tagactactg ttgctaaaag gacctcagag gtcatctggg ccagccctgc ccttttagag 1020
ttgaagaaat ggagtccaga gaagtaaaat ctgttgccca atgtcacaca gtattgaagc 1080
ttaggaatag gtctcgtggc tcccactcta gtgtttttttg ctccacaccg gtcatttatc 1140
tccttccctt ctatcctccc tgcaatcttt aactttagtc ttggcccagg tcatcctaaa 1200
tattgccatc ttcataatac gtggttctgg ccatgccacg ctcctggcta acatcctcta 1260
aggactcaac ctctgcaggt ggggctgagt gccttggctt ttcatcaagg caggcgagtc 1320
ctgacttagc tttctaagga catgagttca gcaagtcact gcttctctag ccaaactggt 1380
ttacttgtag cccagtgcca gcttcaccca tctctgtcac tgtgcctttg cccaagcggt 1440
cactttccca cccactttcc cagaggggta ccttctccat cttctctctt taagcagatt 1500
ctacctgtgc ctggctcacc tcctccacaa aacagcccga gatagcgtgg gagtaagtca 1560
gacctaggtt caaatcctag ctcttccact taactatgtg atcttggtca aaatgcttaa 1620
cctctctgag cctcagtgtc tgtattttga ttatgagaag gagaacaata gtaatgttct 1680
ccttttgcat ctgtaaatct ctatcatagc cttcaccaca caggtatgta actccctgtt 1740
aatacatacc ctacatgcat gtctctctgc ccctttctag tgctggccat tagaacttgc 1800
tgccataatg gcagtgtagc tacttatgtc tgtggagcac atgaaatgtg gctagtatga 1860
ctgaggaact gaatttttaa ttttaataac catgggtggt tagtggctac cattttggac 1920
aaggtgtctc tagactgtaa gctcagtaag gacagaaacc atgtttttct tgttttggat 1980
tgtatgtcca ataactgcat tgcctaacgc atggtgagta ctgcacacat atttgttgaa 2040
tggatgatag ctgcaatttg ttgcatgctc ccttgtgtcc agcacaacac tacaaactcg 2100
ataaaaggca tttcatatag tcctcatcac agcctctgag gctgggttag attagagaga 2160
gagttttata tagagggcag acacatagta ggggttcaat aaaagttatt attattctaa 2220
ctcctccctc tgaccagccc cactgacttt tgtctcatct ttccttag 2268

<210> SEQ ID NO 196
<211> LENGTH: 602
<212> TYPE: DNA
<213> ORGANISM: homo sapiens
<220> FEATURE:
<223> OTHER INFORMATION: DOK3

<400> SEQUENCE: 196 gtgaggggc cctggagggg ctggcctggg ggagatgcag gccagaacac acaggtccct 60
gagtgttggg ctgaggagcc tgggctgcac cccaggaagg ggagagacag gttggtcttg 120
ggttgtggag agtgctgcat ggaggcccag tggggcagtg gcccctgggg ggatgccaaa 180
ggctggtgat gttcagtggc tcgtgaggtg gagaggagca ggtgaacacg agagagattt 240
cagggagaaa gaaaagcagc aagatggggt gaggcgctca aaccaggacg ccgagtggga 300
aagccaggag ttggctagag aagggtcctg ggtggaggca gggccaggga gtgtcaggcc 360
cagggtgcgc agctgcccgg ggcgggacgg gggaggggcg ggaactcatg actcggggag 420
ccagactgcg atcagacgcg cgtgcccagc tgaaccaggt gcgtgagaag gctgccttca 480
ggtggccggg ggctccctcc aggtaggtgt gggcaccttg ggcagccaga accccaggga 540
ggaaatacat gctgcccccca gcccctgagc tgaagacagg ctcccctccc cccggcctgc 600
ag 602

<210> SEQ ID NO 197
<211> LENGTH: 14420
<212> TYPE: DNA
<213> ORGANISM: homo sapiens
<220> FEATURE:
<223> OTHER INFORMATION: ABCA1

<400> SEQUENCE: 197
agtaagcttg ggtttttcag cagcgggggg ttctctcatt ttttctttgt ggttttgagt 60
tggggattgg aggagggagg gagggaagga agctgtgttg gttttcacac agggattgat 120
ggaatctggc tcttatggac acaggactgt gtggtccgga tatggcatgt ggcttatcat 180

```
agagggcaga tttgcagcca ggtagaaata gtagctttgg tttgtgctac tgcccaggca    240
tgagttctga tccctaggac ctggctccga atcgcccctg agcaccccac tttttccttt    300
tgctgcagcc ctgggagcca cctggctctc caaaagcccc taatgggccc ctgtatttct    360
ggaagctgtg ggtgaagtga gttagtggcc ccactcttag agatcaatac tgggtatctt    420
ggtgtcaatc tggattcttt ccttcaggcc tggaggaata taataactga gacttgtttt    480
atttctgcag agggttctaa gccattcact tcccagatgg gccaataatg ctttgagtaa    540
tctggagatc atctttaatg cgcaggtgaa tggaactctt ccacagaggg atgtgagggc    600
tgtagagcag agtgaactcc ctgaaactca gacgtcagct ctttgtctct ctatctctga    660
acacccttcc ttagagatcc catctctagg atgcatttct ctgtagttag tttctaagtc    720
tcttgttcct gttctgcctt tattttttt tcctggattc taagccagta tccccacttg    780
gctgtcttaa tgtagcttaa catgtctgta atcaaaatga tcatctttct gagattcaaa    840
gggctataag ggactttgga gagaatttca ttcagttttc ctcaaactag aataatgctt    900
gcactgtctg taaaagaaca aaagtgtcaa agcatccttt tgttcactaa atttcctttt    960
ttattatagt gttacttaaa tattaggaag taaaagtagg tataaacttc ttataggctg   1020
ttattataca actatatgac ccatacatat ttacaaatta agtgcagcca aaattgcaaa   1080
atcaatacca ttcaaattaa taccttaaat gtggtgaggc agctgttgtt caactgaaac   1140
caaattataa gttgcatggc agtaaatgct atcatgctga tcattttgag tttggccagt   1200
ctatattatc atgtgctaat gattgaattc tccacccatt tttctacttg tatgacctta   1260
atttgatggc acctgttcca tcctcatgag tttgctacaa ttatactggt gccaacacaa   1320
tcataaacac aaatataaac ttgggctttg aaatcttgtg ccagaacttg gctttaaagt   1380
aagcatttaa aaaatccata tgtgtttatt agactttgtt tagatgactg ttgaaatgaa   1440
aacaaagtgt ttaaaatcct cttagagaac ttaaatataa tccctcagca atatgtatac   1500
agatcttcct ttgagaaaaa ctgattgtgt tcagcctctc atgttacaaa tggggaacct   1560
gaattctgag gtctctagtg agagaacagg gactggaatc tgtggatcct atctgtttta   1620
ataataattg taaagtataa tagataatat tatattaata aaataaaagc aaacacttag   1680
aatgagcttc catgtgtgag gcactaactg attaggcatt attaactaga tttattcctt   1740
ttaaggcccc gcgatgtact gttatttcca catgttgtag ctggggaacg tgctactcag   1800
agaggttaag taacttgtct gaggtccaca ccactaacaa ggagcacagg tagggttcaa   1860
atccagataa tctgactttg gagctggcac tctaactcaa tgtgcctaat cgcttttcag   1920
tggtgtcatt attttgccta ttctccatct gagaatattg aagtttctga ctccttcctt   1980
gcctttctcc ctgcctcccg tggttatccc caggtcttgg tgttccagtc ctctatgtcc   2040
gtccttactc ttattccttt gctacagtgt gatccagggc tcctgcccct tcttatcctg   2100
gtagaggggg cccacttgct gggaaattgt ctccgccatg gtttatccat gttgtgtgtc   2160
cattagtgag tagtgggaag aatcatatca tgttggcaat gaaagggggg ctatggctct   2220
ggggtagtct agtctgaacc tcttatttta cggatgagaa agctgaggta caaagcaggg   2280
aagggatttc ttgaggtcac ccagccagca actgagctgc aaccagaagc tgagatcccc   2340
aggactaggg ccgagcctca ttctgtccca tcacagtgac ttttcttccc tcctccaaac   2400
tatttttatt ttttattttt ttgcagctgc ttagcagctt gaagttagaa gaaagggcag   2460
ggaaaaggtt ttccgtgctt agccagggaa ggaatcctgc aacaggatgt ggggttgggt   2520
cattcaaatt gggccagact ccactggtct tgttgcttct tgcttggtat tgcagatggg   2580
```

```
tttaaaagtg ttaggattag agagataggc aggtttagcc aaaggcagtt tgtagccttg   2640
tggcagagtt ctttttaaag aaggaagtgg gatgcaacac cctgacacaa aggggcttaa   2700
gttgttatac cactgcctgc taacctgttt tccttaactc tcttcctgat ttctaaagga   2760
agtatatttt gctgaatcag aaagaaaagt gatttatttc aggttgctga tgcttagatt   2820
gttagagttg gaaagatctg gcttgcatct tgtacagctg acagaactgg ggctcagggg   2880
ggcacaggtg cccagagttg gtcagtcagg aaagtagcac cagaaccagt ctcctggtgg   2940
ccctacagtt gcagaccctt ttttgctttg ctctctgtgt atactaaagc ttctatgtct   3000
ctgaatctca agttctgact ggtagctact ttccaatcca cctggcttag atttctagat   3060
tatattgttt agacgtcaga acctcttaag ggttttgggg ccacttgtta gctcacatag   3120
tgagaaccag ccctgcccat taggtagggg aagaagttag cagtccatga tagctgttgc   3180
ctgcagcgta tggatgttca ttgcacagtt cctgtctcct gagatcctgg agtgtatacg   3240
cttggcctca gagcccagca cagagcctgg cccttgggac atgcttagta agtatttact   3300
gaatgagtgg gaaatgtctt aaggcccatt agtttgcagg tcttgaggag gctcccttgc   3360
actaggaaga atagaaagca tacataaagc ctgtgtgctg ccgccaggaa gactagaaac   3420
gctatgttca gcctggagct gaatggtata ccccagagca accctgttga aaggcagtgc   3480
ttgccttttc attctgtgtc ctggtttgct ggtaactcct gggtcccctg cctctcctgt   3540
acccccattg tgcagactga gggggacca tcagccaggg ttagttttcc gctgtttctg   3600
ttaggcaaag aataaattga attgagttgt gaaagttggg tgcaaagctc agtttgggtc   3660
caaagtaaca gttaacttgt gtgggtggca ggtattcagt acaaacaggg ctggggacag   3720
gaaggggaag agaacttcag agctttcacg atcctcatct ggttttaggc tgatccagag   3780
gccaaggtcc ccatggaaca aactggacaa agtgagggtg gccacatggc ctcttttctt   3840
ttgcctttat tattaatttt ctcaaataga tctgactagt catgtggctg ggaaaatagt   3900
taattgtgat ttttttttt ttaaactgag tctcactcta ttgcccaggc tggagtgcag   3960
tggtatgatc tcagctcgcc gcaacctctg cctcccggga tcaagcaatt gtcatgcctc   4020
agcctcccgg gtagctggga ttatgggcac acagcaccac gcctggctaa tttttgtatt   4080
tttagtagag acatggtttt agcatgttgg ccaggctggt cttgaactcc tgacctcaag   4140
tgatccaccc acctcagcct tccaatctgc tgggattaca ggcatgagcc actgcaccca   4200
gccagagtac cactatttgg gcattcttta atgaaaaaga atgaactatc caaaaattaa   4260
aactcctcat ttatgagctt ttagagaatt ttacagagta gatggaaact ctctgcatcc   4320
tttccccact tctagtttca cctgacacat ttcttccctg tccttactcc tgggccggca   4380
gcagtggtca tgattccaat cccagcttgg ccaccatctg cctcagtggc ctaggaaaac   4440
tcctttctcc agagctttag ttttctcttc tacggaatga agaaagttaa aacaaataga   4500
catttattgt ttcatttgga taaatatcta ttaagcatct attacttgtg gtatggttag   4560
ctgggtatat agtggtgaag cagctgggca tgagtactgc tttcgtagag cttacagttc   4620
agtgaggcca gcagatgtga aacatatcat cacacaaata aaaatataac tatcaactgt   4680
gatgaggatt atgaaggaaa aaatccggca aactatggta ctggtgttag atactagcag   4740
gtgtgggtag ggatttcatt tagattgaca ggttgtcaca ttaaagctga gagccctgaa   4800
gttcaagcaa tggttagcca ggcaaagatc agaggcttag agatagggaa atccattcca   4860
ggcagagaga ctgggggtgc ctgtccccta ggtcagggaa cagaagaaag ccagtggcac   4920
```

-continued

```
tggtggagtg aataagactg gcgggggatg agttggtagt agacatgacc agatcattta   4980
gggccaattc tcctggggaa ggagaattta atttaatatt tatttattta tttatttatt   5040
tatttattta tttatttatt tatttttcaa gacggagtct agttctgtcg cccaggctgg   5100
agtgcagtgg agcaatctcg gctcactgca acttttgcct cctggtttca agcgattctc   5160
ctgcctcagc ctcctagtag ctgggattac agacgcccac caccatgccc agctaatttt   5220
tgtattttta tagagatgcg gtttcaccat attggccagg ctggtctgaa actcctgacc   5280
ttgtgatcct cctacctcgg cttcccaaag tgctgggatt acaggcgtga cccacagtgc   5340
cccctgagaa tttaatttta ttttatgtgc aagaggattc cctgaggtag tcaggccaca   5400
ttgtctggtg actcttggga tagagggaac ttgaatgaca aaggcccaag aaagcaattg   5460
taatcattac atatacatgg accattttat gctgttttct tctttcattt aacattattt   5520
agtgtgcgtg ttcacatatt tctaaatcat cttctgattt agaataatga tttctgatgt   5580
gtaggctgtg ttttatagtt ttgaaagtaa tactttgata tccattactt tcttgattct   5640
cacagcaatt ctgaggtgta tgcgttgcaa tttctgtttc acagatgaag agagtattgt   5700
taataagtta atggccgggc atggtggctc acacctataa ttccagcact ttgggagacc   5760
aaggtgggcg gatcacttga ggccaggaat ttgagaccag cctggtcaat gtggtgacac   5820
ccatctctac taaaaataca aaaattagcc aggcgtggta gcacttgcct gtaatcccag   5880
ctatttggga gggtgaggca ggagaatttg cttgaacctg gcaggtggaa gttgcagtga   5940
gccaagattg caccactgta ctcctgcctg ggtgacagag cgagactctg tctcaaaaaa   6000
taaaaagttg ctaagaggag ggctgggatc ttttggctcc aaatctactg tgggatgatg   6060
cctttgacat tcctgatagc tgtgcagtaa tccattaaca cagtttttat aagttcaaac   6120
cctgttgcca acatttagat tgttccatgt gtgctgttac aaataaatta ctataaagat   6180
tctatacatt taatctttta ttatttttgt attatttctg taggccaaaa tctgaggaac   6240
aggattacta ggttgaaggg aaatggccct tgaagtgtct gatcagatgt ctttccagag   6300
gatccaacca atttaaatag ccaccatcaa tgcatgagac tttgtagttc agggaaggca   6360
ggcctggttt taaaaatcat ttcccctctc tagcattttt ctgatgtgat ccttaagatt   6420
tcactttagt tttcccaggt ctcattggca tgtatgctgt tagggatggg tctaaaatta   6480
atttttcttc acattcatat catgtcatcc cagtgattat ttaataaata atcacttgat   6540
taaatagtga ttccttttct agttattttt gggacattta ttaaaacctg gatatggtgg   6600
ctcatgcctg tattcccagc actttgggag gctgaggtgg ggggattgct tgagactagg   6660
agttcaacac cagcctgggc agcatagcaa gactccatct ctataaaaat aaggaaatta   6720
gtcaggcatg gtggtacttg cctggagtcc cagctacttg gaaggctgag gtaggagaat   6780
tgcttgagtc caggtggtca aggctgcagt gagctatgac catactactg tactccagcc   6840
tgggcaacag agtgaaactc tgtctgaaaa aaaaaaaaaa aaaaaaaaaa aaaaaaaaaa   6900
aaagatgtgt agggagcaat tttggagtta ttcatttggt catttgatat gtagttttag   6960
ttttggtgct gatagagccc agaatgtacc ctgaatttga tgaacattct gatatatggg   7020
ggagctcatt gtcccccact taccttttttg cctctcagaa tatcttttga tatttttatc   7080
tgttttttcc ccattgaatg ttattacctt atcaagctca aaaaagtacc ctatcgctat   7140
tttaagttca gttgtgttaa atctataaat tagcttggga aatttggata ttaaatgaac   7200
tcatgaagaa gcagagttta gctctcctta attctcatct tcctttattt atcctactac   7260
agttctgtgg ttttctttta tgtaagaagc acatgtttgg ctaagttaat gcctaggttt   7320
```

```
ttttgtttat gtgtccattc tcactgtgga tagtattctc ttttccccac attatattaa   7380
tttaactggt tttcagagac taatagcaat gctattattt aggagaattt accttggttc   7440
tgattaactt acccatactt gcaaatcatt tgcagctttt tagttaactt tgtgagttct   7500
cttagattta cgaccatgcc agaaacagaa aggatatttt catctcttcc tttctgatgt   7560
ttattcttct tgtttccttt ttttatcccc cattatattc tcaagaatct ctcaatacta   7620
agaaatagcg acttcatttt tcagcgcgga gtgcattatt ttggctacca tgattcagaa   7680
gcctcttgcc taaggcccaa ttttattctg ctagttttct ctgttctttg tacatggccc   7740
ttgcgctgcc ctaaccttga attaacgtgg ctaaatctca agaatttaag agcaccgtga   7800
ctgtgtcctc aggctaggga gggaaatggg ttcacagagt gactggattg tggtctatga   7860
acttcggcag ccagcagcaa aagtcaggca tgaataatca agtggacagt gaacatctgt   7920
agtgtgggag atgttggcat aactatgaat gatgattcaa gagtggtttg atgcatattg   7980
aataacatga tgataagtac tagactctgt gctaagcctt ctatgtgaaa tacatttaat   8040
tctcataata actctagagc agtggttctc gaccggggcc ggttatcccc ctaccccacc   8100
ccaccctcac ccttccacca gggacataac atctggagat atttttggtt gtcacaatcc   8160
tgggaatgta tgtgctgata tttagaggtt gaggtcaggg atgctgctga acttcgtaga   8220
attcatagga gagtctctca caacacctat ctggccccaa atgtcagtag ggtcactatc   8280
aagaaaatct gctctagcag tgcctgctca tattatcccc atgttgaaat agcaagatgg   8340
gaagtgcaaa gtggtgcttc ggtactcttg gagcagcttt gactttggtg agaaacgcct   8400
tttaaaaaca atgtttcttc ccatcttccc accccatggg gaggtgtggg gttgggtggg   8460
taggcaccaa agcaagattt agaagagttt tctgtaggaa tttataatgg taaaggatca   8520
acttcatttc caagctattt atgagggttt atgtttagga aaagtgctaa gcttagagaa   8580
ggaggagaaa tctgatttta ttaatgagtg tagccataat ggcatatcct ggcagaagtc   8640
aactttggtt tctagaggga ggctattatg aaaagaaata cctggaacat tcccctgggt   8700
ttggaaggtg agttctaggt tcaatgatgg gaagaatttt agaggtccaa gataaaaggg   8760
caaagattaa attttgtctc tcatgagttc tctggctcag gtggtgtgaa ctttgcagac   8820
agtctcttta attcactcat acatgctagt ctcccagctc agcaagggct ttgagagagc   8880
aggtgtctgt atgctctggt aagtgaaggc aaagtgcata aggaggttgg ggtccataat   8940
ggcgaagaga aggagccctt cagtcagagt ggctttgaat cttggctctg ccatttgcca   9000
atcttggacc attgggcagt gtattaactc tttgaatctc agcttcctct tctgtaaaat   9060
gtgtataaca agagtactaa ttggattgtt tgatgattaa atgagttaat gtgtataaag   9120
cactcacaac cctggtacat agtaagacct ttcattatta ttatcatcat caattttttt   9180
taacctcttt tcctgatctg cttacactca ccagcttcag ctgctccaaa tggcttgtaa   9240
gatttttgt ttgccctttg ctgtcagttg ccatggggaa gatccattca tttttttcag   9300
tcaaccaaca tattttgagc atctgctgcc ctacaggatc ctagatatgg gggctgcaga   9360
gatatccagg aacataagcc ttgattaatt gggtcagatc agtgctcagc agggctggca   9420
agtgctaggt ttcttttaag tggcatatct taaaaggtat atgtcctaaa catagctttg   9480
tgatggcagc atgatgggta caaaagcaca cacttaagtg tcagtagatc tgggttcaaa   9540
cattggtgca gtttcttatg gctcgtaact tgttcaaacc tcagtttctt cacttctaaa   9600
acggtaatga tacaacctac ctcacagggt tattatgaat taaatactgg agatgagata   9660
```

cacaaaacgt cttgagtaca cagtagctgc ccaatattgg ctgtaagtat tataaatcta 9720
caagctgtga attaatttta cctctctgga tcctgttgat atttctagac cattccacct 9780
agtggggcca tttcctacct gagtcacccg tggtgtcaaa tagaatgtca tgtggcctcc 9840
tgagttgggt agaattggct gctcatctca accccgctac tgactatctc tgtgatttac 9900
ccttcctcca gccttagcct tgctacatat aaaatcaaga caataatgtt tcctatctca 9960
cagggttgtc ctgaggatta aattaagtaa ttaatataaa atgtgccttg tacatattgg 10020
gccctaaata aacagtagct actatttatc cttaaagtac aaatggtagt ttcagagctt 10080
caaggctgat ggctatttat cttactcata ctctttgttt agcttcattt ttttccccta 10140
atttcattag tattttcttt tctttttttt tttttttttt tttttttttt tttgaggtga 10200
agtctcactc tgttgcccag gctggagtgc aatggagcga tcttggctca ccccaacctc 10260
tgtctcctgg gttcaaacag ttctcctgcc tcagcctccc gagtagctgg gattacaggc 10320
tcccgccacc atgcccagct atttttttgt attttcagta gagatggggt ttcacccttt 10380
tgaccaggct ggtcttgaac tcctgacctc atgatcaacc cacctcagcc tcccaaagtg 10440
ctgggattac aggtgtgagc caccacgccc ggcctcataa gtattttcta aatttattta 10500
cagtcatgcc atttaaaagg aaagttgtat tcctgtcttt gttaatattt ataagtgatt 10560
ttattcagct acaagcttgg aatggcatat aattttgtat tctgcttttt tcacttaata 10620
ttacatggct aatgatttct gtgtttcata aacattattc tgatgatggc atgatatatt 10680
gttgagtaca tgtaccataa ttgaatcatt tccctattgc tatgcaatta agttgtttcc 10740
aatattttgc aattataatg tttcaatgaa tgaataactt tatgcatata gctttttgat 10800
atcttaagtt cagtttccta ggatgaattt ccaggaatag taattgggca aatgggataa 10860
acatgactct tgaatacgta ttgttaacat tgctttccca aagggctcaa ctgatttata 10920
tttccgtgtt cattatcttt taaaccagct catttactca ccaaacattt ttaaagccat 10980
tatcatgtgg taggcttagt aagaagaaag tgaccctaag ggagaagctt atatataaat 11040
agggtccctg gtgtaccaag tgctgataca gacacaaagt acctggggaa attgagatga 11100
gggagtcctg gctcagctgg gagaaaagtt cattttcata gagtcatggt tttgttcttt 11160
ggcagaaaga aaattgcttt cttccccacc cccacccccca gctttattga ggtataattg 11220
acaaataaaa attgtatatc tttaagatat gcaatgtgat atatatgtat atctcaactt 11280
aaaaaataag ctacagaata aaaaggtgtt tgctattaaa aaaaaagaaa aggctgaatg 11340
tcattcccaa gcttggaaat ttgagtatgt tgcctctttg ggattattta cagaaatatt 11400
agcaagacca gccccatctt tggtcttgag tactccactg tcagcatgct ttcttccaga 11460
gagggatcca tttgccttta tttttcattc tgttgtgccg tctatgcaaa ctattcttga 11520
tagttttatg gtaacagtgt ttttttgttc catgagataa tttatacatg ctcattgtgg 11580
aaaatttaga aaagacagga aagtattaaa aacatcactt tttttttttt tttttttttt 11640
ttttttttaa gagacagagt cttgctctgt cgcccaggcc ggagtgcagt ggcgtgatct 11700
cagctcacag caacctccgc ttcccaggtt taagtgattc tcctgcctca gcctcccaag 11760
tagctgggag tacaggcatg caccaccacg cccggctaat tttgtatttt tagtagagat 11820
ggggtttcac catgttggcc aggctggtct caaactcctg acctcaggtg atccgcctgc 11880
cttggcctcg caaagttctg ggattatagg caggagccac tgcgccagcc acacctacgt 11940
tcttatcatc ctagtacatc cactgtcatt atcttgctgt atttccttct gcccagtctc 12000
actctgatca tgcagtggcg tgatcatgca gtgatctcgg ctcactgcaa cctaggcctt 12060

```
ctgggttcga gtgattctcc tgccttagcc tcctgggttc aagtgattct cttgccttgg  12120
cctcccaagt agctgggatt acaggcatac acccccatgc ccatctaatt tttgtatttt  12180
tagtagacac agcgtttcac taaaattttg tatttttagt agagatgggg tttcaccatg  12240
ttggccaggc tggtctccaa ctcctgacct caggtgatcc gcctgccttg gcctcacaaa  12300
gtgattacag gcatgagcca ctgcatccat cgccaaaaag attttttaaa agagtttaat  12360
gtagaaccat atcaaaggtc tttggaaata aaaaacagtt ttttaaaaat atcagaaata  12420
aaacaacaaa taaataaata aataaaaaca cccaaaacaa tctgaagcac gagcacctag  12480
cagaaaggtt caattatgat ctattcatag agtggaatat caagtagaca ttacaggaca  12540
tgttttaaga ttatatttta tgtcatggga aatgctctcc cagtatgatg ttaaatgaaa  12600
aaacagaata caaaagtata tatgctgcat agtctcaata ttgtagagaa aaaatattat  12660
ttatgtatgc atgaaaaaag acaaaagatg ttaacagaga tccattgtta cttcagttta  12720
ctagggattg tctctgggag gtaggattaa ggtgatttat atttaccttt ttaaactttt  12780
ctgtattttt ttattttcaa attttccata aaaatataag gacttgaaga tcaagaaaaa  12840
atttctgctt tggctcagtg cagtggctca cgcctgtaat cccagcagtt tgggagccct  12900
aggggagagg atcacttgaa cccaagagtt tgacgttcca gtgagctatg atctccggat  12960
cgtaccgcct ggacgatgga gcaagaccct gtctcaaaaa aaaaaatctt tgcttttttt  13020
ttttgtttgt ttttgagacg gagtctctct ctgttgcccc agctggagta cagtggcaca  13080
atctcagctc accgcaacct ctgcctcctg ggttcaagcg attctcttgc ctcagcctcc  13140
caagtacctg ggattccatg cacccaccac tatgcccagc tacttttttg tattttcagt  13200
agagacaggg tttcaccatg ttggccaggc tggtctcgaa ttcctgacct cagctgatcc  13260
accggccttg gcctcccaaa gtgctgggat tacaggcatg agccactgtg cccagcccaa  13320
tcttttgctt tttttaaaaa aagaagacaa aaagggattt tataccagta ttatcttggc  13380
tgtgtgactc tgaagccaca gttgtaagtt ataattactc tgaaacacaa ggccctgtga  13440
ctcttttggg ctctttggtg tttatcttga ttacaacgtt ggaatataga aatgaaagga  13500
atgggagagg tgatagactt caggcagtgt aactagttgt ctgaacacta ctggctcaat  13560
tatattgtgt ctagtgattt ccatcttgtc cgtctgctaa tttatcgcct ggtaactcac  13620
tgaggcaggg ttttcctttg gagaaacctc attgttttaa ccagtgtatc atgcttgttt  13680
agaagttcaa tgatcttttt aactcatcgg agaagatgat gaccagacct ggacagatgg  13740
ggaaggactt tgcactctct ctttacagtc ctgagtgcac acaggtcaat atggaactat  13800
gtgtgaattt tcattgtctt tgagagccct cttctctgcc ccatagggag cagctttgtg  13860
tgcaattaga ggagcaaggg ttgtgtgtat ttagcacagc aggttggcct ggtcctctcc  13920
tctcaacata gtcaccacat acctggcact atgctaaggc tgggaatgca gacagatggg  13980
tgcctgcttt cagagtgctc aatgtgctga ggaagccagc aacagaaaca gatgatttca  14040
ggagctccag gaaaatgcta caggaggagt gtgcctgggt tactggagta gcacaggagg  14100
agggcttcta gctcaggctg agattttagt aaaggaaatt atgccacgat gaatcctgaa  14160
gaatgaatag aagtgaacca gataaagcac gataggaagc atcttccctt acctaaggga  14220
agacacagag gtatatggaa tggtatgtta aaaggttggg actccaaaca gttctgttaa  14280
agcttagaga gtggtgggag agactggaga agttgattaa ttagtaaatg aagttgtctg  14340
tggatttccc agatcccagt ggcattggat atccatatta tttttaaatt tacagtgttc  14400
```

tatcttattt cccactcagt 14420

<210> SEQ ID NO 198
<211> LENGTH: 1448
<212> TYPE: DNA
<213> ORGANISM: homo sapiens
<220> FEATURE:
<223> OTHER INFORMATION: TMEM195

<400> SEQUENCE: 198
gtgagacttt attggaagag gctactctta ttcttgctgc tttcttaata aatggtaagg 60
tcaatctcct tagggttttg ttcactttca ttattcaaat gattacattc taataataat 120
aattcagttt cttaaaggcg tgaagcaaaa gtagaatttc cacttgaatt ttcttacaat 180
ccatagccat cttcacctgt aaattccctc ttttatatgt cactccagaa tatgacaaaa 240
acaaaagttt aaagttttcc tggactccat ggcattgtaa atgtagctat tggaagctca 300
atgacaaata gttacaccac atcagtaaac tttgtaacaa tttcattttt aaatctttca 360
cttgtccacc ccttccaggg aaactatttc ctctttcatt tggtagagta gttcagcaga 420
atgaaggata tgcagcttga ccaggtccag ctctgacttc ctaagtttga atttgaccca 480
agttttcttt gaaactctga agtgctcaga ggcacatttc acttctggtt cctggctatg 540
attggaagtg gaaatatcca gaattagaac ttgaatactg aagttcccca ccctatcaaa 600
gttattccta caacactcac tagttcatgg cagaaataga aaaaaaatga catcatagaa 660
tatgttattg agagttcagt ttagaaagct tcaaaactca tgattagctt ccaaatgagt 720
aaaatccgta tctttttcaa gattagatat tacactttct ttctgagttt ttaagttaaa 780
aaaagtggca ctgatatctt cataaattat tattgtttat actgcaatat caaaccaaat 840
tcaatgctcc atcaccaata gtggagcttt caaaacatct cttattatgt gaaacaaaaa 900
tcaaaaccaa atgaataaaa tctgaatcat gttttaagca aacatgtaaa attaccatat 960
tctctaaaat tctaagcaga aaattgtctc tactctttga atttcatcat tagaaatagt 1020
tctggtaagt ctaatatgaa aaattagaat tatgtgcatc tttaaggaaa gcctcttgaa 1080
gtgggtctaa attatacatg tagagacaat agacctctaa ttatctacct tattctaaat 1140
gtatttttta aactaatttg gaagatgttc ctcttaatct tataatatta taattatcgt 1200
ggttatatct atgattacat ttcatattca aattggatga tagaatttga gcacatgttt 1260
agtgtatgtc taaaataatt agacttcttt accactgtgt aggaagtaat cctctaaaat 1320
gagtgtctac catctcctgc agggcttccc aaatctgggc ctttcaattc tgaaatgact 1380
aatcaggaaa tgtaaaataa tttcatatgg aacataatag catctctttt ctgcaacttc 1440
ctttccag 1448

<210> SEQ ID NO 199
<211> LENGTH: 3633
<212> TYPE: DNA
<213> ORGANISM: homo sapiens
<220> FEATURE:
<223> OTHER INFORMATION: TLR4

<400> SEQUENCE: 199
gtatgtggct ggagtcagct cctctgaact ttccctcact tctgcccaga acttctcact 60
gtgtgccctg gtttgtttat ttttgcaaaa aaaaaaaaga gttaaattac cttaaagact 120
caagaagcca cagagatcaa ataattcatt gttacagggc actagaggca gccattgggg 180
gtttgttcca tttggaaatt ttgagtgcta acaggggcat gagataacat agatctgctt 240

```
aaggtccctg ctctgctacc ttgtggctct gtgaagaaat tatcaaacct gtctgagact    300
agttttcgca tctgtaagag aattataata ccttcttcac tagagagtaa gcagactgct    360
tcagtgtcat ttcttcccac tggtggtctt tacactcagc ttcaagcagt caccctgctc    420
ctttcaatct caggaaaaag atggcttttg tgtgtgtgtc tctagagaaa gaactttcta    480
agtgggtgtc agacttctgt atgcagtaat atagtttagt ccagaggatg aaaaaaataa    540
gagaatgaaa aaggaaaaga gagagagaga gaagaaaaaa gcaagaggga aatatgtata    600
atgtcagcta atgcaacagt ttctttctta gtgaaatacc aatcagctgg ttggtaatct    660
tattcatgat ggatctcttt tgtttttccc ctgcgcagac ttcacagttg ctttagaaac    720
ccatagtaga gccgaacagc taagaaaatg atttacagtg aggcagggtc agaaactcaa    780
gagagaaaaa gccagctgca gtcctgaagt tgaggatata ggagaaaatc aagtaatatt    840
tagcaaagac taattcatta tcttgaagcc atcccttccc tcaattccct gcccatagtc    900
ctcctccttg tcctcttctc tgtatccctc tgctgttagg ttaatggaga tagattttct    960
aattaggctc actgcgagat aaaaccacag ccaaacttga cttcttttcc ccatgtacct   1020
tttcctgtca gtccctgaag cctgtccatc cctgcccatc cccttagttc cactgtaagg   1080
caggccctca tttcccctgg cattgactct tacacactaa ctgctttcct gattccagtc   1140
ttcttccttt aattcattct gcacgttctt gtttgttatg tacttgcatt tgttgttatt   1200
atttttcctt aggcttcaat ctaacaaatt actctcctta aaaactttta ataactctcc   1260
attgccatta gaacagcttt ctaccacagg gcctttgcac tggctatttc ttctacctag   1320
aatgctagat cagtgctatc cattggcaat attatgtgag ccacatatgt acttttaaag   1380
tttttagtag cctcattaaa aaaagaaaca agtgaattta atttcgataa tagttttatt   1440
taacttagcg tatttaaaat aatgtttaaa attttaatat atatttacct attattgata   1500
tttttacatt ccttgtttgg tactaagtct ggaatttagt atatgtttta catttaccac   1560
acttctcaat ttacactatt cacatttctt gtgtttgata actgtgtatg gctagtgact   1620
accgtattgg tcagtgcagc ccaagtcctt ttcatgcttt aatcactcca ttcagatctc   1680
tgattaaatg tcccctcctc agggcagtct tccttgattg ccccatgtag agctctccag   1740
cctcacttat ttgcctcaaa tcccctttata ctgcttaata ttttttttc tagagcacaa   1800
cattttatat ttttgtttgt ttattttctc tctctccctt tgtaatggaa tcggtaagga   1860
ggcaggatca ttgctggttt tatttaccac tatatttcca gtggccagca cacagtagcc   1920
gctagatgtg taagtgataa atgattgaaa taattgctgc aggacaaagt ctgaggccct   1980
cctgatctgg cttgccctct tacttagatt tcaccactcc caccactcac cagctaatct   2040
gagtttgttt tccactcttt acgtgctcac gttgtcctct ccttaggaca tgtttttctt   2100
cccctttcca catatctaaa ccttactcat cttccaagac ccactttaaa atcttccttt   2160
tctgggaagc ctttcctgaa tccagacttg atctctgctt tctctgaacc acagggcata   2220
ttttctaagc ctattttatg gccccttgag atagtgttag ctttgctcct atctaaactc   2280
ttactctaga ctgtgagtcc attgaagtct ggagctgcat catatttttc tttgtaatgc   2340
ccacagcact tggcaggaaa tgcctacaat ttggacttaa gtaaaccttc atttaatcag   2400
ttattcaatc agttagtgat tcagcaaata tttattgagc accaaccatt tgccagacac   2460
cattctgagt gctggagaca aagcagtggg caaacccatc aaacttgcaa tggaatacag   2520
gagatgaaca atacgatgag aacaatcaga tagacaacat aatgttagat ggttgtgctt   2580
```

cccgtgaaag ggaataaaag agggcaaaga aagagtgcct ggcactgttt ctattagaca 2640
atattgtctt tgaggctcca tggcttgcaa catttaagca gacatacgaa tgaagatctg 2700
catgtttgaa ctctgacttt gcgcatatta cttcatttct ttgaatttcc attttcctca 2760
tctttaaatg cttatttgaa gattaagtga aagtatataa caaacaagaa ctatgcaggc 2820
atatggtaag ggattaatga tagatgataa taattaatgt tgacatctat tgatcactta 2880
tactgtagcg ggcttttaaa taaactcttt aaacacctta tctcatttaa tccttcaaac 2940
attctattgg tttcaaacaa cagaaaacta caattagctg gcttctgcaa ggaattttgt 3000
tggaggaaat gagagcattc agaaattaga tgggagcgtt agagaattag gcttacaaag 3060
aatgtgggaa agtaggctag aaagcagtgt aaaaacaaag acagcataaa gcacttgacc 3120
ttatttacta ggttccacca tggaatccca tgcactctaa agatttcccc ctatttctac 3180
atcactttgc tcaagggtca atgagccaag aaaaagaatg cagttgtcaa aatctgggcc 3240
atgactaagg aaggtctgga catcttgact gccagacagt ctccccaatg atatggagta 3300
tttaaaatga tactggatat tttatttatt ttttgtattt tcaactttta agttcagagg 3360
cacatgtgca gagcatgcag gtttattaca taagtaaatg tgtgccatgg tgatttgctg 3420
catagatcat gaaaatatgg aacgcatcat ggatttgtgt gtcatccttg tgcaggggcc 3480
atgctcatct tctctgtatc cttccaattt tagtgtatgt gctactgcag caagcacgat 3540
attggatatt ttattaccta cattttacat atgataaaat gaggctcact gaggtttttc 3600
ttttgttcgt tttattttgt tttgttttta aag 3633

<210> SEQ ID NO 200
<211> LENGTH: 422
<212> TYPE: DNA
<213> ORGANISM: homo sapiens
<220> FEATURE:
<223> OTHER INFORMATION: MR1

<400> SEQUENCE: 200
gtaagtgttt tgagcttatt gtgctgggtg ctagagtagc agggaggaca gacctaagtt 60
gaagattacg ggacaatcta agtgacacct gctatctcag acagagactt cagcatcata 120
gggagccaga gcagggagtt ccaagccgtg ggaactgtga ctctttctta ctgaccctta 180
agcaaaattc taagctccag ggaagcagag gcagcagctt gagctccctg attgaccaga 240
tatgattaat ctttgtttct ctgtgctttg aacatgacta tgctccataa atatttaaaa 300
attgggaata gggtgaagat agatacacca aaaggagcaa gcagtgtctg aaaccagcaa 360
agacttaaaa gttaccgaag aaggtgttca tgctttcatt ttatcttttt tttttaacct 420
ag 422

<210> SEQ ID NO 201
<211> LENGTH: 393
<212> TYPE: DNA
<213> ORGANISM: homo sapiens
<220> FEATURE:
<223> OTHER INFORMATION: FCGR1A (CD64)

<400> SEQUENCE: 201
gtaagttgga ctcagagggg acagttagaa gggtacaggc tgtggctgtt gtgagtcaag 60
agttttgtct tcctgtggta actctgggta gaactcatga gtatgaagca acttgtatct 120
gtgcttccat ggtttattag agcttatttt atgaaaagga tgggaagggc aaccctgagg 180
tagcattaag cctggacgca ccgcagtgaa gtttccttga taaccacctg tagcttgttc 240

```
agttctgtta gtactggatt ttgagaaaga gaaatagaaa ctcaagagat ctgagttgat    300

ccctcagagt ctacattaat tctgtctccc caattctctc ttcctcatta ttttccttgg    360

accaactgat atctttattc tctgatctct tgc                                 393


<210> SEQ ID NO 202
<211> LENGTH: 1273
<212> TYPE: DNA
<213> ORGANISM: homo sapiens
<220> FEATURE:
<223> OTHER INFORMATION: CSF3R

<400> SEQUENCE: 202

gtgagtaggg gatccctaga gaggggctga gccttgggct tgatggagag ctggaatcct     60

ggggccactc cccacagctc tgccaagtgt tcatgtccgg ggtcctaggc ctggggcccg    120

ggattcgtcc tttggaaccc cagccctgga cactgagtct cttttcacag gatgccccta    180

cttttggggg tattgcacca gggaagtcac tcacagccaa gtatctcctt ggggacactg    240

agctgggctg gggacaggca taatcattct cccctcccca tgcctctgtc tctcaggacg    300

tgtgtgtctg tgagttccag ccgcgcaacc cctccccgtc tgggtctcta tttcactctc    360

tgtttccatc tttcctcctc agcttctctc tggcttgcta tctctctgag tttctctgtc    420

tcgcatattt cctgctatct cttgaatctt aaactctcgg taacagacgc ttcccgggct    480

ccaggcctcc gagtgccccc cccccgccca ctctctgggt cggcgtacat tgggcccttt    540

ttctctgtct ctcgatatct ctctggcctc aatcgtcctc ttggcgagtc tctctgtcgt    600

ttcagtctgt gtggatttca gtcaccgcct cactctgtca ctcttcctgt tgctctctct    660

ttttctttat ctgcagcata tctggaaatg cctctcccct ctgtttattc ccagcccccct    720

cctccctccc cacccttccc acagaaagaa tctcgaggtg agagtagaaa cagcaaggga    780

gcgaggggtg tgaagtgggg aagagagtgt gaggggagag ggctgagcgt gatgagggag    840

aaacagaaag agggaatgtg aaggcagcca gcccaggaga catcgagctg tgctgggcca    900

caggagtgag cacctgcaga gcccagcaga gatggccgca gtgacaggag ggccaggggg    960

cccaggagtt aggaggagag gatccagaaa gggggctttg gaactgcgca gtgtggcaca   1020

gacaaaagca aggtggcagt cctgggaggt gtgaccacac aggctgtgag ggaggcaggg   1080

gtgaggggaa aactgaactg tgctggattc tgtgagctgc tgacctgcta tttatggctc   1140

gtgaaaataa cctatggttg ctgagtgcca actccatgca aggcacaggg ctaaatgcct   1200

ttaccaaaat aatctcattt catcctcaca acaacgctga ggagtgagtg ctaatgttat   1260

ttctttccca cag                                                      1273


<210> SEQ ID NO 203
<211> LENGTH: 29639
<212> TYPE: DNA
<213> ORGANISM: homo sapiens
<220> FEATURE:
<223> OTHER INFORMATION: FGD4

<400> SEQUENCE: 203

gtaagtggtt tcattttcta gtagatatat ttttttcttc cccagcgtgg gtcactttat     60

aacactgcat gccgagggat gtaaaagtgg cagagtttgg ttttctttta aagttaataa    120

agctcacatt ggttttcaag ttcaagatta aaatatgtgc tattgatggg ttttggctct    180

ccaggaggct tcttctgggc taaccagata caaatgagtt tgatagttaa gtttctctgg    240
```

```
cttattttta ttatcataag taaagtttgg aaatttggtc attgagggga gaaatataga    300
gaaagaaagg aacagttttc tctttttcct cccatttctg gtgtgaacaa atgttaagaa    360
atatttacca ctaatcattt ttctagtgct actgcacgga gcattgttct gttaaaacaa    420
acaaaaattc ccaccatccc agtcttgttt tggtgaagtt caggggagta agtattattt    480
gtttttctgt aaaagacaac attgtagaga taggcatgag tttgtttttt aaaaattgtt    540
agtggtagta gtattaagcc actgtggtct ctttgagtgt tgtagagagc atattaatga    600
gaaattgagt ctttgaaata gaaatgtaat tcaactgtgt gatagaaatg taatcatgtg    660
acgggaaatg tctgctaaaa atatttttaa tcactgaaat gggttcattt tgtttatttt    720
cccattcgtt tttgactgga tataagcctc actgaaaaat gtccacactg ctgaacaaga    780
taaactacaa cttagaaccg gcagccttca cagttaccag tattctttct gatggtggtg    840
tggctctttc cttccttaag tgtcaggggc atacgctgag tgtggaagcc caaggttggg    900
gttggtgaca gcactgcctc aggagagctg aggcgccact cctgcagctg cacagctggc    960
tccgttccca ggttctagta gctgcgggag ggttaagcag cccagtccat gcctgcccct   1020
gctccctcca tcactcaggc agaagcctga attcttttgc aggcgttcca ccactcttgc   1080
ataaagtttg gaggtcttgt gatctctcca aaatttacca tcatactcta aatatgaaat   1140
taaaaaaaaa aaaagaaatg cagcaaaagg gaagtgtttt ctcaccccaa gcagtgaagt   1200
tttaggttct ctttttcctg aaatagcttc tgtccattct catttatctt caaacagtta   1260
gagatgattg gagagacagt attccctcct ggaaggcagc tcttaattag agaggaaaat   1320
atttctagaa caggaagatg aagcttgaga ggtgaatgtt gataaacata gagaacttgt   1380
tggctcttgt tttctgcttt aatggacagc accctttaga gagtggccac tacaacaata   1440
tggactttat aagttccttt ttaggttttt aaactgagaa gacagtaata tagcacttcc   1500
tgcctacact actggataat tttgttaaat catctaagaa aaattgtaaa tatgcatatt   1560
tagtgcacat gttattttat aacagttttt ttttttaat gacctgaaaa aacttctctt   1620
tctaaagctt acgctttcag gcaaactcct ttcacatgaa agaaatgaaa tatgatagag   1680
tatgatgaat gactcaatag gaaatattat gcagttcttt ggaagaatga taacttggtg   1740
ttcctttaat aaacatccaa atgtacatgt aacctaaact gcaaactagg attaagattt   1800
aaatttaatc agttcttctt agatactaga atagacttga ggaggtcaag agtagatagg   1860
agactcctgg aataatccag ggaaaagttg aagtcattta tttcaaaaat aaaaaggtat   1920
tttcttagat gttttgtgga ccatccctgc ccacttcctg agccaccttc tgataacctt   1980
tactgtaggc acctgtttc tttataaaat aacaagctaa tttttattgg ctaaagtaca   2040
tttgtaaatg tcttcaccct ggtttgtgtg tgttctctga tttatctccc accacagcac   2100
ctgctaagct ctggctagaa cagatccttc catttttatt ccctggcgaa ttgacacaag   2160
ttagttggtt atacgttgaa gcaggcagaa ggaaaacact taggagaaga aaaatagtgt   2220
taatcgtaga atttggtcat tctacatggt ggttattata ataaaacttg gcctggggaa   2280
aatgagtctt tcaccctctt agagaataag tacacacaaa tacattttta aaacatttaa   2340
acaaacaaac aaaaaagact gtgtcactgt ggtcttgtct tttccatgcc attataaagc   2400
agttatttct tttttttctc tctctctttt cttttttttt tttgagacag agtctcgctc   2460
tgtcacccag gctggagtgc agtggcgcta agctccacct ccggggttca caccattctc   2520
ctgcctcagc ctcccgagta gctgggacta caggcacccg ccaccatgcc cggctaattt   2580
tttgcatttt tagtagagac agggtttcac cgtgttagcc aggatggtct caatctcctg   2640
```

```
atctcattat ccgcccacct cggcctccca aagtgctggg attacaggcg tgagccacca   2700
cgcctggcca taaagcagtt attatttctt atgcttagtc ccaaaaacct agtcttcctt   2760
gagtcatttt tctcttatgt acaatctggc aacaaatctt gcttcaagat atatcaaact   2820
gactatgtct tattgcctct actgttactt gccctgcttt aggttacaca cagctttccc   2880
ctggattgct tctactagcc tcctatctac ccttgacctc ctggagtcca ttgtctacct   2940
aacagcctgt gtgcacctct aaaaacggag ggcagataat tgccacttct ctgctcgcag   3000
tccttcagtg aattcccatc tctttcaaag gaaatcccct gttctttcaa tgatgtgcaa   3060
ggccctacct tctctagccc ctatccctat ccctacccct taactttctg acctcagcat   3120
caaatatgct ccctagtcta tccatgttgt cttccttatt tctctttgaa catatcaact   3180
gtgcttctac cttaggattt ttgtagtttt acactttgct tggaatgcta atcctcaaaa   3240
tatgttatgc cttattccct tcatgtctac tcagctagca gagtattagt gagacctcct   3300
tgtcctccct gtatatagga tataataata gcctctcacc taatagcacg cctgttcctt   3360
cacccagctt tactttcgtt atagcagttt ttttgtttgt ttgttttgtt ttgttttgag   3420
acagagtctt tctgtcatcc aggctggagt gcagtggcgc agtcttggct cactgcaacc   3480
tctgcctctc aggctgaaac gatcctccca cctcagcctc cacagtagcc aggacttaca   3540
ggcacacacc accatgcctg gctacttttt atatttttag tagagacatg ggttttgtca   3600
tgttgcccag gcaggtctcg aactcctgag ctcaagcaat tcacctgcct tggtttccca   3660
aaatgctggg attacaggtg tgagccactg tgcctggccc atcatagcac ttttaccatt   3720
tagcatgtta tacaggttat ttttttgttg tggtgttcac tgctatgttc ctagggtcta   3780
gaaaggtaac taatagatac tgggtgcttt gttaatattt gttgattgaa tacatttcta   3840
atattcagtg cctttttctg ttgggaaatg taaaatgagc aggaatataa gaagtttaat   3900
aaattataaa tatttgtagt gttctccatt tcttcccttc agttctcttt taagaataaa   3960
tatccttgct tgctaacctc tggtgtccct tgttgagcag catgtcaata atgagttcct   4020
gctattggaa gcctcacagg ccaagttgat ataaagaagt atgaagaaag tatggagggg   4080
ttagtgggtt agtgagattg gaatctgtgg ctgagcccgt acatgatttt ggatgattaa   4140
ttaatgggct gtgtcgtaag acagaaaaga gatgagggag aagctttggg gtgtgaaacc   4200
aagaaatctg gagcgatact gtctgtgtgg agaaaattgt ggccaagatt ttttgctatt   4260
aaagatgtac ttaggccagg cgcagtggct cacacctgta atcccagcac tttgggaggc   4320
caaggaggga agatcatgag gtcagaagat ccgagaccat cctggctaac accgtgaaac   4380
tccgtctcta gtaaagatac aaaaaatcag ctgggcgtgg tggcacgcac ctgtagtccc   4440
atctactcag taggttgagg caggagaatt gcttgaaccc aggaggtgga ggttgcagtg   4500
agctgagatc gtgctattgc acttcagcct aggtgacaga gggagactct gtctcaataa   4560
ataaaaagat aaaaataaat aagaaaaaga ggtccttaat attttatatt aatgatatac   4620
ttgccccact ttttgttttt tctcttccta catttaagtc atttcactct ttgaagcact   4680
cttgtaggag ggtgatagga aaagtaaaac gattgaataa aaaataatct agaaatattt   4740
ccttagtagt tcctgtaagg cttgatgtgg aatagaaaac caatacacgg gccaggtgcg   4800
gtggctcaca tccgtaatcc cagcacattg ggaggctgag gtgggtggat catctgaggt   4860
tgggagttca agaccagcct gaccaacatg gagaaaccgc atctctacta aaaatatcaa   4920
attagctggg cgtagtggca catgcctata atcccagcta cttgggaggc tgaggcagga   4980
```

```
caatcgcttg aacctgagag gcggaggttg cagtgagctg agatcgcgcc attgcactcc   5040
agcctgggca acaagagcga aactctgtct caggggggaa aaaaaaaaaa gccagtacat   5100
gaattaaagt gtaagaatta tttgtgttta cacttcatgt aatttatttc caaatttatc   5160
tagataattg gaaattgacc tgcattttaa aatctgtagc caacagttaa tgttaaaaaa   5220
aaaagttccc ttccccaaat gcagttaaaa tctatgaact gctgtttgct atttgataat   5280
atacttgatc tgaatagtaa ttatacatta ttagattaca tgacttctta gaaatatgga   5340
atcaattttg actatagcaa aaagaaatta tacaaagctt gaaaataatt ttgttatttt   5400
ataaatgtgt aagcccctta atgtctatca gtagttactg atttattaga aatatcatgt   5460
ttttctctaa tattgcccag taaatttttt ttaaatttat ttccatcaga gttactaatt   5520
tagagtgtaa aatagcaaaa taagaaatat caaggaaaaa aggtatttct ggtaactttt   5580
tatctaaaat tgaccatttt gatacagaat ggtaacaagt catgcttagg gttaggaaat   5640
gtaactgtat tcactatact caatcctaaa aattgtgtaa tacctctatg ttcaaggagg   5700
tttaagttcg cctccctcat agacctctaa atgcagtgac tatgagaaat gtcataggag   5760
aggtacaaaa tatgtttgga gaatagaaaa ggaggaacaa ctgtttcatt gattcaagga   5820
aatttcctca aaaaaggtaa cattggagct agatattgat aaatttgttt aaacaaagac   5880
tttctgtttt ttaagctaaa agaaccaacg tatgcaaaag cagagagaaa catatgaaaa   5940
gagaactgtg ttttccagga atggagaaga tgagaatgtg gctagagtgt taggggtgca   6000
tagttctgag tagatggata ttaggccctt caggagattg acgccttttt ttttctttct   6060
ttcttttctt tttttttttt ttgtgagaca gagtttcact cttgtcgctc aagctggagt   6120
gtgatggtgt gatctcagct caccgcaacc tccacctccc aggttcaagc aattctcctg   6180
cctcagcctc ccgagtagct gggattacag gcatgtgcca ccacccccag ctaattttgt   6240
atttttagta gagatgggat ttctccatgt cggtcaggct ggtctcgaac tcctgacttc   6300
aggtgattcg cccgcctctg cctcccaaag cgctgggatt acaggcaaga ttgatgtctt   6360
aatgtgaagg gtcctttatg caagctagag gttttgaggt tccccctccc catcgagcct   6420
tgcagttcca ttaaaggatt ttaagcaagg gagtaataaa attcgttata tcattgaatg   6480
aataaaatag tcagactttt tatttgtagg agaaaaattg tattagatgt agccaaatat   6540
ggcttaagta atgcagtttt aaaattcaga attggaaaat tggtttatct ttgattaact   6600
ggttcatttt ttttcttcct aacttctttc ttctgtcagc caaaaaaaaa taggaaataa   6660
tggataagct agaagcagta tttgcttttt aagttttgca tgactgaaac aatcccctac   6720
actgttagaa gcctaacaca caatgctatt gtgctctggg tctagaaaaa atgtgaggcc   6780
tgctagtctg attttgcagc agggagtaag gaaagccaat acttaacttt gtaagctgct   6840
aaatattaaa tgtttagtaa aatggggttt atagtaatgt ttttttttgag acagagtctc   6900
actctgttgc caggctggag tacagtggct cagtctcggc tcactgcaac ctctgcctcc   6960
gggttcaagc ggttctcctt cctcagcctc ctgagtagct gggattagag gcgcctgcca   7020
ccacacccag ctaattttttg tatttttagt agagacgggg tttcaccacg ttggccaggc   7080
tggtgtcaat ctcctgacct ggtgatccgc ccgcctcagc ctcccaaagt gctgggaata   7140
caggcgttag ccaccgtgcc cggccagtaa tattttttct taaaaagaga atatcaaaat   7200
aaagaggaga gtcaggagta gagggtatca ccaagccttt tttagagtca cctaatttgt   7260
tacatgtttt tcttaaaatt accaaccatc aaaaagaaga attttgatct atatctatgc   7320
ctaagagatg tcagtagagc agtaaaaata tttctctaat ttataaggaa gttaagtaac   7380
```

tttcccacag tcaaaataat catgtcaaaa atttgacctt tcaaccacta gttttagtaa 7440
tccaccctgc tttttcctc agggaaaaaa aaaaatgtac ttcccagata aacatcacct 7500
tgcgtttcac cgcaggtctg ggtgatcctt accttggaac aaatgatagt gttggtgcat 7560
ttaaagtagc agcttttggg tgactggctg gtcctgagga gtttttccta cttagcagtg 7620
ttcattttat ctattaatgc cgtgaagcaa aatacaggtt gaatgagcag tgttggtaac 7680
tgcaaaacaa agtgttgcaa cacagtaggc tgaggtagtt ttaagcagat aaagtctaca 7740
gaaattagtt tacagaaata gtgttaggct gggatgtttt agctgctaga tttcagattt 7800
agagaaatca agtttagaaa aataaaccag caaagtagta caaaattaat agcaacaatg 7860
tcaggaagaa tttgcttatg aaaaggatct attttccctt ttgtgaagag aaacatttgt 7920
tcacccttgg ttacttgtga ttgagataat taaaaacaat tttatttggt tttagcagcc 7980
tccttgtgaa aacttatgaa atattaggca gtttgatttt cttctcctct ctggacctgc 8040
agataaattt gttgtgaata aatggaaaat agtttggcag tgggcagaag caagggaaaa 8100
gccaagaatc tggtcgattt ataaaccaga cattgtgaat aaatgagttg gctacagctc 8160
ttagaaaaag gcttttgcct ttcgagttct tttcctacat ctgcttttat ttctttcaca 8220
ctttatgaag tcaataaaaa ttttgatttc attgttacag aagtttctcc ttgtatagga 8280
gcttttcatg ccctctgttg gccataaata atttactttt gatttctcaa ggctcctaac 8340
tggtgacttt tcatataagg ggatgtctag gttgtttttg gtagtgatat tatctctttg 8400
tacccagaga acacttctga caccaaatgg ggggttttct tcacagcaac aaccagttct 8460
tcagctctac ctggagttag cgtcagatcc cataggtgaa acgctgagtc ccacaagact 8520
atccccactt tagatgccag tcacaagtcc caggcatccc gtagttctga ctgactcacc 8580
gtaaatcaga ggttcccatg aactcctcat cagatttaat aatttgctag attgggtcac 8640
agaactcagg aaagcacttt actgacattt gcttgtttat tataaaggat actatgaaga 8700
atatagatga acagccagat aaagagagat taatacataa ggtgaggtcc agaagattcc 8760
tgaacatggg tgctcctgtc ccatggggtt agggtaggcc accctccctg cacatggatg 8820
tattcaccaa cttggaagct ctctgatcct tgtcacttag aggtttcatc atgtagacgt 8880
gatcaattat taactcagtc tccaggcact ctccctctcc agaagttggg aggaataggt 8940
ctgaaagttc catgcttctg atcattactt ggtctttctg gcagccacct ccatcctgag 9000
gctacctagg gttacgccaa gagtcatttc atcaaaagag gcttctacca cccaggaagt 9060
gtcaagagat ttaagaactc tccgttagga acaaaagatg ctcctattat ccccaccact 9120
taggaaatta caagagtttt gtttttgaga cagggtctca ctgtgttgcc caggctggag 9180
tgcagtggtg caatctcagc tcactgcaag ctccgcctcc tgggttcatg ccattctcct 9240
gcctcagcct cccaagtagc tgggactaca gatgcccgcc accacgccca gctaattttt 9300
ttgtattttt agtagagacg gggtttcacc atcttagcca ggatggtctt gatctcctga 9360
cctcatgatc cgcccgcctc ggcctcccaa agtgctggga ttacaggtgt gagccaccgc 9420
acccagccgg aaattacaag agatttaagt gctgtccttt gtcagaaacc agagatcaag 9480
tatatatatt tttattatgt cacaaatgga ttctaaaatc agataatctt actattactt 9540
atctgtgaag aggacttcat actttgcaca gaagtatttg ctgtgactta aacaagagtc 9600
acatggtgct atgagcttaa ataattacta gtaaaatttg gccagagcca gcagccatgg 9660
cttatgtctg taatcccagc actttgggag tccgagatgg gtggatctcc tgaggtcagg 9720

```
atttcgagac cagcctggcc aacatggtga aacaaaaaat gtctctacaa aaaatgcaaa   9780
aatgagctgg gcgtggtggt gggtacctgt aatcccagct acttgggagc ctgaggcagg   9840
agaatcactt gaacctggga gggagaggtt gcagtgagcc gagatggtgc cactgcactc   9900
cagcctgggt gacaaagcaa gactctctca aaacaaagaa aattgttttt ggctgggtgc   9960
agtggctcat gcctgtaatc ccagcactct gggaggctga ggcaggtgga tcactttgaa  10020
ctcagtcgtt tgagaccagc ctggtcagta tggtgaaatc ccgtctctac aaaaaaatac  10080
aaaaatgagc cgggcgtggt ggctcacacc tgtggttcca gctactcagg aggctgaggc  10140
tagaggactg cttgagccag gaagtggagg ttgcagtgag ttgagatcgc accattgcac  10200
tccagcctgg tgacagaagg atactctgtc tccaaaaaaa aaaaattact attaaaatta  10260
gtcttcatgg tgttttggtg aactttagct taccagctga aaattatgga attcatttca  10320
tatagcttcc actataaata ctattttgat ccaagcctgt taataacact aagcatggtg  10380
actctcaacc atgactgcac agtgggattg cctgggaagc tttaacatac actgatacct  10440
gggtctcata tcccagagat tgacttaagt ggtttggggt gcaacccagg tattgcagtt  10500
ttctttctta aagttccaca ggtgattcta atgtagtcat ggttgagagc tactgacctt  10560
gagaagcatg attttttaga ggtggctaac ccgttctggt ctactggttt acatgcagta  10620
gagatagttg ggaagataa tttttgctta aaataggaaa gcaactgaca caatcgcatg  10680
gtaggcatgc agggtttaga acagtaagaa actgaagatt ataccatata acactgtgaa  10740
tttattaaat acattccaga gtgggttatc agccaagatg tgctagatca actgtgtatg  10800
gtgctgctaa tgagttcaca gaaacctaga ggtttttact tgcccaaggt cacaccacta  10860
gctggggaca caaccaaaac tggaaaatta tagtggtaat tcatagtttg ttgccttgat  10920
tatttaggtc aagttctgta aactttttct gtgaagggcc agattgtaaa cattttaggc  10980
tttgcaggcc atatggtccc tgttgcaact actcaactct actaacatag taaaaagcat  11040
catacacatt atgtaaatga atgaatgtgt attctagtaa aactttattg acagaagctg  11100
gatttggcct gtgacctgta ggctgcagat ccctgattga ggattgtttt aatcttccca  11160
ttggaaagtt ggctccttaa gagtaggctg aagatgttac tggtcccacg tggtgcctta  11220
cttcctggta ctgttacagt ggcctctgtt gcaaggtgtt agatgagtgc ttgttgaatt  11280
catatctatg cagctcttaa cgtttttctg ttgcttctaa cccttccagt aggggaaaca  11340
gttggcacat attccagctt tggagaggaa atgcttgaag tctgtagcag ggtataattg  11400
ctgaattctt caagcgaatt aaagatctga atttgctcta gggcattcat aattatttta  11460
atttcctgga acagattcta agaattcatt ttaaatctga aagtttttct taaaatctgt  11520
tttatgatac actgtcttta tttttgtgaa tattgttagt ttctcacaac aatatttatt  11580
tcagttcatt tggatctaag atctttgttg tacttatgtg tggccagtag actctttagc  11640
aaaattaaac aaatgctaat gggttcccac agccacccaa atattagaag tacagctcca  11700
gattatgagc ctgtttctct ttttcttttc ttcttctcat tattttaaag agatggagtc  11760
tcagtatgtt gcttaggctg gtctcaaact cctgggctga agccattctc ccgcctcagc  11820
cttccaagta gctgggatta caggcaggag ccaccacccc agacatgaac ccacttctaa  11880
tgcaaaacac atattgacct gacaacaggg ccctcagttg tggtggaaag agcagtgacc  11940
ttggaattaa aagccctgtt gtgactcgtg gctttgccac ttttaaccaa ccctactttt  12000
atttacctat aatgtgcagg tatctgtctc actctttagg gatgccaaag gtgaaatgag  12060
gtgtgctgtc tatgtgacag tgccttgtga gcacttttct gacttctccc tgaggaggtt  12120
```

tgggtcaggc ctagcagaaa ctgcagccat agagcatgga gggaagtagg acttgactag 12180
cataaagtga gtctatgaga gtgtgcccac tggtttccaa agagaatgtc gaagagtcta 12240
caatggtgag gcctcatcag cctcgatttg agaagcaaat gtaggtcaga aatggggagc 12300
agaacaagag gaaaagaaga aggtcaggag tgtgcagagc tgaagaggtg gtgagaagtg 12360
gttcaaagct ggaaacaggc aaggtaatct ggaattctgt cttgatgtct attgagttat 12420
cctaaatcaa gactcatgtt cctcttacct tatatttctt aaattgattt gtttgatgcc 12480
ctgggtattt tgaagctcct agctgcataa tcttgcctaa taaaggcaca gaattagggc 12540
aaatagctgc agtgacttgt gtacctgctc agtgaaagcc aaagaatcaa tagctagaat 12600
ctgtgtccac aaattgctta caaaccacat gtagatatga cattcaacat caggcaaggc 12660
tgggcacggt ggctcagatc tgtaattcca gcactttggg aggccaaggc aggaggatca 12720
ctagagttca ggagtttgag accagcctgg gcaagatgat gagactcagt ctctacaaaa 12780
atgaaaaaaa aaatagctga gtgtggtggc atacacctgt agtcccacct ccttgggagg 12840
ctgaggtgag aggatcactt gagcccagga gtttgaggtt gcagtgagat atggtcatgc 12900
cactatattc cagcctgtct gcatgtaaaa acaaaaaaata cacacacata cacacacacc 12960
ccagcctaac cacttaccac ctcttaatca tctgtataat ggacataaaa atgcctgcta 13020
tactttacat catagtattc ttgagtggag taaatgaaat aatgcatata aggtgctttg 13080
cacaatgtgt gcttgcctca caataaacac tcaatattat tagatatgat ttctaccatt 13140
attactaaca gtagtaagaa tagcagtagt atttaaaagc aagtttgcat tagttttaaa 13200
gcactatgaa atcccaagtc ttttttaaga cggagtctca ctttgttgcc caggctggag 13260
tgcagtggtg cagtctctgc tcactacaat ctccgcctcc cgggttcaag cgattctcct 13320
gcttcagcct cctgagtagc tctgattata ggtacccgcc accacaccca gctaattttt 13380
attttttagt agagacgggg ttttaccatg ttggccagac tggtctcaaa ctgctgacct 13440
caagtgatcc acctgcctcg gcctcccaaa gtgctaggat tacagggatg agccactgca 13500
cccggcctca agttatgatt gttaatattt ttgtgacatt caggataaat atttttttagt 13560 atgctactga aggacatgtc tcagcatcgg tgtatccctt cctgaagcta tatgttacct 13620
tgcatttaca gagttgactt ggtgtccaga gaacaaatca gttgagaaaa ggccattttg 13680
aaaacgattt tttccaggga gcatacgcta gtaccctgtt gcggcatcca tgtgtgaggg 13740
ggtggttgga ttatagatct tcaatgtgaa gtcaagtttc ttatcaaatg aagtgttttg 13800
tccgatctta gagtttaaac ccacaaggag gtaacaaagc aaagggctaa tatatctttt 13860
cgctacttag aactacaggc cagaaatttg cttttgtatt ctgagatctt atgatacttg 13920
tctcaatgaa ataaaactgc atgcattatt ctgcatttcc atattactat tctctgtatt 13980
ggtaattatt atgatacttg cttcctgtac ttaaagcagc atgcagattt attttataat 14040
cacttcaagg aaagaaccag ttcctttgga gatttcctgt ggttccaaag ttgcatgcct 14100
ccaagtctgt taggttgtgg gattttgcat ttgagagaaa tgagggaggt ggagagaatg 14160
aagagaaagt ggactggcag aattacagaa tgtggtttca tctgatcttt taggctgagg 14220
gctactccat ttgtagactc catgcataaa actcaggcat cctgggtcct gccctactgc 14280
tgctttgtgg tcagaacatc gtgagatcat gcagcctcaa ggctgggaac atacgggatc 14340
aggtccaaca gcaggttgga gtttgggttc atgatttcaa agtcagggtc gtgagggcac 14400
ccaagatgat taccgagaag tcaaaagcac gtgccagtaa tggcaatgtg aaggtctggg 14460

-continued

```
aaacagccaa aacgtagctg tcaggaatgt gggacagagt ccctagggca gcttttccca  14520
aaacatgttc caagatatac tagctctatg ggatgttgac ttacaataat atgtggtgaa  14580
aaggttttcc agacaaacac tgagttcaga gttaagcagg tttttttcta ttgcagagct  14640
tgtcagagcc tctgatatgc ccactagtat tgtaagtgta caagatgaag ctttaaaatt  14700
gggcaaataa cagatatttc atacagaatc ctggatgtgg ccaggagtga tgggagatga  14760
aggatcctct tgtcagagta gcactccaca gaacacactt ggggaaaagt tgtcccaggg  14820
cctgtggcat gtgctctgaa ttcattttcg cctggctctt aattctgggg ttcggaagga  14880
actggcaaac acccacagaa gttatctagg atcttattga gtgcttcccc ctcgtccttc  14940
catccgaatc acttggctga tatttgttgc tgctattaac agaattcagg aaatcagccc  15000
ttcttagagg aagaaggaca agtgagacca caaacaacaa aacataatga atggatcaga  15060
gcctgtgtat aattggccct gaattaggca aataggcttt ccccactccc ttaaaatgaa  15120
aacaaaatgg tagtttaaag aaagtaccaa agggactata tctaataata acaatgagat  15180
tgaaaatgag ggcacatggt gtgtttaggg acggctgagg ccagtgaatg tcaaggcaga  15240
ctgcatcttt gacagcctcg cctcactggc tcctgaaatc ctcacacaca aaacagcatt  15300
cttcttgtgt tcttaaagtg aaaggcactg tttccctgtc acactagcaa tgttgcgaag  15360
taaatgtcat cctttcctcc tccttggccc tgccttctac agctagtgcc cctgccagtt  15420
gtttcctcag cacgtctcca gcgttcctct tctcttcccc ctcggcacgg ccttacttct  15480
ggtctcatca tcctatgcct gggctgatgc ctttgcttcc cagctgcagt cggctgggga  15540
tgaatgtggg gttaaggcag gcattccaga tatttataga attgttcatg gttcttttcc  15600
cattagccat gagttacttg agggtgaaga tagtgtctta tttgtctctc tgtctctagt  15660
aattagccaa gtacctggca cttttaatta aggagttatc actcagtaca tttaaatagg  15720
gagaaaaaga aaaaaacaaa gaatggaata aagtaaaagc atgataggtt ttgttactct  15780
ttttgcagtt gatcattggc tattcttaat tcttatagac cagttagtac tttagcagca  15840
tacagataag atatattaaa atcatacact gagtttttaa aaagtagatg ggcatgagtg  15900
gtggctcatg cctgtaatcc catcactttg ggagggcgag gcagtaggat cgcttgagcc  15960
caagagttcg agaccagcct gggcaaaata gtgggacccc gtctctacaa aatatttttt  16020
aaaaattagc cgggtgtgat ggtgcacctg ccgtcctagc tgcttgtgag gctgaagtga  16080
gaggatcact tgagcctgta aggtcagagc tgcagtgagc catgacagtg ccactgcact  16140
ccagcctggg cgacagagca agacactgtc tcaaaaaaaa aaaaaaaaaa aaagaaagag  16200
acaaaaagtt cattagcact taaacatgct tttcagaaaa tgactaatta tcaaaaacta  16260
gcaattgtga tactagcaaa tgaagaaacg tcaaatggag aagaaatgaa aaacgttttt  16320
agaatccagg acacacattt acaagaatgt aaaatattgt gaaaataatt tggaggagaa  16380
ttatgattaa attatttgag acttgaatta cctgcagtaa attcagctgc gtatcggttg  16440
ttaggcattt tatcattact aatcctgtta ccatctttgt tgaataagag attcatactt  16500
gatatacaag gtccatacat ttgtaaataa ttcattatta tattagtttg caagagtcat  16560
gattttgcca gaatttatcc aaaatggtct attggtaatc ccagagagta gcagaggcat  16620
tgggcagtga agctaacagg cggtgctaaa gccagcatga gcaagtgctg ggtggtagga  16680
aaatagaact caggcagtag tgagggcaaa taggagcaga cagggcagac ctagaaggag  16740
acagcaagta agaggcttag gaggctggag gagcagagac taaggaacgc tcccctggca  16800
tcatgcagca ttattacata agtgttagta atttcaaata gttataacta ttttagatat  16860
```

accatgtgct agctactgtt gtagtatgct cactagaatt taatacttga atcctcacag 16920
caacctaggt ggatactatt atgaatccta tgaattttca tttatagatg acaaaattga 16980
agtacaggga aagtaagtca ttcacccagc tgatcatcag taaatggaaa agccatgatt 17040
tgacctcagg aaaatgaggg ttatttgaca gggctgactt gaagaatgtt tagattgctg 17100
tagaactgta tttagtgctt aacgatatat aataactgat acaattggta tccaaacagc 17160
cgaatgtcat gcttttaggg atcaaggaaa gttgcctaag tgtgcatgtg cctagcattt 17220
gagttttgat acggatgatc ataccagaaa aatataccat cagttttcag gcctatctgc 17280
acagtaatat gcgtggagtt cttcatgatg tattcactga tattaaagct caaaactatt 17340
atgaatctta ggctctggcg aaaaaatgtg atcgtttaaa aattcggcat ttatcttatc 17400
ctgtggaatg ggcaacttct caggcccatt tgtcaccacc aacaaagcag taacacgagg 17460
tgttttaata aatctgttgc ccagtctctt ccatattgct atgcttagct gtaaaagaag 17520
ggaccaagaa atgggtgtta agctgaattg gaaacaattt tcagataaag cacagcagtc 17580
tgcgaacctc ctccagctca agatggtgtc aactagaatt gccttttgta agcaggcaga 17640
aagagacaca tgtacttgat tgtggtttct ctttactccc actttccact ctggtcatcc 17700
ctgtagacac agagtaattt gtgtactgta aatagctaga tctttctgta atctttattt 17760
gtttctttgt ttgtttttttg agatggagtc tcacactgtc gcccaggctg gagtgcagtg 17820
gctcaatctc ggctcactgc aacctccacc tcctaggttc aagcgattct cctgcttcag 17880
cctcctgagt agctgggatt acaggcgccc gccgccatgc ccgactaatt tttgcatttt 17940
tttttttttt tttttttttt tgtagtagag acaatgtttc accatgttgg ctaggcttct 18000
ctcgaactcc tgacctcagg tgatccgcct gccttggcct ctcaaagtgc tgggattaca 18060
ggcgtgaacc accactctcg gctttaacca acattcttag ttgaacacag cagaaaggga 18120
aacctccatt agtacatgga actcgggcag tagtgagggc aaatatgagg gagagctgcc 18180
ttcctgttgc agtggtaagt tcagtctcta cctaagaaaa cagcatgcca aggtacagca 18240
gagcacactg gccagctcca atgcaagagt catcatggag tgtacctttt tttttttga 18300
cagagtttcg ctcttgttgc ctaggctgga gtgcaatggc gcgatcttgg ctcaccgcaa 18360
cctccacctc ctgggttcaa gcgattctcc tacctcagcc tcttgagtag ctgggattac 18420
aggcatgcgc caccacgcct ggctaatttt tttttttttt tttttttgta tttttagtag 18480
agacagggtt tctccatgtt ggtcaggctg gtctcaaact ccctacctca ggtgatccac 18540
ccgcctcggc ctcccaaagt gctgggatta caagcatgag ccactgcacc tggccggagt 18600
atgcactttt aacatgtcta tgcagggaca catgtcctct aacaacaaat ggccatcccg 18660
agagtggtgg agcagagtgt tggacctctg gagcccaaat ttttattgta gcaatacaca 18720
gtcttcttat aacaggcact gtggccatgg gtcttatcag ctcctattca aaattggaat 18780
taggacaagt atagcaggtt gtgttctaac agaattctaa cttttaaggt gccacagaca 18840
ataatattct ttagaaatct tagtgttatc ctttttatcc tttcagggta gcaaacaaaa 18900
ggcactcagt aaataattat ggagtataat ttggggaaaa caaaatattt ctagtctgaa 18960
aattattgtt ttaaaaatta tttttgtctt gagaggctgt acatttctgt caactgcgtg 19020
gccacattgt tgatatgctt aagaaagata acagtcaaag ttgccttttt acactttgta 19080
tttgtgctca tccaaccatg agacctttaa aaatattgaa tatctgtagt tatctccctt 19140
caagtcttat tttgagttta tattaccttt gaactcaaaa gatctcaagc catttgcttt 19200
acctgacagt atgacattct ttaattttag gtagcattgt atgatgagtc tcaaatattg 19260
gcagcctata atgcatataa gttagtgatc ctagtaaatg taaataaaat aataaacaga 19320
aacatgctgg gcatggtggc ttatgcctgt aattccgtaa ctttgggagg ctgaggcagg 19380
aggattgctt cacaccagga gttagagacc agcttgggca acagaaaccc caatttttaa 19440
aaaatcagct gaacgtggtg gtgcatgcct gtagtcacag ctactcagga ggctgaggtg 19500
ggaggatcac ttgagctcag attgaggctg cagtgagttg tgagtgcacc tcagtctagg 19560
tggcagagtg aggtcctgtc tcaaaaacat aatgataaat gaaaataata acagaaacat 19620
tcagtcaata actgggattt ttttttactg ttactatttt ttatcaagac aaacatctgg 19680
agagttctac aattccagat gcttaccaat ctgcttctgg gttgtgaaaa aattatttgg 19740
gtatgtatag cttttaactt tttttttgtt tgttttaact gaatattgag gattttggta 19800
gaataacttt gaatgttttg gattttagat ttaaatggaa atatcaaatt ttatataggt 19860
tgggctctag atatttccat attgtcagaa tttagaaaac atcttttatg aaatagaaac 19920
taagaatttt ggcaaacaga gaaagttgcc caaggtctcc agaattcatt tgtttgacaa 19980
atacatattg agcatctacc ctgtgacagg tggtattcct gggatttgtc aggagcacaa 20040
ttgctgcctt cctggagctt acattctaac cagggaaaac tgacaataaa caataaaaaa 20100
agtaagtaaa taatgtagtt tgttagaaag ccataggtgc tacagaaaaa aataaactat 20160
aaagtagggg tcggactagc aataaaacta aatagtgtgg tcagggtagt ccatgtggac 20220
aagatgcaat ttgagccaag atttaaaaaa gataaagcaa ttagcctcaa aataatcggg 20280
gggaagaact ttccagcacc aagtagtttg ctcggcctgt tggaggaata gcaaggagcc 20340
agtgtgcctg gaatggaatg cccaaggggc aatagtggcc ataaggtaaa agtggtaatg 20400
gggctaaggc cagatcctat agagcttaca aactactgca aagaacttga gattttactc 20460
tcagtagaat gtggatccat tggagaattt taagcacagg atctgacttg ggttttaaaa 20520
gggtctctct ggtcctggtt tgacaatatg gactgcactg ggaacaaggg aaggagcagg 20580
ggtcttactg ctgtaattca gttaaaaatt atggtagttt aggctggaat agtagcacca 20640
gagatagtgc tagatggtaa aatctggaaa tattttgaaa gtagagccac caggatttcc 20700
tggtgaatag gatgtagagt atgagagaaa aagaggattt ggggtgtttc caaggtttta 20760
gcctgtgcat aaatggagtt attactattg attcagagaa aaccttaagg cagctacttt 20820
tagataagag ttgggtgatg aggggttcag atatgaatct gttgatagtg agatggctct 20880
tagacatact ggggaagatg ctggtaggca actgcatgtg taaatctgga gacgggtgag 20940
gtctgcagta gagatttaag tgtaggataa tctcaacatg tggaaggcat ggaagtgtgg 21000
gtgcaagtgg gagacgagaa ccaagcacta atccaagtgc acttcaatat ttaattttaa 21060
gagacaaggt cttttttttt ttttttttt cgagatggag tctcgctctg tcacccaggc 21120
tgaagtgcag tggcgccatc tcggctcact gcaagctccg cctcccggtt tcacgccatt 21180
ctcctgcctc agcctcccga gtagctggga ccacaggcgc ccaccaccac gcccggctaa 21240
tttttgtatt tttggtagag acggggtttc accgtgttag ccaggatggt ctcgatctcc 21300
tgacctcatg attcacctgc ctcagcctcc caaagtgcta ggattacagg cgtgagccac 21360
tgcgcccagc cgagacaagg tctttcactc tgttacagct ggagcacagt ggtgcaatca 21420
caggtcactg caatctcaaa ctcctgggct caagtaatct tcccaagtag ctaagactat 21480
aggtgtgcac caccatgccc agctaatttt tttttttact ttttgtagag atagtgtctt 21540
gctgtgttgc cgaagctagt ctcaaactct tatcttaagc agtcctctct ccgtggcgtc 21600
cctaagtgct gggattacag gcatgagcca tcatgcctgg ccaggcactt taattttaaa 21660
gagcctttaa tatggtttct tgccatgtca gagataagaa cagcttaata tttcttgact 21720
tttccttggt taaacaaggg gtatgcttta aaattttttt taattttaat tgtggtaaaa 21780
ggtacttaaa atttgccatc atagccattt ttaaatgtac atttcactgt cattaaatac 21840
attcaccact atcatccaca gaactcttca tcttgcaaaa ctgaattctg cacccactaa 21900
acaataactc ccttttcttc ttcctcccag gtcctcaaaa ccttcattcc attttctgtt 21960
tctatgattt taaagtggaa ttatacagta tttctctttt tgtaactggc ttatttcact 22020
tagcattatg tatgtcctca agattcatcc atgctgtagc atatgataga atttcctgct 22080
gggcgcagtg gctcacacct gtaatcccag cactttggga ggccaaggtg ggtggatcac 22140
ctgaagtcag gagttcgaga ccagcctggc cgacgtggtg aaaccctgtc tctactaaaa 22200
aatacaaaaa ttagctgcac atggtggtgg gcgacacagc ctcccaaagt gttgggatta 22260
caggtgtgag ctgctgcgcc aggcctgctt ctactctttg actattgtga attaatgctg 22320
ctgtgaacat ggatgtacaa atgtaaggga tatgttttttg tttttgttt ttaagatgga 22380
gtctcactct gtcacctagg ctggtgtgca gtggcacagt cttggctcac tgcaacctcc 22440
gcctcccgga ttcaagcaat tctcccacct cagtctcctg agtagctgag attacaggta 22500
cccaccatca tgaccagcta ctttttgtat ttttagtaga aactgggttt caccatgttt 22560
cccaggctgg tcttgaactc ctgacctcag gtgatctgcc cgcctcaccc tcccaaagtg 22620
ttgggattac aggcctgcgc cacgatgccc agcagggata tgcttttttta aaagtctctg 22680
tgatatgtat acttggtgac tttcatagat ttttaaaaat ataagtgata tataaataca 22740
tttttattat aaaagattta aatgatatag ctgttaacag accaaaatat gaaaattctc 22800
attcattctc tcacctcacc tccatctgca attcccaaag ttacatttgg tgtgctatct 22860
tccctctctt tcagtacatt tctatacatt tgtctataac ttattctttt taaaaactga 22920
gatattatac atattctaca gtttaataat gtcttggaga cctctcaatt atttatattt 22980
tggaaatatt cccagtctgc tgcatatgtt ctatagtgtt atatttacct ttacatgtac 23040
agggctatta ctgtagatta gagtcctaga agtgcatgca gttcctaggt ccaaggaact 23100
ttctttaact cttcatcaga ttttcttttt gaagaacctt tgtggcttga taattatgtt 23160
tctagaaaat ttattattca ggtttagaag tttggggagc tgtttgaaat aacactcaaa 23220
taaatttcct ggctatggat ttgttcccca tagcaagaga gttgtaaact atgagtttta 23280
taaccttaat gtcttttttt taaaaaaggc aattgatctc ttaatctagg tgttttagct 23340
agcatatggg agatgtaatc tgcaatctat gggacaaatg ggggagtttt gggagttatg 23400
atagaagact gttgaaaaat gttttataat aatgttttac agtagagaaa cctggtagat 23460
gccacctcat cagccgacca gggttaacat cacatgataa tcatattgct atcatgcagt 23520
gatattaata taataaagtg agatgggtgc attgcctctg tgatattctt accccaaacc 23580
cataaccaca gtctcataat gagaaaataa cagaaaccca atttgaggga cattccacaa 23640
aatacctgac catgttcttc aaaagtgcta tggtgccaaa agtcatgcaa gacaaatcta 23700
agtaattctc acaggttgta gtacactaag gagacagtga aaactaaatg caaataaagt 23760
ggtttttggt tttttaaagt atgtttatcc ttatggacaa tatgctccca taaagatcgt 23820
ctaccctaga aaactgtgtc ttccctctta aatccaagag atgcttgtcc caaagggtgg 23880
accccattga gatctcctgg gctagagacc cagtgcatgg atggatgaga cagtataagc 23940
aagaccgtat aaagctgtga tctgagctca tggacactgt ggtaagaggt caggctcgaa 24000
gaatcagaga actgagtgga ttttgcaatg gatagccaaa gagagggtcc aaacttaaaa 24060
tgcgaaacaa taattcaaga atgatttggt aaaatgtaat ataacagcct ataacagagt 24120
ctagcaaata gtagccaaaa gtcaccctaa ccaatcgtag ggcatatcta ccacacaaaa 24180
gtgtgactta gcgcatgact gtttaaatgc caaaaaagac agataaagga aagttaagcc 24240
atagtggcaa cctctgcagt tggaacgagg gagctatatc agtcaacagt gaggctaatt 24300
gagaatattt gaggttggcg tatgtctagg gattcctata ggagatacaa cccagcaagc 24360
ataggtcagc aacccaaggt cagagtacaa aatgggttaa tactaaaaag tggttaaaaa 24420
gatgaccagt cctcaagagg agatagtatt taaatcggat acctctcctt ccccatgcta 24480
actaacatac tgtaatttgt tatggctgtt tctaaggtaa ctgtttataa ttataaatca 24540
gccctactgg ttcttcttga tattgtaatt tgcaatcaaa gaacctctag agttaatgta 24600
aaacttcttg aatgagagac catctggtta caattttggt ttcaattccc tgttaggcaa 24660
ctgacaccca aataaggact gtttccaaat atgagtaggc taagtcagtc ataaacaaac 24720
aaaaagtttc agtttttgtt gctattatcc aagatgttag cagatgaagt gtttaatgaa 24780
agggtgcttc ttttaggcaa acttctttta ccatgatttg tttaacctat accagtggtc 24840
cgtacatttt tttcctgtaa agggccaaat aattattaat agtattttta gccttgcagc 24900
cacgtatgat ctctatgtat ttgtcattgc ctttttgttt ttttaaacaa atgtttaaaa 24960
atgtaaatgt tctctgtgtc cttcaccatg ttttcatgct ttgtgatagt ggctgaaatt 25020
tagagacttg ttttaataaa caatgttctg aaatgttgat ctaattgcct ctggcaaaag 25080
atgtgtaatc atgactttga tgaacttatt ttaaaaatag atgcacagtt gatctcttat 25140
tgcacgcatt ttggcacatt cgtgggagat attctctgta aacatgacac ttgcgaaacc 25200
taccataccc tgaaagtttg ctgtctagaa attaagtgcc tagttttcat tcaaattaat 25260
atttaggtaa gacatgtttt atttctaaat agactgtcaa acatttttca tattttaatg 25320
tgtaatggtg atgacctttt taaaaagact caacgtaatt tgttttctca tttaacccat 25380
taactgcccc ctttgtgtag tattgttgct gctttctctt ataaattgat gatgtctcag 25440
ggtctcaatt tacaattaca ttagtttctt cctctagttt gtagttgagc tgtggctctg 25500
cactgttggg gcctgtacag ccatccttca ctagaccccg ggaggtggcc tttagtaggc 25560
tcaaaggtgg cctttaagcc attcttagta tcactgtgaa aaagcatcca gattttcccc 25620
ctgaaaggcc aagtggttgc atgatgtgtt gtggatttta gggatatact ttgcctattt 25680
cacatacttt tttccaagaa gatagataag cttacacatg taaaggtttc aactgtattt 25740
cttctgttta taattttatt tattttgaga tggtgtctcg ctctgtcact catttggag 25800
tgcagcgcaa tggtgtgatc acggctcact gtggcctcaa actcccaggt ttaagccatc 25860
ctcgcacctc ggccttctaa gtagctggga ctacagatgt atgccaccac acccagttaa 25920
tgttttttgt atttttttga agagacagga ttttgccatg gctgcctacc tggtctcaaa 25980
ctcctgggct taagtgatct gcctgcctca gcctcgcaaa gtgttgagat tacgtgagcc 26040
actgcaccca gcctttttat aattttaata ataatctgtc aatctttcat tacttttgcc 26100
ttctaaattc ttgttatatt ttactaaaca atgcttaatc tcgctgataa accattttag 26160
cagaagtatg tctgatgagg accaccccctg cctttttttt tcttttctca gagttgcaag 26220
gtctccctct gttgaccagg ctggagtgca gtggtgtgat tatagctcac tgcttcctca 26280
acctcctggg ctcaagagat cctctcacct caacctcccc agtagctggg accacaagcg 26340

```
cgcaccacca tgcccagcta atttttattt tttttaagta aaggcagggt cttatgttgc  26400
ccaggctggt ctcaaattcc tagcgtcatt taatttctgt tttggtattg gctctgaaag  26460
aactgttgag acaatacttg gaactcttga tattttccaa aatctgtttt accaagataa  26520
attttaagga gagcaacaga aaataaagca gaaatgtggt ttctttgttg ggttttgttt  26580
tttttttttt tttttttttt tttgagatgg agtttcactc ttgttgccca ggctggagtg  26640
caatggtgcg atctcagctc actgcaacct ccccccatcc tgggttcagg tgattctcct  26700
gtctcaccct cctgagtagc taggattaca ggcgcccacc accacatctg gctaattttt  26760
gtatttttag tagagacggg gttttaccat gttggccagg ctggtcttga actcctgacc  26820
tcaggtgatc cacccgcctt ggcctcccag agtgctggga ttacaggcat gagccaccgc  26880
acctggccca aatgtggttt ctaatcaata ttatttaata atgaattgga ttaagaattt  26940
tttgggtttt ttttactcaa tagaaagttg attgggtttt ttaaaaatag cttgttttca  27000
ataattaagg cttaaaaaaa tctctgagtt ctctttgaga tatttggatt ctataaaaaa  27060
tgaaactctt tgtttcttaa ccaaatgata attccttaaa ttgcattctt tgattcaatt  27120
atactgaatt tcctggtaga aattttattt tctctgaagc agagtcagtg gtcttaatat  27180
caccatgtca accagaagag aaggaaatct aatatgcata atagagaaca ctgacacatg  27240
acttctttaa aagtctctga aattcaacat ataacttttt ataccagaaa gtgaacaaac  27300
atttaatcct tcctcttcat ctatgtctca tgatgtattt gtgtgatttt aaagaacatt  27360
ttggagtttt tgagttctat ataaatgtga ccatgttatc tgtataatct tgccatcctt  27420
tctttggaaa acatgggtca ccgttagcgt atgtcatgga tgttgatgtg gagtctgagt  27480
aagctagtgg gcgagagggt gtgtgtgtgg acgtgggcgc atgtgtgtat ttgttagttt  27540
caaatcgagc cattcttcta gagtctttag gtcagctgtc acgttgggct ttcctccttt  27600
gttcttttga gttgctctgt gactagccac agacccaaca ctaaaaagga aggcttttaa  27660
cggattaatt ccgtcctttc cttcgcctac attgtagcag ctgcgttctg ccctttctgt  27720
ggccctgcaa ggagaggagg cctgtgtata acagtcttct gtcaacatcc attataagat  27780
tcctaaagca catggaatga gatagttccc aggaaaactc tttgtcaagg ccagcccatg  27840
tgggaaaagt gtttctatgc ttagtcttgt aactatgact gtttttgttt tatggggtca  27900
ggggaaattt aacttatttt atttttcttt tttattgatc attcttgggt gtttctcgca  27960
gagggggatt tggcagggtc ataggacaat agtggaggga aggtcagcag ataaacaagt  28020
gaacaaaggt ctctggtttt cctaggcaga ggaccctgcg gccttccgca gtgtttgtgt  28080
ccctgggtac ttgagattag ggagtggtga tgattcttaa cgagcatgct gccttcaagc  28140
tctgtttaac aaagcacatc ctgcaccgcc cttaatccat ttaaccctga gtggacacag  28200
cacatgtttc agagagcaca gggttggggg taaaaggtca ccgatcaaca ggatcccaag  28260
gcagaagaat ttttcttagt acagaacaaa atgaaaagtc tcccatgtct acttctttct  28320
acacagacac ggcaaccatc cgacttctca atcttttccc cacctttccc ccctttctat  28380
tccacaaaac cgccattgtc atcccggccc gttctcaatg agctgttggg tacacctccc  28440
agacggggtg gtggccgggc agaggggctt ctcacatccc agtaggggcg gccgggcaga  28500
ggtgcccctc acctcccgga cggggcggct ggccgggcgg ggggctgaca cccccacctc  28560
cctcccggac ggggcggctg gccgggcggg gggctgaccc cccccacctc cctcccggac  28620
gggacggctg gcctggcggg ggctgacccc cacctccctc ccggatgggg tggctgccgg  28680
```

gcggagacgc tcctcacttc ccagaggggg tggctgccgg gcagaggggc tcctcacttc 28740
tcagacgggg cggttgccag gcggagggtc tcctcacttc tcagacgggg cggccgggca 28800
gagacgctcc tcacctccca gacggggtcg cggccgggca ggggcgctcc tcacatccca 28860
gacggggtgg cggggcagag gtgctcccca catctcagac gatgggcggc cgggcagaga 28920
cgctcctcag ttcctagatg ggatggcggc cgggaagagg cactcctcac ttcctagatg 28980
agatggcggc caggcagaga cactcctcac tttccagact gggcagccag gcagaggggc 29040
tcctcacgtc ccagacgatg ggcagccggg cagagacgct cctcacttcc cagacggggt 29100
ggcggccggg cagaggctgc aatctcggca ctttgggagg ccaaggcagg cggctgggag 29160
gtggaggttg tagcgagccg cgatcacgcc actgcactcc agcctgggca ccattgagca 29220
ctgagtgaac cagactccat ctgcaatccc ggcacctcgg gaggccgagg ctggcggatc 29280
actcgcggtt aggagctgga gaccagccca gccaacccag cgaaaccccg tctccaccaa 29340
aaaagtacga aaaccaatca ggcatggcgg cgcgggcatg taatcgcagg cactcggcag 29400
gctgaggcag gagaatcagg cagggaggtt gcagtgagcc gagatggcag cagtacagtc 29460
cagcttcggc tcggcatcag agggagaccg tggaaagaga gggagaccgt ggaaagggga 29520
gagggagagg gagggggagg gggagggaga gggagtggga gaggggaaat ttaacttata 29580
aggcagtatt gtgatatgcc tccatactta cctgcccttt ctttctgaac tcttgcagg 29639

<210> SEQ ID NO 204
<211> LENGTH: 8716
<212> TYPE: DNA
<213> ORGANISM: homo sapiens
<220> FEATURE:
<223> OTHER INFORMATION: TSPAN14

<400> SEQUENCE: 204
gtgagtagag cgcggagacc tggctggggc gtcgggccct gcccctttct ttgtctgagg 60
ccgacttccc cgagcgttct ccgggggcga gggctgctcc ttaggtccct gtttggcccc 120
tcagcctccc tccccgcctg cccaggagcg gccccgcggg cggcgctggc tttgtctgcc 180
aggattgctc gctagaggtt ggaggcctcc gccgggaccc cgctgagccg aactccggcg 240
ccgcgcggac gagagccgcg gcgggcccgg ggccggcact cctggttcgg tagccctcgc 300
cccatcagcg cgcccccggcg agtgcgcgcc cgtgccgggc ggggtgaggg cgacgggagc 360
ctggacggcc gctgctgctc ggggctctgc ttctcgtccc cagcagcgag ctcggggatg 420
ggccaccctt tcggctcagt cacccaccct cggctcccag gagatcgggt ccggggtggg 480
ggtgggcgta ggccggggcg ggccgcccct tcctcctgcc ccgccgtggt tgtgctcagt 540
ctcccacgcc gccgtgggtc ccactctgcc cggcttgggt ttgggacggc cggagtttga 600
gtaggcggtg acccagcttc tccgcgttag tcgtgtgggg ttgtgtttgg gagcaaagcc 660
tgacccctga cctagccgga gttctggtag agtgaggttt gtggctgcgg actgtgcttg 720
tcccgggccg ctgctgcttc tcctccaccc ccaggggtgg ggtgcgggtg ggtaggaagt 780
gcctgtgtga gggtgtgtgg agggactttg gccctgggac cgcaggagca cttgtcttgg 840
ggacttaaag ttgatctccg gcgagaaaca gtccgtgcta gggggagtcg ggggaagtcg 900
tgggcccggg tactggcctg gggctgggcg cagagcggtg gtgagtgcgg cggtgtcaca 960
cactcgttgg ctgtgctggc gctgctatcc gggaggtcag gcggtgctgg gcggctgtgc 1020
agagcattgt attggagcct ctgcaggtgt gctcttggca gtggtctgct ctccagggga 1080
tcttcctccc ttccgagagg gagttgctct tgggctagtg agagagtggc ctgccaaatc 1140

```
ctcaaaagta gccttcccct tgccccttga ccttgaagtc cagaagcagt tagtgcctgc   1200
tgagtgctcc ggccacccctt ctctatttgt gaagggaaac ctggggacag gccatcggag   1260
caccccctatg tccttgccac atttcagcta gccgagtggt tggtgggggc ggccgtcttt   1320
ccagggatct tcctgggccc tggcaccccc agaatgaagc ccagactcca ccataatggc   1380
cctgtatgcc cttctatccc cttagctgct ggtgtgatca tagcctcaaa ttgctgggct   1440
caagtgatcc tcccacctca gcctcccaaa gcacagggat tacaggtgtg agccaccacg   1500
cgcagtctga tcccactccg atccctaacg ttatagtgac aggccctgga aacccagggc   1560
caccagatgt attttccctt tccttctcat tgtgttgcac cccaacttca gttggagact   1620
ctggatatat ccatccccac atctctgaac tccactgctt gggccaccta atgtcatcct   1680
cagtttagtt aacaaagcat ggttgagatt tctgtggggt gcgaggcatt gttgcaggca   1740
ctattccaag tctggaaagt ccctcaccag ctatgaactt ggtgtggtct tagaacccag   1800
gctggacatg gcataggtgc tcagtagtgt ttattgatct gagcttgatc tcagcgtagc   1860
aggatcattt agggagacgg ggttgtgggg ggggtctgag cccatgggtg cttctgaagg   1920
tttgtggctg ccccaggaag aaagggcatg gagctgcaga atggttggct gcccagggaa   1980
ttgtcccctt caccagctgg gcagctgtgc tagtctctga ggactggtga aggtccttct   2040
catgtaggaa gtggcagtat gaagtgggag aggagatggc tctgccctga aggttgtggc   2100
ggcagtgaag tgaagttccc atggaggccg gggagcagga aagccctggg ttctggaact   2160
atttcctgag gcctcactct atgccaccat gtgctcagga atttgaccca tttaacttca   2220
actgaggtag aattcctttt agcagtgcct gcaaagtggc attgtgccag gcctgggaaa   2280
cctttgctgg cttaaaattt agtgaaggac aagattattt catagtgata ctaatgtgag   2340
tttattgaga cttacaccct agaagtttga cttgtaataa ctcatttaat ccttgaaaac   2400
agctgtgatg gctgggcgtg atggctcatg cctgtaatcc cagcactttg ggaggccgag   2460
gtgggtggat cacctgaggt caggagttca agaccagcct gaccaacacg gtgaaaccct   2520
gtctctacga aaaatacaaa attagctggg cgtggtggca catgcctata atcccagcta   2580
cttgggaggc tgaggcagga gaattgcttc aatctgggag gtggaggttg cagtgagctg   2640
agatcgcgcc gttgcactcc agcctgggca acaagaatga aactccatct caaaaaaacaa   2700
aaaacaaaaa gcaaaacaac cgtgatgtca acagctccat tttacagatg aggaaactgt   2760
ggtcccgaga ggtcacagag taacttgctt gaagtctcaa tatgagctgg gttttctcat   2820
ttcttttttt ttgatactga gtctcactct attgcccagg ctggagtgca gtggcgtgat   2880
ctcggctcac tgcaacctcc gcctcctggg ttcaagtgat tcttctcctg cctcagcctc   2940
ccaagtagct tggactacag gtgtgcacca ccacacccag ctaatttttg tatttttagt   3000
agagatgggg tttcaccatg ttggccaggc tggtcttgaa ctcctgacct caagtgatcc   3060
gcccgcctcg gcctcccaaa gtgctgggat tacaggcgtg agccactgtg ccggaccagg   3120
ttttctcatt tctaatttag acaatatgtt cctctcagag gtgattaaaa tggattcata   3180
taccaaacaa gcctggccca cagtggaact aatgaatgtt ttcagtgaag gtgcccttgt   3240
atccctgcct ctgaacacat ctcatctgtc cagcacagcc tgggcacata gcaggtaccc   3300
cggaaccccc gctgattggt gatggagctt ctgtctccct aaggccaggg aatgggaaga   3360
ccagcactac cacatgcaga agattgggga gtcactgctt gtgtctgtct ggacagatca   3420
cggtttgctg tggtaacagc aatccccagg tctcagaggc ttaaagcaac agaggtttat   3480
```

ttcttgttca cactgcatgt tcatcactta tctgctttat gttgtcctca ctggggggac 3540
ccatagtgat tagtgggaac acccctggtg gcttggacag agggacagag aacatgatga 3600
tccctgtgtc ctgccactga gtcctggtgg cctttaagat gcctatggga aggggattag 3660
gttcctgctg cctgtctctg ccctgccgtg tcagtccttg gatatcttgc atgttccatc 3720
cgctacctgg atgtggcctg taggggcagc cacctttcct agaagcagga gcaggtagcg 3780
atacccaggc aggcctggtc ctccccactt ttgtgggact cggggattga gcttgcaggc 3840
ataggggtgt agaaagcagt ggtagcgagg tgactgaagg tggactccca ctggggatgg 3900
gattgagtgt ggggctagat ccctggtctg tagaagggag taggaaccct gttagttaaa 3960
ttttccccct caggccacgt tagtaggatt ttgaagagtc agccacactg tggctcttga 4020
ttttgtgcct ggtcacctgc ttggtctctg gtgatttccc tcggggccag cagacactgt 4080
tggaggtggt gaggcctcag gttcttctgc ttcatggtta actcactctg cttaggcata 4140
tttccacctt ttccagggcc tccgtttttc tgccagtgga ttgagaggtg gtggtggtct 4200
ccagcagtgg tctcactctt ggcaggctat cagagtaccc agggagctgc gtagaatgaa 4260
gttttgagag tctttggtct aggtgaatgc cagcgtttca gtttgcttat cttccattat 4320
agtagtgtcc tctgtaactg tgaatcaggg aggttattca taatatctcc acatccattt 4380
tctcccttaa ttgcgtatgc ttttgattta gacagggcaa gtagccattt tggtggagcg 4440
caggccctgg caggggggca gtgtccagtg ccgctctcaa ttaaacgtga agatgtgaag 4500
atgaataaca ctgtccagct tgcagagtgg acggtggtga ggcaagcttt caagttgcac 4560
ctactttcta gttgagtgac ctacacaagt ctttgatttt tttttttttt cttcctggaa 4620
aaaaaaagtt gtctactttt ctcatctgta aagtgagaag aatcaagtct gccttttctg 4680
tctcacgggg ttgcagtgaa gcattagtac cctgagaagc aagatccaaa gcccctgagt 4740
taggcctgac actggtgtga gacagctgcc atctctggcg gcactcagca agtgttcacc 4800
agcagctgat tctgggaacc tcacttcctc cgcccttggg cttggtgggg ttgggtaggg 4860
ttgggtgggg ctgtggtttt cttttaggag gcagcaggcc aggcctggag accagagctt 4920
aagtgggcct gggcaggctg gggttgaaac tcttcacccc ttgcggtctg tactgcctcc 4980
caactgagca gccagggaga aggcctagag cctgtgcctt tcagctagat agctggagga 5040
actggctcct ccctccttag gctgtgctgg cctgagctgg gagcctgaga gctggggcag 5100
ttgtctctaa agtggcttct gggattctgg taagaggtga gctcctggtg ctgcctcaga 5160
gtctttgtgt ttcctggcat ttgggagagc tggagttggg ctgtcctgca tgggtaaggt 5220
ttggggaggg actggaacaa ggggctagtg aaccttctct gggtttttcc tgcctgacta 5280
tgcgttgaca gtcccagctg ttgggcctgt gctcctgtac actgcacggc cttgagagga 5340
gttcggagcc ctaacatcca ggagagaggc cccacagcag tggaaggaaa tgggcctctc 5400
ccgaatctct tgtttgtacc ccgaggtctg agtggtgatc ctggggatgc tatgggactc 5460
tcagcagtag gagtgtgtct gtccccagtc tgggtgccca ccagctgtgc tgagggtcct 5520
ctcctgtgtc cctgggccag gcagacaggg tctttttctg gggcttgtta ggggaggtca 5580
gccacagccc cagaccaagt aatttacaca ccctgagtga ggggtgggag cagtgggtcc 5640
aggaagactt agggagctgg tgaaagaaaa acttaattct gacacttgtt aaactggtaa 5700
ggtagactgt atcaggacta ttacgataga tgtaggaatt atcgcaatgg attttgcagt 5760
agaggggaga gagtgggcca actccaaata caacaaagaa aagtgggaac ttatagccaa 5820
ggagcggagt gtgggggctc ctgaaaattt ctaagagggt agggaaattt ttactaaact 5880

```
tagctaactg aattcttgct gcaggcaggc cagggtgatc aggttttacc tgggagatag   5940
tacaggatga gaaatacgtt cagatatcca gggtgattag atattgaggt tgggggattc   6000
tggttaacag gagttttgct aaaactaggc tcttagagag aatggagtta ggaaccctag   6060
gtcaggacca gatgagtaga gggctcagag gaataaagtt tggtgaggga cagaatctct   6120
gtcagtatcc cgtggttggc agtgtcctgt ccattcttct tgcactggcc tgtccctcag   6180
gagacaggtg tgagtggtcc tgagcttggg ccagtgtaag agtaggggac aggtttctct   6240
ccttgtaggt gtcccttctt gtaagtgtca ctctcttttt ttccagaaac cttggtcctt   6300
ttcagcatct gctggcccct tgtcccttgg ctcccttgct cttggcctgc tggatttccc   6360
ctctgcaccc aggaaatcgc atggacctgg gtccttgttt ccctacagcc caccaatttt   6420
gctgcttttt tctgcccccct gaagctgagc tcctgctgca atttgtgttc cctgctctcc   6480
ctgtcctggg caaaccagtc tgacaacttt gtggttctcg ctcccgcctc catcagcctg   6540
gggattgact gtcccatttg tctgagctgg gcagagggag gtgctgtggg ggatctcttc   6600
ctcttgcctg gactgcacac tcctgctgcc ttctagccgg agctcctggg cattttgcct   6660
atgggagctt caccagcttc cttctgtctg aggcctacaa gtccctgcct ccagcctacc   6720
ttgttcctcc tccatgagtg aggctcctcc ttttctctct ggccctcctg tctacttgat   6780
cagactctgc ctctcttgag ggccggctcc ctccagccta ccctgcacag gtgaccctgt   6840
ttggcctgcc tccttttctt gaggctgatc ttgtctcaac agtcagcttt tcaggaacca   6900
ggcccttgct gttgtaagga aaacctgtcg gctgtggatg gggccttccc tccttcctaa   6960
aggctctgta gccagcttcc acccttgcag tggaacagtg gtggtgccag aaccctgctc   7020
tctgcagcca tcctgcctac cacagtcatt gtgttttgta actctagtag cttcttgtga   7080
aatacaagtg atggtataaa cgtggatagg tttttgaggg gggcatgcca aaatcagagt   7140
tggtggtagt ggtgggggat tcattcccaa gggctctggg gtgctaagtg tgtgagcaaa   7200
gaggaacaag tggcatgtgc ccaggatggg gtggggcggg caggtttagt tgagggctcc   7260
tctggtgtag ggtagccctg acgctcccct ccatggcatg actgatgagg tggcaaaggc   7320
aggtgccagg atttggtgtg ttgaagatta gtgcctgggt tgggctctgc tcactcctgc   7380
agaaagacgg ttggagaggg gctggtcttg gtttcacaga ggattgtggg attacaggca   7440
agacctgctg agggcttgca ctgagccacc gagaggagca gaaagagata cgagggcttc   7500
aggtgccagt atggttctca ctgttgtgag atctcatttg tgcctttttt tttttttcctt   7560
cagacagggt ctcactctgt tgcccaggct ggagtgcagt ggccctatca cagctcactg   7620
aggcctccac cttcctggct caagtgatcc tcccgcctca gcctcctgag tagcagggac   7680
cacaggcatg cagcaccaca cccagctaat ttaaagaatt ttttgtagag attggatctt   7740
gctatgttgc ctaggctggt gtcaaactcc tgggcacttg atttgtgctt cttaattcag   7800
gggctactta ttgaacatat ttagcagtct tcagaaagca tcttattctg taaggggaac   7860
caaatatacc cattcccccct ctctggcctt ctttccctgt ggtctgggcg gtctttgagc   7920
ttgaggtcat taggaggtgt ttatttctgt ccgccctggt ggcctagggc gtaggaatgg   7980
ggtgggatgg gatgggatgg ggtggggtgg ggtggaggag ttattctaca tagatagagt   8040
tctgtttatg cagcactccc tgccatacac atctctcact caaatggtct ggccagtcct   8100
ggttctaatg gtcattgtgt cattcccctc agcagcagga aaggctggaa tggtttttgt   8160
attgttcctt agggggaaaa atcacttgga ggaagtatat cagtgcttct gagtgcagag   8220
```

tatttattga cacgtcagtt aaaggaagct tttaaacaac atatatgtat ctctttagtg 8280
aggaataaat ctacaagtgc atctcacagc tccattttgc agcttccatt tcctggaagg 8340
tacatggagt ttagtggtta gggaatgggg ttttgagctg ggattttgga gaaactgttt 8400
ttagcctgtc cttggaattg ggccaggcct agaaatctgt tgaaatagct ttctttagtt 8460
gctgaaactg ggatgtgttc atagcactag gacctcgagc tccactgatg actgagtggg 8520
gagggctcag agaagggtcc ctgtggatgc ccgggatgcc tgggtttcag tcccgtctcc 8580
tgcatcgcct acattgcctg aatcttaggg tcttacagat ttatcatgaa gtgggcttgg 8640
cagcagatgg tctggtttct tttgtgcctt tgtcagaatc tgttcttgct cttcttagga 8700
aaactttcta tttcag 8716

<210> SEQ ID NO 205
<211> LENGTH: 3812
<212> TYPE: DNA
<213> ORGANISM: homo sapiens
<220> FEATURE:
<223> OTHER INFORMATION: B2M

<400> SEQUENCE: 205
gcgtgagtct ctcctaccct cccgctctgg tccttcctct cccgctctgc accctctgtg 60
gccctcgctg tgctctctcg ctccgtgact tcccttctcc aagttctcct tggtggcccg 120
ccgtggggct agtccagggc tggatctcgg ggaagcggcg gggtggcctg ggagtgggga 180
agggggtgcg cacccgggac gcgcgctact tgcccctttc ggcggggagc aggggagacc 240
tttggcctac ggcgacggga gggtcgggac aaagtttagg gcgtcgataa gcgtcagagc 300
gccgaggttg gggagggtt tctcttccgc tctttcgcgg ggcctctggc tcccccagcg 360
cagctggagt gggggacggg taggctcgtc ccaaaggcgc ggcgctgagg tttgtgaacg 420
cgtggagggg cgcttggggt ctgggggagg cgtcgcccgg gtaagcctgt ctgctgcggc 480
tctgcttccc ttagactgga gagctgtgga cttcgtctag gcgcccgcta agttcgcatg 540
tcctagcacc tctgggtcta tgtggggcca caccgtgggg aggaaacagc acgcgacgtt 600
tgtagaatgc ttggctgtga tacaaagcgg tttcgaataa ttaacttatt tgttcccatc 660
acatgtcact tttaaaaaat tataagaact acccgttatt gacatctttc tgtgtgccaa 720
ggactttatg tgctttgcgt catttaattt tgaaaacagt tatcttccgc catagataac 780
tactatggtt atcttctgcc tctcacagat gaagaaacta aggcaccgag attttaagaa 840
acttaattac acaggggata aatggcagca atcgagattg aagtcaagcc taaccagggc 900
ttttgcggga gcgcatgcct tttggctgta attcgtgcat ttttttttaa gaaaaacgcc 960
tgccttctgc gtgagattct ccagagcaaa ctgggcggca tgggccctgt ggtcttttcg 1020
tacagagggc ttcctctttg gctctttgcc tggttgtttc caagatgtac tgtgcctctt 1080
actttcggtt ttgaaaacat gagggggttg ggcgtggtag cttacgcctg taatcccagc 1140
acttagggag gccgaggcgg gaggatggct tgaggtccgt agttgagacc agcctggcca 1200
acatggtgaa gcctggtctc tacaaaaaat aataacaaaa attagccggg tgtggtggct 1260
cgtgcctgtg gtcccagctg ctccggtggc tgaggcggga ggatctcttg agcttaggct 1320
tttgagctat catggcgcca gtgcactcca gcgtgggcaa cagagcgaga ccctgtctct 1380
caaaaaagaa aaaaaaaaaa aaagaaagag aaaagaaaag aaagaaagaa gtgaaggttt 1440
gtcagtcagg ggagctgtaa aaccattaat aaagataatc caagatggtt accaagactg 1500
ttgaggacgc cagagatctt gagcactttc taagtacctg gcaatacact aagcgcgctc 1560

```
acctttcct ctggcaaaac atgatcgaaa gcagaatgtt ttgatcatga gaaaattgca   1620
tttaatttga atacaattta tttacaacat aaaggataat gtatatatca ccaccattac   1680
tggtatttgc tggttatgtt agatgtcatt ttaaaaaata acaatctgat atttaaaaaa   1740
aaatcttatt ttgaaaattt ccaaagtaat acatgccatg catagaccat ttctggaaga   1800
taccacaaga aacatgtaat gatgattgcc tctgaaggtc tattttcctc ctctgacctg   1860
tgtgtgggtt ttgtttttgt tttactgtgg gcataaatta atttttcagt taagttttgg   1920
aagcttaaat aactctccaa aagtcataaa gccagtaact ggttgagccc aaattcaaac   1980
ccagcctgtc tgatacttgt cctcttctta gaaaagatta cagtgatgct ctcacaaaat   2040
cttgccgcct tccctcaaac agagagttcc aggcaggatg aatctgtgct ctgatccctg   2100
aggcatttaa tatgttctta ttattagaag ctcagatgca aagagctctc ttagctttta   2160
atgttatgaa aaaaatcagg tcttcattag attccccaat ccacctcttg atggggctag   2220
tagcctttcc ttaatgatag ggtgtttcta gagagatata tctggtcaag gtggcctggt   2280
actcctcctt ctccccacag cctcccagac aaggaggagt agctgccttt tagtgatcat   2340
gtaccctgaa tataagtgta tttaaaagaa ttttatacac atatatttag tgtcaatctg   2400
tatatttagt agcactaaca cttctcttca ttttcaatga aaaatataga gtttataata   2460
ttttcttccc acttccccat ggatggtcta gtcatgcctc tcattttgga aagtactgtt   2520
tctgaaacat taggcaatat attcccaacc tggctagttt acagcaatca cctgtggatg   2580
ctaattaaaa cgcaaatccc actgtcacat gcattactcc atttgatcat aatggaaagt   2640
atgttctgtc ccatttgcca tagtcctcac ctatccctgt tgtattttat cgggtccaac   2700
tcaaccattt aaggtatttg ccagctcttg tatgcattta ggttttgttt ctttgttttt   2760
tagctcatga aattaggtac aaagtcagag aggggtctgg catataaaac ctcagcagaa   2820
ataaagaggt tttgttgttt ggtaagaaca taccttgggt tggttgggca cggtggctcg   2880
tgcctgtaat cccaacactt tgggaggcca aggcaggctg atcacttgaa gttgggagtt   2940
caagaccagc ctggccaaca tggtgaaatc ccgtctctac tgaaaataca aaaattaacc   3000
aggcatggtg gtgtgtgcct gtagtcccag gaatcacttg aacccaggag gcggaggttg   3060
cagtgagctg agatctcacc actgcacact gcactccagc ctgggcaatg gaatgagatt   3120
ccatcccaaa aaataaaaaa ataaaaaaat aaagaacata ccttgggttg atccacttag   3180
gaacctcaga taataacatc tgccacgtat agagcaattg ctatgtccca ggcactctac   3240
tagacacttc atacagttta gaaaatcaga tgggtgtaga tcaaggcagg agcaggaacc   3300
aaaaagaaag gcataaacat aagaaaaaaa atggaagggg tggaaacaga gtacaataac   3360
atgagtaatt tgatgggggc tattatgaac tgagaaatga actttgaaaa gtatcttggg   3420
gccaaatcat gtagactctt gagtgatgtg ttaaggaatg ctatgagtgc tgagagggca   3480
tcagaagtcc ttgagagcct ccagagaaag gctcttaaaa atgcagcgca atctccagtg   3540
acagaagata ctgctagaaa tctgctagaa aaaaaacaaa aaaggcatgt atagaggaat   3600
tatgagggaa agataccaag tcacggttta ttcttcaaaa tggaggtggc ttgttgggaa   3660
ggtggaagct catttggcca gagtggaaat ggaattggga gaaatcgatg accaaatgta   3720
aacacttggt gcctgatata gcttgacacc aagttagccc caagtgaaat accctggcaa   3780
tattaatgtg tcttttcccg atattcctca gg                                 3812
```

<210> SEQ ID NO 206

<211> LENGTH: 23
<212> TYPE: DNA
<213> ORGANISM: artificial
<220> FEATURE:
<223> OTHER INFORMATION: SS 3 prime albumin

<400> SEQUENCE: 206
attggcgatt ttctttttag ggc 23

<210> SEQ ID NO 207
<211> LENGTH: 20
<212> TYPE: DNA
<213> ORGANISM: artificial
<220> FEATURE:
<223> OTHER INFORMATION: SS 3 prime consensus

<400> SEQUENCE: 207
tttttttttt tttttttcag 20

<210> SEQ ID NO 208
<211> LENGTH: 7
<212> TYPE: DNA
<213> ORGANISM: artificial
<220> FEATURE:
<223> OTHER INFORMATION: SS 5 prime albumin

<400> SEQUENCE: 208 ggtaggt 7

<210> SEQ ID NO 209
<211> LENGTH: 888
<212> TYPE: DNA
<213> ORGANISM: artificial
<220> FEATURE:
<223> OTHER INFORMATION: anHAL_S100A9

<400> SEQUENCE: 209
ctgacccagc ctcaccgcag tttgggttga caagggagga tgggagtatg ggctacagca 60
atcaagggga agatttgagc tcctggagcc cagccccaag acgcagcgag tgtcctgtta 120
tacagggcag gtgctcacag ttacacagga cgacagggtc aagaaattgc tcaattgaac 180
acctgctatt tgtcgggccc tgttctgggc agagggatgt agtggtaaat ggggagccca 240
ctattccagt ggagggagac acacagtaaa gttgttggcc aataaagagc acagataaag 300
ccaaatgcca ataagtgcct ggaagaaaat gagatagagt gcgctgtggg caatggggct 360
gggtggggtg gaggtgacca gttagggtac atgagaaggg cctctttgag gaggtaacat 420
ttgagctgag ccccgaatgt tggggaggga agcccctgag gatgacactt ggcacaaagc 480
tgaggagacc ctaagcctca ggcgggaact tggggtggaa gacttggggg cttttctaat 540
cctaagggtc tgcggtggaa aatgaatgca taaagagcac atggagagca cctgcacagc 600
actcagggaa ctgggaggtt tttcccccgc tccaaaaatg attaggcagt tctaagaaaa 660
aggctgagca cttccaacag cctttttgtt ttcttttcaa atttggggaa agtcgggaaa 720
cagaggcctg cattaagaag ggtggaacac atgggtctca gtctcagttc cagtcccgga 780
gccagacatc ctggggtagg tccccagccc tcccagtgcc cctccctccg ccttggtaag 840
gtggagaatt gcagccttca gagttagggg ccctgacagc tctccata 888

<210> SEQ ID NO 210
<211> LENGTH: 149
<212> TYPE: DNA
<213> ORGANISM: artificial
<220> FEATURE:
<223> OTHER INFORMATION: Rewriten S100A9 ex1

<400> SEQUENCE: 210
atgacttgca aaatgtcgca gctggaacgc aacatagaga ccatcatcaa caccttccac 60
caatactctg tgaagctggg gcacccagac accctgaacc agggggaatt caaagagctg 120
gtgcgaaaag atctgcaaaa ttttctcaa 149

<210> SEQ ID NO 211
<211> LENGTH: 340
<212> TYPE: DNA
<213> ORGANISM: artificial
<220> FEATURE:
<223> OTHER INFORMATION: anHAR_S100A9

<400> SEQUENCE: 211
ggtggaggcc tcaggcaggc aggatgctgg gtggggtagg caagaaaggg cccagcagag 60
aggccgcatg gcaaaactat cctccatgtg accccctatg cccgcttcac cccccacctg 120
acatccccca ccagaagcaa agcgatgctg tgggaaagga agcagagcct catggatggg 180
ctgcacagga gagtgctcgc attggctggg taccccacag gttctgggag gggacttagc 240
gaggtgactc agccagaggg tggcagagct ggaaccaacc agtgctctct tggaccccgc 300
ctgggtctgg gtcttccacc tcccctgatg tctctccttt 340

<210> SEQ ID NO 212
<211> LENGTH: 895
<212> TYPE: DNA
<213> ORGANISM: artificial
<220> FEATURE:
<223> OTHER INFORMATION: anHAL_CD11b

<400> SEQUENCE: 212
aacttttggg tctgtcataa atagagggcc cagaatatgt aggagtcagt ctggggagag 60
gcaaagggga tttggggaag gagaaagggt tcaagaagaa gcagggagaa cagctagacc 120
cagacaggct ggccagggaa gcctggatga atgaccacat tcatggactg tgcaaggctg 180
cttgccggtc cccttgcttc acacatgagg agacggaggc ccagggagga gaagtgacat 240
ggctcagggt gcgcagcagg tgtgagaccc ctttcctgag tgcttcctcc tggatcccct 300
ctcaccatct ccactttgcc tccggttcta ttttccaagg tcccgggtgc aaatgtttgt 360
tgaatgactg atgaatgaaa atgatttgag tttgttacct tttatgctta tatgttgtgg 420
aaaatgaaat tctcctcaaa agggaaggaa atacttgaga gctgcatagg aaggaaatta 480
tctaattaag aatgtataga aacttcactg ttgggcaaat catcgttgtg acaccggggg 540
aagaagccat ttaggtgctc agaagggagg ctggaattca gagcaggact ggacgtgccc 600
cacgacggtg gttcttaggt caggagtcag caaacagtgg cctgggggcc cgatatggcc 660
cacgacctgt ttttgcacaa cctgccagct agagattgaa gatgaacact gataatcgat 720
ttgatgatag ggagcaccac ccccaaagaa ttctatttgt ctcatttgta aacccgtatt 780
acaaacaaat tgtactcaat cattatgttt gaaatttccc taatgacaaa tttgtggaaa 840
agtattttct gtcttgttat ataagtactt gtacaacata ttctatcagc ctctt 895

<210> SEQ ID NO 213
<211> LENGTH: 28
<212> TYPE: DNA
<213> ORGANISM: artificial
<220> FEATURE:

<223> OTHER INFORMATION: Rewriten CD11b ex1

<400> SEQUENCE: 213
atggctctca gagtccttct gttaacag 28

<210> SEQ ID NO 214
<211> LENGTH: 430
<212> TYPE: DNA
<213> ORGANISM: artificial
<220> FEATURE:
<223> OTHER INFORMATION: anHAR_CD11b

<400> SEQUENCE: 214
ggtctgcaaa acctaaaatt tactatctgg ctgtttacag aataagtgtg ctaatccccg 60
ccccaggcta acagagctgg acctgggagg cagacatctg gatgctgggt tagttagggt 120
gaccgaatgg atgggaaagg gaatggagca ggaagacatg ctgctatctt ttttttttt 180 ttttttttt gatacagggt ctttctctgt tgcccaggct gtagtgcagt ggcatgatca 240
tggttcactg cagccttgac ctcctgggtt caagcaatcc tcccacctca gcctcctgag 300
taccactaca cccggctaat tttttatttt ttgtagagat ggggtctcac tgtgttgcct 360
aggctggtct taaactcctg agcccaggtg atcctcccac gtcagcctct taaattattg 420
ggataacagg 430

<210> SEQ ID NO 215
<211> LENGTH: 3
<212> TYPE: PRT
<213> ORGANISM: artificial
<220> FEATURE:
<223> OTHER INFORMATION: GSG linker

<400> SEQUENCE: 215

Gly Ser Gly
1

<210> SEQ ID NO 216
<211> LENGTH: 19
<212> TYPE: PRT
<213> ORGANISM: artificial
<220> FEATURE:
<223> OTHER INFORMATION: aaP2A

<400> SEQUENCE: 216

Ala Thr Asn Phe Ser Leu Leu Lys Gln Ala Gly Asp Val Glu Glu Asn
1 5 10 15

Pro Gly Pro

<210> SEQ ID NO 217
<211> LENGTH: 18
<212> TYPE: PRT
<213> ORGANISM: artificial
<220> FEATURE:
<223> OTHER INFORMATION: aaT2A

<400> SEQUENCE: 217

Glu Gly Arg Gly Ser Leu Leu Thr Cys Gly Asp Val Glu Glu Asn Pro
1 5 10 15

Gly Pro

<210> SEQ ID NO 218
<211> LENGTH: 239
<212> TYPE: PRT

```
<213> ORGANISM: artificial
<220> FEATURE:
<223> OTHER INFORMATION: aaEGFP

<400> SEQUENCE: 218

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 219
<211> LENGTH: 925
<212> TYPE: PRT
<213> ORGANISM: artificial
<220> FEATURE:
<223> OTHER INFORMATION: TALEN CD11b Left

<400> SEQUENCE: 219

Met Gly Asp Pro Lys Lys Lys Arg Lys Val Ile Asp Ile Ala Asp Leu
1               5                   10                  15

Arg Thr Leu Gly Tyr Ser Gln Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95
```

```
Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
    130                 135                 140

Gly Ala Pro Leu Asn Leu Thr Pro Glu Gln Val Val Ala Ile Ala Ser
145                 150                 155                 160

Asn Ile Gly Gly Lys Gln Ala Leu Glu Thr Val Gln Ala Leu Leu Pro
                165                 170                 175

Val Leu Cys Gln Ala His Gly Leu Thr Pro Glu Gln Val Val Ala Ile
            180                 185                 190

Ala Ser His Asp Gly Gly Lys Gln Ala Leu Glu Thr Val Gln Arg Leu
        195                 200                 205

Leu Pro Val Leu Cys Gln Ala His Gly Leu Thr Pro Glu Gln Val Val
    210                 215                 220

Ala Ile Ala Ser Asn Ile Gly Gly Lys Gln Ala Leu Glu Thr Val Gln
225                 230                 235                 240

Ala Leu Leu Pro Val Leu Cys Gln Ala His Gly Leu Thr Pro Glu Gln
                245                 250                 255

Val Val Ala Ile Ala Ser Asn Ile Gly Gly Lys Gln Ala Leu Glu Thr
            260                 265                 270

Val Gln Ala Leu Leu Pro Val Leu Cys Gln Ala His Gly Leu Thr Pro
        275                 280                 285

Glu Gln Val Val Ala Ile Ala Ser His Asp Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser Asn Ile Gly Gly Lys Gln
                325                 330                 335

Ala Leu Glu Thr Val Gln Ala Leu Leu Pro Val Leu Cys Gln Ala His
            340                 345                 350

Gly Leu Thr Pro Gln Gln Val Val Ala Ile Ala Ser Asn Gly Gly Gly
        355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Ala Leu Leu Pro Val Leu
                405                 410                 415

Cys Gln Ala His Gly Leu Thr Pro Gln Gln Val Val Ala Ile Ala Ser
            420                 425                 430

Asn Gly Gly Gly Lys Gln Ala Leu Glu Thr Val Gln Arg Leu Leu Pro
        435                 440                 445

Val Leu Cys Gln Ala His Gly Leu Thr Pro Gln Gln Val Val Ala Ile
    450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser His Asp Gly Gly Lys Gln Ala Leu Glu Thr Val Gln
            500                 505                 510

Arg Leu Leu Pro Val Leu Cys Gln Ala His Gly Leu Thr Pro Gln Gln
```

```
        515                 520                 525

Val Val Ala Ile Ala Ser Asn Gly Gly Gly Lys Gln Ala Leu Glu Thr
    530                 535                 540

Val Gln Arg Leu Leu Pro Val Leu Cys Gln Ala His Gly Leu Thr Pro
545                 550                 555                 560

Glu Gln Val Val Ala Ile Ala Ser Asn Ile Gly Gly Lys Gln Ala Leu
                565                 570                 575

Glu Thr Val Gln Ala Leu Leu Pro Val Leu Cys Gln Ala His Gly Leu
            580                 585                 590

Thr Pro Gln Gln Val Val Ala Ile Ala Ser Asn Gly Gly Gly Lys Gln
        595                 600                 605

Ala Leu Glu Thr Val Gln Arg Leu Leu Pro Val Leu Cys Gln Ala His
    610                 615                 620

Gly Leu Thr Pro Glu Gln Val Val Ala Ile Ala Ser His Asp Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
        675                 680                 685

Asp Pro Ala Leu Ala Ala Leu Thr Asn Asp His Leu Val Ala Leu Ala
    690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
        755                 760                 765

Met Lys Val Met Glu Phe Phe Met Lys Val Tyr Gly Tyr Arg Gly Lys
    770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
    850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
        915                 920                 925
```

<210> SEQ ID NO 220

<211> LENGTH: 925
<212> TYPE: PRT
<213> ORGANISM: artificial
<220> FEATURE:
<223> OTHER INFORMATION: TALEN CD11b Right

<400> SEQUENCE: 220

```
Met Gly Asp Pro Lys Lys Lys Arg Lys Val Ile Asp Ile Ala Asp Leu
1               5                   10                  15

Arg Thr Leu Gly Tyr Ser Gln Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
    130                 135                 140

Gly Ala Pro Leu Asn Leu Thr Pro Glu Gln Val Val Ala Ile Ala Ser
145                 150                 155                 160

Asn Ile Gly Gly Lys Gln Ala Leu Glu Thr Val Gln Ala Leu Leu Pro
                165                 170                 175

Val Leu Cys Gln Ala His Gly Leu Thr Pro Gln Gln Val Val Ala Ile
            180                 185                 190

Ala Ser Asn Asn Gly Gly Lys Gln Ala Leu Glu Thr Val Gln Arg Leu
        195                 200                 205

Leu Pro Val Leu Cys Gln Ala His Gly Leu Thr Pro Gln Gln Val Val
    210                 215                 220

Ala Ile Ala Ser Asn Gly Gly Gly Lys Gln Ala Leu Glu Thr Val Gln
225                 230                 235                 240

Arg Leu Leu Pro Val Leu Cys Gln Ala His Gly Leu Thr Pro Glu Gln
                245                 250                 255

Val Val Ala Ile Ala Ser Asn Ile Gly Gly Lys Gln Ala Leu Glu Thr
            260                 265                 270

Val Gln Ala Leu Leu Pro Val Leu Cys Gln Ala His Gly Leu Thr Pro
        275                 280                 285

Glu Gln Val Val Ala Ile Ala Ser Asn Ile Gly Gly Lys Gln Ala Leu
    290                 295                 300

Glu Thr Val Gln Ala Leu Leu Pro Val Leu Cys Gln Ala His Gly Leu
305                 310                 315                 320

Thr Pro Glu Gln Val Val Ala Ile Ala Ser Asn Ile Gly Gly Lys Gln
                325                 330                 335

Ala Leu Glu Thr Val Gln Ala Leu Leu Pro Val Leu Cys Gln Ala His
            340                 345                 350

Gly Leu Thr Pro Gln Gln Val Val Ala Ile Ala Ser Asn Gly Gly Gly
        355                 360                 365

Lys Gln Ala Leu Glu Thr Val Gln Arg Leu Leu Pro Val Leu Cys Gln
    370                 375                 380
```

```
Ala His Gly Leu Thr Pro Gln Gln Val Val Ala Ile Ala Ser Asn Gly
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Gln Gln Val Val Ala Ile Ala Ser
            420                 425                 430

Asn Gly Gly Gly Lys Gln Ala Leu Glu Thr Val Gln Arg Leu Leu Pro
        435                 440                 445

Val Leu Cys Gln Ala His Gly Leu Thr Pro Gln Gln Val Val Ala Ile
    450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser Asn Ile Gly Gly Lys Gln Ala Leu Glu Thr Val Gln
            500                 505                 510

Ala Leu Leu Pro Val Leu Cys Gln Ala His Gly Leu Thr Pro Gln Gln
        515                 520                 525

Val Val Ala Ile Ala Ser Asn Asn Gly Gly Lys Gln Ala Leu Glu Thr
    530                 535                 540

Val Gln Arg Leu Leu Pro Val Leu Cys Gln Ala His Gly Leu Thr Pro
545                 550                 555                 560

Gln Gln Val Val Ala Ile Ala Ser Asn Asn Gly Gly Lys Gln Ala Leu
                565                 570                 575

Glu Thr Val Gln Arg Leu Leu Pro Val Leu Cys Gln Ala His Gly Leu
            580                 585                 590

Thr Pro Gln Gln Val Val Ala Ile Ala Ser Asn Gly Gly Gly Lys Gln
        595                 600                 605

Ala Leu Glu Thr Val Gln Arg Leu Leu Pro Val Leu Cys Gln Ala His
    610                 615                 620

Gly Leu Thr Pro Gln Gln Val Val Ala Ile Ala Ser Asn Gly Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
        675                 680                 685

Asp Pro Ala Leu Ala Ala Leu Thr Asn Asp His Leu Val Ala Leu Ala
    690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
        755                 760                 765

Met Lys Val Met Glu Phe Phe Met Lys Val Tyr Gly Tyr Arg Gly Lys
    770                 775                 780

His Leu Gly Gly Ser Arg Lys Pro Asp Gly Ala Ile Tyr Thr Val Gly
785                 790                 795                 800
```

Ser Pro Ile Asp Tyr Gly Val Ile Val Asp Thr Lys Ala Tyr Ser Gly
805 810 815

Gly Tyr Asn Leu Pro Ile Gly Gln Ala Asp Glu Met Gln Arg Tyr Val
820 825 830

Glu Glu Asn Gln Thr Arg Asn Lys His Ile Asn Pro Asn Glu Trp Trp
835 840 845

Lys Val Tyr Pro Ser Ser Val Thr Glu Phe Lys Phe Leu Phe Val Ser
850 855 860

Gly His Phe Lys Gly Asn Tyr Lys Ala Gln Leu Thr Arg Leu Asn His
865 870 875 880

Ile Thr Asn Cys Asn Gly Ala Val Leu Ser Val Glu Glu Leu Leu Ile
885 890 895

Gly Gly Glu Met Ile Lys Ala Gly Thr Leu Thr Leu Glu Glu Val Arg
900 905 910

Arg Lys Phe Asn Asn Gly Glu Ile Asn Phe Ala Ala Asp
915 920 925

<210> SEQ ID NO 221
<211> LENGTH: 925
<212> TYPE: PRT
<213> ORGANISM: artificial
<220> FEATURE:
<223> OTHER INFORMATION: TALEN S100A9 Left

<400> SEQUENCE: 221

Met Gly Asp Pro Lys Lys Lys Arg Lys Val Ile Asp Ile Ala Asp Leu
1 5 10 15

Arg Thr Leu Gly Tyr Ser Gln Gln Gln Gln Glu Lys Ile Lys Pro Lys
20 25 30

Val Arg Ser Thr Val Ala Gln His His Glu Ala Leu Val Gly His Gly
35 40 45

Phe Thr His Ala His Ile Val Ala Leu Ser Gln His Pro Ala Ala Leu
50 55 60

Gly Thr Val Ala Val Lys Tyr Gln Asp Met Ile Ala Ala Leu Pro Glu
65 70 75 80

Ala Thr His Glu Ala Ile Val Gly Val Gly Lys Gln Trp Ser Gly Ala
85 90 95

Arg Ala Leu Glu Ala Leu Leu Thr Val Ala Gly Glu Leu Arg Gly Pro
100 105 110

Pro Leu Gln Leu Asp Thr Gly Gln Leu Leu Lys Ile Ala Lys Arg Gly
115 120 125

Gly Val Thr Ala Val Glu Ala Val His Ala Trp Arg Asn Ala Leu Thr
130 135 140

Gly Ala Pro Leu Asn Leu Thr Pro Gln Gln Val Val Ala Ile Ala Ser
145 150 155 160

Asn Gly Gly Gly Lys Gln Ala Leu Glu Thr Val Gln Arg Leu Leu Pro
165 170 175

Val Leu Cys Gln Ala His Gly Leu Thr Pro Glu Gln Val Val Ala Ile
180 185 190

Ala Ser Asn Ile Gly Gly Lys Gln Ala Leu Glu Thr Val Gln Ala Leu
195 200 205

Leu Pro Val Leu Cys Gln Ala His Gly Leu Thr Pro Gln Gln Val Val
210 215 220

Ala Ile Ala Ser Asn Asn Gly Gly Lys Gln Ala Leu Glu Thr Val Gln
225 230 235 240

```
Arg Leu Leu Pro Val Leu Cys Gln Ala His Gly Leu Thr Pro Gln Gln
                245                 250                 255

Val Val Ala Ile Ala Ser Asn Asn Gly Gly Lys Gln Ala Leu Glu Thr
            260                 265                 270

Val Gln Arg Leu Leu Pro Val Leu Cys Gln Ala His Gly Leu Thr Pro
        275                 280                 285

Gln Gln Val Val Ala Ile Ala Ser Asn Asn Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Gln Gln Val Val Ala Ile Ala Ser Asn Asn Gly Gly Lys Gln
                325                 330                 335

Ala Leu Glu Thr Val Gln Arg Leu Leu Pro Val Leu Cys Gln Ala His
            340                 345                 350

Gly Leu Thr Pro Glu Gln Val Val Ala Ile Ala Ser His Asp Gly Gly
        355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
            420                 425                 430

His Asp Gly Gly Lys Gln Ala Leu Glu Thr Val Gln Arg Leu Leu Pro
        435                 440                 445

Val Leu Cys Gln Ala His Gly Leu Thr Pro Gln Gln Val Val Ala Ile
    450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Asn Gly Gly Lys Gln Ala Leu Glu Thr Val Gln
            500                 505                 510

Arg Leu Leu Pro Val Leu Cys Gln Ala His Gly Leu Thr Pro Glu Gln
        515                 520                 525

Val Val Ala Ile Ala Ser Asn Ile Gly Gly Lys Gln Ala Leu Glu Thr
    530                 535                 540

Val Gln Ala Leu Leu Pro Val Leu Cys Gln Ala His Gly Leu Thr Pro
545                 550                 555                 560

Glu Gln Val Val Ala Ile Ala Ser His Asp Gly Gly Lys Gln Ala Leu
                565                 570                 575

Glu Thr Val Gln Arg Leu Leu Pro Val Leu Cys Gln Ala His Gly Leu
            580                 585                 590

Thr Pro Glu Gln Val Val Ala Ile Ala Ser Asn Ile Gly Gly Lys Gln
        595                 600                 605

Ala Leu Glu Thr Val Gln Ala Leu Leu Pro Val Leu Cys Gln Ala His
    610                 615                 620

Gly Leu Thr Pro Gln Gln Val Val Ala Ile Ala Ser Asn Asn Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
```

```
            660                 665                 670

Gly Gly Arg Pro Ala Leu Glu Ser Ile Val Ala Gln Leu Ser Arg Pro
        675                 680                 685

Asp Pro Ala Leu Ala Ala Leu Thr Asn Asp His Leu Val Ala Leu Ala
    690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
        755                 760                 765

Met Lys Val Met Glu Phe Phe Met Lys Val Tyr Gly Tyr Arg Gly Lys
    770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
    850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
        915                 920                 925


<210> SEQ ID NO 222
<211> LENGTH: 925
<212> TYPE: PRT
<213> ORGANISM: artificial
<220> FEATURE:
<223> OTHER INFORMATION: TALEN S100A9 Right

<400> SEQUENCE: 222

Met Gly Asp Pro Lys Lys Lys Arg Lys Val Ile Asp Ile Ala Asp Leu
1               5                   10                  15

Arg Thr Leu Gly Tyr Ser Gln Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
```

```
            100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
    130                 135                 140

Gly Ala Pro Leu Asn Leu Thr Pro Glu Gln Val Val Ala Ile Ala Ser
145                 150                 155                 160

His Asp Gly Gly Lys Gln Ala Leu Glu Thr Val Gln Arg Leu Leu Pro
                165                 170                 175

Val Leu Cys Gln Ala His Gly Leu Thr Pro Glu Gln Val Val Ala Ile
            180                 185                 190

Ala Ser His Asp Gly Gly Lys Gln Ala Leu Glu Thr Val Gln Arg Leu
        195                 200                 205

Leu Pro Val Leu Cys Gln Ala His Gly Leu Thr Pro Gln Gln Val Val
    210                 215                 220

Ala Ile Ala Ser Asn Gly Gly Gly Lys Gln Ala Leu Glu Thr Val Gln
225                 230                 235                 240

Arg Leu Leu Pro Val Leu Cys Gln Ala His Gly Leu Thr Pro Gln Gln
                245                 250                 255

Val Val Ala Ile Ala Ser Asn Asn Gly Gly Lys Gln Ala Leu Glu Thr
            260                 265                 270

Val Gln Arg Leu Leu Pro Val Leu Cys Gln Ala His Gly Leu Thr Pro
        275                 280                 285

Glu Gln Val Val Ala Ile Ala Ser His Asp Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
                325                 330                 335

Ala Leu Glu Thr Val Gln Arg Leu Leu Pro Val Leu Cys Gln Ala His
            340                 345                 350

Gly Leu Thr Pro Gln Gln Val Val Ala Ile Ala Ser Asn Gly Gly Gly
        355                 360                 365

Lys Gln Ala Leu Glu Thr Val Gln Arg Leu Leu Pro Val Leu Cys Gln
    370                 375                 380

Ala His Gly Leu Thr Pro Gln Gln Val Val Ala Ile Ala Ser Asn Asn
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
            420                 425                 430

His Asp Gly Gly Lys Gln Ala Leu Glu Thr Val Gln Arg Leu Leu Pro
        435                 440                 445

Val Leu Cys Gln Ala His Gly Leu Thr Pro Glu Gln Val Val Ala Ile
    450                 455                 460

Ala Ser His Asp Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Gly Gly Gly Lys Gln Ala Leu Glu Thr Val Gln
            500                 505                 510

Arg Leu Leu Pro Val Leu Cys Gln Ala His Gly Leu Thr Pro Gln Gln
        515                 520                 525
```

Val Val Ala Ile Ala Ser Asn Asn Gly Gly Lys Gln Ala Leu Glu Thr
530 535 540

Val Gln Arg Leu Leu Pro Val Leu Cys Gln Ala His Gly Leu Thr Pro
545 550 555 560

Glu Gln Val Val Ala Ile Ala Ser Asn Ile Gly Gly Lys Gln Ala Leu
565 570 575

Glu Thr Val Gln Ala Leu Leu Pro Val Leu Cys Gln Ala His Gly Leu
580 585 590

Thr Pro Gln Gln Val Val Ala Ile Ala Ser Asn Asn Gly Gly Lys Gln
595 600 605

Ala Leu Glu Thr Val Gln Arg Leu Leu Pro Val Leu Cys Gln Ala His
610 615 620

Gly Leu Thr Pro Gln Gln Val Val Ala Ile Ala Ser Asn Asn Gly Gly
625 630 635 640

Lys Gln Ala Leu Glu Thr Val Gln Arg Leu Leu Pro Val Leu Cys Gln
645 650 655

Ala His Gly Leu Thr Pro Gln Gln Val Val Ala Ile Ala Ser Asn Gly
660 665 670

Gly Gly Arg Pro Ala Leu Glu Ser Ile Val Ala Gln Leu Ser Arg Pro
675 680 685

Asp Pro Ala Leu Ala Ala Leu Thr Asn Asp His Leu Val Ala Leu Ala
690 695 700

Cys Leu Gly Gly Arg Pro Ala Leu Asp Ala Val Lys Lys Gly Leu Gly
705 710 715 720

Asp Pro Ile Ser Arg Ser Gln Leu Val Lys Ser Glu Leu Glu Glu Lys
725 730 735

Lys Ser Glu Leu Arg His Lys Leu Lys Tyr Val Pro His Glu Tyr Ile
740 745 750

Glu Leu Ile Glu Ile Ala Arg Asn Ser Thr Gln Asp Arg Ile Leu Glu
755 760 765

Met Lys Val Met Glu Phe Phe Met Lys Val Tyr Gly Tyr Arg Gly Lys
770 775 780

His Leu Gly Gly Ser Arg Lys Pro Asp Gly Ala Ile Tyr Thr Val Gly
785 790 795 800

Ser Pro Ile Asp Tyr Gly Val Ile Val Asp Thr Lys Ala Tyr Ser Gly
805 810 815

Gly Tyr Asn Leu Pro Ile Gly Gln Ala Asp Glu Met Gln Arg Tyr Val
820 825 830

Glu Glu Asn Gln Thr Arg Asn Lys His Ile Asn Pro Asn Glu Trp Trp
835 840 845

Lys Val Tyr Pro Ser Ser Val Thr Glu Phe Lys Phe Leu Phe Val Ser
850 855 860

Gly His Phe Lys Gly Asn Tyr Lys Ala Gln Leu Thr Arg Leu Asn His
865 870 875 880

Ile Thr Asn Cys Asn Gly Ala Val Leu Ser Val Glu Glu Leu Leu Ile
885 890 895

Gly Gly Glu Met Ile Lys Ala Gly Thr Leu Thr Leu Glu Glu Val Arg
900 905 910

Arg Lys Phe Asn Asn Gly Glu Ile Asn Phe Ala Ala Asp
915 920 925

<210> SEQ ID NO 223
<211> LENGTH: 717

-continued

```
<212> TYPE: DNA
<213> ORGANISM: artificial
<220> FEATURE:
<223> OTHER INFORMATION: polynucleotide EGFP

<400> SEQUENCE: 223

atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaag       717


<210> SEQ ID NO 224
<211> LENGTH: 57
<212> TYPE: DNA
<213> ORGANISM: artificial
<220> FEATURE:
<223> OTHER INFORMATION: polynucleotide P2A

<400> SEQUENCE: 224

gctactaact tcagcctgct gaagcaggct ggagacgtgg aggagaaccc tggacct        57


<210> SEQ ID NO 225
<211> LENGTH: 54
<212> TYPE: DNA
<213> ORGANISM: artificial
<220> FEATURE:
<223> OTHER INFORMATION: polynucleotide T2A

<400> SEQUENCE: 225

gagggcagag gcagcctgct gacctgcggc gacgtcgagg agaaccccgg gccc           54


<210> SEQ ID NO 226
<211> LENGTH: 9
<212> TYPE: DNA
<213> ORGANISM: artificial
<220> FEATURE:
<223> OTHER INFORMATION: GSG polynucleotide linker

<400> SEQUENCE: 226

ggaagcgga                                                              9
```

METHODS TO GENETICALLY MODIFY CELLS FOR DELIVERY OF THERAPEUTIC PROTEINS

SEQUENCE LISTING

The instant application contains a Sequence Listing, which has been submitted electronically in ASCII format and is hereby incorporated by reference in its entirety. Said ASCII copy, created on Apr. 18, 2023, is named 17996701_ST25_2.txt and is 338,526 bytes in size.

FIELD OF THE INVENTION

The present invention generally relates to the field of gene therapy, and more specifically to the treatment and prevention of inherited genetic diseases. In particular, the present disclosure provides methods to genetically modify cells by insertion of an artificial exon (ArtEx) for delivery of therapeutic proteins in specific cell types and more particularly engineered cells for expression of a transgene into the brain of a patient

BACKGROUND

Inborn errors of metabolism are a large class of monogenic disorders due to defects in genes that often code for enzymes. This genetic deficiency leads to the accumulation of un-degraded substrates in various tissues leading to variable clinical manifestations which can often affect the central nervous system. Standard of care for these diseases (if available) often involves intravenous delivery of the therapeutic protein. This improves the condition as the therapeutic protein is taken up by the affected cells which corrects the deficiency. This strategy in which gene products made in one cell (or delivered therapeutically) are taken up by affected cells to correct the deficiency is referred to as cross-correction. However, therapeutic delivery of the protein to the plasma does not resolve the neurological defects seen in these patients as the protein fails to cross the blood-brain barrier (or an inadequate amount of the protein crosses the blood-brain barrier). Thus, any therapeutic strategy for these diseases that delivers the therapeutic protein to the plasma, such as intravenous transfer or converting the liver or any other organ with gene therapy into a therapeutic protein production facility will fail to resolve the neurological symptoms of the disease.

Thus, there is a significant need for methods and therapeutic compositions for delivery to the brain to treat genetic diseases.

This background information is provided for informational purposes only. No admission is necessarily intended, nor should it be construed, that any of the preceding information constitutes prior art against the present invention.

SUMMARY

It is to be understood that both the foregoing general description of the embodiments and the following detailed description are exemplary, and thus do not restrict the scope of the embodiments.

In one aspect, the invention provides genetically modified hematopoietic stem cells (HSC) comprising a therapeutic gene product that is co-expressed at an appropriate locus that is active in multiple hematopoietic lineages, such as macrophages, and more particularly tissue-resident microglial cells that populate the brain. The methods described herein can treat a patient through therapeutic gene product exogenous expression in myeloid lineages and tissues deriving therefrom. The invention is particularly advantageous for cross-expressing healthy alleles into the brain through by the microglial cells that populate the brain derivating from the hematopoietic lineages to obtain cross correction of deleterious alleles.

In another aspect, the invention relies on the ex vivo modification of hematopoietic stem cells (HSC) or iPS cells using programmable nucleases such as transcription activator-like effector nuclease (TALEN), zinc finger nuclease (ZFN), clustered regularly interspaced short palindromic repeats (CRISPR)-Cas, meganucleases and megaTAL (transcription activator-like (TAL) fused to a meganuclease) plus delivery of a repair template for that locus provided with recombinant adeno-associated virus (rAAV) to promote homology directed repair (HDR) of the locus. Any genetic modifications encoded in the repair template DNA can be incorporated at the target locus using this strategy including the incorporation of a therapeutic gene product such as a complementary DNA (cDNA). In some embodiments, the therapeutic gene product will be under the regulatory control of the target locus and promote expression in hematopoietic cells and in particular the microglial cells. The modified cells can subsequently be returned to the patient through adoptive cell transfer or autologous HSC transplantation. This process will deliver the therapeutic gene product systemically to treat the body but also locally in the brain to treat the totality of the symptoms of the disease.

In another aspect, the invention provides a method for expressing a transgene into the brain of a patient comprising:

i) obtaining genetically modified hematopoietic stem cells (HSC), wherein the HSC were isolated from the patient or were obtained from induced pluripotent stem (iPS) cells derived from the patient and differentiated into HSC, wherein the genetically modified HSC have been engineered to comprise a transgene integrated at a locus expressed in microglial cells; and ii) engrafting the genetically modified HSC into the patient in order to have them differentiate into microglial cells expressing the transgene into the patient's brain.

In another aspect, the invention provides a method for expressing a transgene into the brain of a patient comprising:

i) obtaining genetically modified hematopoietic stem cells (HSC), wherein the HSC were isolated from a compatible donor or were obtained from induced pluripotent stem (iPS) cells derived from a compatible donor and differentiated into HSC, wherein the genetically modified HSC have been engineered to comprise a transgene integrated at a locus expressed in microglial cells; and ii) engrafting the genetically modified HSC into the patient in order to have them differentiate into microglial cells expressing the transgene into the patient's brain.

In another aspect, the invention provides an isolated HSC or iPS cell which has a transgene integrated at a locus selected from TMEM119, CD11B, B2m, CX3CR1 or S100A9, said transgene being under the transcriptional control of the endogenous promoter of said genes. In some embodiments, the HSC or iPS cell is for use as a medicament. In some embodiments, the HSC or iPS cell is for use in the treatment a patient who has a deficiency in the expression of an endogenous gene homologous to the transgene (cross correction). In some embodiments, the HSC or iPS cell is for use in the treatment of a lysosomal storage disease.

In some embodiments, the locus expressed in microglial cells is selected from the group consisting of TMEM119, S100A9, CD11B, B2m, Cx3cr1, MERTK, CD164, Tlr4, Tlr7, Cd14, Fcgr1a, Fcgr3a, TBXAS1, DOK3, ABCA1, TMEM195, MR1, CSF3R, FGD4, TSPAN14, TGFBRI, CCR5, GPR34, SERPINE2, SLCO2B1, P2ry12, Olfml3, P2ry13, Hexb, Rhob, Jun, Rab3il1, Ccl2, Fcrls, Scoc, Siglech, Slc2a5, Lrrc3, Plxdc2, Usp2, Ctsf, Cttnbp2nl, Atp8a2, Lgmn, Mafb, Egr1, Bhlhe41, Hpgds, Ctsd, Hspa1a, Lag3, Csf1r, Adamts1, F11r, Golm1, Nuak1, Crybb1, Ltc4s, Sgce, Pla2g15, Ccl3l1, Abhd12, Ang, Ophn1, Sparc, Pros1, P2ry6, Lair1, Il1a, Epb41l2, Adora3, Rilpl1, Pmepa1, Ccl13, Pde3b, Scamp5, Ppp1r9a, Tjp1, Ak1, B4galt4, Gtf2h2, Trem2, Ckb, Acp2, Pon3, Agmo, Tnfrsf17, Fscn1, St3gal6, Adap2, Ccl4, Entpd1, Tmem86a, Kctd12, Dst, Ctsl2, Abcc3, Pdgfb, Pald1, Tubgcp5, Rapgef5, Stab1, Lacc1, Tmc7, Nrip1, Kcnd1, Tmem206, Hps4, Dagla, Extl3, Mlph, Arhgap22, Cxxc5, P4ha1, Cysltr1, Fgd2, Kcnk13, Gbgt1, C18orf1, Cadm1, Bco2, Adrb1, C3ar1, Large, Leprel1, Liph, Upk1b, P2rx7, Slc46a1, Ebf3, Ppp1r15a, Il10ra, Rasgrp3, Fos, Tppp, Slc24a3, Havcr2, Nav2, Apbb2, Clstn1, Blnk, Gnaq, Ptprm, Frmd4a, Cd86, Tnfrsf11a, Spint1, Ppm1l, Tgfbr2, Cmklr1, Tlr6, Gas6, Hist1h2ab, Atf3, Acvr1, Abi3, Lrp12, Ttc28, Plxna4, Adamts16, Rgs1, Icam1, Snx24, Ly96, Dnajb4, and Ppfia4. In some embodiments, multiples copies of the transgene are integrated at the same locus separated by 2A self-cleaving peptide sequences.

As an independent embodiment, the present patent application presents a method for integrating an exogenous coding sequence into an endogenous intronic genomic region, which allows integration of said exogenous coding sequence preferably between the first and second endogenous exons of said genomic region. In some embodiments, this method, illustrated in FIG. 2, has the advantage to preserve stemness of HSCs and their ability to differentiate into various myeloid cells. In some embodiments, the transgene has been inserted into the HSC or iPS cell using a rare cutting endonuclease and/or a viral vector. In some embodiments, the viral vector is an AAV vector. The method, also referred to as "ArtEx" allows the insertion of an artificial Exon encoding transgenes that are placed under transcriptional control of an endogenous locus, preferably into an intronic sequence without having to inactivate the expression of the endogenous exons present at said locus.

The method more particularly comprises one or several of the steps of:

providing cell(s) comprising an endogenous intronic genomic region, introducing into said cell(s) a polynucleotide template comprising an exogenous coding sequence, wherein said polynucleotide template comprises:

a) a first homologous polynucleotide sequence, which is homologous to the intronic sequence upstream of the insertion site, b) a first strong splice site sequence, comprising a branch point and a splice acceptor;

c) a first sequence encoding 2A self-cleaving peptide;

d) an exogenous sequence coding for a protein of interest;

e) a second sequence encoding 2A self-cleaving peptide;

f) a copy of the coding sequence of the first exon;

g) a second strong splice site sequence comprising a splice donor; and h) a second homologous polynucleotide sequence, which is homologous to the intronic sequence downstream of the insertion site; and optionally inducing the integration of said exogenous polynucleotide into said intronic sequence, preferably by homologous recombination, to have said exogenous coding sequence being transcribed at said endogenous locus along with the first and preferably second exon, or a copy thereof.

This method is particularly useful for cross correction of the expression of deficient protein in a large array of genetic disease, especially inherited diseases.

In some embodiments, the transgene is IDUA for treating Mucopolysaccharidosis Type I (Scheie, Hurler-Scheie or Hurler syndrome).

In some embodiments, the transgene is IDS for treating Mucopolysaccharidosis Type II (Hunter).

In some embodiments, the transgene is ARSB for treating Mucopolysaccharidosis Type VI (Maroteaux-Lamy).

In some embodiments, the transgene is GUSB for treating Mucopolysaccharidosis Type VII (Sly).

In some embodiments, the transgene is ABCD1 for treating X-linked Adrenoleukodystrophy.

In some embodiments, the transgene is GALC for treating Globoid Cell Leukodystrophy (Krabbe).

In some embodiments, the transgene is ARSA for treating Metachromatic Leukodystrophy.

In some embodiments, the transgene is GBA for treating Gaucher Disease.

In some embodiments, the transgene is FUCA1 for treating Fucosidosis.

In some embodiments, the transgene is MAN2B1 for treating Alpha-mannosidosis.

In some embodiments, the transgene is AGA for treating Aspartylglucosaminuria.

In some embodiments, the transgene is ASAH1 for treating Farber.

In some embodiments, the transgene is HEXA for treating Tay-Sachs.

In some embodiments, the transgene is GAA for treating Pompe.

In some embodiments, the transgene is SMPD1 for treating Niemann Pick.

In some embodiments, the transgene is LIPA for treating Wolman Syndrome.

In some embodiments, the transgene is CDKL5 for CDKL5-deficiency related disease.

Other objects, in particular vectors, cells and resulting populations of cells, as well as other features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The skilled artisan will understand that the drawings, described below, are for illustration purposes only. The drawings are not intended to limit the scope of the present teachings in any way.

FIG. 14. Schematic representation of the methods of the present invention for treating diseases by ArtEx insertion in HSC or iPS in view of expression of transgenes into different hematopoietic lineages to obtain cross correction of deficient proteins in pathologic cell types. The HSCs are engineered ex-vivo and infused into the patient. By ArtEx is meant that an artificial exon comprising the sequence encoding the protein for cross correction is introduced by gene targeted insertion into an intron at an endogenous locus without altering the expression of the other exons at said locus. The locus is selected for its expression in the respective selected cell lineage or cell type (progenitor cells, blood cells, T-cells, B-cells, platelets, neutrophils, monocytes.).

DETAILED DESCRIPTION

Figure 1:
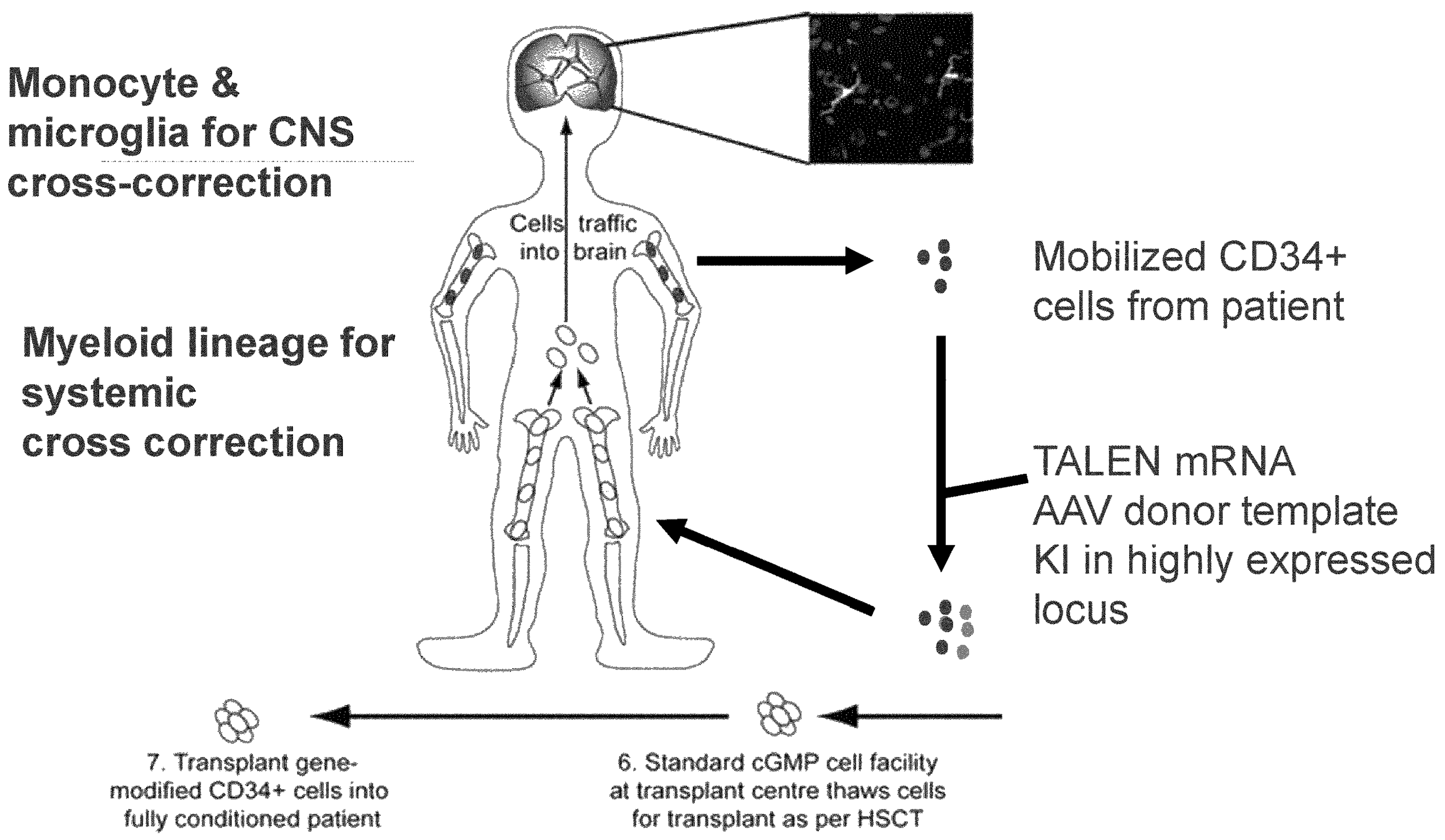
FIG. 1. Schematic of ex vivo gene therapy platform to target therapeutic gene expression to the myeloid lineage including the microglia.

Disclosed herein are methods for expressing a transgene into the brain of a patient. The methods comprise obtaining genetically modified hematopoietic stem cells (HSC) or iPS cells (capable of differentiating into HSC) wherein the cells comprise a transgene encoding a therapeutic protein integrated into the cells at a locus expressed at least in microglial cells. The methods further comprise engrafting genetically modified HSC into a patient whereby the cells differentiate into microglial cells and express the therapeutic protein in the patient's brain. The hematopoietic stem cells or iPS cells can be derived from the patient (autologous approach) or from a donor (allogeneic approach). The invention can be regarded as a method for delivery into a patient of a therapeutic protein to correct a genetic disease or disorder, for example, a metabolic disease or lysosomal storage disease (LSD), wherein the patient expresses a defective copy of the protein. The cell is modified by targeted insertion of a transgene encoding the functional protein into a locus that is expressed at least in microglial cells, thereby treating the disease. The methods of the present invention also permits to address Central Nervous System disease, of genetic origin or not, by delivering therapeutic proteins or enzymes to the brain expressed by microglia originating from genetically engineered HSCs.

The therapeutic protein may be excreted from the microglial cell such that it is able to affect or be taken up by other cells in brain that do not harbor a functional protein corresponding to the transgene. The invention also provides methods for the production of an engineered HSC cell that produces high levels of the therapeutic where the introduction of a population of these engineered cells into a patient will supply the needed protein to treat a disease or condition.

Thus, the methods and compositions of the invention can be used to express from a transgene a therapeutically beneficial protein from a locus that is expressed in microglial cells to replace a protein that is defective in inherited metabolic disease or to deliver a therapeutic protein or enzyme to the brain. For instance, dopa-decarboxylase [EC 4.1.1.28] can be expressed the brain by microglia in order to convert L-Dopa to dopamine, which alleviates Parkinson disease's symptoms.

Additionally, the invention provides methods and compositions for treatment of these diseases by insertion of the sequences into a locus expressed in microglial cells.

In some embodiments, the transgene is introduced into HSC cells isolated from the patient or from a compatible donor. In some embodiments, the transgene is introduced into HSC derived from iPS cells or it is introduced into the iPS cells prior to their differentiation to HSC. As the HSC differentiate into the microglial cells, they will express therapeutically effective amounts of the replacement protein for delivery to cells in the brain.

Reference will now be made in detail to the presently preferred embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

The practice of the present invention employs, unless otherwise indicated, conventional techniques of molecular biology (including recombinant techniques), microbiology, cell biology, biochemistry and immunology, which are within the skill of the art. Such techniques are explained fully in the literature. See, e.g., Sambrook et al. *Molecular Cloning: A Laboratory Manual, 2nd edition* (1989); *Current Protocols in Molecular Biology* (F. M. Ausubel et al. eds. (1987)); the series *Methods in Enzymology* (Academic Press, Inc.); *PCR: A Practical Approach* (M. MacPherson et al. IRL Press at Oxford University Press (1991)); *PCR 2: A Practical Approach* (M. J. MacPherson, B. D. Hames and G. R. Taylor eds. (1995)); *Antibodies, A Laboratory Manual* (Harlow and Lane eds. (1988)); *Using Antibodies, A Laboratory Manual* (Harlow and Lane eds. (1999)); and *Animal Cell Culture* (R. I. Freshney ed. (1987)).

Unless specifically defined herein, all technical and scientific terms used have the same meaning as commonly understood by a skilled artisan in the fields of gene therapy, biochemistry, genetics, immunology, cancer and molecular biology. Definitions of common terms in molecular biology may be found, for example, in Benjamin Lewin, *Genes VII*, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341).

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. As used in the specification and claims, the singular form "a," "an" and "the" include plural references unless the context clearly dictates otherwise. For example, the term "a cell" includes a plurality of cells, including mixtures thereof. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" means plus or minus 10% of the numerical value of the number with which it is being used.

As used herein, the term "hematopoietic stem cells" (or "HSC") refer to immature blood cells having the capacity to self-renew and to differentiate into mature blood cells comprising diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). It is known in the art that such cells may or may not include CD34+ cells. CD34+ cells are immature cells that express the CD34 cell surface marker. In humans, CD34+ cells are believed to include a subpopulation of cells with the stem cell properties defined above, whereas in mice, HSC are CD34−. In addition, HSC also refer to long term repopulating HSC (LT-HSC) and short term repopulating HSC (ST-HSC). LT-HSC and ST-HSC are differentiated, based on functional potential and on cell surface marker expression. For example, in some embodiments, human HSC are a CD34+, CD38−, CD45RA−, CD90+, CD49F+, and lin− (negative for mature lineage markers including CD2, CD3, CD4, CD7, CD8, CD10, CD11B, CD19, CD20, CD56, CD235A). In mice, bone marrow LT-HSC are CD34−, SCA-1+, C-kit+, CD135−, Slamfl/CD150+, CD48−, and lin− (negative for mature lineage markers including Ter119, CD11b, Gr1, CD3, CD4, CD8, B220, IL7ra), whereas ST-HSC are CD34+, SCA-1+, C-kit+, CD135−, Slamfl/CD150+, and lin− (negative for mature lineage markers including Ter119, CD11b, Gr1, CD3, CD4, CD8, B220, IL7ra). In addition, ST-HSC are less quiescent (i.e., more active) and more proliferative than LT-HSC under homeostatic conditions. However, LT-HSC have greater self-renewal potential (i.e., they survive throughout adulthood, and can be serially transplanted through successive recipients), whereas ST-HSC have limited self-renewal (i.e., they survive for only a limited period of time, and do not possess serial transplantation potential). Any of these HSC can be used in any of the methods described herein. In some embodiments, ST-HSC are useful because they are highly proliferative and thus, can more quickly give rise to differentiated progeny.

As used herein, a "recipient" is a patient that receives a transplant, such as a transplant containing a population of hematopoietic stem cells or a population of differentiated cells. The transplanted cells administered to a recipient may be, e.g., autologous, syngeneic, or allogeneic cells.

As used herein, a "donor" is a human or animal from which one or more cells are isolated prior to administration of the cells, or progeny thereof, into a recipient. The one or more cells may be, e.g., a population of hematopoietic stem cells to be expanded, enriched, or maintained according to the methods of the invention prior to administration of the cells or the progeny thereof into a recipient.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound, cell, or population of cells as disclosed herein into a subject by a method or route which results in at least partial delivery of the agent at a desired site. Pharmaceutical compositions comprising the compounds or cells disclosed herein can be administered by any appropriate route which results in an effective treatment in the subject.

As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

By "sequence specific reagent" is meant any active molecule that has the ability to specifically recognize a selected polynucleotide sequence from a genomic locus, preferably of at least 9 bp, more preferably of at least 10 bp and even more preferably of at least 12 pb in length, in view of modifying the expression of said genomic locus. In one embodiment, a sequence specific reagent that induces a stable mutation, is a reagent that has nickase or endonuclease activity.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites."

An "effective amount" or "therapeutically effective amount" refers to that amount of a composition described herein which, when administered to a subject (e.g., human), is sufficient to aid in treating a disease. The amount of a composition that constitutes a "therapeutically effective amount" will vary depending on the cell preparations, the condition and its severity, the manner of administration, and the age of the subject to be treated, but can be determined routinely by one of ordinary skill in the art having regard to his own knowledge and to this disclosure. When referring to an individual active ingredient or composition, administered alone, a therapeutically effective dose refers to that ingredient or composition alone. When referring to a combination, a therapeutically effective dose refers to combined amounts of the active ingredients, compositions or both that result in the therapeutic effect, whether administered serially, concurrently or simultaneously.

Endonucleases can be classified as rare-cutting endonucleases when having typically a polynucleotide recognition site greater than 10 base pairs (bp) in length. In some embodiments the rare-cutting endonuclease has a recognition site of from 14-55 bp. Rare-cutting endonucleases significantly increase homologous recombination by inducing DNA double-strand breaks (DSBs) at a defined locus thereby allowing gene repair or gene insertion therapies (Pingoud, A. and G. H. Silva (2007). *Nat. Biotechnol.* 25(7): 743-4).

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

In some embodiments, the endonuclease is engineered and is not found in nature. In some embodiments, the endonuclease is generated using a process such as phage display, interaction trap or hybrid selection. See e.g., U.S.

Pat. Nos. 5,789,538; 5,925,523; 6,007,988; 6,013,453; 6,200,759; as well as WO 95/19431; WO 96/06166; WO 98/53057; WO 98/54311; WO 00/27878; WO 01/60970; WO 01/88197; WO 02/099084 and U.S. Patent Appl. Publication No. 2011/0301073.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology and generally uses a "donor" molecule (also referred as "polynucleotide template") to be integrated into the endogenous locus ("target" sequence) by homologous recombination or NHEJ repair. This leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

By "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. In some embodiments, the mutation can affect the coding sequence of a gene or its regulatory sequence. It may also affect the structure of the genomic sequence or the structure/stability of the encoded mRNA.

By "vector" is meant a nucleic acid molecule capable of transporting another nucleic acid to which it has been linked. A "vector" in the present invention includes, but is not limited to, a viral vector, a plasmid, an oligonucleotide, a RNA vector or a linear or circular DNA or RNA molecule which may consists of a chromosomal, non-chromosomal, semisynthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available. Viral vectors include retrovirus, adenovirus, parvovirus (e.g., adenoassociated viruses (AAV), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

As used herein, the term "locus" is the specific physical location of a DNA sequence (e.g. of a gene) into a genome. The term "locus" can refer to the specific physical location of a rare-cutting endonuclease target sequence on a chromosome or on an infection agent's genome sequence. Such a locus can comprise a target sequence that is recognized and/or cleaved by a sequence-specific endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA RNA hybrid cleavage can result in the production of either blunt ends or staggered ends.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

"Expansion" in the context of cells refers to increase in the number of a characteristic cell type, or cell types, from an initial cell population of cells, which may or may not be identical. The initial cells used for expansion may not be the same as the cells generated from expansion.

"Cell population" refers to eukaryotic mammalian, preferably human, cells isolated from biological sources, for example, blood product or tissues and derived from more than one cell.

"Enriched" when used in the context of cell population refers to a cell population selected based on the presence of one or more markers, for example, CD34+.

The term "CD34+ cells" refers to cells that express at their surface CD34 marker. CD34+ cells can be detected and counted using for example flow cytometry and fluorescently labeled anti-CD34 antibodies.

"Enriched in CD34+ cells" means that a cell population has been selected based on the presence of CD34 marker. Accordingly, the percentage of CD34+ cells in the cell population after selection method is higher than the percentage of CD34+ cells in the initial cell population before selecting step based on CD34 markers. For example, CD34+ cells may represent at least 50%, 60%, 70%, 80% or at least 90% of the cells in a cell population enriched in CD34+ cells.

The term "subject" or "patient" as used herein includes all members of the animal kingdom including non-human primates and humans.

Where a numerical limit or range is stated herein, the endpoints are included. Also, all values and subranges within a numerical limit or range are specifically included as if explicitly written out.

Therapeutic Methods

In one embodiment, the invention provides a method for expressing a transgene into the brain of a patient comprising:

i) obtaining genetically modified hematopoietic stem cells (HSC), wherein the HSC were isolated from the patient or were obtained from induced pluripotent stem (iPS) cells derived from the patient and differentiated into HSC, wherein the genetically modified HSC have been engineered to comprise a transgene integrated at a locus expressed in microglial cells; and ii) engrafting the genetically modified HSC into the patient in order to have them differentiate into microglial cells expressing the transgene into the patient's brain.

In another embodiment, the invention provides a method for expressing a transgene into the brain of a patient comprising:

i) obtaining genetically modified hematopoietic stem cells (HSC), wherein the HSC were isolated from a compatible donor or were obtained from induced pluripotent stem (iPS) cells derived from a compatible donor and differentiated into HSC, wherein the genetically modified HSC have been engineered to comprise a transgene integrated at a locus expressed in microglial cells; and ii) engrafting the genetically modified HSC into the patient in order to have them differentiate into microglial cells expressing the transgene into the patient's brain.

In another embodiment, the invention provides a method of treating a disease or condition in a patient comprising administering to the patient an effective amount of genetically modified HSC, wherein the genetically modified HSC have been engineered to comprise a transgene integrated at a locus expressed in microglial cells, wherein the genetically modified HSC differentiate into microglial cells in the patient and express the transgene into the patient's brain. In some embodiments, the HSC were isolated from a compatible donor or were obtained from induced pluripotent stem (iPS) cells derived from a compatible donor and differentiated into HSC. In some embodiments, the HSC were isolated from the patient or were obtained from induced pluripotent stem (iPS) cells derived from the patient and differentiated into HSC.

In some embodiments, the patient has a monogenic disease or condition. In some embodiments, the patient has a deficiency in the expression of an endogenous gene homologous to the transgene. In some embodiments, the patient has a lysosomal storage disease. In some embodiments, disease or condition is selected from Mucopolysaccharidosis Type I (Scheie, Hurler-Scheie or Hurler syndrome), Mucopolysaccharidosis Type II (Hunter syndrome), Mucopolysaccharidosis Type VI (Maroteaux-Lamy syndrome), Mucopolysaccharidosis Type VII (Sly disease), X-linked Adrenoleukodystrophy, Globoid Cell Leukodystrophy (Krabbe disease), Metachromatic Leukodystrophy, Gaucher disease, Fucosidosis, Alpha-mannosidosis, Aspartylglucosaminuria, Farber's disease, Tay-Sachs disease, Pompe disease, Niemann Pick disease and Wolman disease. In some embodiments, the patient has a Central Nervous System (CNS) disease. In some embodiments the CNS disease is selected from Alzheimer disease, Parkinson disease, Huntington's disease, multiple sclerosis disease. In some embodiments, the patient has a CDKL5-deficiency related disease. In some embodiments the CDKL5-deficiency disease is selected from Early infantile epileptic encephalopathy (EIEE), Atypical Rett syndrome, CDKL5-related epileptic encephalopathy, and West syndrome.

The methods can be part of an autologous or part of an allogenic treatment. By autologous, it is meant that cells used for treating patients are originating from said patient. By allogeneic is meant that the cells or population of cells used for treating patients are not originating from said patient but from a donor.

In some embodiments, the cells are administrated to patients undergoing an immunosuppressive treatment. In one embodiment, the administered cells have been made resistant to at least one immunosuppressive agent. In some embodiments, the immunosuppressive treatment helps the selection and expansion of the genetically modified HSC within the patient.

The administration of the cells may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions are administered by intravenous injection, where there are capable of migrating to the bone marrow.

While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, the administration of the cells or population of cells comprises administration of about $10^4$-$10^9$ cells per kg body weight. In some embodiments, about $10^5$ to $10^6$ cells/kg body weight are administered. All integer values of cell numbers within those ranges are contemplated.

The cells can be administrated in one or more doses. In another embodiment, am effective amount of cells are administrated as a single dose. In another embodiment, an effective amount of cells are administrated as more than one dose over a period of time. Timing of administration is within the judgment of managing physician and depends on the clinical condition of the patient.

In some embodiments, administering genetically modified HSC cells can include treating the patient with a myeloablative and/or immune suppressive regimen to deplete host bone marrow stem cells and prevent rejection. In some embodiments, the patient is administered chemotherapy and/or radiation therapy. In some embodiments, the patient is administered a reduced dose chemotherapy regimen. In some embodiments, reduced dose chemotherapy regimen with busulfan at 25% of standard dose can be sufficient to achieve significant engraftment of modified cells while reducing conditioning-related toxicity (Aiuti A. et al. (2013), *Science* 23; 341 (6148)). A stronger chemotherapy regimen can be based on administration of both busulfan and fludarabine as depleting agents for endogenous HSC. In some embodiments, the dose of busulfan and fludarabine are approximately 50% and 30% of the ones employed in standard allogeneic transplantation. In another embodiment, the cells are administered following B-cell ablative therapy such as agents that react with CD20, e.g., Rituxan. In some embodiments, the patient is administered chemotherapy agents such as fludarabine, external-beam radiation therapy (XRT), cyclophosphamide, or antibodies such as OKT3 or CAMPATH.

In certain embodiments, the genetically modified cells are administered to the subject as combination therapy comprising immunosuppressive agents. Exemplary immunosuppressive agents include sirolimus, tacrolimus, cyclosporine, mycophenolate, anti-thymocyte globulin, corticosteroids, calcineurin inhibitor, anti-metabolite, such as methotrexate, post-transplant cyclophosphamide or any combination thereof. In some embodiments, the subject is pretreated with only sirolimus or tacrolimus as prophylaxis against GVHD. In some embodiments, the cells are administered to the subject before an immunosuppressive agent. In some embodiments, the cells are administered to the subject after an immunosuppressive agent. In some embodiments, the cells are administered to the subject concurrently with an immunosuppressive agent. In some embodiments, the cells are administered to the subject without an immunosuppressive agent. In some embodiments, the patient receiving genetically modified cells receives immunosuppressive agent for less than 6 months, 5 months, 4 months, 3 months, 2 months, 1 month, 3 weeks, 2 weeks, or 1 week.

Transgenes and Diseases

The transgene as used herein encodes a therapeutic protein of a disease associated gene. A disease associated gene is one that is defective in some manner in a disease. In some embodiments, the disease to be treated and transgene are shown below in Table 1.

TABLE 1

Monogenic diseases and transgenes for their treatment.

| Disease | Transgene | Nucleotide sequence | Amino acid sequence |
|---|---|---|---|
| Mucopolysaccharidosis Type I (Scheie, Hurler-Scheie or Hurler syndrome) | IDUA | SEQ ID NO: 1 | SEQ ID NO: 2 |
| Mucopolysaccharidosis Type II (Hunter syndrome) | IDS | SEQ ID NO: 3 | SEQ ID NO: 4 |
| Mucopolysaccharidosis Type VI (Maroteaux-Lamy syndrome) | ARSB | SEQ ID NO: 5 | SEQ ID NO: 6 |
| Mucopolysaccharidosis Type VII (Sly disease) | GUSB | SEQ ID NO: 7 | SEQ ID NO: 8 |
| X-linked Adrenoleukodystrophy | ABCD1 | SEQ ID NO: 9 | SEQ ID NO: 10 |
| Globoid Cell Leukodystrophy (Krabbe disease) | GALC | SEQ ID NO: 11 | SEQ ID NO: 12 |
| Metachromatic Leukodystrophy | ARSA | SEQ ID NO: 13 | SEQ ID NO: 14 |
| Metachromatic Leukodystrophy | PSAP | SEQ ID NO: 15 | SEQ ID NO: 16 |
| Gaucher disease | GBA | SEQ ID NO: 17 | SEQ ID NO: 18 |
| Fucosidosis | FUCA1 | SEQ ID NO: 19 | SEQ ID NO: 20 |
| Alpha-mannosidosis | MAN2B1 | SEQ ID NO: 21 | SEQ ID NO: 22 |
| Aspartylglucosaminuria | AGA | SEQ ID NO: 23 | SEQ ID NO: 24 |
| Farber's disease | ASAH1 | SEQ ID NO: 25 | SEQ ID NO: 26 |
| Tay-Sachs disease | HEXA | SEQ ID NO: 27 | SEQ ID NO: 28 |
| Pompe disease | GAA | SEQ ID NO: 29 | SEQ ID NO: 30 |
| Niemann Pick disease | SMPD1 | SEQ ID NO: 31 | SEQ ID NO: 32 |
| Wolman disease | LIPA | SEQ ID NO: 33 | SEQ ID NO: 34 |
| CDKL5-deficiency related diseases (e.g., Early infantile epileptic encephalopathy (EIEE) disease, Atypical Rett syndrome, CDKL5-related epileptic encephalopathy disease, or West syndrome disease) | CDKL5 | SEQ ID NO: 35 | SEQ ID NO: 36 |

In some embodiments, the transgene comprises a coding sequence of a gene selected from IDUA, IDS, ARSB, GUSB, ABCD1, GALC, ARSA, PSAP, GBA, FUCA1, MAN2B1, AGA, ASAH1, HEXA, GAA, SMPD1, LIPA and CDKL5.

In some embodiments, the nucleotide sequence of IDUA comprises SEQ ID NO:1 and the amino acid sequence comprises SEQ ID NO:2.

In some embodiments, the nucleotide sequence of IDS comprises SEQ ID NO:3 and the amino acid sequence comprises SEQ ID NO:4.

In some embodiments, the nucleotide sequence of ARSB comprises SEQ ID NO:5 and the amino acid sequence comprises SEQ ID NO:6.

In some embodiments, the nucleotide sequence of GUSB comprises SEQ ID NO:7 and the amino acid sequence comprises SEQ ID NO:8.

In some embodiments, the nucleotide sequence of ABCD1 comprises SEQ ID NO:9 and the amino acid sequence comprises SEQ ID NO:10.

In some embodiments, the nucleotide sequence of GALC comprises SEQ ID NO:11 and the amino acid sequence comprises SEQ ID NO:12.

In some embodiments, the nucleotide sequence of ARSA comprises SEQ ID NO:13 and the amino acid sequence comprises SEQ ID NO:14.

In some embodiments, the nucleotide sequence of PSAP comprises SEQ ID NO:15 and the amino acid sequence comprises SEQ ID NO:16.

In some embodiments, the nucleotide sequence of GBA comprises SEQ ID NO:17 and the amino acid sequence comprises SEQ ID NO:18.

In some embodiments, the nucleotide sequence of FUCA1 comprises SEQ ID NO:19 and the amino acid sequence comprises SEQ ID NO:20.

In some embodiments, the nucleotide sequence of MAN2B1 comprises SEQ ID NO:21 and the amino acid sequence comprises SEQ ID NO:22.

In some embodiments, the nucleotide sequence of AGA comprises SEQ ID NO:23 and the amino acid sequence comprises SEQ ID NO:24.

In some embodiments, the nucleotide sequence of ASAH1 comprises SEQ ID NO:25 and the amino acid sequence comprises SEQ ID NO:26.

In some embodiments, the nucleotide sequence of HEXA comprises SEQ ID NO:27 and the amino acid sequence comprises SEQ ID NO:28.

In some embodiments, the nucleotide sequence of GAA comprises SEQ ID NO:29 and the amino acid sequence comprises SEQ ID NO:30.

In some embodiments, the nucleotide sequence of SMPD1 comprises SEQ ID NO:31 and the amino acid sequence comprises SEQ ID NO:32.

In some embodiments, the nucleotide sequence of LIPA comprises SEQ ID NO:33 and the amino acid sequence comprises SEQ ID NO:34.

In some embodiments, the nucleotide sequence of CDKL5 comprises SEQ ID NO:35 and the amino acid sequence comprises SEQ ID NO:36.

In some embodiments, the transgene comprises one or more copies of a nucleotide sequence selected from any one of SEQ ID NOS:1, 3, 5, 7, 9, 11, 13, 15, 17, 19, 21, 23, 25, 27, 29, 31, 33 and 35.

In some embodiments, the transgene comprises one or more copies of a nucleotide sequence encoding an amino acid sequence selected from any one of SEQ ID NOS:2, 4, 6, 8, 10, 12, 14, 16, 18, 20, 22, 24, 26, 28, 30, 32, 34 and 36.

In some embodiments, the transgene comprises a nucleotide sequence encoding a therapeutic protein that is a variant of any one of SEQ ID NOS:2, 4, 6, 8, 10, 12, 14, 16, 18, 20, 22, 24, 26, 28, 30, 32, 34 and 36.

A particular nucleotide sequence encoding a therapeutic protein may be identical over its entire length to the coding sequence in SEQ ID NOS:1, 3, 5, 7, 9, 11, 13, 15, 17, 19, 21, 23, 25, 27, 29, 31, 33 or 35. Alternatively, a particular nucleotide sequence encoding a therapeutic protein may be an alternate form of SEQ ID NOS: 1, 3, 5, 7, 9, 11, 13, 15, 17, 19, 21, 23, 25, 27, 29, 31, 33 or 35 due to degeneracy in the genetic code or variation in codon usage encoding the polypeptides of SEQ ID NOS:2, 4, 6, 8, 10, 12, 14, 16, 18, 20, 22, 24, 26, 28, 30, 32, 34 and 36. In some embodiments, the transgene comprises a nucleotide sequence that is highly identical, at least 90% identical, with a nucleotide sequence encoding a therapeutic protein or at least 90% identical with the encoding nucleotide sequence set forth in SEQ ID NOS: 1, 3, 5, 7, 9, 11, 13, 15, 17, 19, 21, 23, 25, 27, 29, 31, 33 or 35. In some embodiments, the transgene comprises a nucleotide sequence that is at least 90%, 91%, 92%, 93%, 94%, 95%, 96%, 97%, 98%, or 99% identical to the nucleotide sequence set forth in SEQ ID NOS: 1, 3, 5, 7, 9, 11, 13, 15, 17, 19, 21, 23, 25, 27, 29, 31, 33 or 35.

When a transgene comprising a polynucleotide encoding the therapeutic proteins of the invention is used for the recombinant production of a therapeutic protein, the polynucleotide may include the coding sequence for the full-length polypeptide or a fragment thereof, by itself; the coding sequence for the full-length polypeptide or fragment in reading frame with other coding sequences, such as those encoding a leader or secretory sequence, a pre-, or pro or prepro-protein sequence, or other fusion peptide portions. The polynucleotide may also contain non-coding 5' and 3' sequences, such as transcribed, non-translated sequences, splicing and polyadenylation signals, ribosome binding sites and sequences that stabilize mRNA.

In some embodiments the therapeutic protein can further comprises secretory signal peptides allowing its secretion by the gene edited cells of the present invention. Some Examples of such signal peptides are listed in Table 2 below:

TABLE 2

Examples of useful signal peptides

| SEQ ID NO: # | Origin of the peptide | Polypeptide sequence |
|---|---|---|
| 37 | Human albumin peptide | MKWVTFISLLFLFSSAYS |
| 38 | Human chymotrypsinogen peptide | MAFLWLLSCWALLGTTFG |
| 39 | Human interleukin-2 peptide | MQLLSCIALILALV |
| 40 | Human trypsinogen-2 peptide | MNLLLILTFVAAAVA |
| 41 | Human BM40 peptide | MRAWIFFLLCLAGRALA |
| 42 | Secrecon | MWWRLWWLLLLLLLWPMVWA |
| 43 | Mouse IgK VIII | METDTLLLWVLLLWVPGSTG |
| 44 | Human IgK VIII | MDMRVPAQLLGLLLLWLRGARC |
| 45 | CD33 | MPLLLLLPLLWAGALA |

TABLE 2-continued

Examples of useful signal peptides

| SEQ ID NO: # | Origin of the peptide | Polypeptide sequence |
|---|---|---|
| 46 | tPA | MDAMKRGLCCVLLLCGAVFVSPS |
| 47 | Consensus | MLLLLLLLLLALALA |
| 48 | Native | MLLLLLLLGLRLQLSLG |

In some embodiments the therapeutic protein can further comprise peptide allowing cell uptake, such as cell penetrating peptides (CPP) and Apolipoproteins. Examples of cell penetrating peptides and Apolipoproteins are listed in Table 3 below.

TABLE 3

Examples of useful CPP and Apolipoproteins

| SEQ ID NO: # | Origin of the polypeptide | Polypeptide sequence |
|---|---|---|
| 49 | Penetratin | RQIKIWFQNRRMKWKK |
| 50 | TAT | YGRKKRRQRRR |
| 51 | SynB1 | RGGRLSYSRRRFSTSTGR |
| 52 | SynB3 | RRLSYSRRRF |
| 53 | PTD-4 | PIRRRKKLRRLK |
| 54 | PTD-5 | RRQRRTSKLMKR |
| 55 | FHV Coat | RRRRNRTRRNRRRVR |
| 56 | BMV Gag | KMTRAQRRAAARRNRWTAR |
| 57 | HTLV-II Rex | TRRQRTRRARRNR |
| 58 | D-Tat | GRKKRRQRRRPPQ |
| 59 | R9-Tat | GRRRRRRRRRPPQ |
| 60 | Transportan | GWTLNSAGYLLGKINLKALAALAKKIL |
| 61 | MAP | KLALKLALKLALALKLA |
| 62 | SBP | MGLGLHLLVLAAALQGAWSQPKKKRKV |
| 63 | FBP | GALFLGWLGAAGSTMGAWSQPKKKRKV |
| 64 | MPG ac | GALFLGFLGAAGSTMGAWSQPKKKRKV |
| 65 | MPG(ΔNLS) | GALFLGFLGAAGSTMGAWSQPKSKRKV |
| 66 | Pep-1 | KETWWETWWTEWSQPKKKRKV |
| 67 | Pep-2 | KETWFETWFTEWSQPKKKRKV |
| 68 | ApoE p1 | LRKLRKRLLLRKLRKRLL |
| 69 | ApoE p2 | LRKLRKRLLRDADDLLRKLRKRLLRDADDL |
| 70 | ApoE p3 | LRVRLASHLRKLRKRLL |
| 71 | ApoE p4 | TEELRVRLASHLRKLRKRLL |
| 72 | ApoE p5 | LRVRLASHLRKLRKRLLLRVRLASHLRKLRKRLL |

TABLE 3-continued

Examples of useful CPP and Apolipoproteins

| SEQ ID NO: # | Origin of the polypeptide | Polypeptide sequence |
|---|---|---|
| 73 | ApoE p6 | TEELRVRLASHLRKLRKRLLTEELRVRLASHLRKLRKRLL |
| 74 | Myc Peptide | EQKLISEEDL |
| 75 | ApoB Peptide | SSVIDALQYKLEGTTRLTRKRGLKLATALSLSNKFVEGS |

In some embodiments, the transgene comprises a polynucleotide having a nucleotide sequence at least 90% identical, and more preferably at least 91%, 92%, 93%, 94%, 95%, 96%, 97%, 98% or 99% identical to a nucleotide sequence encoding a therapeutic protein having the amino acid sequence in SEQ ID NOS:2, 4, 6, 8, 10, 12, 14, 16, 18, 20, 22, 24, 26, 28, 30, 32, 34 and 36.

Conventional means utilizing known computer programs such as the BestFit program (Wisconsin Sequence Analysis Package, Version 10 for Unix, Genetics Computer Group. University Research Park, 575 Science Drive, Madison, Wis. 53711) may be utilized to determine if a particular nucleic acid molecule is at least 90%, 91%, 92%, 93%, 94%, 95%, 96%, 97%, 98% or 99% identical to any one of the nucleotide sequences shown in SEQ ID NOS:1, 3, 5, 7, 9, 11, 13, 15, 17, 19, 21, 23, 25, 27, 29, 31, 33 or 35.

In some embodiments, the transgene comprises a polynucleotide encoding a therapeutic protein that has an amino acid sequence of the therapeutic protein of SEQ ID NOS:2, 4, 6, 8, 10, 12, 14, 16, 18, 20, 22, 24, 26, 28, 30, 32, or 34, in which several, 1, 1-2, 1-3, 1-5, 5-10, or 10-20 amino acid residues are substituted, deleted or added, in any combination.

In some embodiments, the transgene comprises a polynucleotide that is at least 90%, 91%, 92%, 93%, 94%, 95%, 96%, 97%, 98% or 99% identical over their entire length to a polynucleotide encoding a therapeutic protein having the amino acid sequence set out in SEQ ID NOS:2, 4, 6, 8, 10, 12, 14, 16, 18, 20, 22, 24, 26, 28, 30, 32, 34 or 36.

In some embodiments, the therapeutic protein expressed by the transgene is identical to a wild-type amino acid sequence of the protein, e.g., any of SEQ ID NOS:2, 4, 6, 8, 10, 12, 14, 16, 18, 20, 22, 24, 26, 28, 30, 32, 34 or 36.

In some embodiments, the therapeutic protein expressed by the transgene is a functional fragment or variant of any of SEQ ID NOS:2, 4, 6, 8, 10, 12, 14, 16, 18, 20, 22, 24, 26, 28, 30, 32, 34 or 36.

In some embodiments, the therapeutic protein comprises the polypeptide of SEQ ID NOS:2, 4, 6, 8, 10, 12, 14, 16, 18, 20, 22, 24, 26, 28, 30, 32, 34 or 36, as well as polypeptides and fragments which have activity and comprise at least 90% identity to the polypeptide of SEQ ID NOS:2, 4, 6, 8, 10, 12, 14, 16, 18, 20, 22, 24, 26, 28, 30, 32, 34 or 36, or the relevant portion and more preferably at least 96%, 97% or 98% identity to the polypeptide of SEQ ID NOS:2, 4, 6, 8, 10, 12, 14, 16, 18, 20, 22, 24, 26, 28, 30, 32, 34 or 36, and still more preferably at least 91%, 92%, 93%, 94%, 95%, 96%, 97%, 98%, 99%, or 100% identity to the polypeptide of SEQ ID NOS:2, 4, 6, 8, 10, 12, 14, 16, 18, 20, 22, 24, 26, 28, 30, 32, 34 or 36.

The therapeutic protein may be a part of a larger protein such as a fusion protein. It is often advantageous to include additional amino acid sequence which contains secretory or leader sequences, pro-sequences, or other sequences which may aid in stability.

In some embodiments, the transgene encodes a biologically active fragment of any of SEQ ID NOS:2, 4, 6, 8, 10, 12, 14, 16, 18, 20, 22, 24, 26, 28, 30, 32, or 34. A fragment is a polypeptide having an amino acid sequence that entirely is the same as part but not all of the amino acid sequence of one of the aforementioned therapeutic protein. As with the full length therapeutic proteins, fragments may be "free-standing," or comprised within a larger polypeptide of which they form a part or region, most preferably as a single continuous region. In some embodiments, a fragment can constitute from about 10 contiguous amino acids identified in SEQ ID NOS:2, 4, 6, 8, 10, 12, 14, 16, 18, 20, 22, 24, 26, 28, 30, 32, 34 or 36.

In some embodiments, fragments include, for example, truncation polypeptides having the amino acid sequence of the therapeutic protein, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Functional fragments are those that mediate protein activity of the wild type protein, including those with a similar activity or an improved activity.

In some embodiments, the fragments can lack from 1-20 amino acids (i.e., 1, 2, 3, 4, 5, 6, 7, 8, 9, 10, 11, 12, 13, 14, 15, 16, 17, 18, 19, or 20 amino acids) of the N-terminus and/or C-terminus of any of SEQ ID NOS:2, 4, 6, 8, 10, 12, 14, 16, 18, 20, 22, 24, 26, 28, 30, 32, 34 or 36.

In some embodiments, the transgene encodes a polypeptide having an amino acid sequence at least 90% identical to that of SEQ ID NOS:2, 4, 6, 8, 10, 12, 14, 16, 18, 20, 22, 24, 26, 28, 30, 32, 34 or 36, or functional fragments thereof with at least 90% identity to the corresponding fragment of SEQ ID NOS:2, 4, 6, 8, 10, 12, 14, 16, 18, 20, 22, 24, 26, 28, 30, 32, 34 or 36, all of which retain the biological activity of the therapeutic protein. Included in this group are variants of the defined sequence and fragment. In some embodiments, variants are those that vary from the reference sequence by conservative amino acid substitutions, i.e. those that substitute a residue with another of like characteristics. Typical substitutions are among Ala, Val, Leu and Ile; among Ser and Thr; among the acidic residues Asp and Glu; among Asn and Gln; and among the basic residues Lys and Arg, or aromatic residues Phe and Tyr. In some embodiments, the transgene encodes a polypeptide variants in which 1-20 amino acids are substituted, deleted, or added in any combination.

CDKL5-Deficiency Related Diseases:

Early Infantile Epileptic Encephalopathy (EIEE) Disease

Early Infantile Epileptic Encephalopathy (EIEE) is a neurological disorder characterized by seizures. The disorder affects newborns, usually within the first three months of life (most often within the first 10 days) in the form of epileptic seizures. Infants have primarily tonic seizures (which cause stiffening of muscles of the body, generally those in the back, legs, and arms), but may also experience partial seizures, and rarely, myoclonic seizures (which cause jerks or twitches of the upper body, arms, or legs). Episodes may occur more than a hundred times per day. Most infants with the disorder show underdevelopment of part or all of the cerebral hemispheres or structural anomalies. Some cases are caused by metabolic disorders or by mutations in several different genes. The cause for many cases can't be determined. There are several types of early infantile epileptic encephalopathy. The EEGs reveal a characteristic pattern of high voltage spike wave discharge followed by little activity. This pattern is known as "burst suppression." The seizures associated with this disease are difficult to treat and the syndrome is severely progressive. Some children with this condition go on to develop other epileptic disorders such as West syndrome and Lennox-Gestaut syndrome.

EWE may be the result of different etiologies. Many cases have been associated with structural brain abnormalities. Some cases are due to metabolic disorders (cytochrome C oxidase deficiency, carnitine palmitoyl transferase II deficiency) or brain malformations (such as porencephaly, or hemimegalencephaly) that may or not be genetic in origin. Genetic variants of EIEE have been associated with mutations in certain genes such as ARX (Xp22.13), CDKL5 (Xp22), SL25A22 (11p15.5) and STXBP1 (9q34.1), among others. The genetic abnormalities are thought to lead to EWE as they are related to neuronal dysfunction or brain dysgenesis.

Atypical Rett Syndrome

Atypical Rett syndrome is a neurodevelopmental disorder that is diagnosed when a child has some of the symptoms of Rett syndrome but does not meet all the diagnostic criteria. Like the classic form of Rett syndrome, atypical Rett syndrome mostly affects girls. Children with atypical Rett syndrome can have symptoms that are either milder or more severe than those seen in Rett syndrome. Several subtypes of atypical Rett syndrome have been defined. The early-onset seizure type is characterized by seizures in the first months of life with later development of Rett features (including developmental problems, loss of language skills, and repeated hand wringing or hand washing movements). It is frequently caused by mutations in the X-linked CDKL5 gene (Xp22).

CDKL5-Related Epileptic Encephalopathy Disease

CDKL5-related epileptic encephalopathy is characterized by a 3-stage evolution consisting of early epilepsy (stage 1), then infantile spasms (stage 2) and, finally, multifocal and refractory myoclonic epilepsy (stage 3). See, e.g., Bahi-Buisson et al. *Epilepsia.* 49:1027-1037 (2008). Genetic abnormalities of cyclin-dependent kinase-like 5 (CDKL5) cause an early-onset epileptic encephalopathy.

West Syndrome Disease

West syndrome is a type of epilepsy characterized by spasms, abnormal brain wave patterns called hypsarrhythmia and sometimes intellectual disability. The spasms that occur may range from violent jackknife or "salaam" movements where the whole body bends in half, or they may be no more than a mild twitching of the shoulder or eye changes. These spasms usually begin in the early months after birth and can sometimes be helped with medication. There are many different causes of West syndrome and if a specific cause can be identified, a diagnosis of symptomatic West syndrome can be made. If a cause cannot be determined, a diagnosis of cryptogenic West syndrome is made. A specific cause for West syndrome can be identified in approximately 70-75% of those affected. X-linked West syndrome (X-linked infantile spasm syndrome or ISSX) can be caused by a mutation in the CDKL5 gene or the ARX gene on the X chromosome.

Mucopolysaccharidoses

Mucopolysaccharidoses (MPSs) are degenerative genetic diseases linked to an enzymatic defect. In particular, MPSs are caused by the deficiency or the inactivity of lysosomal enzymes which catalyze the gradual metabolism of complex sugar molecules called glycosaminoglycans (GAGs). These enzymatic deficiencies cause an accumulation of GAGs in the cells, the tissues and, in particular, the cell lysosomes of affected subjects, leading to permanent and progressive cell damage which affects the appearance, the physical capacities, the organ function and, in most cases, the mental development of affected subjects.

Eleven distinct enzymatic defects have been identified, corresponding to seven distinct clinical categories of MPS. Each MPS is characterized by a deficiency or inactivity of one or more enzymes which degrade mucopolysaccharides, namely heparan sulfate, dermatan sulfate, chondroitin sulfate and keratan sulfate.

MPS I is divided into three subtypes based on severity of symptoms. All three types result from an absence of, or insufficient levels of, the enzyme alpha-L-iduronidase (IDUA). Children born to an MPS I parent carry the defective gene.

MPS I H (also called Hurler syndrome or alpha-L-iduronidase deficiency), is the most severe of the MPS I subtypes. Developmental delay is evident by the end of the first year, and patients usually stop developing between ages 2 and 4. This is followed by progressive mental decline and loss of physical skills. Language may be limited due to hearing loss and an enlarged tongue. In time, the clear layers of the cornea become clouded and retinas may begin to degenerate. Carpal tunnel syndrome (or similar compression of nerves elsewhere in the body) and restricted joint movement are common. Affected children may be quite large at birth and appear normal but may have inguinal (in the groin) or umbilical (where the umbilical cord passes through the abdomen) hernias. Growth in height may be faster than normal but begins to slow before the end of the first year and often ends around age 3. Many children develop a short body trunk and a maximum stature of less than 4 feet. Distinct facial features (including flat face, depressed nasal bridge, and bulging forehead) become more evident in the second year. By age 2, the ribs have widened and are oar-shaped. The liver, spleen, and heart are often enlarged. Children may experience noisy breathing and recurring upper respiratory tract and ear infections. Feeding may be difficult for some children, and many experience periodic bowel problems. Children with Hurler syndrome often die before age 10 from obstructive airway disease, respiratory infections, and cardiac complications.

MPS I S, Scheie syndrome, is the mildest form of MPS 1. Symptoms generally begin to appear after age 5, with diagnosis most commonly made after age 10. Children with Scheie syndrome have normal intelligence or may have mild learning disabilities; some may have psychiatric problems. Glaucoma, retinal degeneration, and clouded corneas may significantly impair vision. Other problems include carpal tunnel syndrome or other nerve compression, stiffjoints, claw hands and deformed feet, a short neck, and aortic valve disease. Some affected individuals also have obstructive airway disease and sleep apnea. Persons with Scheie syndrome can live into adulthood.

MPS I H-S, Hurler-Scheie syndrome, is less severe than Hurler syndrome alone. Symptoms generally begin between ages 3 and 8. Children may have moderate intellectual disability and learning difficulties. Skeletal and systemic irregularities include short stature, marked smallness in the jaws, progressive joint stiffness, compressed spinal cord, clouded corneas, hearing loss, heart disease, coarse facial features, and umbilical hernia. Respiratory problems, sleep apnea, and heart disease may develop in adolescence. Some persons with MPS I H-S need continuous positive airway pressure during sleep to ease breathing. Life expectancy is generally into the late teens or early twenties.

MPS II, also known as Hunter syndrome, is caused by lack of the enzyme iduronate sulfatase. Hunter syndrome has two clinical subtypes and (since it shows X-linked recessive inheritance) is the only one of the mucopolysaccharidoses in which the mother alone can pass the defective gene to a son. The incidence of Hunter syndrome is estimated to be 1 in 100,000 to 150,000 male births.

Mutations in the IDS gene cause MPS II. The IDS gene provides instructions for producing the I2S enzyme, which is involved in the breakdown of large sugar molecules called glycosaminoglycans (GAGs). Specifically, I2S removes a chemical group known as a sulfate from a molecule called sulfated alpha-L-iduronic acid, which is present in two GAGs called heparan sulfate and dermatan sulfate. I2S is located in lysosomes, compartments within cells that digest and recycle different types of molecules.

Mucopolysaccharidosis type VI (MPS VI) or Maroteaux-Lamy disease is a lysosomal storage disease, of the mucopolysaccharidosis group, characterized by severe somatic involvement and an absence of psycho-intellectual regression. The prevalence of this rare mucopolysaccharidosis is between 1/250,000 and 1/600,000 births. In the severe forms, the first clinical manifestations occur between 6 and 24 months and are gradually accentuated: facial dysmorphia (macroglossia, mouth constantly half open, thick features), joint limitations, very severe dysostosis multiplex (platyspondyly, kyphosis, scoliosis, pectus carinatum, genu valgum, long bone deformation), small size (less than 1.10 m), hepatomegaly, heart valve damage, cardiomyopathy, deafness, corneal opacities. Intellectual development is usually normal or virtually normal, but the auditory and ophthalmological damage can cause learning difficulties. The symptoms and the severity of the disease vary considerably from one patient to the other and intermediate forms, or even very moderate forms also exist (spondyloepiphyseal-metaphyseal dysplasia associated with cardiovascular involvement). Like the other mucopolysaccharidoses, Maroteaux-Lamy disease is linked to the defect of an enzyme of mucopolysaccharide metabolism, in the case in point N-acetylgalactosamine-4-sulfatase (also called arylsulfatase B)(ARSB). This enzyme metabolizes the sulfate group of dermatan sulfate (Neufeld et al.: "The mucopolysaccharidoses" The Metabolic Basis of Inherited Diseases, eds. Scriver et al, New York, McGraw-Hill, 1989, p. 1565-1587). This enzymatic defect blocks the gradual degradation of dermatan sulfate, thereby leading to an accumulation of dermatan sulfate in the lysosomes of the storage tissues.

Mucopolysaccharidosis type VII (MPS VII) or Sly disease is a very rare lysosomal storage disease of the mucopolysaccharidosis group. The symptomology is extremely heterogeneous: antenatal forms (nonimmune fetoplacental anasarca), severe neonatal forms (with dysmorphia, hernias, hepatosplenomegaly, club feet, dysostosis, significant hypotonia and neurological problems evolving to retarded growth and a profound intellectual deficiency in the event of survival) and very moderate forms discovered at adolescence or even at adult age (thoracic kyphosis). The disease is due to a defect in beta-D-glucuronidase (GUSB) responsible for accumulation, in the lysosomes, of various glycosaminoglycans: dermatan sulfate, heparan sulfate and chondroitin sulfate. There is at the current time no effective treatment for this disease.

X-Linked Adrenoleukodystrophy

Adrenoleukodystrophy (ALD) is an X-linked disease affecting 1/20,000 males either as cerebral ALD in childhood or as adrenomyleneuropathy (AMN) in adults. Childhood ALD is the more severe form, with onset of neurological symptoms between 5-12 years of age. Central nervous system demyelination progresses rapidly and death occurs within a few years. AMN is a milder form of the disease with onset at 15-30 years of age and a more progressive course. Adrenal insufficiency (Addison's disease) may remain the only clinical manifestation of ALD. The principal biochemical abnormality of ALD is the accumulation of very long chain fatty acids (VLCFA) because of impaired β-oxidation in peroxisomes.

More than 650 mutations in the ABCD1 gene have been found to cause X-linked adrenoleukodystrophy. This condition is characterized by varying degrees of cognitive and movement problems as well as hormone imbalances. The mutations that cause X-linked adrenoleukodystrophy prevent the production of any ALDP in about 75 percent of people with this disorder. Other people with X-linked adrenoleukodystrophy can produce ALDP, but the protein is not able to perform its normal function. With little or no functional ALDP, VLCFAs are not broken down, and they build up in the body. The accumulation of these fats may be toxic to the adrenal glands (small glands on top of each kidney) and to the fatty layer of insulation (myelin) that surrounds many nerves in the body. Research suggests that the accumulation of VLCFAs triggers an inflammatory response in the brain, which could lead to the breakdown of myelin. The destruction of these tissues leads to the signs and symptoms of X-linked adrenoleukodystrophy.

Globoid Cell Leukodystrophy

Infantile globoid cell leucodystrophy (GLD, galactosylceramide lipidosis or Krabbe's disease) is a rare, autosomal recessive hereditary degenerative disorder in the central and peripheral nervous systems. The incidence in the US is estimated to 1:100.000. It is characterized by the presence of globoid cells (cells with multiple nuclei), degeneration of the protective myelin layer of the nerves and loss of cells in the brain. GLD causes severe mental reduction and motoric delay. It is caused by a deficiency in galactocerebroside-β-galactosidase (GALC), which is an essential enzyme in the metabolism of myelin. The disease often affects infants prior to the age of 6 months, but it can also appear during youth or in adults. The symptoms include irritability, fever without any known cause, stiffness in the limbs (hypertony), seizures, problems associated with food intake, vomiting and delayed development of mental and motoric capabilities. Additional symptoms include muscular weakness, spasticity, deafness and blindness.

The galactosylceramidase gene (GALC) is about 60 kb in length and consists of 17 exons. Numerous mutations and polymorphisms have been identified in the murine and human GALC gene, causing GLD with different degrees of severity.

Metachromatic Leukodystrophy

Metachromatic leukodystrophy is an inherited disorder characterized by the accumulation of fats called sulfatides in cells. This accumulation especially affects cells in the nervous system that produce myelin, the substance that insulates and protects nerves. Nerve cells covered by myelin make up a tissue called white matter. Sulfatide accumulation in myelin-producing cells causes progressive destruction of white matter (leukodystrophy) throughout the nervous system, including in the brain and spinal cord (the central nervous system) and the nerves connecting the brain and spinal cord to muscles and sensory cells that detect sensations such as touch, pain, heat, and sound (the peripheral nervous system).

In people with metachromatic leukodystrophy, white matter damage causes progressive deterioration of intellectual functions and motor skills, such as the ability to walk. Affected individuals also develop loss of sensation in the extremities (peripheral neuropathy), incontinence, seizures, paralysis, an inability to speak, blindness, and hearing loss. Eventually they lose awareness of their surroundings and become unresponsive. While neurological problems are the primary feature of metachromatic leukodystrophy, effects of sulfatide accumulation on other organs and tissues have been reported, most often involving the gallbladder.

The most common form of metachromatic leukodystrophy, affecting about 50 to 60 percent of all individuals with this disorder, is called the late infantile form. This form of the disorder usually appears in the second year of life. Affected children lose any speech they have developed, become weak, and develop problems with walking (gait disturbance). As the disorder worsens, muscle tone generally first decreases, and then increases to the point of rigidity. Individuals with the late infantile form of metachromatic leukodystrophy typically do not survive past childhood.

In 20 to 30 percent of individuals with metachromatic leukodystrophy, onset occurs between the age of 4 and adolescence. In this juvenile form, the first signs of the disorder may be behavioral problems and increasing difficulty with schoolwork. Progression of the disorder is slower than in the late infantile form, and affected individuals may survive for about 20 years after diagnosis.

Most individuals with metachromatic leukodystrophy have mutations in the ARSA gene, which provides instructions for making the enzyme arylsulfatase A. This enzyme is located in cellular structures called lysosomes, which are the cell's recycling centers. Within lysosomes, arylsulfatase A helps break down sulfatides. A few individuals with metachromatic leukodystrophy have mutations in the PSAP gene. This gene provides instructions for making a protein that is broken up (cleaved) into smaller proteins that assist enzymes in breaking down various fats. One of these smaller proteins is called saposin B; this protein works with arylsulfatase A to break down sulfatides.

Mutations in the ARSA or PSAP genes result in a decreased ability to break down sulfatides, resulting in the accumulation of these substances in cells. Excess sulfatides are toxic to the nervous system. The accumulation gradually destroys myelin-producing cells, leading to the impairment of nervous system function that occurs in metachromatic leukodystrophy.

In some cases, individuals with very low arylsulfatase A activity show no symptoms of metachromatic leukodystrophy. This condition is called pseudoarylsulfatase deficiency.

The adult form of metachromatic leukodystrophy affects approximately 15 to 20 percent of individuals with the disorder. In this form, the first symptoms appear during the teenage years or later. Often behavioral problems such as alcoholism, drug abuse, or difficulties at school or work are the first symptoms to appear. The affected individual may experience psychiatric symptoms such as delusions or hallucinations. People with the adult form of metachromatic leukodystrophy may survive for 20 to 30 years after diagnosis. During this time there may be some periods of relative stability and other periods of more rapid decline.

Metachromatic leukodystrophy gets its name from the way cells with an accumulation of sulfatides appear when viewed under a microscope. The sulfatides form granules that are described as metachromatic, which means they pick up color differently than surrounding cellular material when stained for examination.

Gaucher Disease

Gaucher disease is an inherited disorder that affects many of the body's organs and tissues. The signs and symptoms of this condition vary widely among affected individuals. Researchers have described several types of Gaucher disease based on their characteristic features.

Type 1 Gaucher disease is the most common form of this condition. Type 1 is also called non-neuronopathic Gaucher disease because the brain and spinal cord (the central nervous system) are usually not affected. The features of this condition range from mild to severe and may appear anytime from childhood to adulthood. Major signs and symptoms include enlargement of the liver and spleen (hepatosplenomegaly), a low number of red blood cells (anemia), easy bruising caused by a decrease in blood platelets (thrombocytopenia), lung disease, and bone abnormalities such as bone pain, fractures, and arthritis.

Types 2 and 3 Gaucher disease are known as neuronopathic forms of the disorder because they are characterized by problems that affect the central nervous system. In addition to the signs and symptoms described above, these conditions can cause abnormal eye movements, seizures, and brain damage. Type 2 Gaucher disease usually causes life-threatening medical problems beginning in infancy. Type 3 Gaucher disease also affects the nervous system, but it tends to worsen more slowly than type 2.

The most severe type of Gaucher disease is called the perinatal lethal form. This condition causes severe or life-threatening complications starting before birth or in infancy. Features of the perinatal lethal form can include extensive swelling caused by fluid accumulation before birth (hydrops fetalis); dry, scaly skin (ichthyosis) or other skin abnormalities; hepatosplenomegaly; distinctive facial features; and serious neurological problems. As its name indicates, most infants with the perinatal lethal form of Gaucher disease survive for only a few days after birth.

Another form of Gaucher disease is known as the cardiovascular type because it primarily affects the heart, causing the heart valves to harden (calcify). People with the cardiovascular form of Gaucher disease may also have eye abnormalities, bone disease, and mild enlargement of the spleen (splenomegaly).

Mutations in the GBA gene cause Gaucher disease. The GBA gene provides instructions for making an enzyme called beta-glucocerebrosidase. This enzyme breaks down a fatty substance called glucocerebroside into a sugar (glucose) and a simpler fat molecule (ceramide). Mutations in the GBA gene greatly reduce or eliminate the activity of beta-glucocerebrosidase. Without enough of this enzyme, glucocerebroside and related substances can build up to toxic levels within cells. Tissues and organs are damaged by the abnormal accumulation and storage of these substances, causing the characteristic features of Gaucher disease.

Fucosidosis

Fucosidosis is a condition that affects many areas of the body, especially the brain. Affected individuals have intellectual disability that worsens with age, and many develop dementia later in life. People with this condition often have delayed development of motor skills such as walking; the skills they do acquire deteriorate over time. Additional signs and symptoms of fucosidosis include impaired growth; abnormal bone development (dysostosis multiplex); seizures; abnormal muscle stiffness (spasticity); clusters of enlarged blood vessels forming small, dark red spots on the skin (angiokeratomas); distinctive facial features that are often described as "coarse"; recurrent respiratory infections; and abnormally large abdominal organs (visceromegaly).

In severe cases, symptoms typically appear in infancy, and affected individuals usually live into late childhood. In milder cases, symptoms begin at age 1 or 2, and affected individuals tend to survive into mid-adulthood.

In the past, researchers described two types of this condition based on symptoms and age of onset, but current opinion is that the two types are actually a single disorder with signs and symptoms that range in severity.

Mutations in the FUCA1 gene cause fucosidosis. The FUCA1 gene provides instructions for making an enzyme called alpha-L-fucosidase. This enzyme plays a role in the breakdown of complexes of sugar molecules (oligosaccharides) attached to certain proteins (glycoproteins) and fats (glycolipids). Alpha-L-fucosidase is responsible for cutting (cleaving) off a sugar molecule called fucose toward the end of the breakdown process.

FUCA1 gene mutations severely reduce or eliminate the activity of the alpha-L-fucosidase enzyme. A lack of enzyme activity results in an incomplete breakdown of glycolipids and glycoproteins. These partially broken down compounds gradually accumulate within various cells and tissues throughout the body and cause cells to malfunction. Brain cells are particularly sensitive to the buildup of glycolipids and glycoproteins, which can result in cell death. Loss of brain cells is thought to cause the neurological symptoms of fucosidosis. Accumulation of glycolipids and glycoproteins also occurs in other organs such as the liver, spleen, skin, heart, pancreas, and kidneys, contributing to the additional symptoms of fucosidosis.

Alpha-Mannosidosis

Alpha-mannosidosis is an autosomal, recessively inherited lysosomal storage disorder that has been clinically well characterized (M. A. Chester et al., 1982, in Genetic Errors of Glycoprotein Metabolism pp 90-119, Springer Verlag, Berlin). Glycoproteins are normally degraded stepwise in the lysosome and one of the steps, namely the cleavage of .alpha.-linked mannose residues from the non-reducing end during the ordered degradation of N-linked glycoproteins is catalysed by the enzyme lysosomal α-mannosidase (EC 3.2.1.24). However, in alpha-mannosidosis, a deficiency of the enzyme α-mannosidase results in the accumulation of mannose rich oligosaccharides. As a result, the lysosomes increase in size and swell, which impairs cell functions.

The symptoms of α-mannosidosis include psychomotor retardation, ataxia, impaired hearing, vacuolized lymphocytes in the peripheral blood and skeletal changes.

Mutations in the MAN2B1 gene cause alpha-mannosidosis. This gene provides instructions for making the enzyme alpha-mannosidase. This enzyme works in the lysosomes, which are compartments that digest and recycle materials in the cell. Within lysosomes, the enzyme helps break down complexes of sugar molecules (oligosaccharides) attached to certain proteins (glycoproteins). In particular, alpha-mannosidase helps break down oligosaccharides containing a sugar molecule called mannose.

Mutations in the MAN2B1 gene interfere with the ability of the alpha-mannosidase enzyme to perform its role in breaking down mannose-containing oligosaccharides. These oligosaccharides accumulate in the lysosomes and cause cells to malfunction and eventually die. Tissues and organs are damaged by the abnormal accumulation of oligosaccharides and the resulting cell death, leading to the characteristic features of alpha-mannosidosis.

Aspartylglucosaminuria

Aspartylglucosaminuria is a condition that causes a progressive decline in mental functioning. Infants with aspartylglucosaminuria appear healthy at birth, and development is typically normal throughout early childhood. The first sign of this condition, evident around the age of 2 or 3, is usually delayed speech. Mild intellectual disability then becomes apparent, and learning occurs at a slowed pace. Intellectual disability progressively worsens in adolescence. Most people with this disorder lose much of the speech they have learned, and affected adults usually have only a few words in their vocabulary. Adults with aspartylglucosaminuria may develop seizures or problems with movement.

People with this condition may also have bones that become progressively weak and prone to fracture (osteoporosis), an unusually large range of joint movement (hypermobility), and loose skin. Affected individuals tend to have a characteristic facial appearance that includes widely spaced eyes (ocular hypertelorism), small ears, and full lips. The nose is short and broad and the face is usually square-shaped. Children with this condition may be tall for their age, but lack of a growth spurt in puberty typically causes adults to be short. Affected children also tend to have frequent upper respiratory infections. Individuals with aspartylglucosaminuria usually survive into mid-adulthood.

Mutations in the AGA gene cause aspartylglucosaminuria. The AGA gene provides instructions for producing an enzyme called aspartylglucosaminidase. This enzyme is active in lysosomes, which are structures inside cells that act as recycling centers. Within lysosomes, the enzyme helps break down complexes of sugar molecules (oligosaccharides) attached to certain proteins (glycoproteins).

AGA gene mutations result in the absence or shortage of the aspartylglucosaminidase enzyme in lysosomes, preventing the normal breakdown of glycoproteins. As a result, glycoproteins can build up within the lysosomes. Excess glycoproteins disrupt the normal functions of the cell and can result in destruction of the cell. A buildup of glycoproteins seems to particularly affect nerve cells in the brain; loss of these cells causes many of the signs and symptoms of aspartylglucosaminuria.

Farber's Disease

Farber's disease is an inherited condition involving the breakdown and use of fats in the body (lipid metabolism). People with this condition have an abnormal accumulation of lipids (fat) throughout the cells and tissues of the body, particularly around the joints. Farber's disease is characterized by three classic symptoms: a hoarse voice or weak cry, small lumps of fat under the skin and in other tissues (lipogranulomas), and swollen and painful joints. Other symptoms may include difficulty breathing, an enlarged liver and spleen (hepatosplenomegaly), and developmental delay. Researchers have described seven types of Farber's disease based on their characteristic features. This condition is caused by mutations in the ASAH1 gene and is inherited in an autosomal recessive manner.

Tay-Sachs Disease

Tay-Sachs disease is a rare inherited disorder that progressively destroys nerve cells (neurons) in the brain and spinal cord.

The most common form of Tay-Sachs disease becomes apparent in infancy. Infants with this disorder typically appear normal until the age of 3 to 6 months, when their development slows and muscles used for movement weaken. Affected infants lose motor skills such as turning over, sitting, and crawling. They also develop an exaggerated startle reaction to loud noises. As the disease progresses, children with Tay-Sachs disease experience seizures, vision and hearing loss, intellectual disability, and paralysis. An eye abnormality called a cherry-red spot, which can be identified with an eye examination, is characteristic of this disorder. Children with this severe infantile form of Tay-Sachs disease usually live only into early childhood.

Other forms of Tay-Sachs disease are very rare. Signs and symptoms can appear in childhood, adolescence, or adulthood and are usually milder than those seen with the infantile form. Characteristic features include muscle weakness, loss of muscle coordination (ataxia) and other problems with movement, speech problems, and mental illness. These signs and symptoms vary widely among people with late-onset forms of Tay-Sachs disease.

Mutations in the HEXA gene cause Tay-Sachs disease. The HEXA gene provides instructions for making part of an enzyme called beta-hexosaminidase A, which plays a critical role in the brain and spinal cord. This enzyme is located in lysosomes, which are structures in cells that break down toxic substances and act as recycling centers. Within lysosomes, beta-hexosaminidase A helps break down a fatty substance called GM2 ganglioside.

Mutations in the HEXA gene disrupt the activity of beta-hexosaminidase A, which prevents the enzyme from breaking down GM2 ganglioside. As a result, this substance accumulates to toxic levels, particularly in neurons in the brain and spinal cord. Progressive damage caused by the buildup of GM2 ganglioside leads to the destruction of these neurons, which causes the signs and symptoms of Tay-Sachs disease.

Because Tay-Sachs disease impairs the function of a lysosomal enzyme and involves the buildup of GM2 ganglioside, this condition is sometimes referred to as a lysosomal storage disorder or a GM2-gangliosidosis.

Pompe Disease

Pompe disease (also known as glycogen storage disease type II; acid alpha-glucosidase deficiency; acid maltase deficiency; GAA deficiency; GSD II; glycogenosis type II; glycogenosis, generalized, cardiac form; cardiomegalia glycogenica diffusa; acid maltase deficiency; AMD; or alpha-1,4-glucosidase deficiency) is an autosomal recessive metabolic genetic disorder characterized by mutations in the gene for the lysomsomal enzyme acid alpha-glucosidase (GAA) (also known as acid maltase). Mutations in the GAA gene eliminate or reduce the ability of the GAA enzyme to hydrolyze the α-1,4 and α-1,6 linkages in glycogen, maltose and isomaltose. As a result, glycogen accumulates in the lysosomes and cytoplasm of cells throughout the body leading to cell and tissue destruction. Tissues that are particularly affected include skeletal muscle and cardiac muscle. The accumulated glycogen causes progressive muscle weakness leading to cardiomegaly, ambulatory difficulties and respiratory insufficiency.

Three forms of Pompe disease have been identified, including the classic infantile-onset disease, non-classic infantile-onset disease and late onset disease. The classic infantile-onset form is characterized by muscle weakness, poor muscle tone, hepatomegaly and cardiac defects. The incidence of the disease is approximately 1 in 140,000 individuals. Patients with this form of the disease often die of heart failure in the first year of life. The non-classic infantile-onset form of the disease is characterized by delayed motor skills, progressive muscle weakness and in some instances cardiomegaly. Patients with this form of the disease often live only into early childhood due to respiratory failure. The late-onset form of the disease may present in late childhood, adolescence or adulthood and is characterized by progressive muscle weakness of the legs and trunk.

Niemann Pick Disease

Niemann-Pick disease is a condition that affects many body systems. It has a wide range of symptoms that vary in severity. Niemann-Pick disease is divided into four main types: type A, type B, type C1, and type C2. These types are classified on the basis of genetic cause and the signs and symptoms of the condition.

Infants with Niemann-Pick disease type A usually develop an enlarged liver and spleen (hepatosplenomegaly) by age 3 months and fail to gain weight and grow at the expected rate (failure to thrive). The affected children develop normally until around age 1 year when they experience a progressive loss of mental abilities and movement (psychomotor regression). Children with Niemann-Pick disease type A also develop widespread lung damage (interstitial lung disease) that can cause recurrent lung infections and eventually lead to respiratory failure. All affected children have an eye abnormality called a cherry-red spot, which can be identified with an eye examination. Children with Niemann-Pick disease type A generally do not survive past early childhood.

Niemann-Pick disease type B usually presents in mid-childhood. The signs and symptoms of this type are similar to type A, but not as severe. People with Niemann-Pick disease type B often have hepatosplenomegaly, recurrent lung infections, and a low number of platelets in the blood (thrombocytopenia). They also have short stature and slowed mineralization of bone (delayed bone age). About one-third of affected individuals have the cherry-red spot eye abnormality or neurological impairment. People with Niemann-Pick disease type B usually survive into adulthood.

Niemann-Pick disease types A and B is caused by mutations in the SMPD1 gene. This gene provides instructions for producing an enzyme called acid sphingomyelinase. This enzyme is found in lysosomes, which are compartments within cells that break down and recycle different types of molecules. Acid sphingomyelinase is responsible for the conversion of a fat (lipid) called sphingomyelin into another type of lipid called ceramide. Mutations in SMPD1 lead to a shortage of acid sphingomyelinase, which results in reduced break down of sphingomyelin, causing this fat to accumulate in cells. This fat buildup causes cells to malfunction and eventually die. Over time, cell loss impairs function of tissues and organs including the brain, lungs, spleen, and liver in people with Niemann-Pick disease types A and B.

Wolman Disease

Lysosomal acid lipase deficiency is an inherited condition characterized by problems with the breakdown and use of fats and cholesterol in the body (lipid metabolism). In affected individuals, harmful amounts of fats (lipids) accumulate in cells and tissues throughout the body, which typically causes liver disease. There are two forms of the condition. The most severe and rarest form begins in infancy. The less severe form can begin from childhood to late adulthood.

In the severe, early-onset form of lysosomal acid lipase deficiency, lipids accumulate throughout the body, particularly in the liver, within the first weeks of life. This accumulation of lipids leads to several health problems, including an enlarged liver and spleen (hepatosplenomegaly), poor weight gain, a yellow tint to the skin and the whites of the eyes (jaundice), vomiting, diarrhea, fatty stool (steatorrhea), and poor absorption of nutrients from food (malabsorption). In addition, affected infants often have calcium deposits in small hormone-producing glands on top of each kidney (adrenal glands), low amounts of iron in the blood (anemia), and developmental delay. Scar tissue quickly builds up in the liver, leading to liver disease (cirrhosis). Infants with this form of lysosomal acid lipase deficiency develop multi-organ failure and severe malnutrition and generally do not survive past 1 year.

In the later-onset form of lysosomal acid lipase deficiency, signs and symptoms vary and usually begin in mid-childhood, although they can appear anytime up to late adulthood. Nearly all affected individuals develop an enlarged liver (hepatomegaly); an enlarged spleen (splenomegaly) may also occur. About two-thirds of individuals have liver fibrosis, eventually leading to cirrhosis. Approximately one-third of individuals with the later-onset form have malabsorption, diarrhea, vomiting, and steatorrhea. Individuals with this form of lysosomal acid lipase deficiency may have increased liver enzymes and high cholesterol levels, which can be detected with blood tests.

Some people with this later-onset form of lysosomal acid lipase deficiency develop an accumulation of fatty deposits on the artery walls (atherosclerosis). Although these deposits are common in the general population, they usually begin at an earlier age in people with lysosomal acid lipase deficiency. The deposits narrow the arteries, increasing the chance of heart attack or stroke. The expected lifespan of individuals with later-onset lysosomal acid lipase deficiency depends on the severity of the associated health problems.

The two forms of lysosomal acid lipase deficiency were once thought to be separate disorders. The early-onset form was known as Wolman disease, and the later-onset form was known as cholesteryl ester storage disease. Although these two disorders have the same genetic cause and are now considered to be forms of a single condition, these names are still sometimes used to distinguish between the forms of lysosomal acid lipase deficiency.

Mutations in the LIPA gene cause lysosomal acid lipase deficiency. The LIPA gene provides instructions for producing an enzyme called lysosomal acid lipase. This enzyme is found in cell compartments called lysosomes, which digest and recycle materials the cell no longer needs. The lysosomal acid lipase enzyme breaks down lipids such as cholesteryl esters and triglycerides. The lipids produced through these processes, cholesterol and fatty acids, are used by the body or transported to the liver for removal.

Mutations in the LIPA gene lead to a shortage (deficiency) of functional lysosomal acid lipase. The severity of the condition depends on how much working enzyme is available. Individuals with the early-onset form of lysosomal acid lipase deficiency have no normal enzyme activity. Those with the later-onset form are thought to have some enzyme activity remaining, and the amount generally determines the severity of signs and symptoms.

Decreased lysosomal acid lipase activity results in the accumulation of cholesteryl esters, triglycerides, and other lipids within lysosomes, causing fat buildup in multiple tissues. The body's inability to produce cholesterol from the breakdown of these lipids leads to an increase in alternative methods of cholesterol production and higher-than-normal levels of cholesterol in the blood. The excess lipids are transported to the liver for removal. Because many of them are not broken down properly, they cannot be removed from the body; instead they accumulate in the liver, resulting in liver disease. The progressive accumulation of lipids in tissues results in organ dysfunction and the signs and symptoms of lysosomal acid lipase deficiency.

Hematopoietic Stem Cells

As used herein, hematopoietic stem cells (HSC) refers to animal, preferably mammalian, more preferably human cells that have the ability to differentiate into any of several types of blood cells, including red blood cells, white blood cells, including lymphoid cells and myeloid cells. HSC can include hematopoietic cells having long-term engrafting potential in vivo. Long term engrafting potential (e.g., long term hematopoietic stem cells) can be determined using animal models or in vitro models. Animal models for long-term engrafting potential of candidate human hematopoietic stem cell populations include the SCID-hu bone model (Kyoizumi et al. (1992) *Blood* 79:1704; Murray et al. (1995) *Blood* 85(2) 368-378) and the in utero sheep model (Zanjani et al. (1992) *J. Clin. Invest.* 89:1179). For a review of animal models of human hematopoiesis, see Srour et al. (1992) *J. Hematother.* 1:143-153 and the references cited therein. An in vitro model for stem cells is the long-term culture-initiating cell (LTCIC) assay, based on a limiting dilution analysis of the number of clonogenic cells produced in a stromal co-culture after 5-8 weeks (Sutherland et al. (1990) *Proc. Nat'l Acad. Sci.* 87:3584-3588). The LTCIC assay has been shown to correlate with another commonly used stem cell assay, the cobblestone area forming cell (CAFC) assay, and with long-term engrafting potential in vivo (Breems et al. (1994) *Leukemia* 8:1095).

Hematopoietic stem cells (HSC) reside in the bone marrow and have the unique ability to give rise to all of the different mature blood cell types and tissues. HSC are self-renewing cells: when they proliferate, at least some of their daughter cells remain as HSC, so that the pool of stem cells is not depleted. The other cells differentiate into common lymphoid progenitor cells that produce lymphocytes and into common myeloid progenitor cells that produce monocytes.

In some embodiments, the hematopoietic stem cells for use in genetic modification herein are isolated from bone marrow. In some embodiments, HSC can be taken from the pelvis, at the iliac crest, using a needle or syringe.

In some embodiments, the hematopoietic stem cells can be derived from human cord blood or mobilized peripheral blood. Hematopoietic stem cells obtained from human peripheral blood may be mobilized by one of a variety of strategies. Exemplary agents that can be used to induce mobilization of hematopoietic stem cells from the bone marrow into peripheral blood include chemokine (C-X-C motif) receptor 4 (CXCR4) antagonists, such as AMD3100 (also known as Plerixafor and MOZOBIL (Genzyme, Boston, Mass.)) and granulocyte colony-stimulating factor (GCSF), the combination of which has been shown to rapidly mobilize CD34+ cells in clinical experiments. Additionally, chemokine (C-X-C motif) ligand 2 (CXCL2, also referred to as GROβ) represents another agent capable of inducing hematopoietic stem cell mobilization to from bone marrow to peripheral blood. Agents capable of inducing mobilization of hematopoietic stem cells for use with the compositions and methods of the invention may be used in combination with one another. For instance, CXCR4 antagonists (e.g., AMD3100), CXCL2, and/or GCSF may be administered to a subject sequentially or simultaneously in a single mixture in order to induce mobilization of hematopoietic stem cells from bone marrow into peripheral blood. The use of these agents as inducers of hematopoietic stem cell mobilization is described, e.g., in Pelus, *Current Opinion in Hematology* 15:285 (2008), the disclosure of which is incorporated herein by reference.

In some embodiments, HSC are harvested from the circulating peripheral blood, while the blood donor is injected with an agent that mobilizes the HSC from the bone marrow. In some embodiments, the agent that mobilizes the HSC from the bone marrow to the peripheral blood is a cytokine, such as granulocyte-colony stimulating factor (GCS-F). In some embodiments, populations of HSC isolated from the peripheral blood are enriched in CD34+ cells, and comprise at least 50%, at least 70%, or at least 90% of CD34+ cells.

In some embodiments, for mobilized peripheral blood (MPB) leukapheresis, CD34+ cells can generally be processed and enriched using immunomagnetic beads such as CliniMACS, Purified CD34+ cells can be seeded on culture bags at $1\times10^6$ cells/ml in serum-free medium in the presence of cells culture grade Stem Cell Factor (SCF), preferably 300 ng/ml (Amgen Inc., Thousand Oaks, CA, USA), preferably with FMS-like tyrosine kinase 3 ligand (FLT3L) 300 ng/ml, and Thrombopoietin (TPO), preferably around 100 ng/ml and further interleukline IL-3, preferably more than 60 ng/ml (all from Cell Genix Technologies) during between preferably 12 and 24 hours before being transferred to an electroporation buffer comprising the sequence specific reagent (e.g., mRNA). Upon electroporation, the cells are transferred back to the culture medium prior to being resuspended in saline and transferred in a syringe for infusion.

Methods for enriching or depleting specific cell populations in a mixture of cells are well known in the art. For example, cell populations can be enriched or depleted by density separation, rosetting tetrameric antibody complex mediated enrichment/depletion, magnetic activated cell sorting (MACS), multi-parameter fluorescence based molecular phenotypes such as fluorescence-activated cell sorting (FACS), or any combination thereof. Collectively, these methods of enriching or depleting cell populations may be referred to generally herein as “sorting” the cell populations or contacting the cells “under conditions” to form or produce an enriched (+) or depleted (−) cell population.

Upon collection of the mobilized cells, the withdrawn hematopoietic stem cells can be genetically modified as described herein and then infused into a patient in need thereof, which may be the donor or another subject, such as a subject that is at least partially HLA-matched to the donor, for the treatment of disease as described herein.

In some embodiments, these cells form a population of cells, which preferably originate from a single donor or patient. These populations of cells can be expanded under closed culture recipients to comply with highest manufacturing practices requirements and can be frozen prior to infusion into a patient, thereby providing “off the shelf” or “ready to use” therapeutic compositions.

In some embodiments, the HSC are CD34+. In some embodiments, the HSC can further be described as CD133+, CD90+, CD38−, CD45RA−, Lin−, or any combination thereof.

In some embodiments, the HSC capable of differentiating into microglial cells are derived from pluripotent stem cells, such as induced pluripotent stem cells (iPS). See, e.g., Abud et al., *Neuron* 94, 278-293 (2017). In some embodiments, the iPS cells are genetically modified as described herein and then differentiated into HSC cells. In some embodiments, the iPS cells are differentiated into HSC and then the HSC are genetically modified as described herein. In further embodiments, cells can be gene edited before being reprogrammed into iPS cells and HSCs as described for instance in Int. Appl. No. PCT/EP2018/083180. In some embodiments, the hematopoietic stem cells can be isolated from the patient to be treated or isolated from a compatible donor.

In some embodiments, hematopoietic stem cells are obtained from induced pluripotent stem (iPS) cells derived from cells of the patient to be treated or from a compatible donor.

In some embodiments, the HSC can be expanded ex vivo prior to genetic modification and/or infusion of these cells into the patient. See, e.g., U.S. Pat. Nos. 9,580,426; 9,956,249; 9,527,828; 9,428,748; 9,394,520; 9,328,085; 9,226,942; 9,115,341; 8,927,281.

In some embodiments, the cells are isolated from a donor that is an HLA matched sibling donor, an HLA matched unrelated donor, a partially matched unrelated donor, a haploidentical related donor, autologous donor, an HLA unmatched donor, a pool of donors or any combination thereof. In some embodiments, the population of therapeutic cells is allogeneic. In some embodiments, the population of therapeutic cells is autologous. In some embodiments, the population of therapeutic cells is haploidentical.

Genetically Modified Cells

In some embodiments, the invention provides genetically modified HSC or iPS cells obtainable according to any one of the embodiments of the methods described herein.

In some embodiments, the invention provides genetically modified HSC or iPS cells comprising a transgene integrated at a locus that is at least transcriptionally active in microglial cells, wherein the transgene is under the transcriptional control of the endogenous promoter of the locus. In some embodiments, the transgene comprises a coding sequence of a gene selected from the group consisting of IDUA, IDS, ARSB, GUSB, ABCD1, GALC, ARSA, PSAP, GBA, FUCA1, MAN2B1, AGA, ASAH1, HEXA, GAA, SMPD1, LIPA and CDKL5.

In some embodiments, multiple copies of the transgene are integrated in the HSC or iPS cell. In some embodiments, the multiple copies are integrated at different loci. In some embodiments, the multiple copies are integrated at the same locus. In some embodiments, the multiple copies integrated at the same locus are separated by 2A self-cleaving peptide sequences.

In some embodiments, the introduced transgene is under the control of the endogenous promoter in the microglial cells. In some embodiments, the locus that is active in microglial cells is selected from the group consisting of TMEM119, S100A9, CD11B, B2m, Cx3cr1, MERTK, CD164, Tlr4, Tlr7, Cd14, Fcgr1a, Fcgr3a, TBXAS1, DOK3, ABCA1, TMEM195, MR1, CSF3R, FGD4, TSPAN14, TGFBRI, CCR5, GPR34, SERPINE2, SLCO2B1, P2ry12, Olfml3, P2ry13, Hexb, Rhob, Jun, Rab3il1, Ccl2, Fcrls, Scoc, Siglech, Slc2a5, Lrrc3, Plxdc2, Usp2, Ctsf, Cttnbp2nl, Atp8a2, Lgmn, Mafb, Egr1, Bhlhe41, Hpgds, Ctsd, Hspa1a, Lag3, Csf1r, Adamts1, F11r, Golm1, Nuak1, Crybb1, Ltc4s, Sgce, Pla2g15, Ccl3l1, Abhd12, Ang, Ophn1, Sparc, Pros1, P2ry6, Lair1, Il1a, Epb41l2, Adora3, Rilpl1, Pmepa1, Ccl13, Pde3b, Scamp5, Ppp1r9a, Tjp1, Ak1, B4galt4, Gtf2h2, Trem2, Ckb, Acp2, Pon3, Agmo, Tnfrsf17, Fscn1, St3gal6, Adap2, Ccl4, Entpd1, Tmem86a, Kctd12, Dst, Ctsl2, Abcc3, Pdgfb, Pald1, Tubgcp5, Rapgef5, Stab1, Lacc1, Tmc7, Nrip1, Kcnd1, Tmem206, Hps4, Dagla, Extl3, Mlph, Arhgap22, Cxxc5, P4ha1, Cysltr1, Fgd2, Kcnk13, Gbgt1, C18orf1, Cadm1, Bco2, Adrb1, C3ar1, Large, Leprel1, Liph, Upk1b, P2rx7, Slc46a1, Ebf3, Ppp1r15a, Il10ra, Rasgrp3, Fos, Tppp, Slc24a3, Havcr2, Nav2, Apbb2, Clstn1, Blnk, Gnaq, Ptprm, Frmd4a, Cd86, Tnfrsf11a, Spint1, Ppm1l, Tgfbr2, Cmklr1, Tlr6, Gas6, Hist1h2ab, Atf3, Acvr1, Abi3, Lrp12, Ttc28, Plxna4, Adamts16, Rgs1, Icam1, Snx24, Ly96, Dnajb4, and Ppfia4.

In some embodiments, the genetically modified HSC or iPS cells comprise a transgene integrated at a locus that is transcriptionally active in microglial cells selected from TMEM119, CD11B, B2m, CX3CR1 or S100A9, wherein the transgene is under the transcriptional control of the endogenous promoter of the locus.

In some embodiments, the genetically modified hematopoietic stem cells are obtained by genetically modifying the hematopoietic stem cells directly. In some embodiments, the genetically modified hematopoietic stem cells are obtained by genetically modifying induced pluripotent stem (iPS) cells and differentiating the iPS cells to become hematopoietic stem cells.

In some embodiments, the hematopoietic stem cells (HSC) or iPS cells are genetically modified such that the cells are capable of expressing the transgene upon their differentiation to microglial cells. In some embodiments, the locus that is genetically modified in the cells is transcriptionally active in microglial cells.

In some embodiments, a population of enriched HSC are subjected to a method to genetically modify the cells. In some embodiments, the enriched population comprises at least 50%, 55%, 60%, 65%, 70%, 75%, 80%, 85%, 90%, 91%, 92%, 93%, 94%, 95%, 96%, 97%, 98%, or 99% or more CD34+ HSC.

In some embodiments, the HSC or iPS cells are genetically modified using a sequence specific reagent. In some embodiments, the sequence specific reagent recognizes one or more sequences that are present in a locus that is expressed in microglial cells. In some embodiments, the sequence specific reagent cleaves a nucleic acid in the cells.

In some embodiments, the invention provides a method for making the genetically modified HSC or iPS cells comprising integrating a transgene into HSC or iPS cells. In some embodiments, the method comprises contacting the cells with a sequence specific reagent that cleaves a nucleic acid sequence at a locus expressed in microglial cells. In some embodiments, the method further comprises contacting the cells with a donor nucleic acid comprising the transgene.

In some embodiments, the sequence-specific reagent used to gene edit the cells of the present invention are rare-cutting endonucleases, such as TALE-nucleases (commercially available under Cellectis trademark TALEN®). Preferred reagents cleave one or several of the target sequences reported in Table 4 of the present specification.

In some embodiments, the sequence specific reagent targets intron of CX3CR1 preferably the first intron of CX3CR1 located between the first coding exon and second coding exon (SEQ ID NO:76). The invention also provides with specific TALE nucleases that preferentially target endogenous polynucleotide sequences of CX3CR1 similar to SEQ ID NO:77 to 87. In some embodiments, the sequence specific reagents are CRISPR-Cas or CRISPR-Cpf using gRNA targeting endogenous sequences similar to SEQ ID NO:97 to 106.

In some embodiments, the sequence specific reagent targets intron of CD11B preferably the first intron of CD11B. The invention also provides with specific TALE nucleases that preferentially target endogenous polynucleotide sequences of CD11B similar to SEQ ID NO:108 to 137. In some embodiment, the sequence specific reagents are CRISPR-Cas or CRISPR-Cpf using gRNA targeting endogenous sequences similar to SEQ ID NO:138 to 147.

In some embodiments, the sequence specific reagent targets intron of S100A9 preferably the first intron of S100A9. The invention also provides with specific TALE nucleases that preferentially target endogenous polynucleotide sequences of S100A9 similar to SEQ ID NO:149 to 178. In some embodiment, the sequence specific reagents are CRISPR-Cas or CRISPR-Cpf using gRNA targeting endogenous sequences similar to SEQ ID NO:179 to 188.

In some embodiments, the polynucleotide template comprises a coding sequence of a transgene as described herein. In some embodiments, the polynucleotide template comprises a coding region of a gene selected from the group consisting of IDUA, IDS, ARSB, GUSB, ABCD1, GALC, ARSA, PSAP, GBA, FUCA1, MAN2B1, AGA, ASAH1, HEXA, GAA, SMPD1, LIPA and CDKL5.

In some embodiments, the donor nucleic acid comprises a nucleotide sequence selected from the group consisting of SEQ ID NOS:1, 3, 5, 7, 9, 11, 13, 15, 17, 19, 21, 23, 25, 27, 29, 31, 33, 35 and variants thereof as described herein.

In some embodiments, the donor nucleic acid encodes a therapeutic protein comprising an amino acid sequence selected from any one of SEQ ID NOS:2, 4, 6, 8, 10, 12, 14, 16, 18, 20, 22, 24, 26, 28, 30, 32, 34, 36 and variants thereof as described herein.

In some embodiments, the sequence specific reagent can be a chimeric polypeptide comprising a DNA binding domain and another domain displaying catalytic activity. Such catalytic activity can be nickase or double nickase to preferentially perform gene insertion by creating cohesive ends to facilitate gene integration by homologous recombination.

In some embodiments, the nuclease reagent induces NHEJ or homologous recombination mechanisms, which has the advantage of introducing stable and inheritable mutations into the genomic locus expressed in microglial cells.

By "nuclease reagent" is meant a nucleic acid molecule that contributes to a nuclease catalytic reaction in the target cell, preferably an endonuclease reaction, by itself or as a subunit of a complex such as a guide RNA Cas9, preferably leading to the cleavage of a nucleic acid sequence target.

The nuclease reagents of the invention are generally "sequence-specific nuclease reagents", meaning that they can induce DNA cleavage in the cells at predetermined loci, referred to by extension as "targeted gene." The nucleic acid sequence which is recognized by the sequence specific reagents is referred to as "target sequence." Said target sequence is usually selected to be rare or unique in the cell's genome, and more extensively in the human genome, as can be determined using software and data available from human genome databases, such as http://www.ensembl.org/index.html.

In some embodiments, the sequence specific nuclease reagent used according to the invention, which specifically cleaves a sequence within the locus can also be used to induce the integration of an exogenous template at the locus. "Exogenous sequence" refers to any nucleotide or nucleic acid sequence that was not initially present at the selected locus. The exogenous sequence preferably comprises a sequence that codes for a therapeutic polypeptide as described herein for treating a disease herein. An endogenous sequence that is genetically modified by the insertion of a polynucleotide according to the method of the present invention, in order to express the polypeptide encoded thereby is broadly referred to as an exogenous coding sequence. In some embodiments, the targeted gene insertion comprises an exogenous sequence encoding a therapeutic polypeptide as described herein.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

DNA domains can be engineered to bind to any sequence of choice in a targeted locus. In some embodiments, the cells are genetically modified with a sequence specific reagent that has been engineered to bind a locus that is transcriptionally active in microglial cells. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, U.S. Pat. Nos. 6,453,242 and 6,534,261, incorporated by reference herein in their entireties. Rational design of TAL-effector domains can also be performed. See, e.g., U.S. Patent Appl. Publication No. 2011/0301073.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Patent Appl. Publication No. 2011/0301073.

The exogenous/donor sequence comprising the transgene is not identical over its entire length to sequences within the locus that is expressed in microglial cells. A donor sequence can contain a non-homologous sequence flanked by two regions of homology to allow for efficient HDR at the location of interest. Alternatively, a donor may have no regions of homology to the targeted location in the DNA and may be integrated by NHEJ-dependent end joining following cleavage at the target site. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

In some embodiments, the sequence specific reagent is a nucleic acid encoding an "engineered" or "programmable" rare-cutting endonuclease, such as a homing endonuclease as described for instance in WO 2004067736, a zing finger nuclease (ZFN) as described, for instance, by Urnov F., et al. (*Nature* 435:646-651 (2005)), a TALE-Nuclease as described, for instance, by Mussolino et al. (*Nucl. Acids Res.*

39(21):9283-9293 (2011)), or a MegaTAL nuclease as described, for instance by Boissel et al. (*Nucleic Acids Research* 42 (4):2591-2601 (2013)).

In some embodiments, the endonuclease reagent is transiently expressed into the cells, meaning that the reagent is not supposed to integrate into the genome or persist over a long period of time, such as the case of RNA, more particularly mRNA, proteins or complexes mixing proteins and nucleic acids (e.g.: Ribonucleoproteins).

In some embodiments, the sequence specific reagent is a nuclease that introduces DNA double strand break at a targeted locus, whose subsequent repair is exploited to achieve different outcomes. In some embodiments, a repair pathway based on homologous recombination can be used to copy information from an introduced DNA homology template. Such homology directed repair (HDR) can promote a specific addition of exogenous polynucleotide sequence (See, e.g., U.S. Pat. No. 8,921,332), e.g., a transgene as described herein, that can be expressed under the control of a promoter present on the exogenous polynucleotide sequence. In some embodiments, the transgene as described herein, can be expressed under the control of an endogenous promoter and at the same time that gene disruption is achieved. In some embodiments where gene disruption is achieved, the transgene is inserted at the stop codon of the endogenous gene and comprises a self-cleaving 2A peptide or IRES sequence. In a more preferred embodiments, the transgene is expressed under the control of an endogenous promoter without gene disruption. In some embodiments, the non-homologous end joining (NHEJ) repair pathway can be utilized (See, e.g., U.S. Pat. No. 9,458,439; He et al., *Nucleic Acids Research,* 44 e85, https://doi.org/10.1093/nar/gkw064).

In some embodiments, one or more targeted nucleases (e.g., CRISPR/Cas, ZFNS or TALENs) creates a double-stranded break in the target sequence (e.g., cellular chromatin) at a locus that is expressed in microglial cells. In some embodiments, a donor polynucleotide that comprises the transgene encoding the therapeutic protein and homology to the nucleotide sequence flanking the region of the break is introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a sequence in cellular chromatin at a locus expressed in microglial cells can be altered and, in certain embodiments, can be modified to comprise a sequence present in a donor polynucleotide.

In some embodiments, the exogenous nucleotide sequence (the "donor sequence" that comprises the transgene) can contain sequences that are homologous, but not identical, to genomic sequences in the locus of interest expressed in microglial cells, thereby stimulating homologous recombination to insert a non-identical sequence in the locus of interest. In some embodiments, portions of the donor sequence that are homologous to sequences in the locus of interest exhibit between about 70 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. A non-homologous portion of the donor sequence contains sequences not present in the locus of interest, such that new sequence, viz., sequence encoding the transgene, are introduced into the locus of interest. In some embodiments, the non-homologous sequence is generally flanked by sequences of 50-1,000 base pairs (or any integral value therebetween) or any number of base pairs greater than 1,000, that are homologous or identical to sequences in the locus of interest. In some embodiments, the donor sequence is non-homologous to the first sequence, and is inserted into the genome by non-homologous recombination mechanisms.

The nucleases can target a gene that is active in microglial cells for the insertion of the transgene. In some embodiments, the nuclease is non-naturally occurring, i.e., engineered in the DNA-binding domain and/or cleavage domain. For example, the DNA-binding domain of a naturally-occurring nuclease or nuclease system may be altered to bind to a selected target site (e.g., a meganuclease that has been engineered to bind to site different than the cognate binding site or a CRISPR/Cas system utilizing an engineered single guide RNA). In other embodiments, the nuclease comprises heterologous DNA-binding and cleavage domains (e.g., zinc finger nucleases; TAL-effector nucleases; meganuclease DNA-binding domains with heterologous cleavage domains).

In some embodiments, the nuclease is a meganuclease (homing endonuclease). Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In some embodiments, the nuclease comprises an engineered (non-naturally occurring) homing endonuclease (meganuclease). In some embodiments, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In some embodiments, the DNA-binding domain comprises a naturally occurring or engineered (non-naturally occurring) TAL effector DNA binding domain. See, e.g., U.S. Patent Application Publication No. 2011/0301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (Kay et al. (2007) Science 318:648-651). These proteins contain a DNA binding domain and a transcriptional activation domain. One of the most well characterized TALEs is AvrBs3 from *Xanthomonas campestgris* pv. *vesicatoria* (see Bonas et al. (1989) *Mol Gen Genet* 218: 127-136 and WO 2010/079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al. (2006) *J Plant Physiol* 163(3): 256-272). In addition, in the phytopathogenic bacteria *Ralstonia solancearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al. (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas.*

In some embodiments, the DNA binding domain that binds to a target site in a target locus is an engineered domain from a TAL effector similar to those derived from the plant pathogens *Xanthomonas* (see Boch et al. (2009) *Science* 326: 1509-1512 and Moscou and Bogdanove (2009) *Science* 326: 1501) and *Ralstonia* (see Heuer et al. (2007) *Applied and Environmental Microbiology* 73(13): 4379-4384); U.S. Pat. Nos. 8,420,782 and 8,440,431 and U.S. Patent Appl. Publication No. 2011/0301073.

In some embodiments, the DNA binding domain comprises a zinc finger protein. In some embodiments, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Appl. Publication Nos. 2005/0064474; 2007/0218528; 2005/0267061, all incorporated herein by reference in their entireties.

An engineered zinc finger binding or TALE domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

In some embodiments, DNA domains (e.g., multi-fingered zinc finger proteins or TALE domains) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The DNA binding proteins described herein may include any combination of suitable linkers between the individual zinc fingers of the protein. In addition, enhancement of binding specificity for zinc finger binding domains has been described, for example, in co-owned WO 02/077227.

DNA-binding domains and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496 and U.S. Patent Appl. Publication No. 2011/0301073.

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. More recently, ZFNs have been used for genome modification in a variety of organisms. See, for example, United States Patent Appl. Pub. Nos.: 2003/0232410; 2005/0208489; 2005/0026157; 2005/0064474; 2006/0188987; 2006/0063231; and International Publication WO 07/014275. Likewise, TALE DNA-binding domains have been fused to nuclease domains to create TALENs. See, e.g., U.S. Patent Appl. Publication No. 2011/0301073.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

In some embodiments, the dimerized cleavage half domains comprise one inactive cleavage domain and one active cleavage domain such that the targeted DNA is nicked on one strand rather than being completely cleaved (a "nickase", see U.S. Patent Appl. Publication No. 2010/0047805). In other embodiments, two pairs of such nickases are used to cleave a target that is nicked on both DNA strands.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994) *Proc. Natl. Acad. Sci. USA* 91:883-887; Kim et al. (1994) *J. Biol. Chem.* 269:31,978-31,982. In one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a Fok I cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domains (also referred to as dimerization domain mutants) that minimize or prevent homodimerization, as described, for example, in U.S. Patent Appl Publication Nos. 2005/0064474; 2006/0188987 and 2008/0131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:1538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In some embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Appl. Publication No. 2011/0201055, incorporated by reference herein). Engineered cleavage half-domains described herein can be prepared using any suitable method, for example, by site-directed mutagenesis of wild-type cleavage half-domains (Fok I) as described in U.S. Patent Appl. Publication Nos. 2005/0064474; 2008/0131962; and 2011/0201055.

In some embodiments, nucleases may be assembled in vivo at the nucleic acid target site using so-called "split-enzyme" technology (see, e.g. U.S. Patent Application Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 2009/0068164. Nuclease expression constructs can be readily designed using methods known in the art. See, e.g., United States Patent Appl. Publication Nos.: 2003/0232410; 2005/0208489; 2005/0026157; 2005/0064474; 2006/0188987; 2006/0063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

In some embodiments, the endonuclease reagent is a RNA-guide to be used in conjunction with a RNA guided endonuclease, such as Cas9 or Cpf1, as per, inter alia, the teaching by Doudna, J. et al., (*Science* 346 (6213): 1077) (2014)) and Zetsche, B. et al. (*Cell* 163(3): 759-771 (2015)) the teaching of which is incorporated herein by reference.

In some embodiments, the cells are genetically modified using the CRISPR (Clustered Regularly Interspaced Short Palindromic Repeats)/Cas (CRISPR Associated) nuclease system. The CRISPR/Cas is an engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer". Cas9 cleaves the DNA to generate blunt ends at the DSB at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al. (2012) *Science* 337, p. 816-821, Jinek et al., (2013), *eLife* 2:e00471, and David Segal, (2013) *eLife* 2:e00563).

The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Wastson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. Is also encompassed in RNA-guided endonucleases in the meaning of the present invention, the endonuclease Cpf1 as taught by Zetsche, B. et al. (Cell 163(3): 759-771 (2015)).

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al., (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA).

Delivery Methods

The nucleases, polynucleotides encoding these nucleases, donor polynucleotides and compositions comprising the proteins and/or polynucleotides described herein for genetically modifying the cells may be delivered in vivo or ex vivo by any suitable means.

In some embodiments, polypeptides may be synthesized in situ in the cell as a result of the introduction of polynucleotides encoding the polypeptides into the cell. In some embodiments, the polypeptides can be produced outside the cell and then introduced into the cell. Methods for introducing a polynucleotide construct into cells are known in the art and include, as non-limiting examples, stable transformation methods wherein the polynucleotide construct is integrated into the genome of the cell, transient transformation methods wherein the polynucleotide construct is not integrated into the genome of the cell and virus mediated methods. In some embodiments, the polynucleotides may be introduced into a cell by recombinant viral vectors (e.g. retroviruses, adenoviruses), liposomes and the like. For example, transient transformation methods include, for example microinjection, electroporation or particle bombardment. The polynucleotides can be included in vectors, more particularly plasmids or virus, in view of being expressed in cells.

In some embodiments, the cells are transfected with a nucleic acid encoding an endonuclease reagent. In some embodiments, 80% of the endonuclease reagent is degraded by 30 hours, preferably by 24, more preferably by 20 hours after transfection.

In some embodiments, an endonuclease encoded by mRNA can be synthetized with a cap to enhance its stability according to techniques well known in the art, as described, for instance, by Kore A. CL., et al. (Locked nucleic acid (LNA)-modified dinucleotide mRNA cap analogue: synthesis, enzymatic incorporation, and utilization (2009) *J Am Chem Soc.* 131 (18):6364-5).

In some embodiments, nucleases and/or donor constructs as described herein may also be delivered using vectors containing sequences encoding one or more of the CRISPR/Cas system(s), zinc finger or TALEN protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues.

Viral vector delivery systems include DNA and RNA viruses, which have either episomal or integrated genomes after delivery to the cell. For a review of gene therapy procedures, see Anderson, *Science* 256:808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, *Biotechnology* 6(10): 1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology*, Doerfler and Bohm (eds.) (1995); and Yu et al., *Gene Therapy* 1:13-26 (1994).

In some embodiments, methods of non-viral delivery of nucleic acids include electroporation, lipofection, microinjection, biolistics, virosomes, liposomes, immunoliposomes, polycation or lipid:nucleic acid conjugates, naked DNA, naked RNA, capped RNA, artificial virions, and agent-enhanced uptake of DNA. Sonoporation using, e.g., the Sonitron 2000 system (Rich-Mar) can also be used for delivery of nucleic acids.

In some embodiments, electroporation steps can be used to transfect cells. In some embodiments, these steps are typically performed in closed chambers comprising parallel plate electrodes producing a pulse electric field between said parallel plate electrodes greater than 100 volts/cm and less than 5,000 volts/cm, substantially uniform throughout the treatment volume such as described in WO 2004/083379, which is incorporated by reference, especially from page 23, line 25 to page 29, line 11. One such electroporation chamber preferably has a geometric factor ($cm^{-1}$) defined by the quotient of the electrode gap squared ($cm^2$) divided by the chamber volume ($cm^3$), wherein the geometric factor is less than or equal to 0.1 $cm^{-1}$, wherein the suspension of the cells and the sequence specific reagent is in a medium which is adjusted such that the medium has conductivity in a range spanning 0.01 to 1.0 milliSiemens. In general, the suspension of cells undergoes one or more pulsed electric fields. With the method, the treatment volume of the suspension is scalable, and the time of treatment of the cells in the chamber is substantially uniform.

In some embodiments, different transgenes or multiple copies of the transgene can be included in one vector. The vector can comprise a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of *General Virology* 82: 1013-1025 (2001); Donnelly et al., *J. of Gen. Virology* 78: 13-21 (1997); Doronina et al., *Mol. And. Cell. Biology* 28(13): 4227-4239 (2008); Atkins et al., *RNA* 13: 803-810 (2007)).

By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

In one embodiment, a polynucleotide encoding a sequence specific reagent according to the present invention can be mRNA which is introduced directly into the cells, for example by electroporation. In some embodiments, the cells can be electroporated using cytoPulse technology which allows, by the use of pulsed electric fields, to transiently permeabilize living cells for delivery of material into the cells. The technology, based on the use of PulseAgile (BTX Havard Apparatus, 84 October Hill Road, Holliston, Mass. 01746, USA) electroporation waveforms grants the precise control of pulse duration, intensity as well as the interval between pulses (see U.S. Pat. No. 6,010,613 and published International Application WO 2004/083379). All these parameters can be modified in order to reach the best conditions for high transfection efficiency with minimal mortality. The first high electric field pulses allow pore formation, while subsequent lower electric field pulses allow moving the polynucleotide into the cell.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam and Lipofectin). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

In some embodiments, the donor sequence and/or sequence specific reagent is encoded by a viral vector. In some embodiments, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., Gene Ther. 9:748-55 (1996)). Other AAV serotypes, including by non-limiting example, AAV1, AAV3, AAV4, AAV5, AAV6, AAV8, AAV 8.2, AAV9, and AAV rh10 and pseudotyped AAV such as AAV2/8, AAV2/5 and AAV2/6 can also be used in accordance with the present invention.

In some embodiments, the cells are administered an effective amount of one or more caspase inhibitors in combination with an AAV vector.

The nuclease-encoding sequences and donor constructs can be delivered using the same or different systems. For example, a donor polynucleotide can be carried by a viral vector, while the one or more nucleases can be delivered as mRNA compositions.

In some embodiments, one or more reagents can be delivered to cells using nanoparticles. In some embodiments, nanoparticles are coated with ligands, such as antibodies, having a specific affinity towards HSC surface proteins, such as CD105 (Uniprot #P17813). In some embodiments, the nanoparticles are biodegradable polymeric nanoparticles in which the sequence specific reagents under polynucleotide form are complexed with a polymer of polybeta amino ester and coated with polyglutamic acid (PGA).

Strategy for Exon Integration into Endogenous Intronic Genomic Loci

As a particular embodiment, the present patent application presents a method for integrating an exogenous coding sequence into an endogenous intronic genomic region, which allows to integrate said exogenous coding sequence preferably between the first and second endogenous coding exons of said genomic region.

Figure 2:
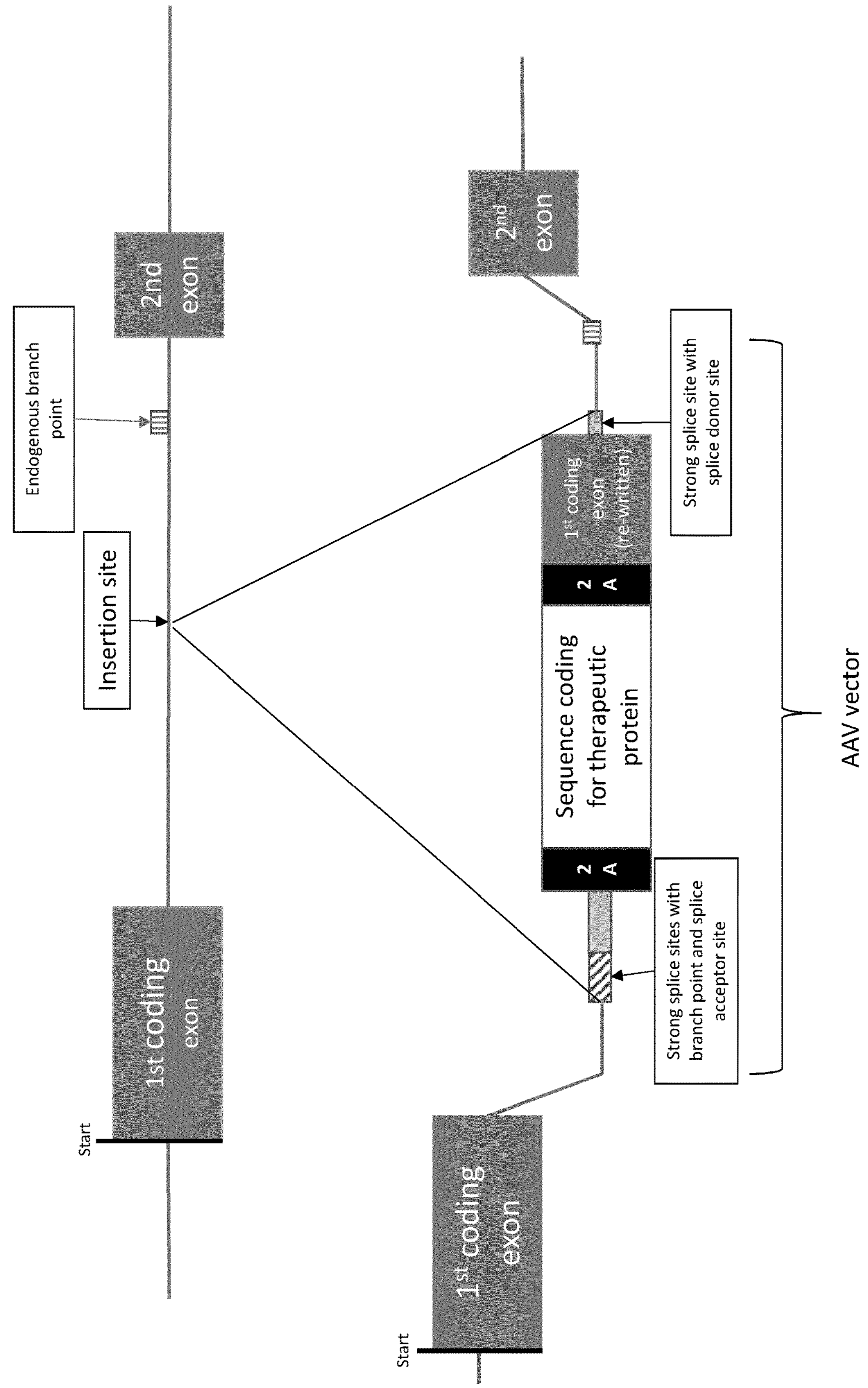
FIG. 2. Schematic representation of one gene editing strategy to obtain therapeutic gene expression to tissue-resident myeloid cells, including microglial cells, as per the present invention. The proposed strategy targets the intronic sequences of selected endogenous loci, among which TMEM119, MERTK, CD164, TLR7, CD14, FCGR3A (CD16), TBXAS1, DOK3, ABCA1, TMEM195, TLR4, MR1, FCGR1A (CD64), CSF3R, FGD4, TSPAN14, CXCR3, CD11B, S100A9 and B2M are preferred loci. This strategy specified in this application enables exogenous therapeutic gene insertion into the endogenous intronic sequences for transcription and expression of the therapeutic protein in the myeloid cells under the transcriptional control of the endogenous promoters present at said loci.
Figure 3:
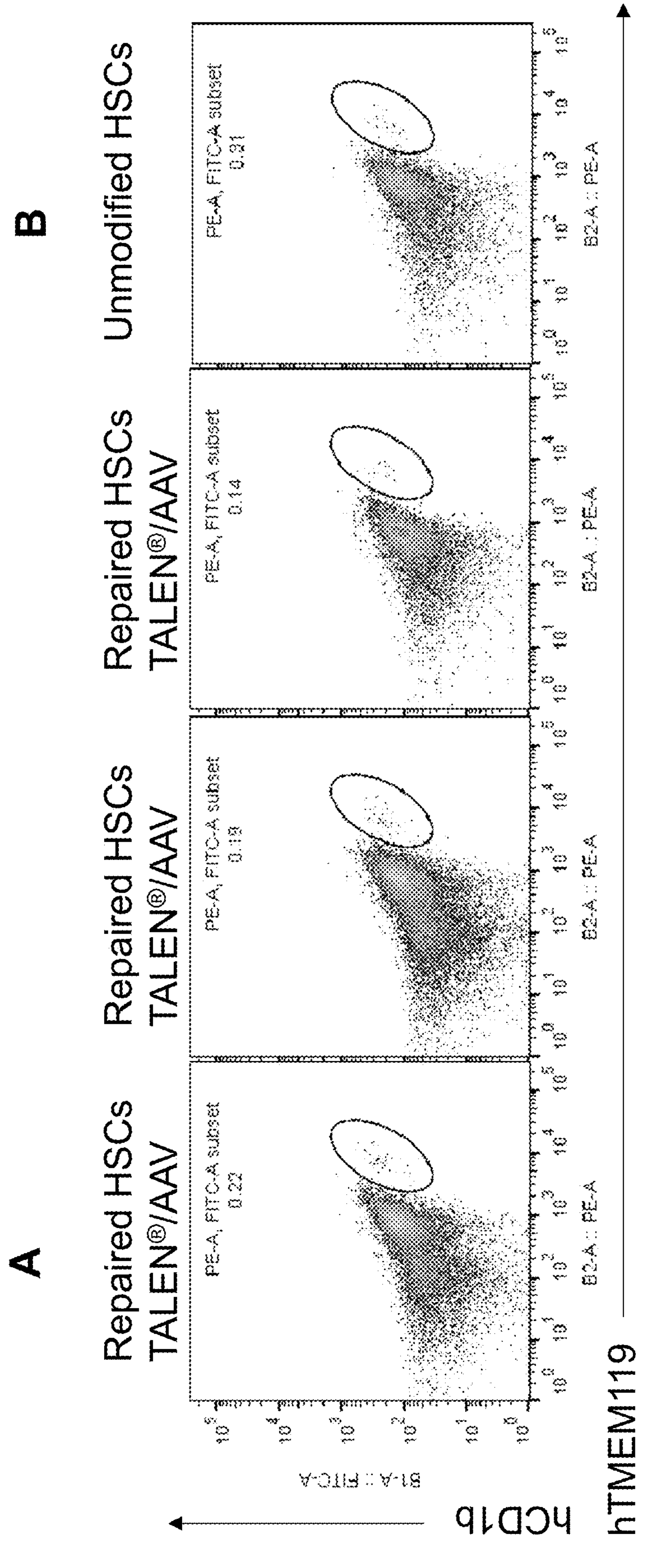
FIG. 3. Expression pattern of the targeted loci (TMEM119) in microglia. Human primary HSCs, were transplanted to NBSGW mice in order to differentiate to human microglial cells. CD11b marker is used as established microglial cell specific differentiation marker. A: 3 replicates of engineered cells (site directed insertion using AAV as polynucleotide template and TALE-nucleases as a rare-cutting endonuclease at the CCR5 locus). B: non-engineered primary HSCs. These experiments show that human HSCs can contribute to microglial cell turnover in the brain to serve as a vehicle for therapeutic molecular delivery to the brain as per the present invention.
Figure 4:
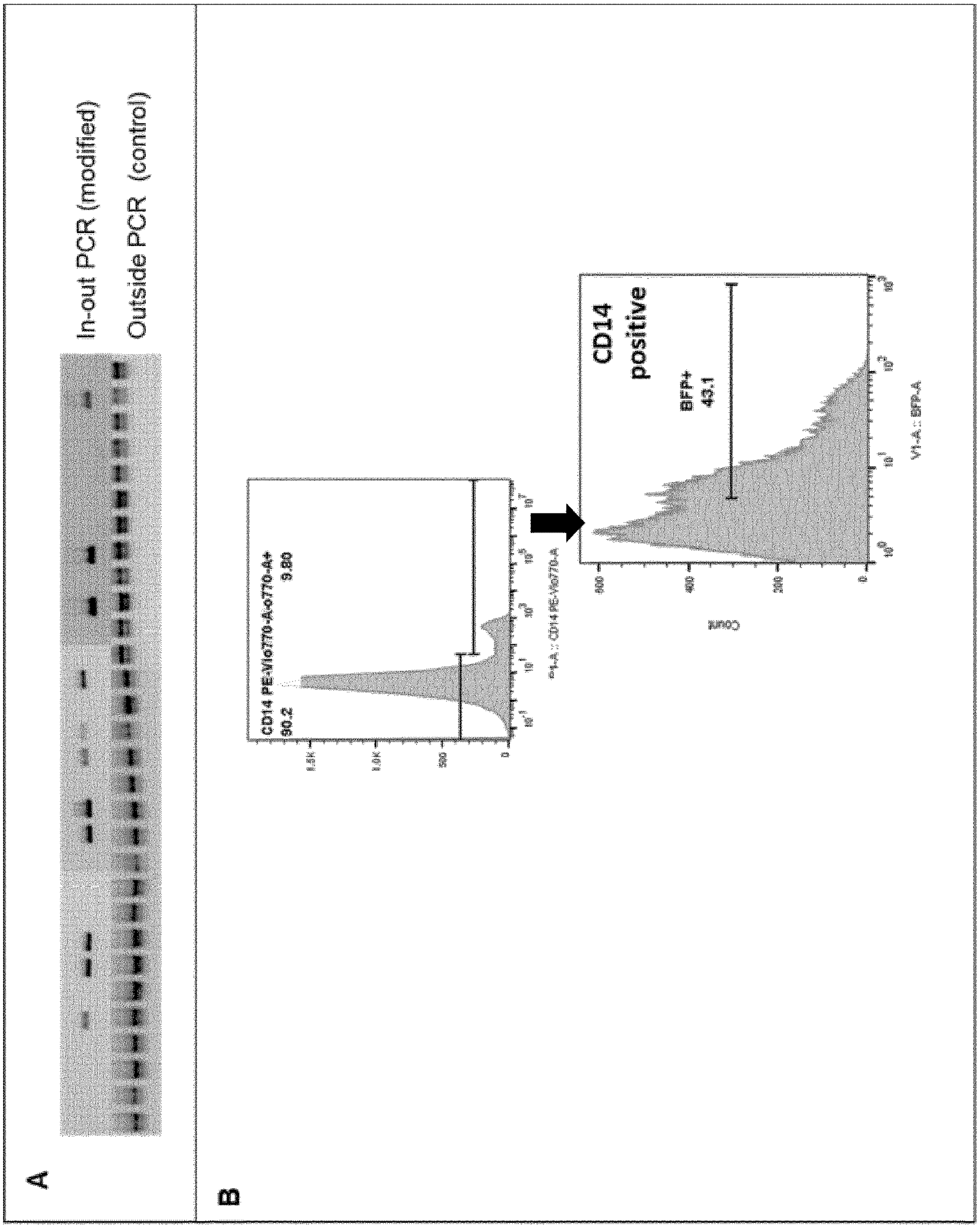
FIG. 4. PCR Experiments performed on engineered HSC cells. BFP reporter gene was inserted at the CCR5 locus. A: PCR positive results showing integration of the transgene at the expected locus. B: BFP flow cytometry measurements show that genomic modification rate did not affect expression and correlated with myeloid specific differentiation (CD14 marker).
Figure 5:
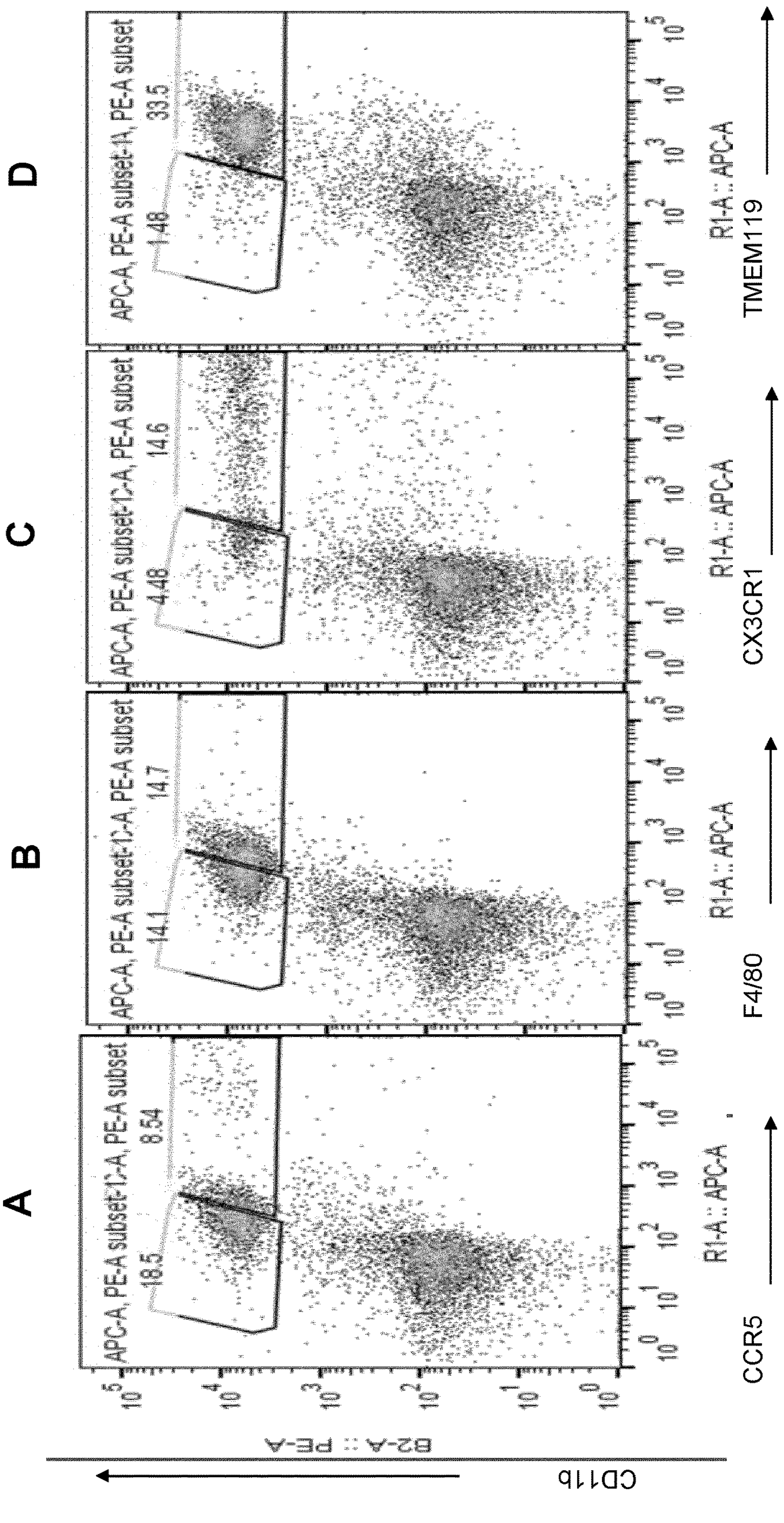
FIG. 5. Expression patterns in microglia from mice brain homogenate. CD11b marker was used as established microglial cell specific differentiation marker. A: CD11b/CCR5. B: CD11B/F4-80 was used as a control. C: CD11b/CX3CR1. D: CD11b/TMEM119. Results show that CX3CR1 and TMEM119 are either more uniformly expressed (TMEM119) or at least comparable (CX3CR1) to F4-80 expression levels and thus appear as more appropriate loci than CCR5 to express transgenes in microglia for therapeutic polypeptide delivery to the brain as per the methods of the present invention.
Figure 6:
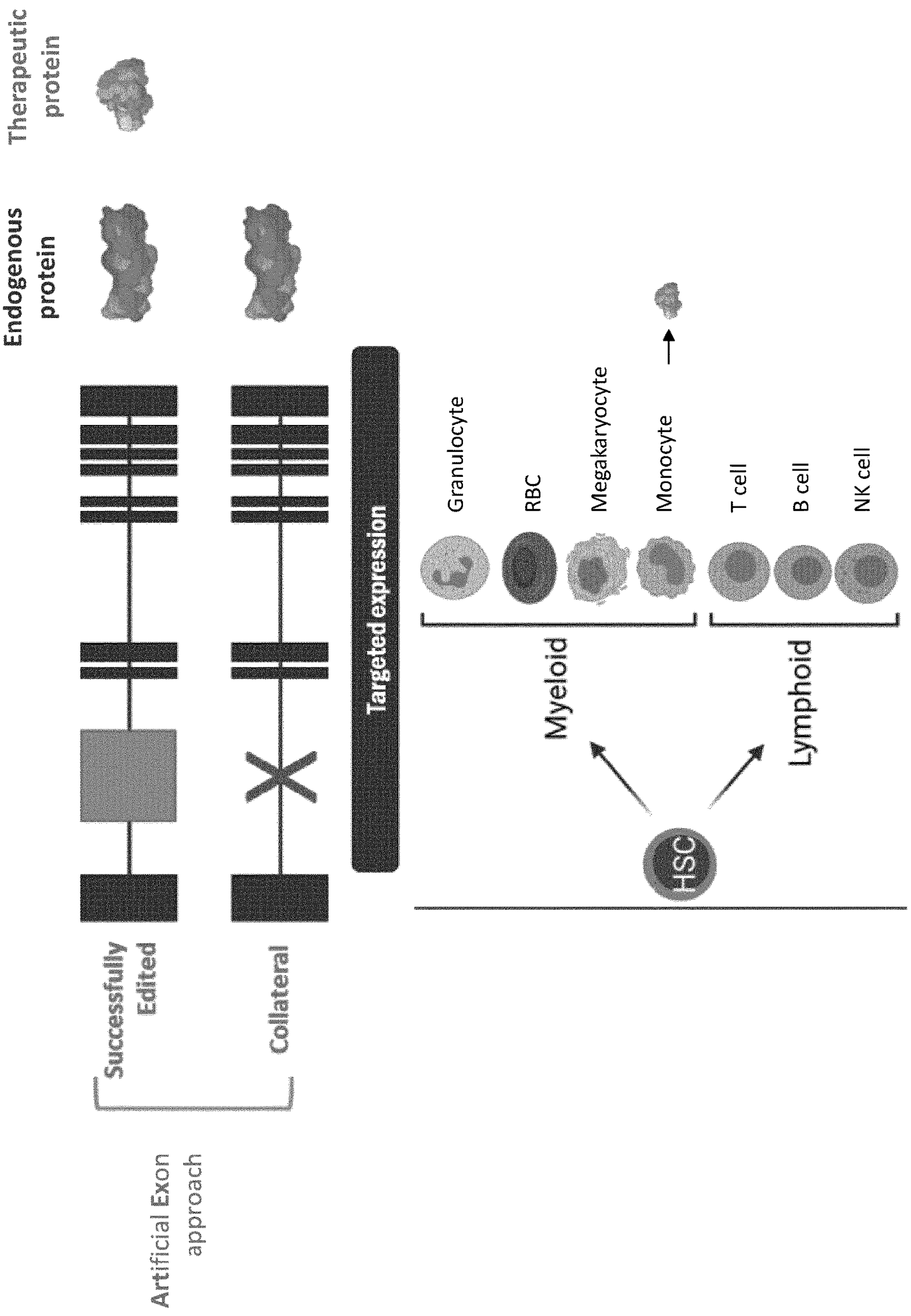
FIG. 6. Schematic representation of gene editing strategy to obtain specific expression of the therapeutic gene in myeloid cells by targeting intronic sequence. This strategy has a major advantage that it will avoid collateral effect (NHEJ events).
Figure 7:
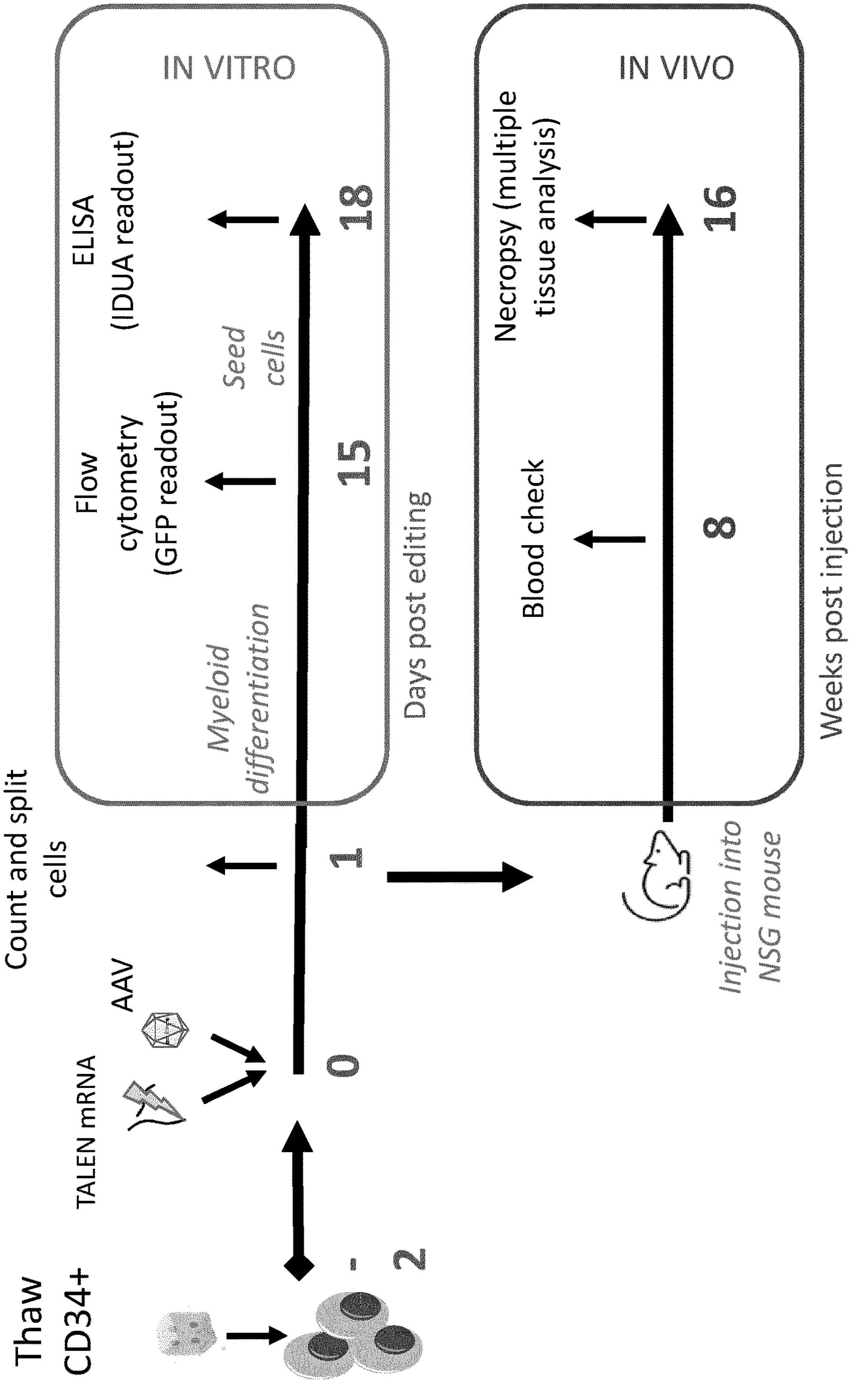
FIG. 7. Schematic representation of the experimental set up depicted in examples.

Said method is particularly useful, for instance, when said exons into said genomic regions are generally actively transcribed from a common endogenous promoter located upstream the first exon, such as illustrated in FIG. 2.

Said method has the advantage of preventing disruption of the transcript encoding the endogenous exonic regions, while allowing their transcription together with the exogenous coding sequence.

In general, said method comprises one or several of the following steps:

- providing cell(s) comprising an endogenous intronic genomic region,
- introducing into said cell(s) a polynucleotide template comprising an exogenous coding sequence,
- said polynucleotide template comprising or consisting of, in the 5' to 3' orientation:
  - a first homologous polynucleotide sequence, which is homologous to the intronic sequence upstream of the insertion site,
- while said first polynucleotide sequence does not preferably comprise a branch point;
  - a first strong splice site sequence, preferably comprising a branch point and a splice acceptor;
  - a first sequence encoding 2A self-cleaving peptide;
  - an exogenous sequence coding for a protein of interest;
  - a second sequence encoding 2A self-cleaving peptide;
  - a copy of the coding sequence of the first exon, optionally rewritten;
  - a second strong splice site sequence preferably comprising a splice donor; and
  - a second homologous polynucleotide sequence, which is homologous to the intronic sequence downstream of the insertion site;
- inducing the integration of said exogenous polynucleotide into said intronic sequence, preferably by homologous recombination, to have said exogenous coding sequence being transcribed at said endogenous locus along with the first exon and preferably second (endogenous) exon, or a copy thereof.

In general, the second homologous polynucleotide, downstream of the copy of the first exon comprises a branch point, preferably that initially present in the endogenous sequence, in order to allow proper RNA splicing and expression of the second exon.

As a preferred embodiment, the copy of the sequence of said first exon can be rewritten at the polynucleotide level for codon optimization and/or reducing nucleotide sequence homologies with the endogenous locus sequences.

Each of the above steps can be performed by using methods well known in the art. According to a preferred embodiment, also in accordance with the delivery of therapeutic protein by HSCs or cells differentiated therefrom, the cells may originate from the patient himself, donors or from iPS cells, for instance as per the methods described in WO2018/189360, which are incorporated by reference.

The steps of the present method are generally performed ex-vivo, which means that the cells are cultivated and manufactured outside the human body. In general, the cells are not germinal cells or cells originating from human embryos and the methods are not intended to modify the germline or the genetic identity of human beings.

Integration of the polynucleotide template into said intronic sequence by homologous recombination can be facilitated by cleavage of a rare-cutting endonuclease at the insertion site. Accordingly, said method for exon integration may thus comprise the step of introducing or expressing into the cell a rare-cutting endonuclease, in particular TALE-nuclease, Zinc-Finger nuclease, meganuclease, CRISPR such as already described in this application to cleave said intronic sequence at the insertion site.

Insertion sites are thus generally determined by the target sequences of said rare-cutting endonucleases. Insertion sites are thus comprised within the rare-cutting endonuclease target sequences, which are themselves comprised into the intronic sequences of the selected loci, and more particularly into the loci contemplated by the present invention for the engineering of the HSCs as disclosed herein.

Preferred loci are those selected for the expression and delivery of the therapeutic proteins which comprise at least two endogenous exon sequences, in particular one of the intron sequences selected from CXCR3 (SEQ ID NO:76), CD11B (SEQ ID NO:107), S100A9 (SEQ ID NO:148) TMEM119 (SEQ ID NO:189), MERTK (SEQ ID NO:190), CD164 (SEQ ID NO:191), TLR7 (SEQ ID NO:192), CD14 (SEQ ID NO:193), FCGR3A (CD16) (SEQ ID NO:194), TBXAS1 (SEQ ID NO:195), DOK3 (SEQ ID NO:196), ABCA1 (SEQ ID NO:197), TMEM195 (SEQ ID NO:198), TLR4 (SEQ ID NO:199), MR1 (SEQ ID NO:200), FCGR1A (CD64) (SEQ ID NO:201), CSF3R (SEQ ID NO:202), FGD4 (SEQ ID NO: 203) and TSPAN14 (SEQ ID NO:204), and B2M (SEQ ID NO:205).

The polynucleotide template used for integrating the exogenous coding sequence usually includes a first and second polynucleotide sequence homologous to the intronic sequences referred to above, or at least 80%, preferably at least 75%, at least 80%, at least 90 or even preferably at least 95% identical to said polynucleotide sequences. The first and second homologous sequences are generally respectively homologous to the endogenous sequences upstream and downstream of the insertion site preferably over more than 50 base pairs (bp), more preferably over more than 100 bp, 200 bp, 500 bp and even more preferably between 50 et 500 bp.

As per the proposed method, the polynucleotide template to be inserted into the endogenous intronic genomic sequence comprises strong splice site sequences upstream and downstream of the exogenous coding sequence. Splice sites are particular motifs by which spliceosome identifies exons and removes intervening introns. Exogenous splice sites sequences can be introduced by cloning or alternatively by introducing mutations into the homologous sequences. Criteria to identify or design strong splice sites and examples of such sequences are provided in the literature, for instance in Shepard, P. J et al. [Efficient internal exon recognition depends on near equal contributions from the 3' and 5' splice sites (2011) *Nucleic acids research,* 39(20), 8928-37].

The first homologous sequence (i.e. upstream homologous sequence or left homology arm) is generally selected to exclude a branch point, which is generally located between 10 and 100 bp, preferably between 20 to 50 bp upstream of the second exon sequence. Human consensus for branch point sequences is generally yUnAy, where A is the branch point and the lowercase pyrimidines ('y') are not as well conserved as the uppercase U and A. Branch points are usually located 21-34 nucleotides upstream of the 3' end of an intron, whereas so-called polypyrimidine tract spans 4-24 nucleotides downstream of the branch point [Gao, K., et al. (2008). Human branch point consensus sequence is yUnAy. *Nucleic acids research,* 36(7), 2257-67].

2A self-cleaving peptides, or 2A peptides, is a class of 18-22 aa-long peptides, which can induce the cleaving of the recombinant protein in cell. 2A peptides are derived from the 2A region in the genome of virus. Four members of 2A peptides family are frequently used in life science research: P2A, E2A, F2A and T2A. F2A, which is more commonly used, is derived from foot-and-mouth disease virus 18; E2A is derived from equine rhinitis A virus; P2A is derived from Porcine teschovirus-1 2A; T2A is derived from Thosea asigna virus 2A [Liu et al. (2017). "Systematic comparison of 2A peptides for cloning multi-genes in a polycistronic vector". *Scientific Reports.* 7 (1)].

The present method for integrating an exogenous coding sequence into an endogenous intronic genomic region can be regarded as an invention in itself, as it is broadly applicable to any types of cells not being restricted to HSCs and irrespective the type of exogenous coding sequence that can inserted at the endogenous locus.

However, said method has been found to be particularly adapted to HSCs to produce therapeutic cells as described herein. There are significant advantages to use the above method for integrating corrected copy(ies) or additional copy(ies) of a gene, for their subsequent expression in differentiated HSCs to obtain cross correction of genetic deficiencies. Indeed, this preserves as much as possible the expression of the endogenous gene locus targeted by the insertion and thus is less susceptible to disturb cell differentiation and cell function of the resulting cells. This is especially sought with engineered HSCs that are intended to differentiate into macrophages to fulfill microglial function in the brain.

The present invention thus encompasses cells obtainable by the method described above and illustrated in FIG. 2 for integrating an exogenous coding sequence into an endogenous intronic genomic region, especially cells dedicated to gene therapy, and especially for cross correction of deficient alleles. This genetic insertion can be performed in HSCs to obtain expression in more differentiated stages, such as those cells used for the delivery of therapeutic proteins to the brain, in particular macrophages and microglial cells, for the treatment of disease, as more particularly described in FIG. 14.

As mentioned before, the present invention is drawn to a general method for integrating an exogenous coding sequence into an endogenous intronic genomic region or locus, without inactivating the expression of the endogenous exons present at this locus, especially sequences downstream the insertion site. This method thus prevents so-called "polar effects" generally observed in transgene genomic integration.

Said method comprises the following steps:

providing cell(s) comprising an endogenous intronic genomic region, introducing into said cell(s) a polynucleotide template comprising an exogenous coding sequence, wherein said polynucleotide template comprises:

a) a first homologous polynucleotide sequence, which is homologous to the intronic sequence upstream of the insertion site, b) a first strong splice site sequence, comprising a branch point and a splice acceptor;

c) a first sequence encoding 2A self-cleaving peptide;

d) an exogenous sequence coding for a protein of interest;

e) a second sequence encoding 2A self-cleaving peptide;
f) a copy of the coding sequence of the first exon(s);
g) a second strong splice site sequence comprising a splice donor; and
h) a second homologous polynucleotide sequence, which is homologous to the intronic sequence downstream of the insertion site; and optionally
inducing the integration of said exogenous polynucleotide into said intronic sequence, preferably by homologous recombination, to have said exogenous coding sequence being transcribed at said endogenous locus along with the first exon(s) or a copy thereof.

By the method of the invention, the above integration forms an artificial exon (Artex) that can be introduced into a hematopoietic stem cell (HSC) in order to obtain for instance expression of an exogenous coding sequence into at least one hematopoietic cell lineage.

In some preferred embodiments, said exogenous coding sequence encodes a protein of interest for treating a genetic disease for its expression in progenitor cells, red blood cells, granulocytes, megacaryocytes, monocytes, B-cells and/or T-cells as shown in FIG. 14.

According to some embodiments, this method is used for expression of a protein selected from FANCA, FANCC or FANCG in progenitor cells.

According to some embodiments, this method is used for expression of a protein selected from HBB, PKLR or RPS19 in red blood cells.

According to some embodiments, this method is used for expression of a protein selected from HAX1, CYBA, CYBB, NCF1, NCF2 or NCF4 in granulocytes.

According to some embodiments, this method is used for expression of a protein selected from Factor 8, Factor 9, Factor 11 or WAS in megakaryocytes.

According to some embodiments, this method is used for expression of a protein selected from IDUA, IDS, ARSB, GUSB, ABCD1, GALC, ARSA, PSAP, GBA, FUCA1, MAN2B1, AGA, ASAH1, HEXA, GAA, SMPD1, LIPA and CDKL5 in Monocytes.

According to some embodiments, this method is used for expression of a protein selected from from ADA, IL2RG, WAS or BTK in B-cells.

According to some embodiments, this method is used for expression of a protein selected from from ADA, IL2RG, WAS, BTK or CCR5 in T-cells.

Accordingly the expression of said exogenous coding sequence results into a protein of interest allowing the cross correction of an endogenous deficient protein. This method can be performed ex-vivo to produce engineered therapeutic cells for the treatment of at least one of the disease listed in FIG. 14, especially the multiple forms of lysosomal storage disease (LSD) identified so far.

The present invention is also drawn to insertion vectors that can be used to carry out the above methods, such as an AAV vector, preferably AAV6, characterized in that it comprises an exogenous polynucleotide sequence for insertion at an endogenous locus comprising the following sequences:
a) a first homologous polynucleotide sequence, which is homologous to the intronic sequence upstream of the insertion site,
b) a first strong splice site sequence, comprising a branch point and a splice acceptor;
c) a first sequence encoding 2A self-cleaving peptide;
d) an exogenous sequence coding for a protein of interest;
e) a second sequence encoding 2A self-cleaving peptide;
f) a copy of the coding sequence of the first exon;
g) a second strong splice site sequence comprising a splice donor; and
h) a second homologous polynucleotide sequence, which is homologous to the intronic sequence downstream of the insertion site.

In preferred embodiments, said first and second homologous sequences are homologous to an endogenous locus selected from: tmem119, s100a9, cd11b, b2m, cx3cr1, mertk, cd164, tlr4, tlr7, cd14, fcgr1a, fcgr3a, tbxas1, dok3, abca1, tmem195, mr1, csf3r, fgd4, tspan14, tgfbri, ccr5, gpr34, serpine2, slco2b1, p2ry12, olfml3, p2ry13, hexb, rhob, jun, rab3il1, ccl2, fcrls, scoc, siglech, slc2a5, lrrc3, plxdc2, usp2, ctsf, cttnbp2nl, atp8a2, lgmn, mafb, egr1, bhlhe41, hpgds, ctsd, hspa1a, lag3, csf1r, adamts1, f11r, golm1, nuak1, crybb1, ltc4s, sgce, pla2g15, ccl3l1, abhd12, ang, ophn1, sparc, pros1, p2ry6, lair1, il1a, epb41l2, adora3, rilpl1, pmepa1, ccl13, pde3b, scamp5, ppp1r9a, tjp1, ak1, b4galt4, gtf2h2, trem2, ckb, acp2, pon3, agmo, tnfrsf17, fscn1, st3gal6, adap2, ccl4, entpd1, tmem86a, kctd12, dst, ctsl2, abcc3, pdgfb, pald1, tubgcp5, rapgef5, stab1, lacc1, tmc7, nrip1, kcnd1, tmem206, hps4, dagla, extl3, mlph, arhgap22, cxxc5, p4ha1, cysltr1, fgd2, kcnk13, gbgt1, c18orf1, cadm1, bco2, adrb1, c3ar1, large, leprel1, liph, upk1b, p2rx7, slc46a1, ebf3, ppp1r15a, il10ra, rasgrp3, fos, tppp, slc24a3, havcr2, nav2, apbb2, clstn1, blnk, gnaq, ptprm, frmd4a, cd86, tnfrsf11a, spint1, ppm1l, tgfbr2, cmklr1, tlr6, gash, hist1h2ab, atf3, acvr1, abi3, lrp12, ttc28, plxna4, adamts16, rgs1, icam1, snx24, ly96, dnajb4, and ppfia4.

The present invention also encompasses an engineered cell obtainable by any of the previous methods, and more particularly one characterized in that an exogenous polynucleotide sequence has been inserted into an intron at an endogenous locus, wherein said polynucleotide sequence preferably comprises:
a first strong splice site sequence comprising a branch point and an acceptor site;
a first sequence encoding 2A self-cleaving peptide;
an exogenous sequence coding for a protein of interest, such as a therapeutic protein;
a second sequence encoding 2A self-cleaving peptide;
a copy of the coding sequence of the preceding exon endogenous to said locus;
a second strong splice site sequence comprising a splice donor site;

2. Still according to some preferred embodiments, said exogenous polynucleotide sequence in said engineered cell can inserted at an endogenous locus selected from: tmem119, s100a9, cd11b, B2m, Cx3cr1, mertk, cd164, tlr4, tlr7, cd14, fcgr1a, fcgr3a, tbxas1, dok3, abca1, tmem195, mr1, csf3r, fgd4, tspan14, tgfbri, ccr5, gpr34, serpine2, slco2b1, P2ry12, Olfml3, P2ry13, Hexb, Rhob, Jun, Rab3il1, Ccl2, Fcrls, Scoc, Siglech, Slc2a5, Lrrc3, Plxdc2, Usp2, Ctsf, Cttnbp2n1, Atp8a2, Lgmn, Mafb, Egr1, Bhlhe41, Hpgds, Ctsd, Hspa1a, Lag3, Csf1r, Adamts1, F11r, Golm1, Nuak1, Crybb1, Ltc4s, Sgce, Pla2g15, Ccl3l1, Abhd12, Ang, Ophn1, Sparc, Pros1, P2ry6, Lair1, Il1a, Epb41l2, Adora3, Rilpl1, Pmepa1, Ccl13, Pde3b, Scamp5, Ppp1r9a, Tjp1, Ak1, B4galt4, Gtf2h2, Trem2, Ckb, Acp2, Pon3, Agmo, Tnfrsf17, Fscn1, St3gal6, Adap2, Ccl4, Entpd1, Tmem86a, Kctd12, Dst, Ctsl2, Abcc3, Pdgfb, Pald1, Tubgcp5, Rapgef5, Stab1, Lacc1, Tmc7, Nrip1, Kcnd1, Tmem206, Hps4, Dagla, Extl3, Mlph, Arhgap22, Cxxc5, P4ha1, Cysltr1, Fgd2, Kcnk13, Gbgt1, C18orf1, Cadm1, Bco2, Adrb1, C3ar1, Large, Leprel1, Liph, Upk1b, P2rx7, Slc46a1, Ebf3, Ppp1r15a, Il10ra, Rasgrp3, Fos, Tppp, Slc24a3, Havcr2, Nav2, Apbb2, Clstn1, Blnk, Gnaq, Ptprm, Frmd4a, Cd86, Tnfrsf11a, Spint1, Ppm1l, Tgfbr2, Cmk1r1, Tlr6, Gas6, Hist1h2ab, Atf3, Acvr1, Abi3, Lrp12, Ttc28, Plxna4, Adamts16, Rgs1, Icam1, Snx24, Ly96, Dnajb4, and Ppfia4. Preferred endogenous gene loci are S100A9 or CD11b According to some preferred embodiments of the present invention, said exogenous polynucleotide sequence is inserted into an intron located between the first and second endogenous coding exons as illustrated in FIG. 2. The first and second encoding 2 self-cleaving peptide are generally different to avoid undesirable rare recombination events, which can be selected from SEQ ID NO:216 and SEQ ID NO:217.

According to some preferred embodiments, the first splice site referred to above comprises SEQ ID NO:206 or SEQ ID NO:207 as shown in the examples.

The coding sequences, in particular that of the first endogenous exon which can be replaced by homologous recombination as a result of the present method of integration as illustrated in FIG. 2, can be codon optimized (i.e. rewritten) to add polynucleotide sequence diversity and prevent undesired recombination events at the endogenous locus. The present invention thus more particularly provides engineered cells in which one exogenous sequence encoding a therapeutic protein selected from IDUA, IDS, ARSB, GUSB, ABCD1, GALC, ARSA, PSAP, GBA, FUCA1, MAN2B1, AGA, ASAH1, HEXA, GAA, SMPD1, LIPA and CDKL5 (SEQ ID NO:1 to SEQ ID NO:35—see Table 1) is integrated at one locus selected from TMEM119, MERTK, CD164, TLR7, CD14, FCGR3A (CD16), TBXAS1, DOK3, ABCA1, TMEM195, TLR4, MR1, FCGR1A (CD64), CSF3R, FGD4, TSPAN14, CXCR3, CD11B, S100A9 and B2M, more particularly into their intronic polynucleotide sequences or any intronic sequences, at least 80%, preferably at least 75%, at least 80%, at least 90 or at least 95% identical to said polynucleotide sequences (to take into account the variability of these sequences throughout the animal kingdom and more particularly the human species).

The invention is thus more specifically directed to one of the following types of engineered cells, wherein:

- IDUA is introduced at the CXCR3 locus, preferably into SEQ ID NO:76;
- IDS is introduced at the CXCR3 locus, preferably into SEQ ID NO:76;
- ARSB is introduced at the CXCR3 locus, preferably into SEQ ID NO:76;
- GUSB is introduced at the CXCR3 locus, preferably into SEQ ID NO:76;
- ABCD1 is introduced at the CXCR3 locus, preferably into SEQ ID NO:76;
- GALC is introduced at the CXCR3 locus, preferably into SEQ ID NO:76;
- ARSA is introduced at the CXCR3 locus, preferably into SEQ ID NO:76;
- PSAP is introduced at the CXCR3 locus, preferably into SEQ ID NO:76;
- GBA is introduced at the CXCR3 locus, preferably into SEQ ID NO:76;
- FUCA1 is introduced at the CXCR3 locus, preferably into SEQ ID NO:76;
- MAN2B1 is introduced at the CXCR3 locus, preferably into SEQ ID NO:76;
- AGA is introduced at the CXCR3 locus, preferably into SEQ ID NO:76;
- ASAH1 is introduced at the CXCR3 locus, preferably into SEQ ID NO:76;
- HEXA is introduced at the CXCR3 locus, preferably into SEQ ID NO:76;
- GAA is introduced at the CXCR3 locus, preferably into SEQ ID NO:76;
- SMPD1 is introduced at the CXCR3 locus, preferably into SEQ ID NO:76;
- LIPA is introduced at the CXCR3 locus, preferably into SEQ ID NO:76;
- CDKL5 is introduced at the CXCR3 locus, preferably into SEQ ID NO:76;
- IDUA is introduced at the CD11B locus, preferably into SEQ ID NO:107;
- IDS is introduced at the CD11B locus, preferably into SEQ ID NO:107;
- ARSB is introduced at the CD11B locus, preferably into SEQ ID NO:107;
- GUSB is introduced at the CD11B locus, preferably into SEQ ID NO:107;
- ABCD1 is introduced at the CD11B locus, preferably into SEQ ID NO:107;
- GALC is introduced at the CD11B locus, preferably into SEQ ID NO:107;
- ARSA is introduced at the CD11B locus, preferably into SEQ ID NO:107;
- PSAP is introduced at the CD11B locus, preferably into SEQ ID NO:107;
- GBA is introduced at the CD11B locus, preferably into SEQ ID NO:107;
- FUCA1 is introduced at the CD11B locus, preferably into SEQ ID NO:107;
- MAN2B1 is introduced at the CD11B locus, preferably into SEQ ID NO:107;
- AGA is introduced at the CD11B locus, preferably into SEQ ID NO:107;
- ASAH1 is introduced at the CD11B locus, preferably into SEQ ID NO:107;
- HEXA is introduced at the CD11B locus, preferably into SEQ ID NO:107;
- GAA is introduced at the CD11B locus, preferably into SEQ ID NO:107;
- SMPD1 is introduced at the CD11B locus, preferably into SEQ ID NO:107;
- LIPA is introduced at the CD11B locus, preferably into SEQ ID NO:107;
- CDKL5 is introduced at the CD11B locus, preferably into SEQ ID NO:107;
- IDUA is introduced at the S100A9 locus, preferably into SEQ ID NO:148;
- IDS is introduced at the S100A9 locus, preferably into SEQ ID NO:148;
- ARSB is introduced at the S100A9 locus, preferably into SEQ ID NO:148;
- GUSB is introduced at the S100A9 locus, preferably into SEQ ID NO:148;
- ABCD1 is introduced at the S100A9 locus, preferably into SEQ ID NO:148;
- GALC is introduced at the S100A9 locus, preferably into SEQ ID NO:148;
- ARSA is introduced at the S100A9 locus, preferably into SEQ ID NO:148;
- PSAP is introduced at the S100A9 locus, preferably into SEQ ID NO:148;
- GBA is introduced at the S100A9 locus, preferably into SEQ ID NO:148;
- FUCA1 is introduced at the S100A9 locus, preferably into SEQ ID NO:148;

MAN2B1 is introduced at the S100A9 locus, preferably into SEQ ID NO:148;
AGA is introduced at the S100A9 locus, preferably into SEQ ID NO:148;
ASAH1 is introduced at the S100A9 locus, preferably into SEQ ID NO:148;
HEXA is introduced at the S100A9 locus, preferably into SEQ ID NO:148;
GAA is introduced at the S100A9 locus, preferably into SEQ ID NO:148;
SMPD1 is introduced at the S100A9 locus, preferably into SEQ ID NO:148;
LIPA is introduced at the S100A9 locus, preferably into SEQ ID NO:148;
CDKL5 is introduced at the S100A9 locus, preferably into SEQ ID NO:148;
IDUA is introduced at the TMEM119 locus, preferably into SEQ ID NO:189;
IDS is introduced at the TMEM119 locus, preferably into SEQ ID NO:189;
ARSB is introduced at the TMEM119 locus, preferably into SEQ ID NO:189;
GUSB is introduced at the TMEM119 locus, preferably into SEQ ID NO:189;
ABCD1 is introduced at the TMEM119 locus, preferably into SEQ ID NO:189;
GALC is introduced at the TMEM119 locus, preferably into SEQ ID NO:189;
ARSA is introduced at the TMEM119 locus, preferably into SEQ ID NO:189;
PSAP is introduced at the TMEM119 locus, preferably into SEQ ID NO:189;
GBA is introduced at the TMEM119 locus, preferably into SEQ ID NO:189;
FUCA1 is introduced at the TMEM119 locus, preferably into SEQ ID NO:189;
MAN2B1 is introduced at the TMEM119 locus, preferably into SEQ ID NO:189;
AGA is introduced at the TMEM119 locus, preferably into SEQ ID NO:189;
ASAH1 is introduced at the TMEM119 locus, preferably into SEQ ID NO:189;
HEXA is introduced at the TMEM119 locus, preferably into SEQ ID NO:189;
GAA is introduced at the TMEM119 locus, preferably into SEQ ID NO:189;
SMPD1 is introduced at the TMEM119 locus, preferably into SEQ ID NO:189;
LIPA is introduced at the TMEM119 locus, preferably into SEQ ID NO:189;
CDKL5 is introduced at the TMEM119 locus, preferably into SEQ ID NO:189;
IDUA is introduced at the MERTK locus, preferably into SEQ ID NO:190;
IDS is introduced at the MERTK locus, preferably into SEQ ID NO: 190;
ARSB is introduced at the MERTK locus, preferably into SEQ ID NO: 190;
GUSB is introduced at the MERTK locus, preferably into SEQ ID NO: 190;
ABCD1 is introduced at the MERTK locus, preferably into SEQ ID NO: 190;
GALC is introduced at the MERTK locus, preferably into SEQ ID NO: 190;
ARSA is introduced at the MERTK locus, preferably into SEQ ID NO: 190;
PSAP is introduced at the MERTK locus, preferably into SEQ ID NO: 190;
GBA is introduced at the MERTK locus, preferably into SEQ ID NO: 190;
FUCA1 is introduced at the MERTK locus, preferably into SEQ ID NO:190;
MAN2B1 is introduced at the MERTK locus, preferably into SEQ ID NO:190;
AGA is introduced at the MERTK locus, preferably into SEQ ID NO: 190;
ASAH1 is introduced at the MERTK locus, preferably into SEQ ID NO: 190;
HEXA is introduced at the MERTK locus, preferably into SEQ ID NO: 190;
GAA is introduced at the MERTK locus, preferably into SEQ ID NO:190;
SMPD1 is introduced at the MERTK locus, preferably into SEQ ID NO: 190;
LIPA is introduced at the MERTK locus, preferably into SEQ ID NO: 190;
CDKL5 is introduced at the MERTK locus, preferably into SEQ ID NO: 190;
IDUA is introduced at the CD164 locus, preferably into SEQ ID NO:191;
IDS is introduced at the CD164 locus, preferably into SEQ ID NO: 191;
ARSB is introduced at the CD164 locus, preferably into SEQ ID NO: 191;
GUSB is introduced at the CD164 locus, preferably into SEQ ID NO: 191;
ABCD1 is introduced at the CD164 locus, preferably into SEQ ID NO: 191;
GALC is introduced at the CD164 locus, preferably into SEQ ID NO: 191;
ARSA is introduced at the CD164 locus, preferably into SEQ ID NO: 191;
PSAP is introduced at the CD164 locus, preferably into SEQ ID NO: 191;
GBA is introduced at the CD164 locus, preferably into SEQ ID NO: 191;
FUCA1 is introduced at the CD164 locus, preferably into SEQ ID NO:191;
MAN2B1 is introduced at the CD164 locus, preferably into SEQ ID NO:191;
AGA is introduced at the CD164 locus, preferably into SEQ ID NO: 191;
ASAH1 is introduced at the CD164 locus, preferably into SEQ ID NO: 191;
HEXA is introduced at the CD164 locus, preferably into SEQ ID NO: 191;
GAA is introduced at the CD164 locus, preferably into SEQ ID NO:191;
SMPD1 is introduced at the CD164 locus, preferably into SEQ ID NO:191;
LIPA is introduced at the CD164 locus, preferably into SEQ ID NO:191;
CDKL5 is introduced at the CD164 locus, preferably into SEQ ID NO:191;
IDUA is introduced at the TLR7 locus, preferably into SEQ ID NO:192;
IDS is introduced at the TLR7 locus, preferably into SEQ ID NO: 192;
ARSB is introduced at the TLR7 locus, preferably into SEQ ID NO: 192;
GUSB is introduced at the TLR7 locus, preferably into SEQ ID NO: 192;

ABCD1 is introduced at the TLR7 locus, preferably into SEQ ID NO: 192;
GALC is introduced at the TLR7 locus, preferably into SEQ ID NO: 192;
ARSA is introduced at the TLR7 locus, preferably into SEQ ID NO: 192;
PSAP is introduced at the locus TLR7, preferably into SEQ ID NO: 192;
GBA is introduced at the TLR7 locus, preferably into SEQ ID NO: 192;
FUCA1 is introduced at the TLR7 locus, preferably into SEQ ID NO:192;
MAN2B1 is introduced at the TLR7locus, preferably into SEQ ID NO:192;
AGA is introduced at the TLR7 locus, preferably into SEQ ID NO: 192;
ASAH1 is introduced at the TLR7 locus, preferably into SEQ ID NO: 192;
HEXA is introduced at the TLR7 locus, preferably into SEQ ID NO: 192;
GAA is introduced at the TLR7 locus, preferably into SEQ ID NO:192;
SMPD1 is introduced at the TLR7 locus, preferably into SEQ ID NO:192;
LIPA is introduced at the TLR7 locus, preferably into SEQ ID NO:192;
CDKL5 is introduced at the TLR7 locus, preferably into SEQ ID NO:192;
IDUA is introduced at the CD14 locus, preferably into SEQ ID NO:193;
IDS is introduced at the CD14 locus, preferably into SEQ ID NO: 193;
ARSB is introduced at the CD14 locus, preferably into SEQ ID NO: 193;
GUSB is introduced at the CD14 locus, preferably into SEQ ID NO: 193;
ABCD1 is introduced at the CD14 locus, preferably into SEQ ID NO: 193;
GALC is introduced at the CD14 locus, preferably into SEQ ID NO: 193;
ARSA is introduced at the CD14 locus, preferably into SEQ ID NO: 193;
PSAP is introduced at the locus CD14, preferably into SEQ ID NO: 193;
GBA is introduced at the CD14 locus, preferably into SEQ ID NO: 193;
FUCA1 is introduced at the CD14 locus, preferably into SEQ ID NO:193;
MAN2B1 is introduced at the CD14 locus, preferably into SEQ ID NO:193;
AGA is introduced at the CD14 locus, preferably into SEQ ID NO: 193;
ASAH1 is introduced at the CD14 locus, preferably into SEQ ID NO: 193;
HEXA is introduced at the CD14 locus, preferably into SEQ ID NO: 193;
GAA is introduced at the CD14 locus, preferably into SEQ ID NO:193;
SMPD1 is introduced at the CD14 locus, preferably into SEQ ID NO:193;
LIPA is introduced at the CD14 locus, preferably into SEQ ID NO:193;
CDKL5 is introduced at the CD14 locus, preferably into SEQ ID NO:193;
IDUA is introduced at the FCGR3A locus, preferably into SEQ ID NO:194;
IDS is introduced at the FCGR3A locus, preferably into SEQ ID NO: 194;
ARSB is introduced at the FCGR3A locus, preferably into SEQ ID NO: 194;
GUSB is introduced at the FCGR3A locus, preferably into SEQ ID NO: 194;
ABCD1 is introduced at the FCGR3A locus, preferably into SEQ ID NO: 194;
GALC is introduced at the FCGR3A locus, preferably into SEQ ID NO: 194;
ARSA is introduced at the FCGR3A locus, preferably into SEQ ID NO: 194;
PSAP is introduced at the FCGR3A locus, preferably into SEQ ID NO: 194;
GBA is introduced at the FCGR3A locus, preferably into SEQ ID NO: 194;
FUCA1 is introduced at the FCGR3A locus, preferably into SEQ ID NO:194;
MAN2B1 is introduced at the FCGR3A locus, preferably into SEQ ID NO:194;
AGA is introduced at the FCGR3A locus, preferably into SEQ ID NO: 194;
ASAH1 is introduced at the FCGR3A locus, preferably into SEQ ID NO: 194;
HEXA is introduced at the FCGR3A locus, preferably into SEQ ID NO: 194;
GAA is introduced at the FCGR3A locus, preferably into SEQ ID NO:194;
SMPD1 is introduced at the FCGR3A locus, preferably into SEQ ID NO:194;
LIPA is introduced at the FCGR3A locus, preferably into SEQ ID NO:194;
CDKL5 is introduced at the FCGR3A locus, preferably into SEQ ID NO:194;
IDUA is introduced at the TBXAS1 locus, preferably into SEQ ID NO:195;
IDS is introduced at the TBXAS1 locus, preferably into SEQ ID NO: 195;
ARSB is introduced at the TBXAS1 locus, preferably into SEQ ID NO: 195;
GUSB is introduced at the TBXAS1 locus, preferably into SEQ ID NO: 195;
ABCD1 is introduced at the TBXAS1 locus, preferably into SEQ ID NO: 195;
GALC is introduced at the TBXAS1 locus, preferably into SEQ ID NO: 195;
ARSA is introduced at the TBXAS1 locus, preferably into SEQ ID NO: 195;
PSAP is introduced at the TBXAS1 locus, preferably into SEQ ID NO: 195;
GBA is introduced at the TBXAS1 locus, preferably into SEQ ID NO: 195;
FUCA1 is introduced at the TBXAS1 locus, preferably into SEQ ID NO:195;
MAN2B1 is introduced at the TBXAS1 locus, preferably into SEQ ID NO:195;
AGA is introduced at the TBXAS1 locus, preferably into SEQ ID NO: 195;
ASAH1 is introduced at the TBXAS1 locus, preferably into SEQ ID NO: 195;
HEXA is introduced at the TBXAS1 locus, preferably into SEQ ID NO: 195;
GAA is introduced at the TBXAS1 locus, preferably into SEQ ID NO:195;
SMPD1 is introduced at the TBXAS1 locus, preferably into SEQ ID NO:195;

LIPA is introduced at the TBXAS1 locus, preferably into SEQ ID NO:195;

CDKL5 is introduced at the TBXAS1 locus, preferably into SEQ ID NO:195;

IDUA is introduced at the DOK3 locus, preferably into SEQ ID NO:196;

IDS is introduced at the DOK3 locus, preferably into SEQ ID NO: 196;

ARSB is introduced at the DOK3 locus, preferably into SEQ ID NO: 196;

GUSB is introduced at the DOK3 locus, preferably into SEQ ID NO: 196;

ABCD1 is introduced at the DOK3 locus, preferably into SEQ ID NO: 196;

GALC is introduced at the DOK3 locus, preferably into SEQ ID NO: 196;

ARSA is introduced at the DOK3 locus, preferably into SEQ ID NO: 196;

PSAP is introduced at the DOK3 locus, preferably into SEQ ID NO: 196;

GBA is introduced at the DOK3 locus, preferably into SEQ ID NO: 196;

FUCA1 is introduced at the DOK3 locus, preferably into SEQ ID NO:196;

MAN2B1 is introduced at the DOK3 locus, preferably into SEQ ID NO:196;

AGA is introduced at the DOK3 locus, preferably into SEQ ID NO: 196;

ASAH1 is introduced at the DOK3 locus, preferably into SEQ ID NO: 196;

HEXA is introduced at the DOK3 locus, preferably into SEQ ID NO: 196;

GAA is introduced at the DOK3 locus, preferably into SEQ ID NO:196;

SMPD1 is introduced at the DOK3 locus, preferably into SEQ ID NO:196;

LIPA is introduced at the DOK3 locus, preferably into SEQ ID NO:196;

CDKL5 is introduced at the DOK3 locus, preferably into SEQ ID NO:196;

IDUA is introduced at the ABCA1 locus, preferably into SEQ ID NO:197;

IDS is introduced at the ABCA1 locus, preferably into SEQ ID NO: 197;

ARSB is introduced at the ABCA1 locus, preferably into SEQ ID NO: 197;

GUSB is introduced at the ABCA1 locus, preferably into SEQ ID NO: 197;

ABCD1 is introduced at the ABCA1 locus, preferably into SEQ ID NO: 197;

GALC is introduced at the ABCA1 locus, preferably into SEQ ID NO: 197;

ARSA is introduced at the ABCA1 locus, preferably into SEQ ID NO: 197;

PSAP is introduced at the ABCA1 locus, preferably into SEQ ID NO: 197;

GBA is introduced at the ABCA1 locus, preferably into SEQ ID NO: 197;

FUCA1 is introduced at the ABCA1 locus, preferably into SEQ ID NO:197;

MAN2B1 is introduced at the ABCA1 locus, preferably into SEQ ID NO:197;

AGA is introduced at the ABCA1 locus, preferably into SEQ ID NO: 197;

ASAH1 is introduced at the ABCA1 locus, preferably into SEQ ID NO: 197;

HEXA is introduced at the ABCA1 locus, preferably into SEQ ID NO: 197;

GAA is introduced at the ABCA1 locus, preferably into SEQ ID NO:197;

SMPD1 is introduced at the ABCA1 locus, preferably into SEQ ID NO:197;

LIPA is introduced at the ABCA1 locus, preferably into SEQ ID NO:197;

CDKL5 is introduced at the ABCA1 locus, preferably into SEQ ID NO:197;

IDUA is introduced at the TMEM195 locus, preferably into SEQ ID NO:198;

IDS is introduced at the TMEM195 locus, preferably into SEQ ID NO: 198;

ARSB is introduced at the TMEM195 locus, preferably into SEQ ID NO: 198;

GUSB is introduced at the TMEM195 locus, preferably into SEQ ID NO: 198;

ABCD1 is introduced at the TMEM195 locus, preferably into SEQ ID NO: 198;

GALC is introduced at the TMEM195 locus, preferably into SEQ ID NO: 198;

ARSA is introduced at the TMEM195 locus, preferably into SEQ ID NO: 198;

PSAP is introduced at the TMEM195 locus, preferably into SEQ ID NO: 198;

GBA is introduced at the TMEM195 locus, preferably into SEQ ID NO: 198;

FUCA1 is introduced at the TMEM195 locus, preferably into SEQ ID NO:198;

MAN2B1 is introduced at the TMEM195 locus, preferably into SEQ ID NO:198;

AGA is introduced at the TMEM195 locus, preferably into SEQ ID NO: 198;

ASAH1 is introduced at the TMEM195 locus, preferably into SEQ ID NO: 198;

HEXA is introduced at the TMEM195 locus, preferably into SEQ ID NO: 198;

GAA is introduced at the TMEM195 locus, preferably into SEQ ID NO:198;

SMPD1 is introduced at the TMEM195 locus, preferably into SEQ ID NO:198;

LIPA is introduced at the TMEM195 locus, preferably into SEQ ID NO:198;

CDKL5 is introduced at the TMEM195 locus, preferably into SEQ ID NO:198;

IDUA is introduced at the TLR4 locus, preferably into SEQ ID NO:199;

IDS is introduced at the TLR4 locus, preferably into SEQ ID NO: 199;

ARSB is introduced at the TLR4 locus, preferably into SEQ ID NO: 199;

GUSB is introduced at the TLR4 locus, preferably into SEQ ID NO: 199;

ABCD1 is introduced at the TLR4 locus, preferably into SEQ ID NO: 199;

GALC is introduced at the TLR4 locus, preferably into SEQ ID NO: 199;

ARSA is introduced at the TLR4 locus, preferably into SEQ ID NO: 199;

PSAP is introduced at the TLR4 locus, preferably into SEQ ID NO: 199;

GBA is introduced at the TLR4 locus, preferably into SEQ ID NO: 199;

FUCA1 is introduced at the TLR4 locus, preferably into SEQ ID NO:199;

MAN2B1 is introduced at the TLR4 locus, preferably into SEQ ID NO:199;
AGA is introduced at the TLR4 locus, preferably into SEQ ID NO: 199;
ASAH1 is introduced at the TLR4 locus, preferably into SEQ ID NO: 199;
HEXA is introduced at the TLR4 locus, preferably into SEQ ID NO: 199;
GAA is introduced at the TLR4 locus, preferably into SEQ ID NO:199;
SMPD1 is introduced at the TLR4 locus, preferably into SEQ ID NO:199;
LIPA is introduced at the TLR4 locus, preferably into SEQ ID NO:199;
CDKL5 is introduced at the TLR4 locus, preferably into SEQ ID NO:199;
IDUA is introduced at the MR1 locus, preferably into SEQ ID NO:200;
IDS is introduced at the MR1 locus, preferably into SEQ ID NO: 200;
ARSB is introduced at the MR1 locus, preferably into SEQ ID NO: 200;
GUSB is introduced at the MR1 locus, preferably into SEQ ID NO: 200;
ABCD1 is introduced at the MR1 locus, preferably into SEQ ID NO: 200;
GALC is introduced at the MR1 locus, preferably into SEQ ID NO: 200;
ARSA is introduced at the MR1 locus, preferably into SEQ ID NO: 200;
PSAP is introduced at the MR1 locus, preferably into SEQ ID NO: 200;
GBA is introduced at the MR1 locus, preferably into SEQ ID NO: 200;
FUCA1 is introduced at the MR1 locus, preferably into SEQ ID NO: 200;
MAN2B1 is introduced at the MR1 locus, preferably into SEQ ID NO: 200;
AGA is introduced at the MR1 locus, preferably into SEQ ID NO: 200;
ASAH1 is introduced at the MR1 locus, preferably into SEQ ID NO: 200;
HEXA is introduced at the MR1 locus, preferably into SEQ ID NO: 200;
GAA is introduced at the MR1 locus, preferably into SEQ ID NO: 200;
SMPD1 is introduced at the MR1 locus, preferably into SEQ ID NO: 200;
LIPA is introduced at the MR1 locus, preferably into SEQ ID NO: 200;
CDKL5 is introduced at the MR1 locus, preferably into SEQ ID NO: 200;
IDUA is introduced at the FCGR1A locus, preferably into SEQ ID NO:201;
IDS is introduced at the FCGR1A locus, preferably into SEQ ID NO: 201;
ARSB is introduced at the FCGR1A locus, preferably into SEQ ID NO: 201;
GUSB is introduced at the FCGR1A locus, preferably into SEQ ID NO: 201;
ABCD1 is introduced at the FCGR1A locus, preferably into SEQ ID NO: 201;
GALC is introduced at the FCGR1A locus, preferably into SEQ ID NO: 201;
ARSA is introduced at the FCGR1A locus, preferably into SEQ ID NO: 201;
PSAP is introduced at the FCGR1A locus, preferably into SEQ ID NO: 201;
GBA is introduced at the FCGR1A locus, preferably into SEQ ID NO: 201;
FUCA1 is introduced at the FCGR1A locus, preferably into SEQ ID NO: 201;
MAN2B1 is introduced at the FCGR1A locus, preferably into SEQ ID NO: 201;
AGA is introduced at the FCGR1A locus, preferably into SEQ ID NO: 201;
ASAH1 is introduced at the FCGR1A locus, preferably into SEQ ID NO: 201;
HEXA is introduced at the FCGR1A locus, preferably into SEQ ID NO: 201;
GAA is introduced at the FCGR1A locus, preferably into SEQ ID NO: 201;
SMPD1 is introduced at the FCGR1A locus, preferably into SEQ ID NO: 201;
LIPA is introduced at the FCGR1A locus, preferably into SEQ ID NO: 201;
CDKL5 is introduced at the FCGR1A locus, preferably into SEQ ID NO: 201;
IDUA is introduced at the CSF3R locus, preferably into SEQ ID NO:202;
IDS is introduced at the CSF3R locus, preferably into SEQ ID NO: 202;
ARSB is introduced at the CSF3R locus, preferably into SEQ ID NO: 202;
GUSB is introduced at the CSF3R locus, preferably into SEQ ID NO: 202;
ABCD1 is introduced at the CSF3R locus, preferably into SEQ ID NO: 202;
GALC is introduced at the CSF3R locus, preferably into SEQ ID NO: 202;
ARSA is introduced at the CSF3R locus, preferably into SEQ ID NO: 202;
PSAP is introduced at the CSF3R locus, preferably into SEQ ID NO: 202;
GBA is introduced at the CSF3R locus, preferably into SEQ ID NO: 202;
FUCA1 is introduced at the CSF3R locus, preferably into SEQ ID NO: 202;
MAN2B1 is introduced at the CSF3R locus, preferably into SEQ ID NO: 202;
AGA is introduced at the CSF3R locus, preferably into SEQ ID NO: 202;
ASAH1 is introduced at the CSF3R locus, preferably into SEQ ID NO: 202;
HEXA is introduced at the CSF3R locus, preferably into SEQ ID NO: 202;
GAA is introduced at the CSF3R locus, preferably into SEQ ID NO: 202;
SMPD1 is introduced at the CSF3R locus, preferably into SEQ ID NO: 202;
LIPA is introduced at the CSF3R locus, preferably into SEQ ID NO: 202;
CDKL5 is introduced at the CSF3R locus, preferably into SEQ ID NO: 202;
IDUA is introduced at the FGD4 locus, preferably into SEQ ID NO:203;
IDS is introduced at the FGD4 locus, preferably into SEQ ID NO: 203;
ARSB is introduced at the FGD4 locus, preferably into SEQ ID NO: 203;
GUSB is introduced at the FGD4 locus, preferably into SEQ ID NO: 203;

ABCD1 is introduced at the FGD4 locus, preferably into SEQ ID NO: 203;
GALC is introduced at the FGD4 locus, preferably into SEQ ID NO: 203;
ARSA is introduced at the FGD4 locus, preferably into SEQ ID NO: 203;
PSAP is introduced at the FGD4 locus, preferably into SEQ ID NO: 203;
GBA is introduced at the FGD4 locus, preferably into SEQ ID NO: 203;
FUCA1 is introduced at the FGD4 locus, preferably into SEQ ID NO: 203;
MAN2B1 is introduced at the FGD4 locus, preferably into SEQ ID NO: 203;
AGA is introduced at the FGD4 locus, preferably into SEQ ID NO: 203;
ASAH1 is introduced at the FGD4 locus, preferably into SEQ ID NO: 203;
HEXA is introduced at the FGD4 locus, preferably into SEQ ID NO: 203;
GAA is introduced at the FGD4 locus, preferably into SEQ ID NO: 203;
SMPD1 is introduced at the FGD4 locus, preferably into SEQ ID NO: 203;
LIPA is introduced at the FGD4 locus, preferably into SEQ ID NO: 203;
CDKL5 is introduced at the FGD4 locus, preferably into SEQ ID NO: 203;
IDUA is introduced at the TSPAN14 locus, preferably into SEQ ID NO:204;
IDS is introduced at the TSPAN14 locus, preferably into SEQ ID NO: 204;
ARSB is introduced at the TSPAN14 locus, preferably into SEQ ID NO: 204;
GUSB is introduced at the TSPAN14 locus, preferably into SEQ ID NO: 204;
ABCD1 is introduced at the TSPAN14 locus, preferably into SEQ ID NO: 204;
GALC is introduced at the TSPAN14 locus, preferably into SEQ ID NO: 204;
ARSA is introduced at the TSPAN14 locus, preferably into SEQ ID NO: 204;
PSAP is introduced at the TSPAN14 locus, preferably into SEQ ID NO: 204;
GBA is introduced at the TSPAN14 locus, preferably into SEQ ID NO: 204;
FUCA1 is introduced at the TSPAN14 locus, preferably into SEQ ID NO: 204;
MAN2B1 is introduced at the TSPAN14 locus, preferably into SEQ ID NO: 204;
AGA is introduced at the TSPAN14 locus, preferably into SEQ ID NO: 204;
ASAH1 is introduced at the TSPAN14 locus, preferably into SEQ ID NO: 204;
HEXA is introduced at the TSPAN14 locus, preferably into SEQ ID NO: 204;
GAA is introduced at the TSPAN14locus, preferably into SEQ ID NO: 204;
SMPD1 is introduced at the TSPAN14 locus, preferably into SEQ ID NO: 204;
LIPA is introduced at the TSPAN14 locus, preferably into SEQ ID NO: 204;
CDKL5 is introduced at the TSPAN14 locus, preferably into SEQ ID NO: 204;
IDUA is introduced at the B2M locus, preferably into SEQ ID NO:205;
IDS is introduced at the B2M locus, preferably into SEQ ID NO: 205;
ARSB is introduced at the B2M locus, preferably into SEQ ID NO: 205;
GUSB is introduced at the B2M locus, preferably into SEQ ID NO: 205;
ABCD1 is introduced at the B2M locus, preferably into SEQ ID NO: 205;
GALC is introduced at the B2M locus, preferably into SEQ ID NO: 205;
ARSA is introduced at the B2M locus, preferably into SEQ ID NO: 205;
PSAP is introduced at the B2M locus, preferably into SEQ ID NO: 205;
GBA is introduced at the B2M locus, preferably into SEQ ID NO: 205;
FUCA1 is introduced at the B2M locus, preferably into SEQ ID NO: 205;
MAN2B1 is introduced at the B2M locus, preferably into SEQ ID NO: 205;
AGA is introduced at the B2M locus, preferably into SEQ ID NO: 205;
ASAH1 is introduced at the B2M locus, preferably into SEQ ID NO: 205;
HEXA is introduced at the B2M locus, preferably into SEQ ID NO: 205;
GAA is introduced at the B2M locus, preferably into SEQ ID NO: 205;
SMPD1 is introduced at the B2M locus, preferably into SEQ ID NO: 205;
LIPA is introduced at the B2M locus, preferably into SEQ ID NO: 205; and
CDKL5 is introduced at the B2M locus, preferably into SEQ ID NO: 205.

Such engineered cells, preferably human cells, are more particularly characterized in that they include at one endogenous locus a polynucleotide sequence comprising the following:

a first strong splice site sequence preferably comprising a branch point and an acceptor site;
a first sequence encoding 2A self-cleaving peptide;
an exogenous sequence coding for a protein of interest, such as a therapeutic protein;
a second sequence encoding 2A self-cleaving peptide;
a copy of the coding sequence of the preceding exon endogenous to said locus, preferably rewritten;
optionally, a second strong splice site sequence, preferably comprising a splice donor site.

The invention also pertains to the DNA template or any polynucleotides, which can be used as insertion vectors useful to perform the engineering of the above cells, especially AAV vectors, more preferably AAV6 vectors as described by Ling, C. et al. [High-Efficiency Transduction of Primary Human Hematopoietic Stem/Progenitor Cells by AAV6 Vectors: Strategies for Overcoming Donor-Variation and Implications in Genome Editing (2016) *Scientific Reports* 6: 35495]. Such polynucleotides are characterized in that they comprise one or several of the following sequences:

a first strong splice site comprising a branch point and an acceptor site;
a first sequence encoding 2A self-cleaving peptide;
an exogenous sequence coding for a protein of interest;
a second sequence encoding 2A self-cleaving peptide;
a copy of the coding sequence of the preceding exon endogenous to said locus, preferably rewritten;

optionally, a second strong splice site comprising a splice donor site.

According to a preferred embodiment, said polynucleotide also comprises upstream and downstream sequences, which are homologous to the endogenous locus as previously described. In general, at least one or both of these upstream and downstream sequences are homologous to intronic sequences, especially those intronic sequences referred to herein as SEQ ID NO:76, SEQ ID NO:107, SEQ ID NO:148 and SEQ ID NO:189 to SEQ ID NO:205, and more preferably exclusively homologous to such intronic sequences (i.e. with spanning exon sequences present at the locus).

Compositions

The invention is also drawn to a composition comprising an effective amount of genetically engineered HSC or iPS cells as described herein. In some embodiments, the invention provides a pharmaceutical composition comprising an effective amount of genetically engineered HSC or iPS cells as described herein.

In some embodiments, the composition can be used as a medicament. In some embodiments, the composition can be used for treating a monogenic disease as described herein.

In some embodiments, the composition comprises a population of cells, wherein at least 40% of the cells in the population have been modified according to any one the methods described herein. In some embodiments, at least 50%, 60%, 70%, 80%, 85%, 90%, 91%, 92%, 93%, 94%, 95%, 96%, 97%, 98%, 99% of the cells in the population have been modified according to any one the methods described herein. In some embodiments, the composition comprises a pure population of cells wherein 100% of the cells have been genetically modified as described herein.

The genetically modified cells can be administered either alone, or as a pharmaceutical composition in combination with diluents and/or with other components. In some embodiments, pharmaceutical compositions can comprise genetically modified HSC or iPS cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g. aluminum hydroxide); and preservatives. In some embodiments, compositions are formulated for intravenous administration.

The genetically modified HSC or iPS cells can be used as a medicament in the treatment of disease. In some embodiments, the genetically modified HSC or iPS cell is for use in the treatment a patient who has a deficiency in the expression of an endogenous gene homologous to the transgene (cross correction). In some embodiments, the genetically modified HSC or iPS cell is for use in the treatment of a lysosomal storage disease. In some embodiments, the genetically modified HSC or iPS cell is for use in the treatment of a disease selected from Mucopolysaccharidosis Type I (Scheie, Hurler-Scheie or Hurler syndrome), Mucopolysaccharidosis Type II (Hunter syndrome), Mucopolysaccharidosis Type VI (Maroteaux-Lamy syndrome), Mucopolysaccharidosis Type VII (Sly disease), X-linked Adrenoleukodystrophy, Globoid Cell Leukodystrophy (Krabbe disease), Metachromatic Leukodystrophy, Gaucher disease, Fucosidosis, Alpha-mannosidosis, Aspartylglucosaminuria, Farber's disease, Tay-Sachs disease, Pompe disease, Niemann Pick disease and Wolman disease.

In some embodiments, the HSC and iPS cells as described herein can be cryopreserved. In some embodiments, the cells can be cryopreserved after their isolation from subjects and prior to any genetic modification. In some embodiments, the genetically modified cells are cryopreserved after genetic modification and prior to infusion in subjects. In some embodiments, the genetically modified cells are cryopreserved after they have been expanded ex vivo.

In one embodiment, the invention provides a cryopreserved pharmaceutical composition comprising: (a) a viable composition of genetically modified HSC or iPS cells (b) an amount of cryopreservative sufficient for the cryopreservation of the HSC or iPS cells; and (c) a pharmaceutically acceptable carrier.

As used herein, "cryopreservation" refers to the preservation of cells by cooling to low sub-zero temperatures, such as (typically) 77 K or −196° C. (the boiling point of liquid nitrogen). Cryopreservation also refers to storing the cells at a temperature between 0°-10° C. in the absence of any cryopreservative agents. At these low temperatures, any biological activity, including the biochemical reactions that would lead to cell death, is effectively stopped. Cryoprotective agents are often used at sub-zero temperatures to preserve the cells from damage due to freezing at low temperatures or warming to room temperature.

In some embodiments, the injurious effects associated with freezing can be circumvented by (a) use of a cryoprotective agent, (b) control of the freezing rate, and (c) storage at a temperature sufficiently low to minimize degradative reactions.

Cryoprotective agents which can be used include but are not limited to dimethyl sulfoxide (DMSO), glycerol, polyvinylpyrrolidine, polyethylene glycol, albumin, dextran, sucrose, ethylene glycol, i-erythritol, D-Sorbitol, D-mannitol, D-sorbitol, i-inositol, D-lactose, choline chloride, amino acids, methanol, acetamide, glycerol monoacetate, and inorganic salts. In a preferred embodiment, DMSO is used, a liquid which is nontoxic to cells in low concentration. Being a small molecule, DMSO freely permeates the cell and protects intracellular organelles by combining with water to modify its freezability and prevent damage from ice formation. Addition of plasma (e.g., to a concentration of 20-25%) can augment the protective effect of DMSO. After the addition of DMSO, cells should be kept at 0-4° C. until freezing, since DMSO concentrations of about 1% are toxic at temperatures above 4° C.

Different cryoprotective agents (Rapatz, G., et al., 1968, *Cryobiology* 5(1):18-25) and different cell types have different optimal cooling rates (see e.g., Rowe, A. W. and Rinfret, A. P., 1962, *Blood* 20:636; Rowe, A. W., 1966, *Cryobiology* 3(1):12-18; Lewis, J. P., et al., 1967, *Transfusion* 7(1):17-32; and Mazur, P., 1970, *Science* 168:939-949 for effects of cooling velocity on survival of marrow-stem cells and on their transplantation potential). The heat of fusion phase where water turns to ice should be minimal. The cooling procedure can be carried out by use of, e.g., a programmable freezing device or a methanol bath procedure.

After thorough freezing, cells can be rapidly transferred to a long-term cryogenic storage vessel. In one embodiment, the expanded HSC or IPs cells can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum In a particular embodiment, the cryopreservation procedure described in *Current Protocols in Stem Cell Biology,* 2007, (Mick Bhatia, et. al., ed., John Wiley and Sons, Inc.) is used and is hereby incorporated by reference. Mainly when the HSC on a 10-cm tissue culture plate have reached approximately 50% confluency, the media within the plate is aspirated and the HSC s are rinsed with phosphate buffered saline. The adherent HSC are then detached by 3 ml of 0.025% trypsin/0.04% EDTA treatment. The trypsin/EDTA is neutralized by 7 ml of media and the detached HSC are collected by centrifugation at 200×g for 2 min. The supernatant is aspirated off and the pellet of HSC is resuspended in 1.5 ml of media. An aliquot of 1 ml of 100% DMSO is added to the suspension of HSC and gently mixed. Then 1 ml aliquots of this suspension of HSC in DMSO are dispensed into CRYULES in preparation for cryopreservation. The sterilized storage CRYULES preferably have their caps threaded inside, allowing easy handling without contamination. Suitable racking systems are commercially available and can be used for cataloguing, storage, and retrieval of individual specimens.

Considerations and procedures for the manipulation, cryopreservation, and long-term storage of HSC, particularly from bone marrow or peripheral blood can be found, for example, in the following references, incorporated by reference herein: Gorin, N.C., 1986, *Clinics In Haematology* 15(1):19-48; Bone-Marrow Conservation, Culture and Transplantation, Proceedings of a Panel, Moscow, Jul. 22-26, 1968, International Atomic Energy Agency, Vienna, pp. 107-186.

Other methods of cryopreservation of viable cells, or modifications thereof, are available and envisioned for use (e.g., cold metal-minor techniques; Livesey, S. A. and Linner, J. G., 1987, Nature 327:255; Linner, J. G., et al., 1986, *J. Histochem. Cytochem.* 34(9):1123-1135; U.S. Pat. Nos. 4,199,022, 3,753,357, and 4,559,298 and all of these are incorporated hereby reference in their entirety.

In some embodiments, the frozen HSC or iPS cells are thawed quickly (e.g., in a water bath maintained at 37°–41° C.) and chilled on ice immediately upon thawing. In particular, the cryogenic vial containing the frozen HSC or iPS cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

In one embodiment, the thawing procedure after cryopreservation is described in *Current Protocols in Stem Cell Biology* 2007 (Mick Bhatia, et al., ed., John Wiley and Sons, Inc.) and is hereby incorporated by reference. Immediately after removing the cryogenic vial from the cryo-freezer, the vial is rolled between the hands for 10 to 30 sec until the outside of the vial is frost free. The vial is then held upright in a 37° C. water-bath until the contents are visibly thawed. The vial is immersed in 95% ethanol or sprayed with 70% ethanol to kill microorganisms from the water-bath and air dry in a sterile hood. The contents of the vial are then transferred to a 10-cm sterile culture containing 9 ml of media using sterile techniques. The HSC can then be cultured and further expanded in an incubator at 37° C. with 5% humidified $CO_2$.

It may be desirable to treat the HSC or IPs cells in order to prevent cellular clumping upon thawing. To prevent clumping, various procedures can be used, including but not limited to, the addition before and/or after freezing of DNase (Spitzer, G., et al., 1980, *Cancer* 45:3075-3085), low molecular weight dextran and citrate, hydroxyethyl starch (Stiff, P. J., et al., 1983, *Cryobiology* 20:17-24).

The cryoprotective agent, if toxic in humans, should be removed prior to therapeutic use of the thawed HSC or iPS cells. In an embodiment employing DMSO as the cryopreservative, it is preferable to omit this step in order to avoid cell loss, since DMSO has no serious toxicity. However, where removal of the cryoprotective agent is desired, the removal is preferably accomplished upon thawing.

One way in which to remove the cryoprotective agent is by dilution to an insignificant concentration. This can be accomplished by addition of medium, followed by, if necessary, one or more cycles of centrifugation to pellet the cells, removal of the supernatant, and resuspension of the cells. For example, the intracellular DMSO in the thawed cells can be reduced to a level (less than 1%) that will not adversely affect the recovered cells. This is preferably done slowly to minimize potentially damaging osmotic gradients that occur during DMSO removal.

After removal of the cryoprotective agent, cell count (e.g., by use of a hemocytometer) and viability testing (e.g., by trypan blue exclusion; Kuchler, R. J. 1977, *Biochemical Methods in Cell Culture and Virology*, Dowden, Hutchinson & Ross, Stroudsburg, Pa., pp. 18-19; 1964, Methods in Medical Research, Eisen, H. N., et al., eds., Vol. 10, Year Book Medical Publishers, Inc., Chicago, pp. 39-47) can be done to confirm cell survival.

In one embodiment, thawed cells are tested by standard assays of viability (e.g., trypan blue exclusion) and of microbial sterility as described herein, and tested to confirm and/or determine their identity relative to the recipient.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

TABLE 4

Preferred target sequences defined to gene edit the cells of the present invention

| SEQ ID NO # | Name of sequence-specific reagent | Target sequence |
|---|---|---|
| 77 | CX3CR1_T01 | TCTTTCCTCTGTAGCATGGTCCAGATGGCTCATAGCAGGGACCATGATA |
| 78 | CX3CR1_T02 | TATGCTGGGTGAGCACCCACTGCATGCACCCACTGTGCCAGCACTGAGA |

TABLE 4-continued

Preferred target sequences defined to gene edit the cells of the present invention

| SEQ ID NO # | Name of sequence-specific reagent | Target sequence |
|---|---|---|
| 79 | CX3CR1_T03 | TGCTGGGTGAGCACCCACTGCATGCACCCACTGTGCCAGCACTGAGAGA |
| 80 | CX3CR1_T04 | TGAGAGACTCCTGTGGGAGCCACAGCAATTCTAGGGTCTTCACTGGGGA |
| 81 | CX3CR1_T05 | TCCTGTGGGAGCCACAGCAATTCTAGGGTCTTCACTGGGGACTCTGAGA |
| 82 | CX3CR1_T06 | TGGGAGCCACAGCAATTCTAGGGTCTTCACTGGGGACTCTGAGACAGCA |
| 83 | CX3CR1_T07 | TCGTCTGCCCTCACTGAGCAGACCCCCTGGATGGCAGGGAGCAGTCCCA |
| 84 | CX3CR1_T08 | TGCCCTCACTGAGCAGACCCCCTGGATGGCAGGGAGCAGTCCCAAGCCA |
| 85 | CX3CR1_T09 | TGGATGGCAGGGAGCAGTCCCAAGCCAGATGGATGCCCATAACCAGCCA |
| 86 | CX3CR1_T10 | TCTCAATACATAATATCACCACGTATCAGGCAAAACCATCCTGCCCAGA |
| 87 | CX3CR1_T11 | TATCAGGCAAAACCATCCTGCCCAGAGCATTATCTGAATTTGCATCCCA |
| 88 | CX3CR1_T12 | TCCTGCCCAGAGCATTATCTGAATTTGCATCCCATCTGCAGAAGATACA |
| 89 | CX3CR1_T13 | TCTGAATTTGCATCCCATCTGCAGAAGATACATTCACCCACTTCTTCCA |
| 90 | CX3CR1_T14 | TTCCATTCTGTCTTAATCAAAGTCTTTATGTGAATTTTCCCCATTGAGA |
| 91 | CX3CR1_T15 | TCCATTCTGTCTTAATCAAAGTCTTTATGTGAATTTTCCCCATTGAGAA |
| 92 | CX3CR1_T16 | TTCTGTCTTAATCAAAGTCTTTATGTGAATTTTCCCCATTGAGAAGACA |
| 93 | CX3CR1_T17 | TCTGTCTTAATCAAAGTCTTTATGTGAATTTTCCCCATTGAGAAGACAA |
| 94 | CX3CR1_T18 | TTTATGTGAATTTTCCCCATTGAGAAGACAAGCCCCTTCCTGGCTTAGA |
| 95 | CX3CR1_T19 | TTCCTGGCTTAGACTGTACCTGACTGATCTTTTCATGAGCTCCTTGCCA |
| 96 | CX3CR1_T20 | TCCTGGCTTAGACTGTACCTGACTGATCTTTTCATGAGCTCCTTGCCAA |
| 97 | CX3CR1_gRNA1 | GTACAGTCTAAGCCAGGAAGGGG |
| 98 | CX3CR1_gRNA2 | GGGAGCAGTCCCAAGCCAGATGG |
| 99 | CX3CR1_gRNA3 | GACTGCTCCCTGCCATCCAGGGG |
| 100 | CX3CR1_gRNA4 | GTGAATGTATCTTCTGCAGATGG |
| 101 | CX3CR1_gRNA5 | GTCTCTCAGTGCTGGCACAGTGG |
| 102 | CX3CR1_gRNA6 | GACAGCAGGGAGCTAGGATGAGG |
| 103 | CX3CR1_gRNA7 | GAAGGGGCTTGTCTTCTCAATGG |
| 104 | CX3CR1_gRNA8 | GCAAATTCAGATAATGCTCTGGG |
| 105 | CX3CR1_gRNA9 | GAGCAGACCCCCTGGATGGCAGG |
| 106 | CX3CR1_gRNA10 | GAACTCATAGAAAGCGATATTGG |
| 108 | CD11b_T01 | TTCAGAGCAGGACTGGACGTGCCCCACGACGGTGGTTCTTAGGTCAGGA |
| 109 | CD11b_T02 | TATGGCCCACGACCTGTTTTTGCACAACCTGCCAGCTAGAGATTGAAGA |
| 110 | CD11b_T03 | TGATGATAGGGAGCACCACCCCCAAAGAATTCTATTTGTCTCATTTGTA |
| 111 | CD11b_T04 | TTCTATTTGTCTCATTTGTAAACCCGTATTACAAACAAATTGTACTCAA |
| 112 | CD11b_T05 | TATTTGTCTCATTTGTAAACCCGTATTACAAACAAATTGTACTCAATCA |
| 113 | CD11b_T06 | TTTGTAAACCCGTATTACAAACAAATTGTACTCAATCATTATGTTTGAA |
| 114 | CD11b_T07 | TTGTAAACCCGTATTACAAACAAATTGTACTCAATCATTATGTTTGAAA |
| 115 | CD11b_T08 | TACAAACAAATTGTACTCAATCATTATGTTTGAAATTTCCCTAATGACA |
| 116 | CD11b_T09 | TTGTACTCAATCATTATGTTTGAAATTTCCCTAATGACAAATTTGTGGA |

TABLE 4-continued

Preferred target sequences defined to gene edit the cells of the present invention

| SEQ ID NO # | Name of sequence-specific reagent | Target sequence |
|---|---|---|
| 117 | CD11b_T10 | TGTACTCAATCATTATGTTTGAAATTTCCCTAATGACAAATTTGTGGAA |
| 118 | CD11b_T11 | TACTCAATCATTATGTTTGAAATTTCCCTAATGACAAATTTGTGGAAAA |
| 119 | CD11b_T12 | TTTCCCTAATGACAAATTTGTGGAAAAGTATTTTCTGTCTTGTTATATA |
| 120 | CD11b_T13 | TTCCCTAATGACAAATTTGTGGAAAAGTATTTTCTGTCTTGTTATATAA |
| 121 | CD11b_T14 | TTGTGGAAAAGTATTTTCTGTCTTGTTATATAAGTACTTGTACAACATA |
| 122 | CD11b_T15 | TGTTATATAAGTACTTGTACAACATATTCTATCAGCCTCTTGGTCTGCA |
| 123 | CD11b_T16 | TTATATAAGTACTTGTACAACATATTCTATCAGCCTCTTGGTCTGCAAA |
| 124 | CD11b_T17 | TATATAAGTACTTGTACAACATATTCTATCAGCCTCTTGGTCTGCAAAA |
| 125 | CD11b_T18 | TACAACATATTCTATCAGCCTCTTGGTCTGCAAAACCTAAAATTTACTA |
| 126 | CD11b_T19 | TCTTGGTCTGCAAAACCTAAAATTTACTATCTGGCTGTTTACAGAATAA |
| 127 | CD11b_T20 | TGCAAAACCTAAAATTTACTATCTGGCTGTTTACAGAATAAGTGTGCTA |
| 128 | CD11b_T21 | TGAAAATGATTTGAGTTTGTTACCTTTTATGCTTATATGTTGTGGAAAA |
| 129 | CD11b_T22 | TTTGTTACCTTTTATGCTTATATGTTGTGGAAAATGAAATTCTCCTCAA |
| 130 | CD11b_T23 | TTGTTACCTTTTATGCTTATATGTTGTGGAAAATGAAATTCTCCTCAAA |
| 131 | CD11b_T24 | TGTTACCTTTTATGCTTATATGTTGTGGAAAATGAAATTCTCCTCAAAA |
| 132 | CD11b_T25 | TTTATGCTTATATGTTGTGGAAAATGAAATTCTCCTCAAAAGGGAAGGA |
| 133 | CD11b_T26 | TTATGCTTATATGTTGTGGAAAATGAAATTCTCCTCAAAAGGGAAGGAA |
| 134 | CD11b_T27 | TATGCTTATATGTTGTGGAAAATGAAATTCTCCTCAAAAGGGAAGGAAA |
| 135 | CD11b_T28 | TGCTTATATGTTGTGGAAAATGAAATTCTCCTCAAAAGGGAAGGAAATA |
| 136 | CD11b_T29 | TGGAAAATGAAATTCTCCTCAAAAGGGAAGGAAATACTTGAGAGCTGCA |
| 137 | CD11b_T30 | TACTTGAGAGCTGCATAGGAAGGAAATTATCTAATTAAGAATGTATAGA |
| 138 | CD11b_gRNA1 | GGTTGTGCAAAAACAGGTCGTGG |
| 139 | CD11b_gRNA2 | GGGAGGCTGGAATTCAGAGCAGG |
| 140 | CD11b_gRNA3 | GGAGTCAGCAAACAGTGGCCTGG |
| 141 | CD11b_gRNA4 | GAGTCAGCAAACAGTGGCCTGGG |
| 142 | CD11b_gRNA5 | GACCTAAGAACCACCGTCGTGGG |
| 143 | CD11b_gRNA6 | GCAAATCATCGTTGTGACACCGG |
| 144 | CD11b_gRNA7 | GAGACAAATAGAATTCTTTGGGG |
| 145 | CD11b_gRNA8 | GCCCCACGACGGTGGTTCTTAGG |
| 146 | CD11b_gRNA9 | GAAATACTTGAGAGCTGCATAGG |
| 147 | CD11b_gRNA10 | GGTCAGGAGTCAGCAAACAGTGG |
| 149 | S100A9_T01 | TTTCCCCGTTGTATTGGTTGAAATAAGTTTCACTAATTGGTAACCTCCA |
| 150 | S100A9_T02 | TATTGGTTGAAATAAGTTTCACTAATTGGTAACCTCCAGAGGGAAGGGA |
| 151 | S100A9_T03 | TTTCACTAATTGGTAACCTCCAGAGGGAAGGGAAGGGAGGGCAGGGGAA |
| 152 | S100A9_T04 | TGGAACTGGCCTCTAAGTCAGATCTGAATTTGCATGCCCTCAATAGTCA |
| 153 | S100A9_T05 | TCTAAGTCAGATCTGAATTTGCATGCCCTCAATAGTCAAGCTGTGAAAA |

TABLE 4-continued

Preferred target sequences defined to gene edit the cells of the present invention

| SEQ ID NO # | Name of sequence-specific reagent | Target sequence |
|---|---|---|
| 154 | S100A9_T06 | TGCATGCCCTCAATAGTCAAGCTGTGAAAACTAATGACCCTCTCTAGGA |
| 155 | S100A9_T07 | TGAAAACTAATGACCCTCTCTAGGACTGGTTTCAAGTCTTCCTCCAGGA |
| 156 | S100A9_T08 | TCTTCCTCCAGGAAGATACCATTCCTAGCTGTTAAAGTTGTTATAAGGA |
| 157 | S100A9_T09 | TCCTCCAGGAAGATACCATTCCTAGCTGTTAAAGTTGTTATAAGGACCA |
| 158 | S100A9_T10 | TTCCTAGCTGTTAAAGTTGTTATAAGGACCAAATGAGGTGACATTTCCA |
| 159 | S100A9_T11 | TTAAAGTTGTTATAAGGACCAAATGAGGTGACATTTCCAGGCTTACTCA |
| 160 | S100A9_T12 | TGACCAGGGCAAGACCCTGGAACTCAGCTTCCTCTTCTATAAATAGAGA |
| 161 | S100A9_T13 | TTCCTCTTCTATAAATAGAGAATCAGCACCCAAGTCACAGGGTCATGGA |
| 162 | S100A9_T14 | TCTTCTATAAATAGAGAATCAGCACCCAAGTCACAGGGTCATGGAGGGA |
| 163 | S100A9_T15 | TCTATAAATAGAGAATCAGCACCCAAGTCACAGGGTCATGGAGGGAATA |
| 164 | S100A9_T16 | TATAAATAGAGAATCAGCACCCAAGTCACAGGGTCATGGAGGGAATAAA |
| 165 | S100A9_T17 | TGGAGAGCGTTTGGTATGTGCTCAGTGTCTGCTCCATTGTGCGCACTCA |
| 166 | S100A9_T18 | TGGTATGTGCTCAGTGTCTGCTCCATTGTGCGCACTCAGCCTATGGTCA |
| 167 | S100A9_T19 | TTGTGCGCACTCAGCCTATGGTCATTTTTAATTTTTAAATCCAGCCCCA |
| 168 | S100A9_T20 | TTCCCTTGTACATTTGCCAGCTGGTCATTTACTGTGCTCCCAGTCCCCA |
| 169 | S100A9_T21 | TTTTGTTTTCTTTTCAAATTTGGGGAAAGTCGGGAAACAGAGGCCTGCA |
| 170 | S100A9_T22 | TTTCTTTTCAAATTTGGGGAAAGTCGGGAAACAGAGGCCTGCATTAAGA |
| 171 | S100A9_T23 | TTCTTTTCAAATTTGGGGAAAGTCGGGAAACAGAGGCCTGCATTAAGAA |
| 172 | S100A9_T24 | TTGGGGAAAGTCGGGAAACAGAGGCCTGCATTAAGAAGGGTGGAACACA |
| 173 | S100A9_T25 | TAGGTCCCCAGCCCTCCCAGTGCCCCTCCCTCCGCCTTGGTAAGGTGGA |
| 174 | S100A9_T26 | TTCAGAGTTAGGGGCCCTGACAGCTCTCCATAGGTGGAGGCCTCAGGCA |
| 175 | S100A9_T27 | TTAGGGGCCCTGACAGCTCTCCATAGGTGGAGGCCTCAGGCAGGCAGGA |
| 176 | S100A9_T28 | TCCATAGGTGGAGGCCTCAGGCAGGCAGGATGCTGGGTGGGGTAGGCAA |
| 177 | S100A9_T29 | TAGGTGGAGGCCTCAGGCAGGCAGGATGCTGGGTGGGGTAGGCAAGAAA |
| 178 | S100A9_T30 | TGGGTGGGGTAGGCAAGAAAGGGCCCAGCAGAGAGGCCGCATGGCAAAA |
| 179 | S100A9_gRNA1 | GCACAGGAGAGTGCTCGCATTGG |
| 180 | S100A9_gRNA2 | GGTACCCCACAGGTTCTGGGAGG |
| 181 | S100A9_gRNA3 | GGAGCCAGACATCCTGGGGTAGG |
| 182 | S100A9_gRNA4 | GGAGAGTGCTCGCATTGGCTGGG |
| 183 | S100A9_gRNA5 | GGAAGCAGAGCCTCATGGATGGG |
| 184 | S100A9_gRNA6 | GGCTTACTCATGCCATGACCAGG |
| 185 | S100A9_gRNA7 | GGGAAACACCTAGAAAAACTAGG |
| 186 | S100A9_gRNA8 | GTGGGGGGTGAAGCGGGCATAGG |
| 187 | S100A9_gRNA9 | GGGGGGTGAAGCGGGCATAGGGG |
| 188 | S100A9_gRNA10 | GAGGGCTGGGGACCTACCCCAGG |

As per the present disclosure, the present invention more particularly encompass the following items:

1. A method for expressing a transgene into the brain of a patient comprising:
   i) obtaining genetically modified hematopoietic stem cells (HSC), wherein the HSC were isolated from the patient or were obtained from induced pluripotent stem (iPS) cells derived from the patient and differentiated into HSC, wherein the genetically modified HSC have been engineered to comprise a transgene integrated at a locus expressed in microglial cells; and
   ii) engrafting the genetically modified HSC into the patient in order to have them differentiate into microglial cells expressing the transgene into the patient's brain.
2. A method for expressing a transgene into the brain of a patient comprising:
   i) obtaining genetically modified hematopoietic stem cells (HSC), wherein the HSC were isolated from a compatible donor or were obtained from induced pluripotent stem (iPS) cells derived from a compatible donor and differentiated into HSC, wherein the genetically modified HSC have been engineered to comprise a transgene integrated at a locus expressed in microglial cells; and
   ii) engrafting the genetically modified HSC into the patient in order to have them differentiate into microglial cells expressing the transgene into the patient's brain.
3. The method according to item 1 or 2, wherein said locus is selected from the group consisting of TMEM119, S100A9, CD11B, B2m, Cx3cr1, MERTK, CD164, Tlr4, Tlr7, Cd14, Fcgr1a, Fcgr3a, TBXAS1, DOK3, ABCA1, TMEM195, MR1, CSF3R, FGD4, TSPAN14, TGFBRI, CCR5, GPR34, SERPINE2, SLCO2B1, P2ry12, Olfml3, P2ry13, Hexb, Rhob, Jun, Rab3il1, Ccl2, Fcrls, Scoc, Siglech, Slc2a5, Lrrc3, Plxdc2, Usp2, Ctsf, Cttnbp2nl, Atp8a2, Lgmn, Math, Egr1, Bhlhe41, Hpgds, Ctsd, Hspa1a, Lag3, Csf1r, Adamts1, F11r, Golm1, Nuak1, Crybb1, Ltc4s, Sgce, Pla2g15, Ccl3l1, Abhd12, Ang, Ophn1, Sparc, Pros1, P2ry6, Lair1, Il1a, Epb41l2, Adora3, Rilpl1, Pmepa1, Ccl13, Pde3b, Scamp5, Ppp1r9a, Tjp1, Ak1, B4galt4, Gtf2h2, Trem2, Ckb, Acp2, Pon3, Agmo, Tnfrsf17, Fscn1, St3gal6, Adap2, Ccl4, Entpd1, Tmem86a, Kctd12, Dst, Ctsl2, Abcc3, Pdgfb, Pald1, Tubgcp5, Rapgef5, Stab1, Lacc1, Tmc7, Nrip1, Kcnd1, Tmem206, Hps4, Dagla, Extl3, Mlph, Arhgap22, Cxxc5, P4ha1, Cysltr1, Fgd2, Kcnk13, Gbgt1, C18orf1, Cadm1, Bco2, Adrb1, C3ar1, Large, Leprel1, Liph, Upk1b, P2rx7, Slc46a1, Ebf3, Ppp1r15a, Il10ra, Rasgrp3, Fos, Tppp, Slc24a3, Havcr2, Nav2, Apbb2, Clstn1, Blnk, Gnaq, Ptprm, Frmd4a, Cd86, Tnfrsf11a, Spint1, Ppm1l, Tgfbr2, Cmklr1, Tlr6, Gas6, Hist1h2ab, Atf3, Acvr1, Abi3, Lrp12, Ttc28, Plxna4, Adamts16, Rgs1, Icam1, Snx24, Ly96, Dnajb4, and Ppfia4.
4. The method according to any of items 1-3, wherein said locus is cx3cr1.
5. The method according to any of items 1-3, wherein said locus is cd11b.
6. The method according to any of items 1-3, wherein said locus is tmem119.
7. The method according to any of items 1-3, wherein said locus is s100a9.
8. The method of any of items 1-7, wherein the cells have been genetically modified using a sequence specific reagent and a donor sequence comprising the transgene.
9. The method of item 8, wherein the donor sequence comprising the transgene is provided to the cells in a viral vector.
10. The method of item 9, wherein the viral vector is an AAV vector.
11. The method of any of items 8-10, wherein the sequence specific reagent comprises an engineered rare-cutting endonuclease.
12. The method of item 11, wherein the engineered rare-cutting endonuclease is selected from the group consisting of transcription activator-like effector nuclease (TALEN), zinc finger nuclease (ZFN), clustered regularly interspaced short palindromic repeats (CRISPR)-Cas, meganuclease and megaTAL.
13. The method of item 12, wherein the sequence specific reagent is provided to cells as a nucleic acid.
14. The method of item 13, wherein the nucleic acid is mRNA.
15. The method according to any one items 1 to 14, wherein said transgene comprises IDUA for treating Mucopolysaccharidosis Type I (Scheie, Hurler-Scheie or Hurler syndrome).
16. The method according to any one items 1 to 14, wherein said transgene comprises IDS for treating Mucopolysaccharidosis Type II (Hunter).
17. The method according to any one items 1 to 14, wherein said transgene comprises ARSB for treating Mucopolysaccharidosis Type VI (Maroteaux-Lamy).
18. The method according to any one items 1 to 14, wherein said transgene comprises GUSB for treating Mucopolysaccharidosis Type VII (Sly).
19. The method according to any one items 1 to 14, wherein said transgene comprises ABCD1 for treating X-linked Adrenoleukodystrophy.
20. The method according to any one items 1 to 14, wherein said transgene comprises GALC for treating Globoid Cell Leukodystrophy (Krabbe).
21. The method according to any one items 1 to 14, wherein said transgene comprises ARSA for treating Metachromatic Leukodystrophy.
22. The method according to any one items 1 to 14, wherein said transgene comprises GBA for treating Gaucher Disease.
23. The method according to any one items 1 to 14, wherein said transgene comprises FUCA1 for treating Fucosidosis.
24. The method according to any one items 1 to 14, wherein said transgene comprises MAN2B1 for treating Alpha-mannosidosis.
25. The method according to any one items 1 to 14, wherein said transgene comprises AGA for treating Aspartylglucosaminuria.
26. The method according to any one items 1 to 14, wherein said transgene comprises ASAH1 for treating Farber.
27. The method according to any one items 1 to 14, wherein said transgene comprises HEXA for treating Tay-Sachs.
28. The method according to any one items 1 to 14, wherein said transgene comprises GAA for treating Pompe.

29. The method according to any one items 1 to 14, wherein said transgene comprises SMPD1 for treating Niemann Pick.
30. The method according to any one items 1 to 14, wherein said transgene comprises LIPA for treating Wolman Syndrome.
31. The method according to any one items 1 to 14, wherein said transgene comprises CDKL5 for treating CDKL5-deficiency related disease.
32. A genetically modified HSC or iPS cell which has a transgene integrated at a locus selected from tmem119, cd11b or cx3cr1, said transgene being under the transcriptional control of the endogenous promoter of said genes.
33. A HSC or iPS cell according to item 32 for use as a medicament.
34. A HSC or iPS cell according to item 32, for use in the treatment a patient who has a deficiency in the expression of an endogenous gene homologous to said transgene (cross correction).
35. A HSC or iPS cell according to item 33, for use in the treatment of a lysosomal storage disease.
36. A HSC or iPS cell according to item 32, wherein said transgene comprises IDUA for its use in the treatment of Mucopolysaccharidosis Type I (Scheie, Hurler-Scheie or Hurler syndrome).
37. A HSC or iPS cell according to item 32, wherein said transgene comprises IDS for its use in the treatment of Mucopolysaccharidosis Type II (Hunter).
38. A HSC or iPS cell according to item 32, wherein said transgene comprises ARSB for its use in the treatment of Mucopolysaccharidosis Type VI (Maroteaux-Lamy).
39. A HSC or iPS cell according to item 32, wherein said transgene comprises GUSB for its use in the treatment of Mucopolysaccharidosis Type VII (Sly).
40. A HSC or iPS cell according to item 32, wherein said transgene comprises ABCD1 for treating X-linked Adrenoleukodystrophy.
41. A HSC or iPS cell according to item 32, wherein said transgene comprises GALC for its use in the treatment of Globoid Cell Leukodystrophy (Krabbe).
42. A HSC or iPS cell according to item 32, wherein said transgene comprises ARSA for its use in the treatment of Metachromatic Leukodystrophy.
43. A HSC or iPS cell according to item 32, wherein said transgene comprises GBA for its use in the treatment of Gaucher Disease.
44. A HSC or iPS cell according to item 32, wherein said transgene comprises FUCA1 for its use in the treatment of Fucosidosis.
45. A HSC or iPS cell according to item 32, wherein said transgene comprises MAN2B1 for its use in the treatment of Alpha-mannosidosis.
46. A HSC or iPS cell according to item 32, wherein said transgene comprises AGA for its use in the treatment of Aspartylglucosaminuria.
47. A HSC or iPS cell according to item 32, wherein said transgene comprises ASAH1 for its use in the treatment of Farber.
48. A HSC or iPS cell according to item 32, wherein said transgene comprises HEXA for treating Tay-Sachs.
49. A HSC or iPS cell according to item 32, wherein said transgene comprises GAA for its use in the treatment of Pompe.
50. A HSC or iPS cell according to item 32, wherein said transgene comprises SMPD1 for its use in the treatment of Niemann Pick.
51. A HSC or iPS cell according to item 32, wherein said transgene comprises LIPA for its use in the treatment of Wolman Syndrome.
52. A HSC or iPS cell according to item 32, wherein said transgene comprises CDKL5 for its use in the treatment of CDKL5-deficicey related disease
53. A HSC or iPS cell according to any one of items 32-50, wherein multicopies of said transgene are integrated at the same locus separated by 2A self-cleaving peptide sequences.
54. A pharmaceutical composition comprising an HSC or iPS cell according to any of items 32-51.
55. A method for integrating an exogenous coding sequence into an endogenous intron genomic region at an insertion site comprising the following steps:
  providing cell(s) comprising an endogenous intronic genomic region,
  introducing into said cell(s) a polynucleotide template comprising an exogenous coding sequence, wherein said polynucleotide template comprises:
  a) a first homologous polynucleotide sequence, which is homologous to the intronic sequence upstream of the insertion site,
  b) a first strong splice site sequence, comprising a branch point and a splice acceptor;
  c) a first sequence encoding 2A self-cleaving peptide;
  d) an exogenous sequence coding for a protein of interest;
  e) a second sequence encoding 2A self-cleaving peptide;
  f) a copy of the coding sequence of the first exon;
  g) a second strong splice site sequence comprising a splice donor; and
  h) a second homologous polynucleotide sequence, which is homologous to the intronic sequence downstream of the insertion site;
  inducing the integration of said exogenous polynucleotide into said intronic sequence, preferably by homologous recombination, to have said exogenous coding sequence being transcribed at said endogenous locus along with the first and preferably second exon, or a copy thereof
56. An insertion vector, such as an AAV vector, characterized in that it comprises an exogenous polynucleotide sequence for insertion at an endogenous locus comprising the following sequences:
  a) a first homologous polynucleotide sequence, which is homologous to the intronic sequence upstream of the insertion site,
  b) a first strong splice site sequence, comprising a branch point and a splice acceptor;
  c) a first sequence encoding 2A self-cleaving peptide;
  d) an exogenous sequence coding for a protein of interest;
  e) a second sequence encoding 2A self-cleaving peptide;
  f) a copy of the coding sequence of the first exon;
  g) a second strong splice site sequence comprising a splice donor; and
  h) a second homologous polynucleotide sequence, which is homologous to the intronic sequence downstream of the insertion site.
57. An insertion vector according to item 56, wherein said first and second homologous sequences are homologous to an endogenous locus selected from: tmem119, s100a9, cd11b, b2m, cx3cr1, mertk, cd164, tlr4, tlr7, cd14, fcgr1a, fcgr3a, tbxas1, dok3, abca1, tmem195, mr1, csf3r, fgd4, tspan14, tgfbri, ccr5, gpr34, serpine2, slco2b1, p2ry12, olfml3, p2ry13, hexb, rhob, jun, rab3il1, ccl2, fcrls, scoc, siglech, slc2a5, lrrc3, plxdc2, usp2, ctsf, cttnbp2nl, atp8a2, lgmn, mafb, egr1, bhlhe4l, hpgds, ctsd, hspa1a, lag3, csf1r, adamts1, f11r, golm1, nuak1, crybb1, ltc4s, sgce, pla2g15, ccl3l1, abhd12, ang, ophn1, sparc, pros1, p2ry6, lair1, il1a, epb41l2, adora3, rilpl1, pmepa1, ccl13, pde3b, scamp5, ppp1r9a, tjp1, ak1, b4galt4, gtf2h2, trem2, ckb, acp2, pon3, agmo, tnfrsf17, fscn1, st3gal6, adap2, ccl4, entpd1, tmem86a, kctd12, dst, ctsl2, abcc3, pdgfb, pald1, tubgcp5, rapgef5, stab1, lacc1, tmc7, nrip1, kcnd1, tmem206, hps4, dagla, extl3, mlph, arhgap22, cxxc5, p4ha1, cysltr1, fgd2, kcnk13, gbgt1, c18orf1, cadm1, bco2, adrb1, c3ar1, large, leprel1, liph, upk1b, p2rx7, slc46a1, ebf3, ppp1r15a, il10ra, rasgrp3, fos, tppp, slc24a3, havcr2, nav2, apbb2, clstn1, blnk, gnaq, ptprm, frmd4a, cd86, tnfrsf11a, spint1, ppm1l, tgfbr2, cmklr1, tlr6, gash, hist1h2ab, atf3, acvr1, abi3, lrp12, ttc28, plxna4, adamts16, rgs1, icam1, snx24, ly96, dnajb4, and ppfia4.

58. An insertion according to item 56 or 57, wherein said therapeutic protein encoded by said exogenous coding sequence has at least 80% polypeptide sequence identity with IDUA, IDS, ARSB, GUSB, ABCD1, GALC, ARSA, PSAP, GBA, FUCA1, MAN2B1, AGA, ASAH1, HEXA, GAA, SMPD1, LIPA and CDKL5 (SEQ ID NO:1 to SEQ ID NO:35—see Table 1)
59. An engineered cell, characterized in that an exogenous polynucleotide sequence has been inserted at an endogenous locus comprising the following:
    - a first strong splice site sequence comprising a branch point and an acceptor site;
    - a first sequence encoding 2A self-cleaving peptide;
    - an exogenous sequence coding for a protein of interest, such as a therapeutic protein;
    - a second sequence encoding 2A self-cleaving peptide;
    - a copy of the coding sequence of the preceding exon endogenous to said locus;
    - a second strong splice site sequence comprising a splice donor site;
60. An engineered cell according to item 59, wherein said exogenous polynucleotide sequence is inserted at an endogenous locus selected from: tmem119, s100a9, cd11b, B2m, Cx3cr1, mertk, cd164, tlr4, tlr7, cd14, fcgr1a, fcgr3a, tbxas1, dok3, abca1, tmem195, mr1, csf3r, fgd4, tspan14, tgfbri, ccr5, gpr34, serpine2, slco2b1, P2ry12, Olfml3, P2ry13, Hexb, Rhob, Jun, Rab3il1, Ccl2, Fcrls, Scoc, Siglech, Slc2a5, Lrrc3, Plxdc2, Usp2, Ctsf, Cttnbp2nl, Atp8a2, Lgmn, Math, Egr1, Bhlhe4l, Hpgds, Ctsd, Hspa1a, Lag3, Csf1r, Adamts1, F11r, Golm1, Nuak1, Crybb1, Ltc4s, Sgce, Pla2g15, Ccl3l1, Abhd12, Ang, Ophn1, Sparc, Pros1, P2ry6, Lair1, Il1a, Epb41l2, Adora3, Rilpl1, Pmepa1, Ccl13, Pde3b, Scamp5, Ppp1r9a, Tjp1, Ak1, B4galt4, Gtf2h2, Trem2, Ckb, Acp2, Pon3, Agmo, Tnfrsf17, Fscn1, St3gal6, Adap2, Ccl4, Entpd1, Tmem86a, Kctd12, Dst, Ctsl2, Abcc3, Pdgfb, Pald1, Tubgcp5, Rapgef5, Stab1, Lacc1, Tmc7, Nrip1, Kcnd1, Tmem206, Hps4, Dagla, Extl3, Mlph, Arhgap22, Cxxc5, P4ha1, Cysltr1, Fgd2, Kcnk13, Gbgt1, C18orf1, Cadm1, Bco2, Adrb1, C3ar1, Large, Leprel1, Liph, Upk1b, P2rx7, Slc46a1, Ebf3, Ppp1r15a, Il10ra, Rasgrp3, Fos, Tppp, Slc24a3, Havcr2, Nav2, Apbb2, Clstn1, Blnk, Gnaq, Ptprm, Frmd4a, Cd86, Tnfrsf11a, Spint1, Ppm1l, Tgfbr2, Cmklr1, Tlr6, Gas6, Hist1h2ab, Atf3, Acvr1, Abi3, Lrp12, Ttc28, Plxna4, Adamts16, Rgs1, Icam1, Snx24, Ly96, Dnajb4, and Ppfia4.
61. An engineered cell according to item 59 or 60, wherein said therapeutic protein encoded by said exogenous coding sequence has at least 80% polypeptide sequence identity with IDUA, IDS, ARSB, GUSB, ABCD1, GALC, ARSA, PSAP, GBA, FUCA1, MAN2B1, AGA, ASAH1, HEXA, GAA, SMPD1, LIPA and CDKL5 (SEQ ID NO:1 to SEQ ID NO:35—see Table 1).

Having generally described this invention, a further understanding can be obtained by reference to certain specific examples, which are provided herein for purposes of illustration only, and are not intended to limit the scope of the claimed invention.

EXAMPLES

Example 1: Materials and Method

Cell Culture:

HSC culture: HSCs prepared from GCS-F mobilized Leukopak (Miltenyi), were thawed and seeded at $0.4\times10^6$ cells/ml into HSC media composed of STEM Span II media (cat. #09655, Stemcell Technologies), with 1×final concentrations of CD34+ expansion cocktail (#02691, Stemcell Technologies) and Pen-Strep (#15140-122, Gibco Life Technologies). The cells were incubated at 37° C. and 5% $CO_2$ for 48 hrs for recovery after thawing before TALEN transfection and AAV transduction.

Repair Template Constructs:

For S100A9, AAV6 particles obtained from Vigene were used to insert the synthetic exon sequence into the first intron of the S100A9 locus. This donor contains a left homology arm for this intronic region (SEQ ID NO: 209), followed by the 3' albumin splicing signal sequence (SEQ ID NO: 206), followed by a sequence encoding a GSG linker (SEQ ID NO: 215), followed by a sequence encoding a P2A peptide (SEQ ID NO: 224), followed by a sequence encoding EGFP (SEQ ID NO: 218) or IDUA (SEQ ID NO: 2) without a stop codon, followed by the T2A self-cleaving peptide (SEQ ID NO: 225), followed by the first exon of S100A9 (SEQ ID NO: 210), followed by the 5' albumin splicing signal sequence (SEQ ID NO: 208), followed by a right homology arm (SEQ ID NO: 211) for this intronic region.

For CD11b, AAV6 particles obtained from Vigene were used to insert the synthetic exon sequence into the first intron of the CD11b locus. This donor contains a left homology arm for this intronic region (SEQ ID NO: 212), followed by the 3' albumin splicing signal sequence (SEQ ID NO: 206), followed by a sequence encoding a GSG linker (SEQ ID NO: 215), followed by a P2A self-cleaving peptide (SEQ ID NO: 224), followed by a sequence encoding EGFP (SEQ ID NO: 218) or IDUA (SEQ ID NO: 2) without a stop codon, followed by the T2A self-cleaving peptide (SEQ ID NO: 225), followed by the first exon of CD11b rewritten (SEQ ID NO: 213), followed by the 5' albumin splicing signal sequence (SEQ ID NO: 208), followed by a right homology arm for this intronic region (SEQ ID NO: 214).

TALE-Nucleases Reagents:

mRNA encoding TALE-Nucleases targeting CD11b (SEQ ID NO: TALEN_CD11B Left and SEQ ID NO: TALEN_CD11B Right), and S100A9 (SEQ ID NO: TALENS100A9 Left and SEQ ID NO: TALEN S100A9 Right) were produced according to previously described protocol (Poirot et al. 2015). The targeted sequences are TACAACATATTCTATCAgcctcttggtctgcaAAACCTAAAATTTACTA (SEQ ID NO: 125) for CD11b and TTAGGGGCCCTGACAGCtctccataggtggagGCCTCAGGCAGGCAGGA (SEQ ID NO: 175) for the S100A9 loci. (TALEN is a trademark designating TALE-nucleases heterodimers designed by Cellectis (8 rue de la Croix Jarry, Paris, France) comprising Fok-1 nuclease catalytic head as described in WO2011072246.

Gene Editing Protocols: Transfection

Forty-eight hours after thawing, HSC were gene edited. For this, HSCs were harvested, washed once with PBS, and resuspended in High Performance electroporation buffer (#45-0802, BTX) at a concentration of $10\times10^6$ cells/ml. TALEN mRNAs were mixed with cell suspension at 5 μg for each TALEN arm and per million cells. The cell and mRNA mixtures were electroporated on BTX PulseAgile, using the program shown in Table 5. The HSCs were transferred into the prewarmed expansion media in a final concentration of $2\times10^6$ cells/ml.

TABLE 5

BTX PulseAgile settings for HSCs

| Settings | Group1 | Group2 | Group3 |
|---|---|---|---|
| Amplitude (V) | 1000 | 1000 | 130 |
| Duration (ms) | 0.1 | 0.1 | 0.2 |
| Interval (ms) | 0.2 | 100 | 2 |
| Number | 1 | 1 | 4 |

Gene Editing: AAV Preparation and Transduction:

Immediately after electroporation, HSCs were transduced with AAV at various doses including 0.3e4, 1e4, or 3.2e4 viral genome per cell (vg/cell), incubated for 15 min at 37 C and transferred to 30° C. for 22h for recovery. The following day cells were counted and diluted at $0.2\text{-}0.6\times10^6$ cells/ml in expansion media and cultivated at 37° C.

Myeloid Differentiation

Myeoid genes like CD11b and S100A9 are not expressed in HSC. In order to see a phenotypic expression of these edited loci, HSC were incubated in myeloid differentiation media. Twenty-four hours after transfection/transduction, HSCs were counted and resuspended in myeloid expansion supplement (Stemcell Technologies, cat. no. 02694) diluted in STEM Span II (Stemcell Technologies, cat. no. 09655) and supplemented with Pen/strep at 2e5 cells/mL. Cells in myeloid expansion media were then plated in non-tissue culture treated plates and split every 3-4 days, seeded at approximately 2e5 cells/mL. After 14 days in culture, cells were recovered for flow cytometry staining, and/or seeded for IDUA secretion.

IDUA Secretion Assay Fourteen days after myeloid differentiation, cells were seeded in equal numbers (2e5 cells/well) in non-tissue culture 96-well culture plates and incubated in myeloid media at 37° C. Four days after seeding, supernatant were collected and the amount of IDUA was characterized using a commercial ELISA (G-Biosciences, cat: IT2013).

In Vivo Mouse Experiments

Six-week old female NSG mice were ordered from Jackson Laboratories and housed with ad libitum water and food. Mice were pre-conditioned for HSC transplant with busulfan (Sigma Aldrich, cat. no. B3625) reconstituted in DMSO and further diluted in PBS, freshly made on first day of injection. Busulfan was then sterilized using 0.2 um syringe filters. Mice were injected with 15 mg/kg busulfan i.p. once daily for 3 consecutive days prior to injection with HSCs. On the day of injection, animals were anesthetized with 3% isoflorine and injected with 1.5e6 HSC by retro-orbital injection. Engraftment was assessed 16 weeks after injection by analyzing for the presence of human cells in blood, bone marrow and brain.

Brain Isolation

Mice were first anesthetized with isofluorane 4% and perfused with 50 mL cold PBS. Brain was extracted and placed in 5 mL DMEM with 5% FBS+Pen/Strep and kept on ice while all mice and tissue are being processed. Once all brains have been extracted, brain was cut into small pieces using sterile scissors and passed through 16 g needle 3 times to homogenize. To further digest brain tissue, 500 ug/mL papain and 20 U/mL DNase I was added to brain homogenate and incubated for 30 minutes at 37° C. After incubation, remaining brain tissue was passed through 40 μM cell strainer and washed with fresh DMEM. Cells were then resuspended in 30% Percoll gradient, underlay with 70% Percoll gradient, and spun for 25 minutes at 600 g to remove myelin. Cells in the interphase of Percoll gradient were recovered, washed, and stained for flow cytometry or kept for genomic DNA extraction.

Flow Cytometry

Cells were spun down at 400×g for 5 minutes. Supernatant was removed and cells were washed once in FACS buffer (1 mM EDTA+0.5% BSA in PBS). After wash, cells were resuspended in 504, Fc block (BD Bioscience, cat. no. 564220) diluted at 5 μg/mL in FACS buffer. After 5 minutes incubation at 4° C., 504, of surface antibodies master mix diluted in FACS buffer was added to cells and incubated for an additional 30 minutes at 4° C. Cells were then washed twice in FACS buffer, followed by fixation in 100 μuL Fixative/Perm solution (BD Bioscience, cat. no. 554722) for 20 minutes at 4° C. Cells were washed once in Permeabilization buffer, followed by incubation in intracellular antibodies mix (diluted in Permeabilization buffer) for 30 minutes at 4° C. Cells were washed once again in Permeabilization buffer and resuspended in 100-200 μL FACS buffer prior to analysis on BD Canto.

For in vitro myeloid differentiation, the following antibodies were used: CD11b APC (Miltenyi 130-110-554), CD14 VioBlue (Miltenyi 130-113-152), and S100A9 PE (Invitrogen MA5-28130). For staining of bone marrow cells, the following antibodies were used: hCD45 PE-Cy7 (BD 103114), mCD45 V450 (BD 560501), CD33 PE (Miltenyi 130-113-349), CD3 PerCP-Cy5.5 (BD 560835), CD34 APC-V770 (Miltenyi 130-113-180), CD19 FITC (BD 555412). For staining of isolated brain cells, the following antibodies were used: hCD45 FITC (Miltenyi 130-113-117), mCD45 APC-Cy7 (BD 557659), P2RY12 BV421 (Biolegend 392106), purified TMEM119 (Biolegend 853302), anti-mIgG2b AF647 (Biolegend 406716), CD11b PE (Biolegend 101208). For each antibody, fluorescence minus one (FMO) controls and single stain compensation beads were included.

Example 2: An Artificial Exon (ArtEx) for the Expression of GFP can be Inserted Between Exon #1 and #2 and Adequately Processed for Expression—In Vitro Results Insertion of an artificial exon in between the 2 first exons of the myeloid genes S100A9 or CD11b, should achieve expression of a therapeutic protein from the myeloid lineage, without compromising the endogenous expression of S100A9 or CD11b. For a proof of concept, we generated TALEN targeting the intronic region of each gene, as well AAV donors carrying a GFP cassettes allowing expression monitoring. As a control for lineage specific expression of our approach, we also generated reagents to insert a promoter containing GFP cassette into the AAVS1 locus as a more traditional safe harbor approach that will be expressed in all blood lineages.

Pre-stimulated HSCs were transfected with TALEN mRNA targeting the AAVS1, S100A9 and CD11b loci, and transduced with an increasing dose of the corresponding AAV-GFP repair template. Edited HSC were then differentiated in myeloid-like cells. Fourteen days after, differentiated cells were screened by flow cytometry to characterize GFP expression in different cellular subsets.

Figure 8:
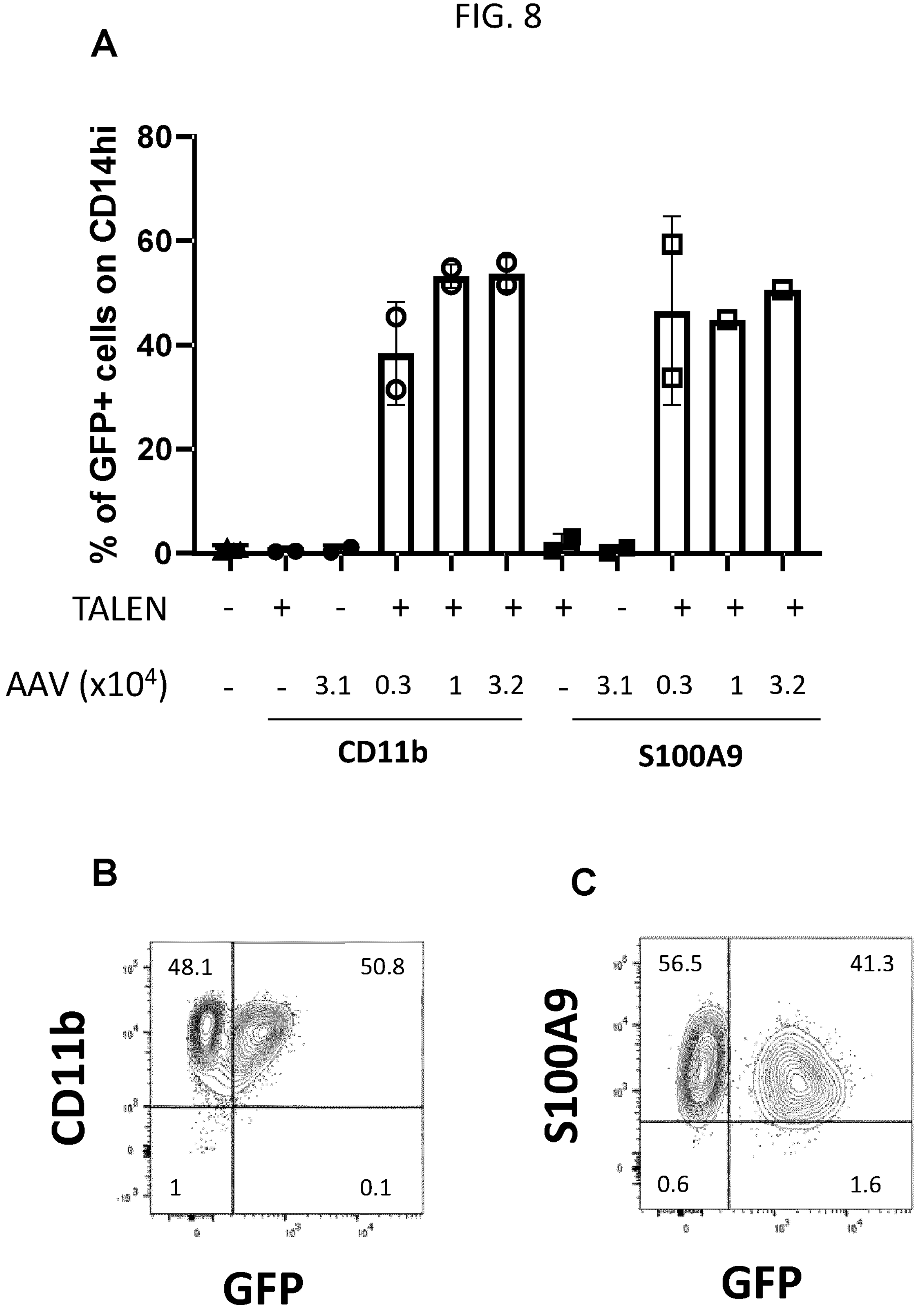
FIG. 8. A. Percentage of GFP+ cells among CD14hi HSCs after targeted integration of GFP at CD11b or S100A9 locus. B. Flow Cytometry results of CD14hi HSCs for CD11b and GFP after GFP targeted integration at CD11b locus. C. Flow Cytometry results of CD14hi HSCs for S110A9 and GFP after GFP targeted integration at S100A9 locus.

Fourteen days after differentiation between 40-60% of cells were CD14+. Among CD14high cells, gene editing rates defined by GFP expression ranged from 26% to 60% largely depending on the AAV dose used, achieving a maximum value of 56%, and 60% for CD11b and S100A9 locus, respectively (FIG. 8A). We also evaluated the expression of the endogenous S100A9 and CD11b in CD14 high cells. All CD14 high cells were positive for CD11b and S100A9, regardless of whether they were edited (GFP+) or not (GFP−) (FIGS. 8B and 8C).

The presence of a substantial amount of GFP cells in either loci, demonstrate that the GFP cassette was adequately inserted in between the first 2 exons, and that our added splicing signals were adequately processed by the splicing cellular machinery. This ArtEx strategy allows expression of a bi-functional mRNA molecule able to translated for both the inserted gene (i.e. GFP) protein and the endogenous CD11b or S100A9 proteins.

Figure 9:
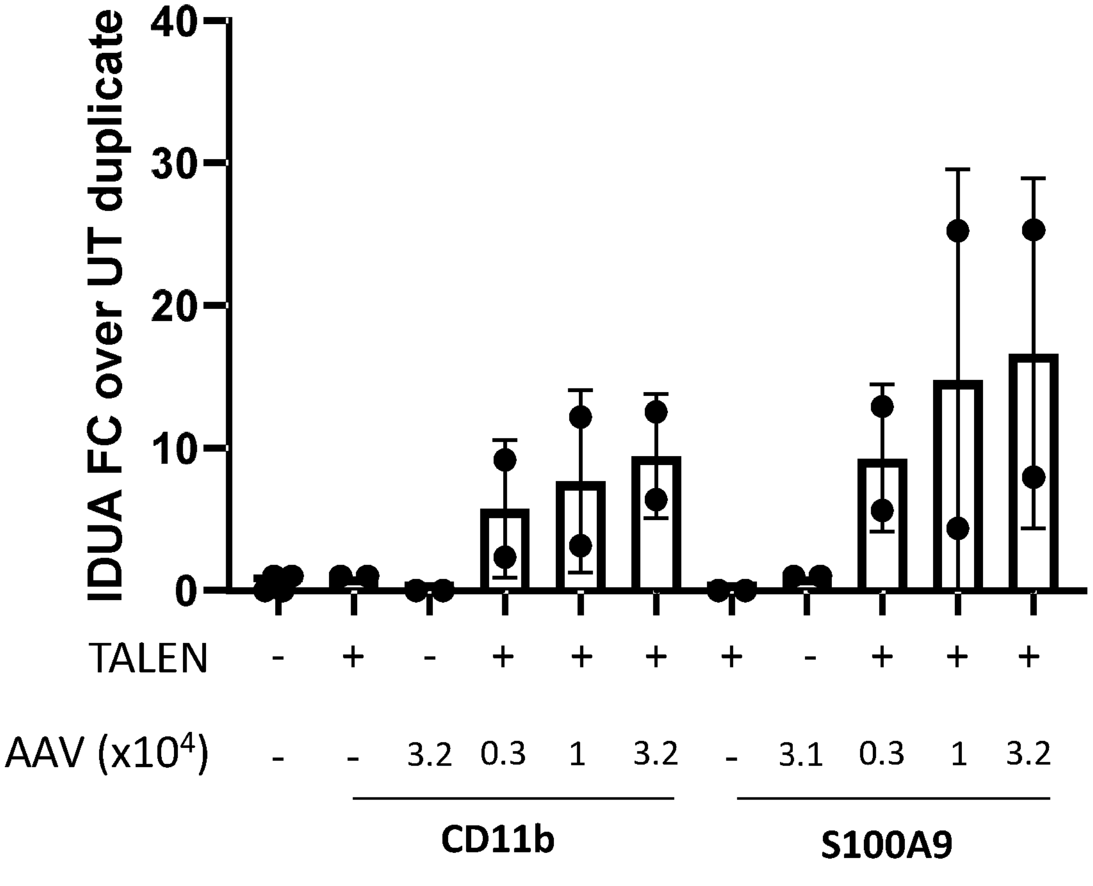
FIG. 9. IDUA quantification results after targeted integration of IDUA gene at CD11b or S100A9 locus.

Example 3: An Artificial Exon for the Expression of IDUA can be Inserted Between Exon #1 and #2 and Adequately Processed for Expression and Secretion—In Vitro Results Pre-stimulated HSCs were transfected with TALEN mRNA targeting S100A9 and CD11b loci, and transduced with the increasing dose of the corresponding AAV-IDUA repair template. Edited HSC were placed into myeloid differentiation media. Fourteen days after, myeloid-like differentiated cells were seeded for IDUA production without any enrichment (% of myeloid between 40-60%). Cell supernatants were collected 3 days after and IDUA was quantified by ELISA. We observed that cells edited at CD11b and S100A9 loci secreted 10× and 15× fold more IDUA than unedited controls, respectively (FIG. 9).

These results confirm that ArtEx strategy allows a specific expression and secretion of therapeutic proteins.

Example 4: Edited HSC Successfully Engrafted in Blood and Bone Marrow of an Animal Model: In Vivo Results One of the more relevant characteristics of HSC, basis of our therapeutic approach, is their ability to provide a lifelong supply of edited cells after a single intervention. To do so, HSC need to engraft in the bone marrow, proliferate and produce blood cells that will later populate multiple tissues in the body.

To provide some insight of this HSC ability, an immunodeficient animal model was used. The edited HSC with the abovementioned GFP cassettes targeted at the S100A9 locus were injected 24h post editing into conditioned NSG females. This animal model has shown to sustain the engraftment of human HSC in the animal bone marrow.

Figure 10:
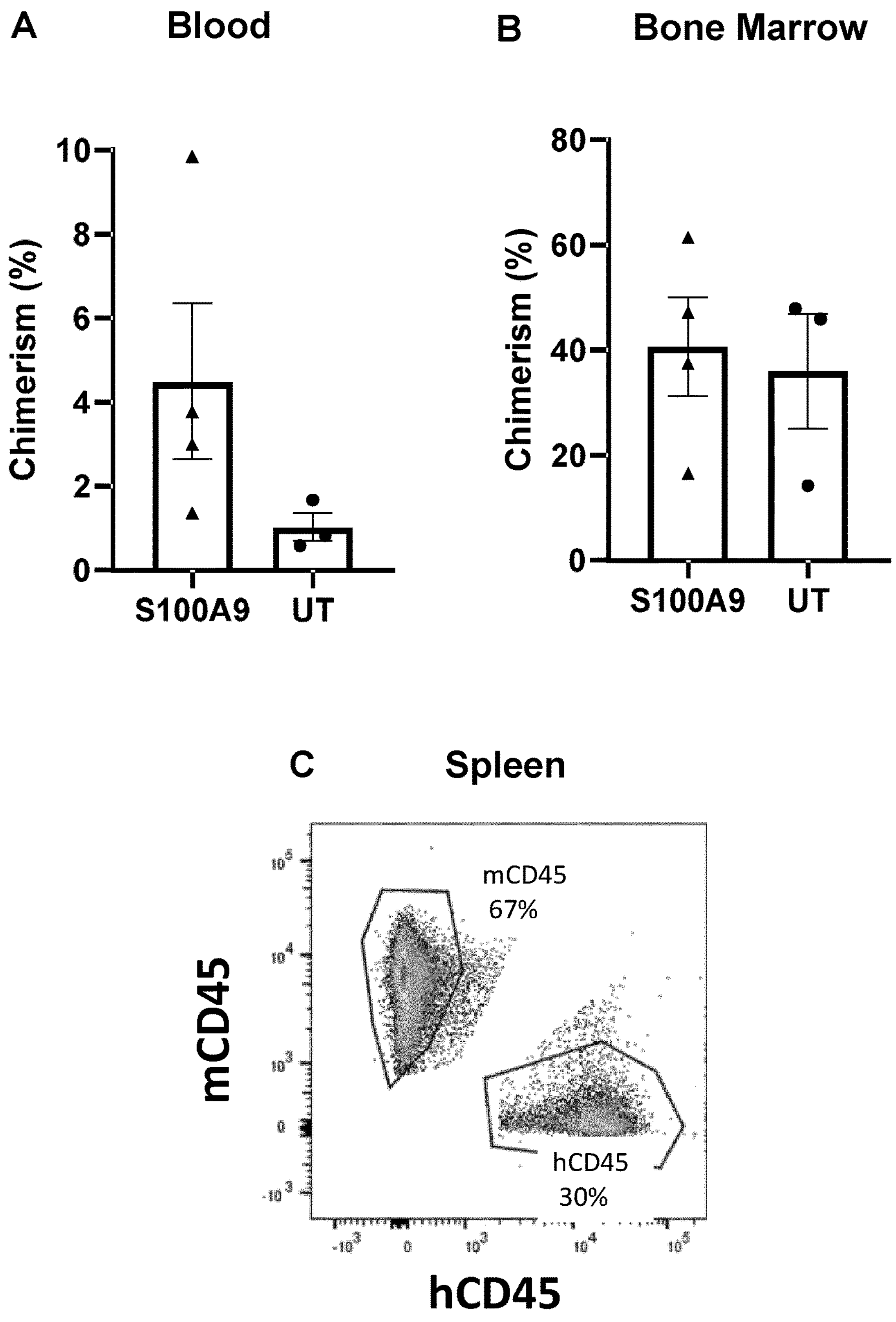
FIG. 10. Percentage of chimerism characterized by the % age of human cells detected in blood (A) or in bone marrow (B) after targeted integration of GFP at S100A9 locus compared to untreated (UT) cells. Example of flow cytometry showing chimerism in the spleen by quantification of mouse and human CD45 positive cells.

Sixteen weeks after the injection of edited HSC, engraftment in blood and bone marrow was detected in all animals at similar levels among study groups, averaging 3.3% in blood and 40.8% in bone marrow (FIGS. 10A and B). In addition, between 24 and 30% of human cells could be detected in the spleens of animals (FIG. 10C). More importantly, edited cells in all these compartments could be detected.

Figure 11:
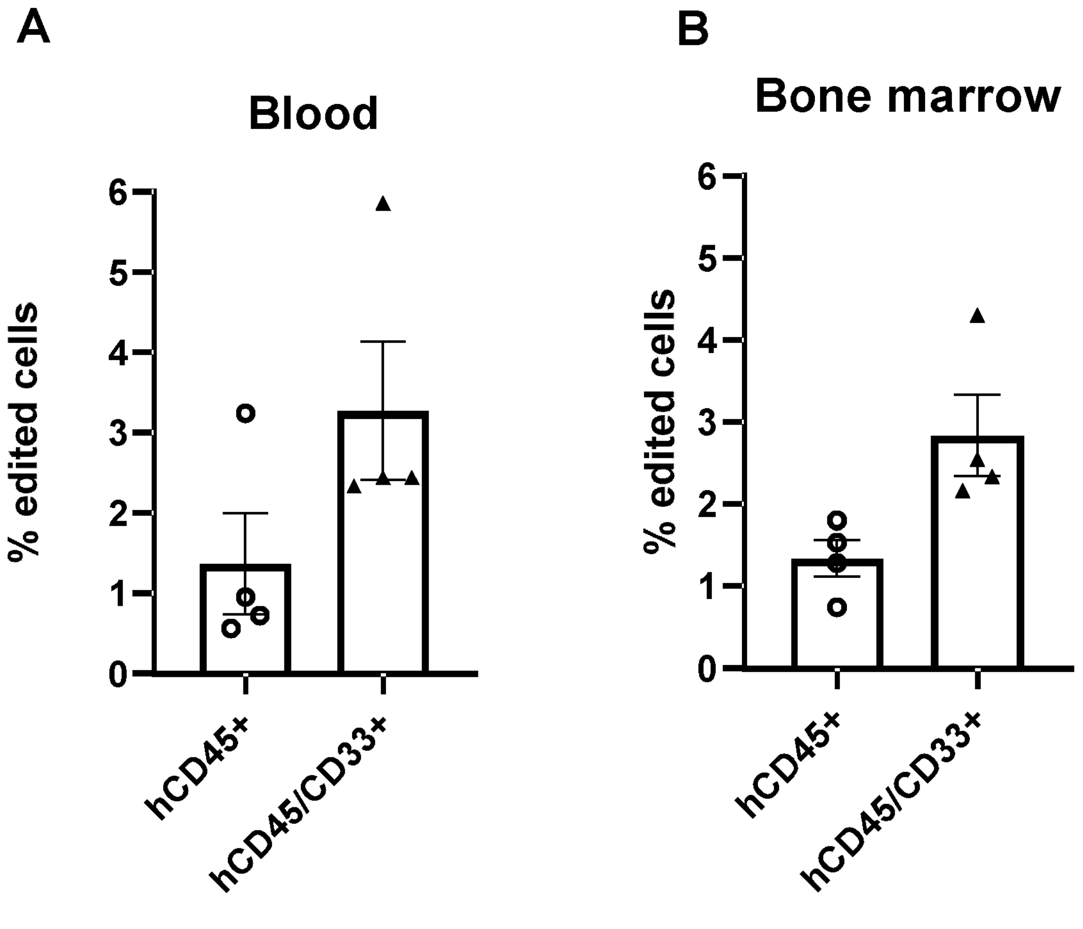
FIG. 11. Percentage of targeted integration of GFP at S100A9 locus in hCD45+ or hCD45 and hCD33+ cells in Blood (A) or in Bone Marrow (B).

The presence of edited cells in blood of these animals was analyzed. On bulk human CD45 cells, we found an average of 1.4% of GFP+ cells in blood of animals injected with HSC edited at the S100A9 locus. However, when analyzing into the myeloid compartment, defined in this model as CD33+ cells, the editing rate increased up to 3.3%, twice as higher than in bulk population (FIG. 11A).

The percentage of edited cells was also analyzed in the bone marrow, and 1.3% of human cells were GFP+. In addition, 2.8% of hCD45+ and CD33+ human cells in the bone marrow were GFP+(FIG. 10B)

Example 5: Edited HSC Successfully Engrafted in the Brain of an Animal Model: In Vivo Results Another potential advantage of this therapeutic approach is the ability that HSC derived microglia can secrete a deficient LSD enzyme in the brain compartment, enabling the treatment of the devastating neurological symptoms associated with these LSD diseases. To investigate about this potential feature, the presence of human cells in the brains of the aforementioned animals was analyzed.

Figure 12:
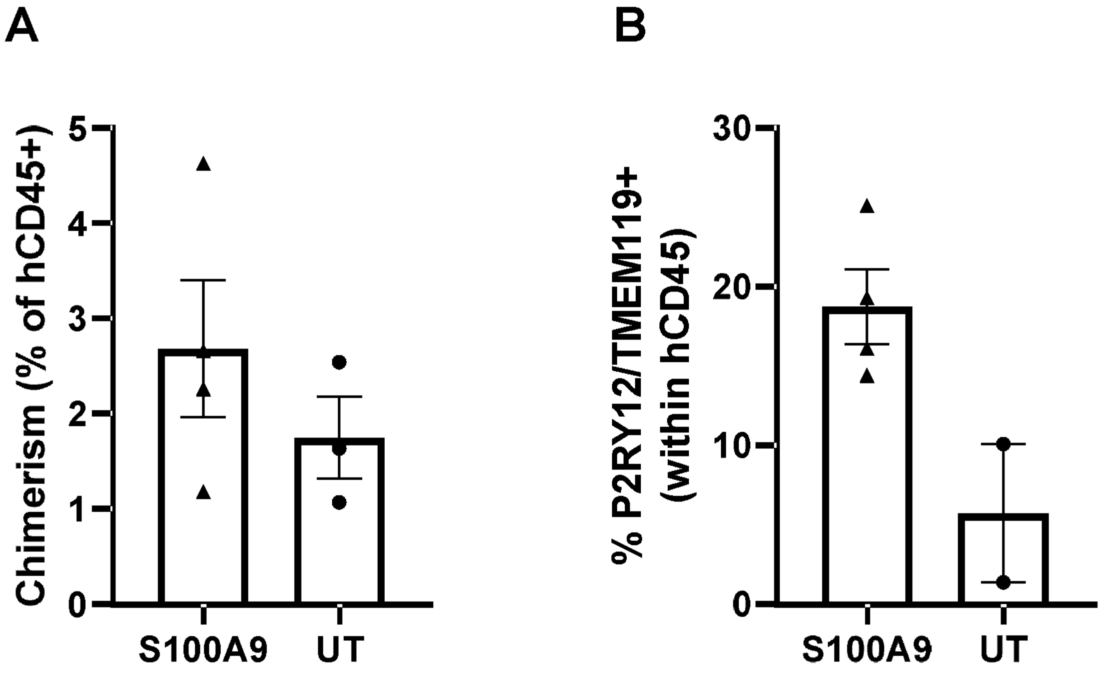
FIG. 12. A. Percentage of chimerism (percentage of human cells) in the brain. B. Percentage of microglial cells (P2RY12/TMEM119+ cells) within human cells detected in the brain.

After isolation of mouse brains and cell processing, significant amount of human cells in mouse brains could be detected. On average 2.7% of cells in the brain had human origin (FIG. 12A). More importantly, 18.5% of these human cells contained derived microglia, using P2RY12 and TMEM119 microglial markers (FIG. 12B). Since these 2 markers were not found in any human cells present in the peripheral blood of these animals, it ruled out any potential contamination of brain isolate with peripheral blood cells during extraction.

In this brain compartment, GFP positive cells represented at least 1.2% and 1.6% of all human cells and of the human microglial cells, respectively.

Example 6: ArtEx Edited HSCs have High Secretion Profile

ArtEx edited HSCs were compared to classical lentiviral edited HSCs for their ability to secrete the therapeutic protein.

Untreated HSCs, HSCs transduced with a lentiviral vector allowing the expression of IDUA and HSCs with targeted integration of IDUA at the S100A9 or CD11b loci as described in preceding examples. Edited HSC were placed into myeloid differentiation media. Fourteen days after, myeloid-like differentiated cells were seeded for IDUA production. Cell supernatants were collected 3 days after and IDUA was quantified by ELISA. We observed that cells edited at CD11b and S100A9 loci secreted 10× and 15× fold more IDUA than unedited controls, respectively (FIG. 13A).

Results demonstrate that ArtEx edited HSCs were able to stimulate IDUA secretion by a 10fold factor whereas HSCs transduced with a lentivirus vector stimulate IDUA secretion by a 5 fold factor.

Figure 13:
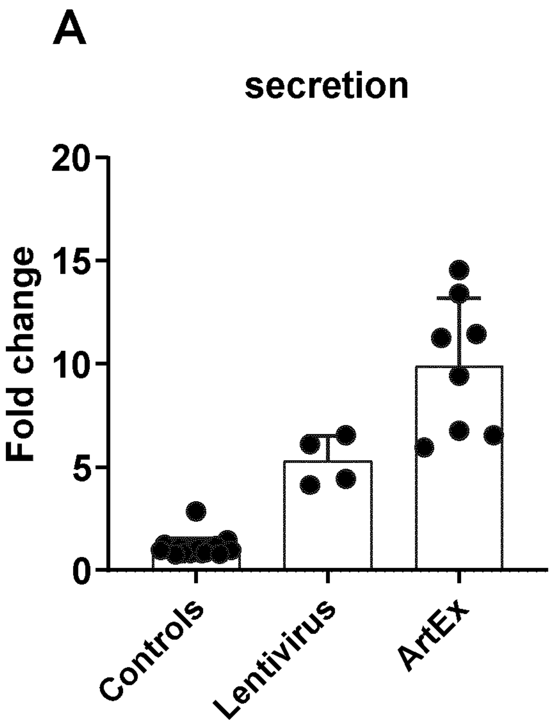
FIG. 13. A. Increased expression of IDUA by HSCs edited lentivirus vector or by targeted artificial exon insertion in CD11b or S100A9 loci compared to untreated HSC (controls). B. Chimerism percentage of human cells detected in Blood, Spleen, Bone Marow after transplantation of edited HSCs. C. Detection in the brain of human cells and of human microglial cells (TMEM119+ and P2RY12+).
Figure 13:
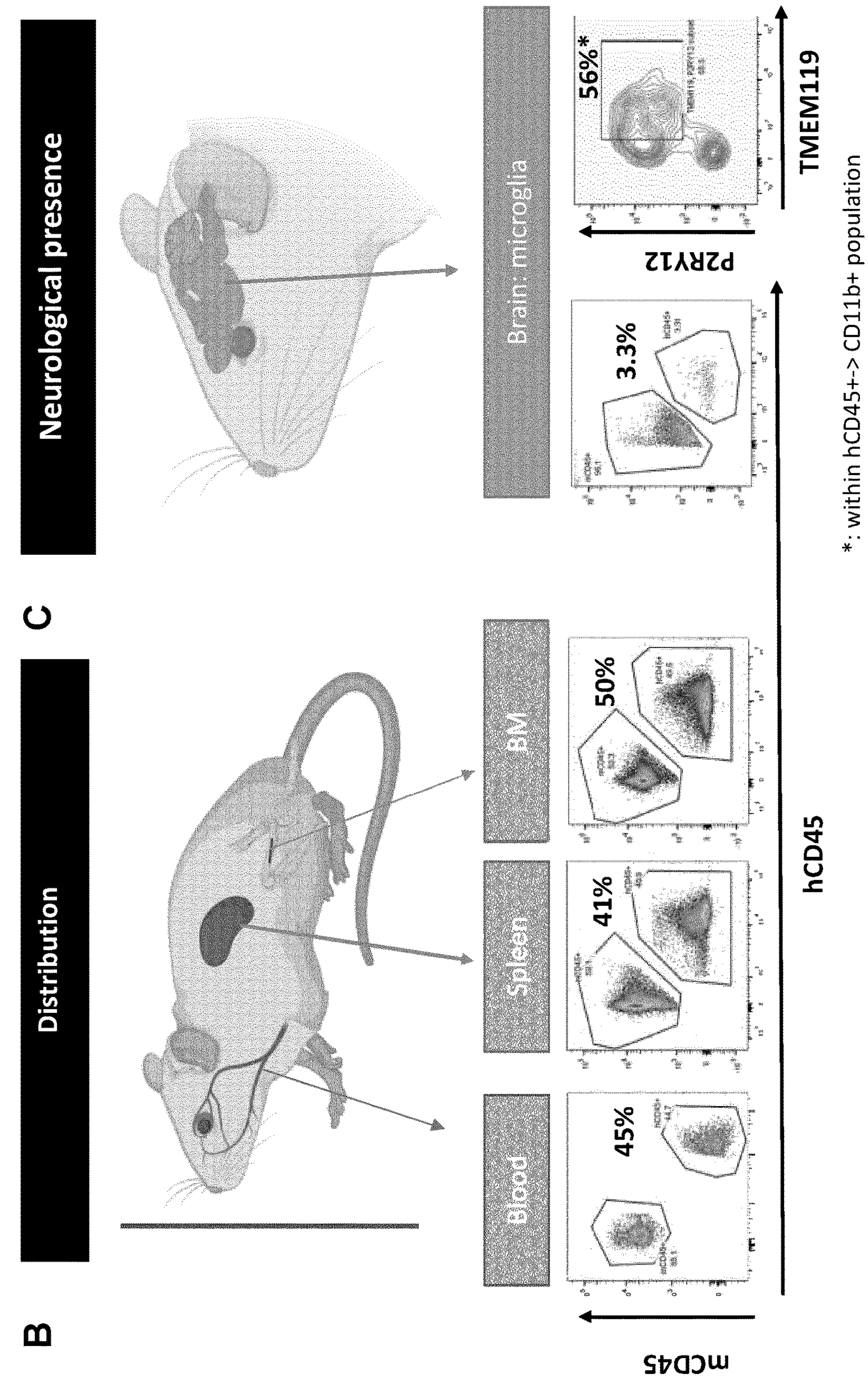

In addition the HSCs were tested for engraftment efficacy in mice and as previously observed the edited HSCs could engraft efficiently into the bone marrow (50%), the spleen (41%) and the blood (45%) and most importantly into the brain up to 3,3% with a significant amount of microglial cells (FIG. 13B ad C).

All together these results reveal the potential of ArtEx strategy to secret high level of therapeutic protein even in the brain.

The invention claimed is:

1. A method for integrating an exogenous coding sequence into an endogenous intronic genomic region at an insertion site comprising the following steps:

providing cell(s) comprising an endogenous intronic genomic region, introducing into said cell(s) a polynucleotide template comprising an exogenous coding sequence, wherein said polynucleotide template comprises the following, in order:

a) a first homologous polynucleotide sequence, which is homologous to the intronic sequence upstream of the insertion site, b) a first strong splice site sequence, comprising a branch point and a splice acceptor;

c) a first sequence encoding 2A self-cleaving peptide;

d) an exogenous sequence coding for a protein of interest;

e) a second sequence encoding 2A self-cleaving peptide;

f) a copy of the coding sequence of a first exon(s);

g) a second strong splice site sequence comprising a splice donor; and h) a second homologous polynucleotide sequence, which is homologous to the intronic sequence downstream of the insertion site;

inducing the integration of said exogenous polynucleotide into said intronic sequence, homologous recombination to have said exogenous coding sequence being transcribed at said endogenous locus along with the first exon(s) or a copy thereof.

2. The method according to claim 1, wherein said integration forms an artificial exon (Artex) and is introduced into a hematopoietic stem cell (HSC) in order to obtain expression of said exogenous coding sequence into at least one hematopoietic cell lineage.

3. The method according to claim 1, wherein said exogenous coding sequence encodes a protein of interest for treating a genetic disease.

4. The method according to claim 1, wherein said exogenous coding sequence is for expression in progenitor cells and expresses a protein selected from FANCA, FANCC or FANCG.

5. The method according to claim 1, wherein said exogenous coding sequence allows expression of the protein of interest in red blood cells and expresses a protein selected from HBB, PKLR or RPS19.

6. The method according to claim 1, wherein said exogenous coding sequence is for expression in granulocyte and expresses a protein selected from HAX1, CYBA, CYBB, NCF1, NCF2 or NCF4.

7. The method according to claim 1, wherein said exogenous coding sequence is for expression in megakaryocyte and expresses a protein selected from Factor 8, Factor 9, Factor 11 or WAS.

8. The method according to claim 1, wherein said exogenous coding sequence is for expression in Monocytes and expresses a protein selected from IDUA, IDS, ARSB, GUSB, ABCD1 GALC, ARSA, PSAP, GBA, FUCA1, MAN2B1, AGA, ASAH1, HEXA, GAA, SMPD1, LIPA and CDKL5.

9. The method according to claim 1, wherein said exogenous coding sequence is for expression in B-cells and expresses a protein selected from ADA, IL2RG, WAS or BTK.

10. The method according to claim 1, wherein said exogenous coding sequence is for expression in T-cells and expresses a protein selected from ADA, IL2RG, WAS, BTK or CCR5.

11. The method according to claim 1, wherein said expression of said exogenous sequence also allows expression of said endogenous locus, downstream the insertion site.

12. The method according to claim 1, wherein the expression of said exogenous coding sequence results into a protein of interest allowing the cross correction of an endogenous deficient protein.

13. An AAV insertion vector characterized in that it comprises an exogenous polynucleotide sequence for insertion at an endogenous locus comprising the following sequences, in order:

a) a first homologous polynucleotide sequence, which is homologous to the intronic sequence upstream of the insertion site, b) a first strong splice site sequence, comprising a branch point and a splice acceptor;

c) a first sequence encoding 2A self-cleaving peptide;

d) an exogenous sequence coding for a protein of interest;

e) a second sequence encoding 2A self-cleaving peptide;

f) a copy of the coding sequence of the first exon;

g) a second strong splice site sequence comprising a splice donor; and h) a second homologous polynucleotide sequence, which is homologous to the intronic sequence downstream of the insertion site.

14. The insertion vector according to claim 13, wherein said first and second homologous sequences are homologous to an endogenous locus selected from: tmem119, s100a9, cd11b, b2m, cx3cr1, mertk, cd164, tlr4, tlr7, cd14, fcgr1a, fcgr3a, tbxas1, dok3, abca1, tmem195, mr1, csf3r, fgd4, tspan14, tgfbri, ccr5, gpr34, serpine2, slco2b1, p2ryl2, olfml3, p2ryl3, hexb, rhob, jun, rab3il1, ccl2, fcrls, scoc, siglech, slc2a5, lrrc3, plxdc2, usp2, ctsf, cttnbp2nl, atp8a2, lgmn, mafb, egr1, bhlhe41, hpgds, ctsd, hspa1a, lag3, csf1r, adamts1, f11r, golm1, nuak1, crybb1, ltc4s, sgce, pla2g15, ccl311, abhd12, ang, ophn1, sparc, pros1, p2ry6, lair1, il1a, epb4112, adora3, rilpl1, pmepa1, ccl13, pde3b, scamp5, ppp1r9a, tjp1, ak1, b4galt4, gtf2h2, trem2, ckb, acp2, pon3, agmo, tnfrsf17, fscn1, st3gal6, adap2, ccl4, entpd1, tmem86a, kctd12, dst, ctsl2, abcc3, pdgfb, pald1, tubgcp5, rapgef5, stab1, lacc1, tmc7, nrip1, kcnd1, tmem206, hps4, dagla, extl3, mlph, arhgap22, cxxc5, p4ha1, cysltr1, fgd2, kcnk13, gbgt1, c18orf1, cadm1, bco2, adrb1, c3ar1, large, leprel1, liph, upk1b, p2rx7, slc46a1, ebf3, ppp1r15a, il10ra, rasgrp3, fos, tppp, slc24a3, havcr2, nav2, apbb2, clstn1, bink, gnaq, ptprm, frmd4a, cd86, tnfrsf11a, spint1, ppm1l, tgfbr2, cmklr1, tlr6, gas6, hist1h2ab, atf3, acvr1, abi3, lrp12, ttc28, plxna4, adamts16, rgs1, icam1, snx24, ly96, dnajb4, and ppfia4.

15. The insertion vector according to claim 13, wherein said therapeutic protein encoded by said exogenous coding sequence has at least 80% polypeptide sequence identity with IDUA, IDS, ARSB, GUSB, ABCD1, GALC, ARSA, PSAP, GBA, FUCA1, MAN2B1, AGA, ASAH1, HEXA, GAA, SMPD1, LIPA and CDKL5 (SEQ ID NO:1 to SEQ ID NO: 35).

16. An engineered cell, characterized in that it is obtainable according to the method of claim 1.

17. An engineered cell, characterized in that an exogenous polynucleotide sequence has been inserted into an intron at an endogenous locus, said polynucleotide sequence comprising, in order:

a first strong splice site sequence comprising a branch point and an acceptor site;

a first sequence encoding 2A self-cleaving peptide;

an exogenous sequence coding for a protein of interest, such as a therapeutic protein;

a second sequence encoding 2A self-cleaving peptide;

a copy of the coding sequence of the preceding exon endogenous to said locus;

a second strong splice site sequence comprising a splice donor site.

18. An engineered cell, according to claim 17, wherein said protein of interest is IDUA, IDS, ARSA, ARSB, GUSB, ABCD1, GALC, ARSA, PSAP, GBA, FUCA1, MAN2B1, AGA, ASAH1, HEXA, GAA, SMPD1, LIPA, CDKL5, FANCA, FANCC, FANCG, HBB, PKLR, RPS19, HAX1, CYBA, CYBB, NCF1, NCF2, NCF4, Factor 8, Factor 9, Factor 11, WAS, IL2RG or BTK.

19. The engineered cell according to claim 17, wherein said coding sequence of the preceding exons endogenous to said locus has been rewritten.

* * * * *